US010851342B2

(12) United States Patent
Kato et al.

(10) Patent No.: US 10,851,342 B2
(45) Date of Patent: Dec. 1, 2020

(54) METHOD FOR PRODUCING PLURIPOTENT STEM CELLS

(71) Applicant: SAITAMA MEDICAL UNIVERSITY, Saitama (JP)

(72) Inventors: Hidemasa Kato, Saitama (JP); Yosuke Moriyama, Saitama (JP); Keiko Hiraki, Saitama (JP); Akihiko Okuda, Saitama (JP)

(73) Assignee: Saitama Medical University, Saitama (JP)

( * ) Notice: Subject to any disclaimer, the term of this patent is extended or adjusted under 35 U.S.C. 154(b) by 461 days.

(21) Appl. No.: 15/842,701

(22) Filed: Dec. 14, 2017

(65) Prior Publication Data
US 2018/0094239 A1 Apr. 5, 2018

Related U.S. Application Data

(62) Division of application No. 14/439,037, filed as application No. PCT/JP2013/079311 on Oct. 29, 2013, now Pat. No. 9,868,934.

(30) Foreign Application Priority Data

Oct. 29, 2012 (JP) ................... 2012-237734

(51) Int. Cl.
C12N 15/85 (2006.01)
C12N 15/63 (2006.01)
C12N 5/074 (2010.01)
C12N 9/02 (2006.01)

(52) U.S. Cl.
CPC ......... *C12N 5/0607* (2013.01); *C12N 5/0696* (2013.01); *C12N 9/0071* (2013.01); *C12Y 114/11* (2013.01); *C12N 2501/71* (2013.01); *C12N 2510/00* (2013.01)

(58) Field of Classification Search
None
See application file for complete search history.

(56) References Cited

U.S. PATENT DOCUMENTS

2014/0249208 A1 9/2014 Bancel
2015/0232810 A1 8/2015 Luo et al.

FOREIGN PATENT DOCUMENTS

| JP | 2013-126412 | | 6/2013 |
| WO | WO2007047796 | * | 4/2007 |
| WO | WO 2010/037001 A2 | | 4/2010 |
| WO | WO 2011/075627 A1 | | 6/2011 |
| WO | WO 2011/130624 A2 | | 10/2011 |

OTHER PUBLICATIONS

Arnesen et al, Proteomics analyses reveal the evolutionary conservation and divergence of N-terminal acetyltransferases from yeast and humans, PNAS, 106(20):8157-8162 (May 2009).
Branco et al., Uncovering the role of 5-hydroxymethylcytosine in the epigenome, Nature Reviews, Genetics, 13:7-13, (Jan. 2012).
Cimmino et al., TET Family Proteins and Their Role in Stem Cell Differentiation and Transformation, Cell Stem Cell, 9:193-204, (Sep. 2011).
Costa et al., NANOG-dependent function of TET1 and TET2 in establishment of Pluripotency, Nature, 495:370-374 (2013).
Dawlaty et al., Tet1 Is Dispensable for Maintaining Pluripotency and Its Loss Is Compatible with Embryonic and Postnatal Development, Cell Stem Cell, 9(2):166-175 (2011).
Extended European Search Report for corresponding EP App. No. 13851495.5, dated Apr. 14, 2016 (10 pages).
Fan et al., Effects of TET1 knockdown on gene expression and DNA methylation in porcine induced pluripotent stem cells, Reproduction, 146 569-579 (Dec. 1, 2013).
Gao et al., Replacement of Oct4 by Tet1 during iPSC Induction Reveals an Important Role of DNA Methylation and Hydroxymethylation in Reprogramming, Cell Stem Cell, 12(4):453-469 (2013).
Hackett et al., Germline DNA demethylation dynamics and imprint erasure through 5-hydroxymethylcytosine., Science, 339(6118):448-452 (2013).
Hwang et al., N-Terminal Acetylation of Cellular Proteins Creates Specific Degradation Signals Science, 327(5968):973-977 (Feb. 2010).
International Preliminary Report on Patentability for International App No. PCT/JP2013/079311, dated May 14, 2015 (with English translation) (6 pages).
International Search Report dated Feb. 4, 2014 for PCT/JP2013/079311 (2 pages).
Ito et al., Role of Tet proteins in 5mC to 5hmC conversion, ES-cell self-renewal and inner cell mass specification, Nature, 466:1129-1135, (Aug. 2010).
Kato, et al., TET1 compensates a defect of currently available human iPS cells, to dramatically increase efficiency of cell differentiation, Regenerative Medicine, (Journal of the Japanese Society for Regenerative Medicine) Program of the 12th Congress of the Japanese Society for Regenerative Medicine, vol. 12, p. 232, O-64-3 (Feb. 28, 2013) (with English Translation).
Koh et al., Tet1 and Tet2 Regulate 5-Hydroxymethylcytosine Production and Cell Lineage Specification in Mouse Embryonic Stem Cells, Cell Stem Cell, 8:200-213, (Feb. 2011).
Lecchi, Identification of a new dysfunctional platelet P2Y12 receptor variant associated with bleeding diathesis, Blood, 125(6):1006-1013 (2015).

(Continued)

Primary Examiner — Maria G Leavitt
(74) Attorney, Agent, or Firm — Fish & Richardson P.C.

(57) ABSTRACT

The present invention allows a TET1 protein to be more stably expressed in human pluripotent stem cells than in the past by, inter alia, substituting the second amino acid from the amino terminal of a TET1 protein with a different amino acid. Furthermore, upon differentiation of said pluripotent stem cells, it is possible to quickly eliminate the expression of, inter alia, NANOG, which is an inhibitor of differentiation and promote the expression of factors related to differentiation by introducing a variant TET1 protein to a pluripotent stem cell. The present invention provides a method for manufacturing pluripotent stem cells with increased differentiation potential, and a substance that is useful to said method.

7 Claims, 53 Drawing Sheets

Specification includes a Sequence Listing.

(56) References Cited

OTHER PUBLICATIONS

Lee et al., Tumorigenicity as a clinical hurdle for pluripotent stem cell therapies, Nature Medicine, 19(8):998-1004 (Aug. 2013).
Moreadith et al., Gene targeting in embryonic stem cells: the new physiology and metabolism, J Mol Med 75:208-216 (1997).
Ngo, et al., Computational Complexity, Protein Structure Prediction, and the Levinthal Paradox, The Protein Folding Problem and Tertiary Structure Prediction, Merz et al. (eds.), Birkhauser Boston: Boston, MA, pp. 433 and 492-495 (1994).
Office Action dated Feb. 9, 2016 in corresponding Japanese patent application No. 2014-544531 (with partial English translation) (9 pages).
Okashita et al., PRDM14 maintains pluripotency of embryonic stem cells through TET-mediated active DNA demethylation, Biochemical and Biophysical Research Communications, 466:138-145.
Okashita et al., PRDM14 promotes active DNA demethylation through the Teneleventranslocation (TET)-mediated base excision repair pathway in embryonic stem cells, Stem Cells And Regeneration Development, 141:269-280 (2014).
Osafune et al., Marked differences in differentiation propensity among human embryonic stem cell lines, Nat Biotechnol. 26(3):313-5 (Mar. 2008).
Polevoda and Sherman, N-terminal Acetyltransferases and Sequence Requirements for N-terminal Acetylation of Eukaryotic Proteins, J. Mol. Biol. 325:595-622 (2003).
Rudinger J., Characteristics of the amino acids as components of a peptide hormone sequence, in Peptide Hormones, Parsons (ed.), University Park Press: Baltimore, MD, pp. 1-7 (1976).
Xu et al., Genome-wide Regulation of 5hmC, 5mC, and Gene Expression by Tet1 Hydroxylase in Mouse Embryonic Stem Cells, Molecular Cell, 42(4):451-464 (2011).
Yan et al., Two-amino acid molecular switch in an epithelial morphogen that regulates binding to two distinct receptors, Science, 290(5491):523-7 (Oct. 2000).

* cited by examiner

SEQUENCE LISTING

```
<160> NUMBER OF SEQ ID NOS: 46

<210> SEQ ID NO 1
<211> LENGTH: 9601
<212> TYPE: DNA
<213> ORGANISM: Homo sapiens
<220> FEATURE:
<221> NAME/KEY: CDS
<222> LOCATION: (506)..(6916)

<400> SEQUENCE: 1
agacactgct gctccggggg gctgacctgg cggggagtgg ccgcgcagtc tgctccggcg      60
ccgctttgtg cgcgcagccg ctggcccctc tactcccggg tctgcccccc gggacacccc     120
tctgcctcgc ccaagtcatg cagccctacc tgcctctcca ctgtgtgacct ttgggaaccg    180 actcctcacc tcggggctc gggccttgac tgtgctggga gccggtaggc gtcctccgcg      240 accgcccgc gccctcgcg cccgccgggg ccccgggctc caaagttgtg gggaccggcg       300
cgagttggaa agtttgcccg agggctggtg caggcttgga gctgggggcc gtgcgctgcc    360
ctgggaatgt gacccggcca gcgaccaaaa ccttgtgtga ctgagctgaa gagcagtgca    420
tccagattct cctcagaagt gagactttcc aaaggaccaa tgactctgtt tcctgcgccc    480
tttcattttt tcctactctg tagct atg tct cga tcc cgc cat gca agg cct     532
                             Met Ser Arg Ser Arg His Ala Arg Pro
                              1               5 tcc aga tta gtc agg aag gaa gat gta aac aaa aaa aag aaa aac agc      580
Ser Arg Leu Val Arg Lys Glu Asp Val Asn Lys Lys Lys Lys Asn Ser
 10              15                  20                  25 caa cta cga aag aca acc aag gga gcc aac aaa aat gtg gca tca gtc     628
Gln Leu Arg Lys Thr Thr Lys Gly Ala Asn Lys Asn Val Ala Ser Val
             30                  35                  40 aag act tta agc cct gga aaa tta aag caa tta att caa gaa aga gat     676
Lys Thr Leu Ser Pro Gly Lys Leu Lys Gln Leu Ile Gln Glu Arg Asp
         45                  50                  55 gtt aag aaa aaa aca gaa cct aaa cca ccc gtg cca gtc aga agc ctt     724
Val Lys Lys Lys Thr Glu Pro Lys Pro Pro Val Pro Val Arg Ser Leu
     60                  65                  70 ctg aca aga gct gga gca gca cgc atg aat ttg gat agg act gag gtt     772
Leu Thr Arg Ala Gly Ala Ala Arg Met Asn Leu Asp Arg Thr Glu Val
 75                  80                  85 ctt ttt cag aac cca gag tcc tta acc tgc aat ggg ttt aca atg gcg     820
Leu Phe Gln Asn Pro Glu Ser Leu Thr Cys Asn Gly Phe Thr Met Ala
 90                  95                 100                 105 cta cga agc acc tct ctt agc agg cga ctc tcc caa ccc cca ctg gtc     868
Leu Arg Ser Thr Ser Leu Ser Arg Arg Leu Ser Gln Pro Pro Leu Val
            110                 115                 120 gta gcc aaa tcc aaa aag gtt cca ctt tct aag ggt tta gaa aag caa     916
Val Ala Lys Ser Lys Lys Val Pro Leu Ser Lys Gly Leu Glu Lys Gln
        125                 130                 135 cat gat tgt gat tat aag ata ctc cct gct ttg gga gta aag cac tca     964
His Asp Cys Asp Tyr Lys Ile Leu Pro Ala Leu Gly Val Lys His Ser
    140                 145                 150
```

-continued

| | | |
|---|---|---|
| gaa aat gat tcg gtt cca atg caa gac acc caa gtc ctt cct gat ata<br>Glu Asn Asp Ser Val Pro Met Gln Asp Thr Gln Val Leu Pro Asp Ile<br>155                   160                   165 | 1012 |
| gag act cta att ggt gta caa aat ccc tct tta ctt aaa ggt aag agc<br>Glu Thr Leu Ile Gly Val Gln Asn Pro Ser Leu Leu Lys Gly Lys Ser<br>170                   175                   180                   185 | 1060 |
| caa gag aca act cag ttt tgg tcc caa aga gtt gag gat tcc aag atc<br>Gln Glu Thr Thr Gln Phe Trp Ser Gln Arg Val Glu Asp Ser Lys Ile<br>190                   195                   200 | 1108 |
| aat atc cct acc cac agt ggc cct gca gct gag atc ctt cct ggg cca<br>Asn Ile Pro Thr His Ser Gly Pro Ala Ala Glu Ile Leu Pro Gly Pro<br>205                   210                   215 | 1156 |
| ctg gaa ggg aca cgc tgt ggt gaa gga cta ttc tct gaa gag aca ttg<br>Leu Glu Gly Thr Arg Cys Gly Glu Gly Leu Phe Ser Glu Glu Thr Leu<br>220                   225                   230 | 1204 |
| aat gat acc agt ggt tcc cca aaa atg ttt gct cag gac aca gtg tgt<br>Asn Asp Thr Ser Gly Ser Pro Lys Met Phe Ala Gln Asp Thr Val Cys<br>235                   240                   245 | 1252 |
| gct cct ttt ccc caa aga gca acc ccc aaa gtt acc tct caa gga aac<br>Ala Pro Phe Pro Gln Arg Ala Thr Pro Lys Val Thr Ser Gln Gly Asn<br>250                   255                   260                   265 | 1300 |
| ccc agc att cag tta gaa gag ttg ggt tca cga gta gaa tct ctt aag<br>Pro Ser Ile Gln Leu Glu Glu Leu Gly Ser Arg Val Glu Ser Leu Lys<br>270                   275                   280 | 1348 |
| tta tct gat tct tac ctg gat ccc att aaa agt gaa cat gat tgc tac<br>Leu Ser Asp Ser Tyr Leu Asp Pro Ile Lys Ser Glu His Asp Cys Tyr<br>285                   290                   295 | 1396 |
| ccc acc tcc agt ctt aat aag gtt ata cct gac ttg aac ctt aga aac<br>Pro Thr Ser Ser Leu Asn Lys Val Ile Pro Asp Leu Asn Leu Arg Asn<br>300                   305                   310 | 1444 |
| tgc ttg gct ctt ggt ggg tct acg tct cct acc tct gta ata aaa ttc<br>Cys Leu Ala Leu Gly Gly Ser Thr Ser Pro Thr Ser Val Ile Lys Phe<br>315                   320                   325 | 1492 |
| ctc ttg gca ggc tca aaa caa gcg acc ctt ggt gct aaa cca gat cat<br>Leu Leu Ala Gly Ser Lys Gln Ala Thr Leu Gly Ala Lys Pro Asp His<br>330                   335                   340                   345 | 1540 |
| caa gag gcc ttc gaa gct act gca aat caa cag gaa gtt tct gat acc<br>Gln Glu Ala Phe Glu Ala Thr Ala Asn Gln Gln Glu Val Ser Asp Thr<br>350                   355                   360 | 1588 |
| acc tct ttc cta gga cag gcc ttt ggt gct atc cca cat caa tgg gaa<br>Thr Ser Phe Leu Gly Gln Ala Phe Gly Ala Ile Pro His Gln Trp Glu<br>365                   370                   375 | 1636 |
| ctt cct ggt gct gac cca gtt cat ggt gag gcc ctg ggt gag acc cca<br>Leu Pro Gly Ala Asp Pro Val His Gly Glu Ala Leu Gly Glu Thr Pro<br>380                   385                   390 | 1684 |
| gat cta cca gag att cct ggt gct att cca gtc caa gga gag gtc ttt<br>Asp Leu Pro Glu Ile Pro Gly Ala Ile Pro Val Gln Gly Glu Val Phe<br>395                   400                   405 | 1732 |
| ggt act att tta gac caa caa gaa act ctt ggt atg agt ggg agt gtt<br>Gly Thr Ile Leu Asp Gln Gln Glu Thr Leu Gly Met Ser Gly Ser Val<br>410                   415                   420                   425 | 1780 |
| gtc cca gac ttg cct gtc ttc ctt cct gtt cct cca aat cca att gct<br>Val Pro Asp Leu Pro Val Phe Leu Pro Val Pro Pro Asn Pro Ile Ala<br>430                   435                   440 | 1828 |
| acc ttt aat gct cct tcc aaa tgg cct gag ccc caa agc act gtc tca<br>Thr Phe Asn Ala Pro Ser Lys Trp Pro Glu Pro Gln Ser Thr Val Ser<br>445                   450                   455 | 1876 |
| tat gga ctt gca gtc cag ggt gct ata cag att ttg cct ttg ggc tca<br>Tyr Gly Leu Ala Val Gln Gly Ala Ile Gln Ile Leu Pro Leu Gly Ser<br>460                   465                   470 | 1924 |

```
gga cac act cct caa tca tca aac tca gag aaa aat tca tta cct         1972
Gly His Thr Pro Gln Ser Ser Ser Asn Ser Glu Lys Asn Ser Leu Pro
        475                 480                 485 cca gta atg gct ata agc aat gta gaa aat gag aag cag gtt cat ata     2020
Pro Val Met Ala Ile Ser Asn Val Glu Asn Glu Lys Gln Val His Ile
490                 495                 500                 505 agc ttc ctg cca gct aac act cag ggg ttc cca tta gcc cct gag aga     2068
Ser Phe Leu Pro Ala Asn Thr Gln Gly Phe Pro Leu Ala Pro Glu Arg
                510                 515                 520 gga ctc ttc cat gct tca ctg ggt ata gcc caa ctc tct cag gct ggt     2116
Gly Leu Phe His Ala Ser Leu Gly Ile Ala Gln Leu Ser Gln Ala Gly
            525                 530                 535 cct agc aaa tca gac aga ggg agc tcc cag gtc agt gta acc agc aca     2164
Pro Ser Lys Ser Asp Arg Gly Ser Ser Gln Val Ser Val Thr Ser Thr
        540                 545                 550 gtt cat gtt gtc aac acc aca gtg gtg act atg cca gtg cca atg gtc     2212
Val His Val Val Asn Thr Thr Val Val Thr Met Pro Val Pro Met Val
555                 560                 565 agt acc tcc tct tct tcc tat acc act ttg cta ccg act ttg gaa aag     2260
Ser Thr Ser Ser Ser Ser Tyr Thr Thr Leu Leu Pro Thr Leu Glu Lys
570                 575                 580                 585 aag aaa aga aag cga tgt ggg gtc tgt gaa ccc tgc cag cag aag acc     2308
Lys Lys Arg Lys Arg Cys Gly Val Cys Glu Pro Cys Gln Gln Lys Thr
                590                 595                 600 aac tgt ggt gaa tgc act tac tgc aag aac aga aag aac agc cat cag     2356
Asn Cys Gly Glu Cys Thr Tyr Cys Lys Asn Arg Lys Asn Ser His Gln
            605                 610                 615 atc tgt aag aaa aga aaa tgt gag gag ctg aaa aag aaa cca tct gtt     2404
Ile Cys Lys Lys Arg Lys Cys Glu Glu Leu Lys Lys Lys Pro Ser Val
        620                 625                 630 gtt gtg cct ctg gag gtt ata aag gaa aac aag agg ccc cag agg gaa     2452
Val Val Pro Leu Glu Val Ile Lys Glu Asn Lys Arg Pro Gln Arg Glu
    635                 640                 645 aag aag ccc aaa gtt tta aag gca gat ttt gac aac aaa cca gta aat     2500
Lys Lys Pro Lys Val Leu Lys Ala Asp Phe Asp Asn Lys Pro Val Asn
650                 655                 660                 665 ggc ccc aag tca gaa tcc atg gac tac agt aga tgt ggt cat ggg gaa     2548
Gly Pro Lys Ser Glu Ser Met Asp Tyr Ser Arg Cys Gly His Gly Glu
                670                 675                 680 gaa caa aaa ttg gaa ttg aac cca cat act gtt gaa aat gta act aaa     2596
Glu Gln Lys Leu Glu Leu Asn Pro His Thr Val Glu Asn Val Thr Lys
            685                 690                 695 aat gaa gac agc atg aca ggc atc gag gtg gag aag tgg aca caa aac     2644
Asn Glu Asp Ser Met Thr Gly Ile Glu Val Glu Lys Trp Thr Gln Asn
        700                 705                 710 aag aaa tca cag tta act gat cac gtg aaa gga gat ttt agt gct aat     2692
Lys Lys Ser Gln Leu Thr Asp His Val Lys Gly Asp Phe Ser Ala Asn
    715                 720                 725 gtc cca gaa gct gaa aaa tcg aaa aac tct gaa gtt gac aag aaa cga     2740
Val Pro Glu Ala Glu Lys Ser Lys Asn Ser Glu Val Asp Lys Lys Arg
730                 735                 740                 745 acc aaa tct cca aaa ttg ttt gta caa acc gta aga aat ggc att aaa     2788
Thr Lys Ser Pro Lys Leu Phe Val Gln Thr Val Arg Asn Gly Ile Lys
                750                 755                 760 cat gta cac tgt tta cca gct gaa aca aat gtt tca ttt aaa aaa ttc     2836
His Val His Cys Leu Pro Ala Glu Thr Asn Val Ser Phe Lys Lys Phe
            765                 770                 775 aat att gaa gaa ttc ggc aag aca ttg gaa aac aat tct tat aaa ttc     2884
Asn Ile Glu Glu Phe Gly Lys Thr Leu Glu Asn Asn Ser Tyr Lys Phe
```

-continued

|  |  |  |  | 780 |  |  |  | 785 |  |  |  | 790 |  |  |  |  |
|---|---|---|---|---|---|---|---|---|---|---|---|---|---|---|---|---|
| cta | aaa | gac | act | gca | aac | cat | aaa | aac | gct | atg | agc | tct | gtt | gct | act | 2932 |
| Leu | Lys | Asp | Thr | Ala | Asn | His | Lys | Asn | Ala | Met | Ser | Ser | Val | Ala | Thr |  |
|  | 795 |  |  |  |  | 800 |  |  |  |  | 805 |  |  |  |  |  |
| gat | atg | agt | tgt | gat | cat | ctc | aag | ggg | aga | agt | aac | gtt | tta | gta | ttc | 2980 |
| Asp | Met | Ser | Cys | Asp | His | Leu | Lys | Gly | Arg | Ser | Asn | Val | Leu | Val | Phe |  |
| 810 |  |  |  |  | 815 |  |  |  |  | 820 |  |  |  |  | 825 |  |
| cag | cag | cct | ggc | ttt | aac | tgc | agt | tcc | att | cca | cat | tct | tca | cac | tcc | 3028 |
| Gln | Gln | Pro | Gly | Phe | Asn | Cys | Ser | Ser | Ile | Pro | His | Ser | Ser | His | Ser |  |
|  |  |  |  | 830 |  |  |  |  | 835 |  |  |  |  | 840 |  |  |
| atc | ata | aat | cat | cat | gct | agt | ata | cac | aat | gaa | ggt | gat | caa | cca | aaa | 3076 |
| Ile | Ile | Asn | His | His | Ala | Ser | Ile | His | Asn | Glu | Gly | Asp | Gln | Pro | Lys |  |
|  |  |  |  | 845 |  |  |  |  | 850 |  |  |  |  | 855 |  |  |
| act | cct | gag | aat | ata | cca | agt | aaa | gaa | cca | aaa | gat | gga | tct | ccc | gtt | 3124 |
| Thr | Pro | Glu | Asn | Ile | Pro | Ser | Lys | Glu | Pro | Lys | Asp | Gly | Ser | Pro | Val |  |
|  |  | 860 |  |  |  |  | 865 |  |  |  |  | 870 |  |  |  |  |
| caa | cca | agt | ctc | tta | tcg | tta | atg | aaa | gat | agg | aga | tta | aca | ttg | gag | 3172 |
| Gln | Pro | Ser | Leu | Leu | Ser | Leu | Met | Lys | Asp | Arg | Arg | Leu | Thr | Leu | Glu |  |
|  | 875 |  |  |  |  | 880 |  |  |  |  | 885 |  |  |  |  |  |
| caa | gtg | gta | gcc | ata | gag | gcc | ctg | act | caa | ctc | tca | gaa | gcc | cca | tca | 3220 |
| Gln | Val | Val | Ala | Ile | Glu | Ala | Leu | Thr | Gln | Leu | Ser | Glu | Ala | Pro | Ser |  |
| 890 |  |  |  |  | 895 |  |  |  |  | 900 |  |  |  |  | 905 |  |
| gag | aat | tcc | tcc | cca | tca | aag | tca | gag | aag | gat | gag | gaa | tca | gag | cag | 3268 |
| Glu | Asn | Ser | Ser | Pro | Ser | Lys | Ser | Glu | Lys | Asp | Glu | Glu | Ser | Glu | Gln |  |
|  |  |  |  | 910 |  |  |  |  | 915 |  |  |  |  | 920 |  |  |
| aga | aca | gcc | agt | ttg | ctt | aat | agc | tgc | aaa | gct | atc | ctc | tac | act | gta | 3316 |
| Arg | Thr | Ala | Ser | Leu | Leu | Asn | Ser | Cys | Lys | Ala | Ile | Leu | Tyr | Thr | Val |  |
|  |  |  | 925 |  |  |  |  | 930 |  |  |  |  | 935 |  |  |  |
| aga | aaa | gac | ctc | caa | gac | cca | aac | tta | cag | gga | gag | cca | cca | aaa | ctt | 3364 |
| Arg | Lys | Asp | Leu | Gln | Asp | Pro | Asn | Leu | Gln | Gly | Glu | Pro | Pro | Lys | Leu |  |
|  |  | 940 |  |  |  |  | 945 |  |  |  |  | 950 |  |  |  |  |
| aat | cac | tgt | cca | tct | ttg | gaa | aaa | caa | agt | tca | tgc | aac | acg | gtg | gtt | 3412 |
| Asn | His | Cys | Pro | Ser | Leu | Glu | Lys | Gln | Ser | Ser | Cys | Asn | Thr | Val | Val |  |
|  | 955 |  |  |  |  | 960 |  |  |  |  | 965 |  |  |  |  |  |
| ttc | aat | ggg | caa | act | act | acc | ctt | tcc | aac | tca | cat | atc | aac | tca | gct | 3460 |
| Phe | Asn | Gly | Gln | Thr | Thr | Thr | Leu | Ser | Asn | Ser | His | Ile | Asn | Ser | Ala |  |
| 970 |  |  |  |  | 975 |  |  |  |  | 980 |  |  |  |  | 985 |  |
| act | aac | caa | gca | tcc | aca | aag | tca | cat | gaa | tat | tca | aaa | gtc | aca | aat | 3508 |
| Thr | Asn | Gln | Ala | Ser | Thr | Lys | Ser | His | Glu | Tyr | Ser | Lys | Val | Thr | Asn |  |
|  |  |  |  | 990 |  |  |  |  | 995 |  |  |  |  | 1000 |  |  |
| tca | tta | tct | ctt | ttt | ata | cca | aaa | tca | aat | tca | tcc | aag | att | gac |  | 3553 |
| Ser | Leu | Ser | Leu | Phe | Ile | Pro | Lys | Ser | Asn | Ser | Ser | Lys | Ile | Asp |  |  |
|  |  |  | 1005 |  |  |  |  | 1010 |  |  |  |  | 1015 |  |  |  |
| acc | aat | aaa | agt | att | gct | caa | ggg | ata | att | act | ctt | gac | aat | tgt |  | 3598 |
| Thr | Asn | Lys | Ser | Ile | Ala | Gln | Gly | Ile | Ile | Thr | Leu | Asp | Asn | Cys |  |  |
|  |  | 1020 |  |  |  |  | 1025 |  |  |  |  | 1030 |  |  |  |  |
| tcc | aat | gat | ttg | cat | cag | ttg | cca | cca | aga | aat | aat | gaa | gtg | gag |  | 3643 |
| Ser | Asn | Asp | Leu | His | Gln | Leu | Pro | Pro | Arg | Asn | Asn | Glu | Val | Glu |  |  |
|  | 1035 |  |  |  |  | 1040 |  |  |  |  | 1045 |  |  |  |  |  |
| tat | tgc | aac | cag | tta | ctg | gac | agc | agc | aaa | aaa | ttg | gac | tca | gat |  | 3688 |
| Tyr | Cys | Asn | Gln | Leu | Leu | Asp | Ser | Ser | Lys | Lys | Leu | Asp | Ser | Asp |  |  |
|  |  |  | 1050 |  |  |  |  | 1055 |  |  |  |  | 1060 |  |  |  |
| gat | cta | tca | tgt | cag | gat | gca | acc | cat | acc | caa | att | gag | gaa | gat |  | 3733 |
| Asp | Leu | Ser | Cys | Gln | Asp | Ala | Thr | His | Thr | Gln | Ile | Glu | Glu | Asp |  |  |
|  |  | 1065 |  |  |  |  | 1070 |  |  |  |  | 1075 |  |  |  |  |
| gtt | gca | aca | cag | ttg | aca | caa | ctt | gct | tcg | ata | att | aag | atc | aat |  | 3778 |
| Val | Ala | Thr | Gln | Leu | Thr | Gln | Leu | Ala | Ser | Ile | Ile | Lys | Ile | Asn |  |  |
|  | 1080 |  |  |  |  | 1085 |  |  |  |  | 1090 |  |  |  |  |  |
| tat | ata | aaa | cca | gag | gac | aaa | aaa | gtt | gaa | agt | aca | cca | aca | agc |  | 3823 |

```
                Tyr Ile Lys Pro Glu Asp Lys Lys Val Glu Ser Thr Pro Thr Ser
                        1095            1100                1105 ctt gtc aca tgt aat gta cag caa aaa tac aat cag gag aag ggc           3868
Leu Val Thr Cys Asn Val Gln Gln Lys Tyr Asn Gln Glu Lys Gly
        1110                1115                1120 aca ata caa cag aaa cca cct tca agt gta cac aat aat cat ggt           3913
Thr Ile Gln Gln Lys Pro Pro Ser Ser Val His Asn Asn His Gly
        1125                1130                1135 tca tca tta aca aaa caa aag aac cca acc cag aaa aag aca aaa           3958
Ser Ser Leu Thr Lys Gln Lys Asn Pro Thr Gln Lys Lys Thr Lys
        1140                1145                1150 tcc acc cca tca aga gat cgg cgg aaa aag aag ccc aca gtt gta           4003
Ser Thr Pro Ser Arg Asp Arg Arg Lys Lys Lys Pro Thr Val Val
        1155                1160                1165 agt tat caa gaa aat gat cgg cag aag tgg gaa aag ttg tcc tat           4048
Ser Tyr Gln Glu Asn Asp Arg Gln Lys Trp Glu Lys Leu Ser Tyr
        1170                1175                1180 atg tat ggc aca ata tgc gac att tgg ata gca tcg aaa ttt caa           4093
Met Tyr Gly Thr Ile Cys Asp Ile Trp Ile Ala Ser Lys Phe Gln
        1185                1190                1195 aat ttt ggg caa ttt tgt cca cat gat ttt cct act gta ttt ggg           4138
Asn Phe Gly Gln Phe Cys Pro His Asp Phe Pro Thr Val Phe Gly
        1200                1205                1210 aaa att tct tcc tcg acc aaa ata tgg aaa cca ctg gct caa acg           4183
Lys Ile Ser Ser Ser Thr Lys Ile Trp Lys Pro Leu Ala Gln Thr
        1215                1220                1225 agg tcc att atg caa ccc aaa aca gta ttt cca cca ctc act cag           4228
Arg Ser Ile Met Gln Pro Lys Thr Val Phe Pro Pro Leu Thr Gln
        1230                1235                1240 ata aaa tta cag aga tat cct gaa tca gca gag gaa aag gtg aag           4273
Ile Lys Leu Gln Arg Tyr Pro Glu Ser Ala Glu Glu Lys Val Lys
        1245                1250                1255 gtt gaa cca ttg gat tca ctc agc tta ttt cat ctt aaa acg gaa           4318
Val Glu Pro Leu Asp Ser Leu Ser Leu Phe His Leu Lys Thr Glu
        1260                1265                1270 tcc aac ggg aag gca ttc act gat aaa gct tat aat tct cag gta           4363
Ser Asn Gly Lys Ala Phe Thr Asp Lys Ala Tyr Asn Ser Gln Val
        1275                1280                1285 cag tta acg gtg aat gcc aat cag aaa gcc cat cct ttg acc cag           4408
Gln Leu Thr Val Asn Ala Asn Gln Lys Ala His Pro Leu Thr Gln
        1290                1295                1300 ccc tct tct cca cct aac cag tgt gct aac gtg atg gca ggc gat           4453
Pro Ser Ser Pro Pro Asn Gln Cys Ala Asn Val Met Ala Gly Asp
        1305                1310                1315 gac caa ata cgg ttt cag cag gtt gtt aag gag caa ctc atg cat           4498
Asp Gln Ile Arg Phe Gln Gln Val Val Lys Glu Gln Leu Met His
        1320                1325                1330 cag aga ctg cca aca ttg cct ggt atc tct cat gaa aca ccc tta           4543
Gln Arg Leu Pro Thr Leu Pro Gly Ile Ser His Glu Thr Pro Leu
        1335                1340                1345 ccg gag tca gca cta act ctc agg aat gta aat gta gtg tgt tca           4588
Pro Glu Ser Ala Leu Thr Leu Arg Asn Val Asn Val Val Cys Ser
        1350                1355                1360 ggt gga att aca gtg gtt tct acc aaa agt gaa gag gaa gtc tgt           4633
Gly Gly Ile Thr Val Val Ser Thr Lys Ser Glu Glu Glu Val Cys
        1365                1370                1375 tca tcc agt ttt gga aca tca gaa ttt tcc aca gtg gac agt gca           4678
Ser Ser Ser Phe Gly Thr Ser Glu Phe Ser Thr Val Asp Ser Ala
        1380                1385                1390
```

```
                                -continued cag aaa aat ttt aat gat tat gcc atg aac ttc ttt act aac cct      4723
Gln Lys Asn Phe Asn Asp Tyr Ala Met Asn Phe Phe Thr Asn Pro
        1395            1400                1405 aca aaa aac cta gtg tct ata act aaa gat tct gaa ctg ccc acc      4768
Thr Lys Asn Leu Val Ser Ile Thr Lys Asp Ser Glu Leu Pro Thr
    1410                1415                1420 tgc agc tgt ctt gat cga gtt ata caa aaa gac aaa ggc cca tat      4813
Cys Ser Cys Leu Asp Arg Val Ile Gln Lys Asp Lys Gly Pro Tyr
        1425            1430                1435 tat aca cac ctt ggg gca gga cca agt gtt gct gct gtc agg gaa      4858
Tyr Thr His Leu Gly Ala Gly Pro Ser Val Ala Ala Val Arg Glu
    1440                1445                1450 atc atg gag aat agg tat ggt caa aaa gga aac gca ata agg ata      4903
Ile Met Glu Asn Arg Tyr Gly Gln Lys Gly Asn Ala Ile Arg Ile
        1455            1460                1465 gaa ata gta gtg tac acc ggt aaa gaa ggg aaa agc tct cat ggg      4948
Glu Ile Val Val Tyr Thr Gly Lys Glu Gly Lys Ser Ser His Gly
    1470                1475                1480 tgt cca att gct aag tgg gtt tta aga aga agc agt gat gaa gaa      4993
Cys Pro Ile Ala Lys Trp Val Leu Arg Arg Ser Ser Asp Glu Glu
        1485            1490                1495 aaa gtt ctt tgt ttg gtc cgg cag cgt aca ggc cac cac tgt cca      5038
Lys Val Leu Cys Leu Val Arg Gln Arg Thr Gly His His Cys Pro
    1500                1505                1510 act gct gtg atg gtg gtg ctc atc atg gtg tgg gat ggc atc cct      5083
Thr Ala Val Met Val Val Leu Ile Met Val Trp Asp Gly Ile Pro
        1515            1520                1525 ctt cca atg gcc gac cgg cta tac aca gag ctc aca gag aat cta      5128
Leu Pro Met Ala Asp Arg Leu Tyr Thr Glu Leu Thr Glu Asn Leu
    1530                1535                1540 aag tca tac aat ggg cac cct acc gac aga aga tgc acc ctc aat      5173
Lys Ser Tyr Asn Gly His Pro Thr Asp Arg Arg Cys Thr Leu Asn
        1545            1550                1555 gaa aat cgt acc tgt aca tgt caa gga att gat cca gag act tgt      5218
Glu Asn Arg Thr Cys Thr Cys Gln Gly Ile Asp Pro Glu Thr Cys
    1560                1565                1570 gga gct tca ttc tct ttt ggc tgt tca tgg agt atg tac ttt aat      5263
Gly Ala Ser Phe Ser Phe Gly Cys Ser Trp Ser Met Tyr Phe Asn
        1575            1580                1585 ggc tgt aag ttt ggt aga agc cca agc ccc aga aga ttt aga att      5308
Gly Cys Lys Phe Gly Arg Ser Pro Ser Pro Arg Arg Phe Arg Ile
    1590                1595                1600 gat cca agc tct ccc tta cat gaa aaa aac ctt gaa gat aac tta      5353
Asp Pro Ser Ser Pro Leu His Glu Lys Asn Leu Glu Asp Asn Leu
        1605            1610                1615 cag agt ttg gct aca cga tta gct cca att tat aag cag tat gct      5398
Gln Ser Leu Ala Thr Arg Leu Ala Pro Ile Tyr Lys Gln Tyr Ala
    1620                1625                1630 cca gta gct tac caa aat cag gtg gaa tat gaa aat gtt gcc cga      5443
Pro Val Ala Tyr Gln Asn Gln Val Glu Tyr Glu Asn Val Ala Arg
        1635            1640                1645 gaa tgt cgg ctt ggc agc aag gaa ggt cgt ccc ttc tct ggg gtc      5488
Glu Cys Arg Leu Gly Ser Lys Glu Gly Arg Pro Phe Ser Gly Val
    1650                1655                1660 act gct tgc ctg gac ttc tgt gct cat ccc cac agg gac att cac      5533
Thr Ala Cys Leu Asp Phe Cys Ala His Pro His Arg Asp Ile His
        1665            1670                1675 aac atg aat aat gga agc act gtg gtt tgt acc tta act cga gaa      5578
Asn Met Asn Asn Gly Ser Thr Val Val Cys Thr Leu Thr Arg Glu
    1680                1685                1690
```

```
gat aac cgc tct ttg ggt gtt att cct caa gat gag cag ctc cat         5623
Asp Asn Arg Ser Leu Gly Val Ile Pro Gln Asp Glu Gln Leu His
            1695                1700                1705 gtg cta cct ctt tat aag ctt tca gac aca gat gag ttt ggc tcc         5668
Val Leu Pro Leu Tyr Lys Leu Ser Asp Thr Asp Glu Phe Gly Ser
        1710                1715                1720 aag gaa gga atg gaa gcc aag atc aaa tct ggg gcc atc gag gtc         5713
Lys Glu Gly Met Glu Ala Lys Ile Lys Ser Gly Ala Ile Glu Val
    1725                1730                1735 ctg gca ccc cgc cgc aaa aaa aga acg tgt ttc act cag cct gtt         5758
Leu Ala Pro Arg Arg Lys Lys Arg Thr Cys Phe Thr Gln Pro Val
1740                1745                1750 ccc cgt tct gga aag aag agg gct gcg atg atg aca gag gtt ctt         5803
Pro Arg Ser Gly Lys Lys Arg Ala Ala Met Met Thr Glu Val Leu
                1755                1760                1765 gca cat aag ata agg gca gtg gaa aag aaa cct att ccc cga atc         5848
Ala His Lys Ile Arg Ala Val Glu Lys Lys Pro Ile Pro Arg Ile
            1770                1775                1780 aag cgg aag aat aac tca aca aca aca aac aac agt aag cct tcg         5893
Lys Arg Lys Asn Asn Ser Thr Thr Thr Asn Asn Ser Lys Pro Ser
        1785                1790                1795 tca ctg cca acc tta ggg agt aac act gag acc gtg caa cct gaa         5938
Ser Leu Pro Thr Leu Gly Ser Asn Thr Glu Thr Val Gln Pro Glu
    1800                1805                1810 gta aaa agt gaa acc gaa ccc cat ttt atc tta aaa agt tca gac         5983
Val Lys Ser Glu Thr Glu Pro His Phe Ile Leu Lys Ser Ser Asp
1815                1820                1825 aac act aaa act tat tcg ctg atg cca tcc gct cct cac cca gtg         6028
Asn Thr Lys Thr Tyr Ser Leu Met Pro Ser Ala Pro His Pro Val
                1830                1835                1840 aaa gag gca tct cca ggc ttc tcc tgg tcc ccg aag act gct tca         6073
Lys Glu Ala Ser Pro Gly Phe Ser Trp Ser Pro Lys Thr Ala Ser
            1845                1850                1855 gcc aca cca gct cca ctg aag aat gac gca aca gcc tca tgc ggg         6118
Ala Thr Pro Ala Pro Leu Lys Asn Asp Ala Thr Ala Ser Cys Gly
        1860                1865                1870 ttt tca gaa aga agc agc act ccc cac tgt acg atg cct tcg gga         6163
Phe Ser Glu Arg Ser Ser Thr Pro His Cys Thr Met Pro Ser Gly
    1875                1880                1885 aga ctc agt ggt gcc aat gca gct gct gct gat ggc cct ggc att         6208
Arg Leu Ser Gly Ala Asn Ala Ala Ala Ala Asp Gly Pro Gly Ile
1890                1895                1900 tca cag ctt ggc gaa gtg gct cct ctc ccc acc ctg tct gct cct         6253
Ser Gln Leu Gly Glu Val Ala Pro Leu Pro Thr Leu Ser Ala Pro
                1905                1910                1915 gtg atg gag ccc ctc att aat tct gag cct tcc act ggt gtg act         6298
Val Met Glu Pro Leu Ile Asn Ser Glu Pro Ser Thr Gly Val Thr
            1920                1925                1930 gag ccg cta acg cct cat cag cca aac cac cag ccc tcc ttc ctc         6343
Glu Pro Leu Thr Pro His Gln Pro Asn His Gln Pro Ser Phe Leu
        1935                1940                1945 acc tct cct caa gac ctt gcc tct tct cca atg gaa gaa gat gag         6388
Thr Ser Pro Gln Asp Leu Ala Ser Ser Pro Met Glu Glu Asp Glu
    1950                1955                1960 cag cat tct gaa gca gat gag cct cca tca gac gaa ccc cta tct         6433
Gln His Ser Glu Ala Asp Glu Pro Pro Ser Asp Glu Pro Leu Ser
1965                1970                1975 gat gac ccc ctg tca cct gct gag gag aaa ttg ccc cac att gat         6478
Asp Asp Pro Leu Ser Pro Ala Glu Glu Lys Leu Pro His Ile Asp
```

|  |  |  |  |  |  |  |  |  |  |  |  |
|---|---|---|---|---|---|---|---|---|---|---|---|
|  | 1980 |  |  | 1985 |  |  |  | 1990 |  |  |  |
| gag | tat | tgg | tca | gac | agt | gag | cac | atc | ttt | ttg | gat | gca | aat | att | 6523 |
| Glu | Tyr | Trp | Ser | Asp | Ser | Glu | His | Ile | Phe | Leu | Asp | Ala | Asn | Ile |  |
|  | 1995 |  |  | 2000 |  |  |  | 2005 |  |  |  |
| ggt | ggg | gtg | gcc | atc | gca | cct | gct | cac | ggc | tcg | gtt | ttg | att | gag | 6568 |
| Gly | Gly | Val | Ala | Ile | Ala | Pro | Ala | His | Gly | Ser | Val | Leu | Ile | Glu |  |
|  | 2010 |  |  | 2015 |  |  |  | 2020 |  |  |  |
| tgt | gcc | cgg | cga | gag | ctg | cac | gct | acc | act | cct | gtt | gag | cac | ccc | 6613 |
| Cys | Ala | Arg | Arg | Glu | Leu | His | Ala | Thr | Thr | Pro | Val | Glu | His | Pro |  |
|  | 2025 |  |  | 2030 |  |  |  | 2035 |  |  |  |
| aac | cgt | aat | cat | cca | acc | cgc | ctc | tcc | ctt | gtc | ttt | tac | cag | cac | 6658 |
| Asn | Arg | Asn | His | Pro | Thr | Arg | Leu | Ser | Leu | Val | Phe | Tyr | Gln | His |  |
|  | 2040 |  |  | 2045 |  |  |  | 2050 |  |  |  |
| aaa | aac | cta | aat | aag | ccc | caa | cat | ggt | ttt | gaa | cta | aac | aag | att | 6703 |
| Lys | Asn | Leu | Asn | Lys | Pro | Gln | His | Gly | Phe | Glu | Leu | Asn | Lys | Ile |  |
|  | 2055 |  |  | 2060 |  |  |  | 2065 |  |  |  |
| aag | ttt | gag | gct | aaa | gaa | gct | aag | aat | aag | aaa | atg | aag | gcc | tca | 6748 |
| Lys | Phe | Glu | Ala | Lys | Glu | Ala | Lys | Asn | Lys | Lys | Met | Lys | Ala | Ser |  |
|  | 2070 |  |  | 2075 |  |  |  | 2080 |  |  |  |
| gag | caa | aaa | gac | cag | gca | gct | aat | gaa | ggt | cca | gaa | cag | tcc | tct | 6793 |
| Glu | Gln | Lys | Asp | Gln | Ala | Ala | Asn | Glu | Gly | Pro | Glu | Gln | Ser | Ser |  |
|  | 2085 |  |  | 2090 |  |  |  | 2095 |  |  |  |
| gaa | gta | aat | gaa | ttg | aac | caa | att | cct | tct | cat | aaa | gca | tta | aca | 6838 |
| Glu | Val | Asn | Glu | Leu | Asn | Gln | Ile | Pro | Ser | His | Lys | Ala | Leu | Thr |  |
|  | 2100 |  |  | 2105 |  |  |  | 2110 |  |  |  |
| tta | acc | cat | gac | aat | gtt | gtc | acc | gtg | tcc | cct | tat | gct | ctc | aca | 6883 |
| Leu | Thr | His | Asp | Asn | Val | Val | Thr | Val | Ser | Pro | Tyr | Ala | Leu | Thr |  |
|  | 2115 |  |  | 2120 |  |  |  | 2125 |  |  |  |
| cac | gtt | gcg | ggg | ccc | tat | aac | cat | tgg | gtc | tga | aggcttttct |  | 6926 |
| His | Val | Ala | Gly | Pro | Tyr | Asn | His | Trp | Val |  |  |  |
|  | 2130 |  |  | 2135 |  |  |  |  |  |  |  |

```
ccccctctta atgcctttgc tagtgcagtg tattttttca aggtgctgtt aaaagaaagt      6986
catgttgtcg tttactatct tcatctcacc catttcaagt ctgaggtaaa aaataataa        7046 tgataacaaa acggggtggg tattcttaac tgtgactata ttttgacaat tggtagaagg      7106
tgcacatttt aagcaaaaat aaaagtttta tagttttaaa tacataaaga aatgtttcag      7166
ttaggcatta accttgatag aatcactcag tttggtgctt taaattaagt ctgtttacta      7226
tgaaacaaga gtcatttta gaggatttta acaggttcat gttctatgat gtaaaatcaa       7286
gacacacagt gttaactcta cacagcttct ggtgcttaac cacatccaca cagttaaaaa      7346
taagctgaat tattattca tggtgccatt gttccaacat cttccaatca ttgctagaaa       7406
attggcatat tcctttgaaa taaacttatg aaatgttttc tctcttaaaa tatttctcct      7466
gtgtaaaata aatcattgtt gttagtaatg gttggaggct gttcataaat tgtaaatata      7526
tattttaaaa gcactttcta tttttaaaag taacttgaaa taatatagta taagaatcct      7586
attgtctatt gtttgtgcat atttgcatac aagagaaatc atttatcctt gctgtgtaga      7646
gttccatctt gttaactgca gtatgtattc taatcatgta tatggtttgt gttcttttac      7706
tgtgtcctct cacattcaag tattagcaac ttgcagtata taaaatagtt agataatgag      7766
aagttgttaa ttatctctaa aattggaatt aggaagcata tcaccaatac tgattaacat      7826
tctctttgga actaggtaag agtggtctct tcttattgaa caacctcaat ttagtttcat      7886
cccacctttc tcagtataat ccatgagagg tgtttccaaa aggagatgag ggaacaggat      7946
aggtttcaga agagtcaaat gcttctaatg tctcaaggtg ataaaataca aaaactaagt      8006
agacagatat ttgtactgaa gtctgataca gaattagaaa aaaaaaattc ttgttgaaat      8066
```

-continued

```
attttgaaaa caaattccct actatcatca catgcctccc caaccccaag tcaaaaacaa      8126
gaggaatggt actacaaaca tggctttgtc cattaagagc taattcattt gtttatctta      8186
gcatactaga tttgggaaaa tgataactca tcttttctga taattgccta tgttctaggt      8246
aacaggaaaa caggcattaa gtttatttta gtcttcccat tttcttccta ttactttatt      8306
gactcatttt attgcaaaac aaaaaggatt acccaaacaa catgtttcga acaaggagaa      8366
ttttcaatga aatacttgat tctgttaaaa tgcagaggtg ctataacatt caaagtgtca      8426
gattccttgg gagtatggaa aacctaatgg tgcttctccc ttggaaatgc cataggaagc      8486
ccacaaccgc taacacttac aattttggtg caaaagcaaa cagttccagc aggctctcta      8546
aagaaaaact cattgtaact tattaaaata atatctggtg caaagtatct gttttgagct      8606
tttgactaat ccaagtaaag gaatatgaag ggattgtaaa aaacaaaatg tccattgata      8666
gaccatcgtg tacaagtaga tttctgcttg ttgaatatgt aaaatagggt aattcattga      8726
cttgttttag tattttgtgt gccttagatt tccgttttaa gacatgtata ttttttgtgag     8786
cctaaggttt cttatataca tataagtata taaataagtg attgtttatt gcttcagctg      8846
cttcaacaag atatttacta gtattagact atcaggaata cacccttgcg agattatgtt      8906
ttagatttta ggccttagct cccactagaa attatttctt caccagattt aatggataaa      8966
gttttatggc tctttatgca tccactcatc tactcattct tcgagtctac acttattgaa      9026
tgcctgcaaa atcaagtat cacttttatt tttctttgga tcaccaccta tgacatagta       9086
aacttgaaga ataaaaacta ccctcagaaa tatttttaaa agaagtagca aattatcttc      9146
agtataatcc atggtaatgt atgcagtaat tcaaattgat ctctctctca ataggtttct     9206
taacaatcta aacttgaaac atcaatgtta attttttggaa ctattgggat tgtgacgct     9266
tgttgcagtt taccaaaaca agtatttgaa aatatatagt atcaactgaa atgtttccat      9326
tccgttgttg tagttaacat catgaatgga cttcttaagc tgattacccc actgtgggaa      9386
ccaaattgga ttcctacttt gttggactct cttttcctgat tttaacaatt taccatccca    9446
ttctctgccc tgtgattttt tttaaaagct tattcaatgt tctgcagcat tgtgattgta     9506
tgctggctac actgctttta gaatgctctt tctcatgaag caaggaaata aatttgtttg      9566
aaatgacatt ttctctcaaa aaaaaaaaaa aaaaa                                 9601
```

<210> SEQ ID NO 2
<211> LENGTH: 2136
<212> TYPE: PRT
<213> ORGANISM: Homo sapiens

<400> SEQUENCE: 2

```
Met Ser Arg Ser Arg His Ala Arg Pro Ser Arg Leu Val Arg Lys Glu
1               5                   10                  15

Asp Val Asn Lys Lys Lys Lys Asn Ser Gln Leu Arg Lys Thr Thr Lys
                20                  25                  30

Gly Ala Asn Lys Asn Val Ala Ser Val Lys Thr Leu Ser Pro Gly Lys
            35                  40                  45

Leu Lys Gln Leu Ile Gln Glu Arg Asp Val Lys Lys Thr Glu Pro
        50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95
```

```
Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
            115                 120                 125

Pro Leu Ser Lys Gly Leu Glu Lys Gln His Asp Cys Asp Tyr Lys Ile
            130                 135                 140

Leu Pro Ala Leu Gly Val Lys His Ser Glu Asn Asp Ser Val Pro Met
145                 150                 155                 160

Gln Asp Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
            195                 200                 205

Pro Ala Ala Glu Ile Leu Pro Gly Pro Leu Glu Gly Thr Arg Cys Gly
            210                 215                 220

Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
            275                 280                 285

Pro Ile Lys Ser Glu His Asp Cys Tyr Pro Thr Ser Ser Leu Asn Lys
            290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
            340                 345                 350

Ala Asn Gln Gln Glu Val Ser Asp Thr Thr Ser Phe Leu Gly Gln Ala
            355                 360                 365

Phe Gly Ala Ile Pro His Gln Trp Glu Leu Pro Gly Ala Asp Pro Val
370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
            420                 425                 430

Leu Pro Val Pro Pro Asn Pro Ile Ala Thr Phe Asn Ala Pro Ser Lys
            435                 440                 445

Trp Pro Glu Pro Gln Ser Thr Val Ser Tyr Gly Leu Ala Val Gln Gly
            450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
            500                 505                 510

Gln Gly Phe Pro Leu Ala Pro Glu Arg Gly Leu Phe His Ala Ser Leu
```

```
            515                 520                 525
Gly Ile Ala Gln Leu Ser Gln Ala Gly Pro Ser Lys Ser Asp Arg Gly
        530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                    565                 570                 575

Thr Thr Leu Leu Pro Thr Leu Glu Lys Lys Arg Lys Arg Cys Gly
            580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
        610                 615                 620

Glu Glu Leu Lys Lys Lys Pro Ser Val Val Pro Leu Glu Val Ile
625                 630                 635                 640

Lys Glu Asn Lys Arg Pro Gln Arg Glu Lys Lys Pro Lys Val Leu Lys
                    645                 650                 655

Ala Asp Phe Asp Asn Lys Pro Val Asn Gly Pro Lys Ser Glu Ser Met
            660                 665                 670

Asp Tyr Ser Arg Cys Gly His Gly Glu Glu Gln Lys Leu Glu Leu Asn
        675                 680                 685

Pro His Thr Val Glu Asn Val Thr Lys Asn Glu Asp Ser Met Thr Gly
        690                 695                 700

Ile Glu Val Glu Lys Trp Thr Gln Asn Lys Lys Ser Gln Leu Thr Asp
705                 710                 715                 720

His Val Lys Gly Asp Phe Ser Ala Asn Val Pro Glu Ala Glu Lys Ser
                    725                 730                 735

Lys Asn Ser Glu Val Asp Lys Lys Arg Thr Lys Ser Pro Lys Leu Phe
            740                 745                 750

Val Gln Thr Val Arg Asn Gly Ile Lys His Val His Cys Leu Pro Ala
        755                 760                 765

Glu Thr Asn Val Ser Phe Lys Lys Phe Asn Ile Glu Glu Phe Gly Lys
770                 775                 780

Thr Leu Glu Asn Asn Ser Tyr Lys Phe Leu Lys Asp Thr Ala Asn His
785                 790                 795                 800

Lys Asn Ala Met Ser Ser Val Ala Thr Asp Met Ser Cys Asp His Leu
                    805                 810                 815

Lys Gly Arg Ser Asn Val Leu Val Phe Gln Gln Pro Gly Phe Asn Cys
            820                 825                 830

Ser Ser Ile Pro His Ser Ser His Ser Ile Ile Asn His His Ala Ser
        835                 840                 845

Ile His Asn Glu Gly Asp Gln Pro Lys Thr Pro Glu Asn Ile Pro Ser
        850                 855                 860

Lys Glu Pro Lys Asp Gly Ser Pro Val Gln Pro Ser Leu Leu Ser Leu
865                 870                 875                 880

Met Lys Asp Arg Arg Leu Thr Leu Glu Gln Val Val Ala Ile Glu Ala
                    885                 890                 895

Leu Thr Gln Leu Ser Glu Ala Pro Ser Glu Asn Ser Ser Pro Ser Lys
            900                 905                 910

Ser Glu Lys Asp Glu Glu Ser Glu Gln Arg Thr Ala Ser Leu Leu Asn
        915                 920                 925

Ser Cys Lys Ala Ile Leu Tyr Thr Val Arg Lys Asp Leu Gln Asp Pro
        930                 935                 940
```

```
Asn Leu Gln Gly Glu Pro Pro Lys Leu Asn His Cys Pro Ser Leu Glu
945                 950                 955                 960

Lys Gln Ser Ser Cys Asn Thr Val Val Phe Asn Gly Gln Thr Thr Thr
                965                 970                 975

Leu Ser Asn Ser His Ile Asn Ser Ala Thr Asn Gln Ala Ser Thr Lys
            980                 985                 990

Ser His Glu Tyr Ser Lys Val Thr Asn Ser Leu Ser Leu Phe Ile Pro
        995                 1000                1005

Lys Ser Asn Ser Ser Lys Ile Asp Thr Asn Lys Ser Ile Ala Gln
    1010                1015                1020

Gly Ile Ile Thr Leu Asp Asn Cys Ser Asn Asp Leu His Gln Leu
    1025                1030                1035

Pro Pro Arg Asn Asn Glu Val Glu Tyr Cys Asn Gln Leu Leu Asp
    1040                1045                1050

Ser Ser Lys Lys Leu Asp Ser Asp Asp Leu Ser Cys Gln Asp Ala
    1055                1060                1065

Thr His Thr Gln Ile Glu Glu Asp Val Ala Thr Gln Leu Thr Gln
    1070                1075                1080

Leu Ala Ser Ile Ile Lys Ile Asn Tyr Ile Lys Pro Glu Asp Lys
    1085                1090                1095

Lys Val Glu Ser Thr Pro Thr Ser Leu Val Thr Cys Asn Val Gln
    1100                1105                1110

Gln Lys Tyr Asn Gln Glu Lys Gly Thr Ile Gln Lys Pro Pro
    1115                1120                1125

Ser Ser Val His Asn Asn His Gly Ser Ser Leu Thr Lys Gln Lys
    1130                1135                1140

Asn Pro Thr Gln Lys Lys Thr Lys Ser Thr Pro Ser Arg Asp Arg
    1145                1150                1155

Arg Lys Lys Lys Pro Thr Val Val Ser Tyr Gln Glu Asn Asp Arg
    1160                1165                1170

Gln Lys Trp Glu Lys Leu Ser Tyr Met Tyr Gly Thr Ile Cys Asp
    1175                1180                1185

Ile Trp Ile Ala Ser Lys Phe Gln Asn Phe Gly Gln Phe Cys Pro
    1190                1195                1200

His Asp Phe Pro Thr Val Phe Gly Lys Ile Ser Ser Ser Thr Lys
    1205                1210                1215

Ile Trp Lys Pro Leu Ala Gln Thr Arg Ser Ile Met Gln Pro Lys
    1220                1225                1230

Thr Val Phe Pro Pro Leu Thr Gln Ile Lys Leu Gln Arg Tyr Pro
    1235                1240                1245

Glu Ser Ala Glu Glu Lys Val Lys Val Glu Pro Leu Asp Ser Leu
    1250                1255                1260

Ser Leu Phe His Leu Lys Thr Glu Ser Asn Gly Lys Ala Phe Thr
    1265                1270                1275

Asp Lys Ala Tyr Asn Ser Gln Val Gln Leu Thr Val Asn Ala Asn
    1280                1285                1290

Gln Lys Ala His Pro Leu Thr Gln Pro Ser Ser Pro Pro Asn Gln
    1295                1300                1305

Cys Ala Asn Val Met Ala Gly Asp Asp Gln Ile Arg Phe Gln Gln
    1310                1315                1320

Val Val Lys Glu Gln Leu Met His Gln Arg Leu Pro Thr Leu Pro
    1325                1330                1335
```

-continued

```
Gly Ile Ser His Glu Thr Pro Leu Pro Glu Ser Ala Leu Thr Leu
    1340                1345                1350

Arg Asn Val Asn Val Val Cys Ser Gly Ile Thr Val Val Ser
    1355                1360                1365

Thr Lys Ser Glu Glu Val Cys Ser Ser Phe Gly Thr Ser
    1370                1375                1380

Glu Phe Ser Thr Val Asp Ser Ala Gln Lys Asn Phe Asn Asp Tyr
    1385                1390                1395

Ala Met Asn Phe Phe Thr Asn Pro Thr Lys Asn Leu Val Ser Ile
    1400                1405                1410

Thr Lys Asp Ser Glu Leu Pro Thr Cys Ser Cys Leu Asp Arg Val
    1415                1420                1425

Ile Gln Lys Asp Lys Gly Pro Tyr Tyr Thr His Leu Gly Ala Gly
    1430                1435                1440

Pro Ser Val Ala Ala Val Arg Glu Ile Met Glu Asn Arg Tyr Gly
    1445                1450                1455

Gln Lys Gly Asn Ala Ile Arg Ile Glu Ile Val Val Tyr Thr Gly
    1460                1465                1470

Lys Glu Gly Lys Ser Ser His Gly Cys Pro Ile Ala Lys Trp Val
    1475                1480                1485

Leu Arg Arg Ser Ser Asp Glu Glu Lys Val Leu Cys Leu Val Arg
    1490                1495                1500

Gln Arg Thr Gly His His Cys Pro Thr Ala Val Met Val Val Leu
    1505                1510                1515

Ile Met Val Trp Asp Gly Ile Pro Leu Pro Met Ala Asp Arg Leu
    1520                1525                1530

Tyr Thr Glu Leu Thr Glu Asn Leu Lys Ser Tyr Asn Gly His Pro
    1535                1540                1545

Thr Asp Arg Arg Cys Thr Leu Asn Glu Asn Arg Thr Cys Thr Cys
    1550                1555                1560

Gln Gly Ile Asp Pro Glu Thr Cys Gly Ala Ser Phe Ser Phe Gly
    1565                1570                1575

Cys Ser Trp Ser Met Tyr Phe Asn Gly Cys Lys Phe Gly Arg Ser
    1580                1585                1590

Pro Ser Pro Arg Arg Phe Arg Ile Asp Pro Ser Ser Pro Leu His
    1595                1600                1605

Glu Lys Asn Leu Glu Asp Asn Leu Gln Ser Leu Ala Thr Arg Leu
    1610                1615                1620

Ala Pro Ile Tyr Lys Gln Tyr Ala Pro Val Ala Tyr Gln Asn Gln
    1625                1630                1635

Val Glu Tyr Glu Asn Val Ala Arg Glu Cys Arg Leu Gly Ser Lys
    1640                1645                1650

Glu Gly Arg Pro Phe Ser Gly Val Thr Ala Cys Leu Asp Phe Cys
    1655                1660                1665

Ala His Pro His Arg Asp Ile His Asn Met Asn Asn Gly Ser Thr
    1670                1675                1680

Val Val Cys Thr Leu Thr Arg Glu Asp Asn Arg Ser Leu Gly Val
    1685                1690                1695

Ile Pro Gln Asp Glu Gln Leu His Val Leu Pro Leu Tyr Lys Leu
    1700                1705                1710

Ser Asp Thr Asp Glu Phe Gly Ser Lys Glu Gly Met Glu Ala Lys
    1715                1720                1725

Ile Lys Ser Gly Ala Ile Glu Val Leu Ala Pro Arg Arg Lys Lys
```

```
                1730             1735             1740
Arg Thr Cys Phe Thr Gln Pro Val Pro Arg Ser Gly Lys Lys Arg
    1745             1750             1755

Ala Ala Met Met Thr Glu Val Leu Ala His Lys Ile Arg Ala Val
    1760             1765             1770

Glu Lys Lys Pro Ile Pro Arg Ile Lys Arg Lys Asn Asn Ser Thr
    1775             1780             1785

Thr Thr Asn Asn Ser Lys Pro Ser Ser Leu Pro Thr Leu Gly Ser
    1790             1795             1800

Asn Thr Glu Thr Val Gln Pro Glu Val Lys Ser Glu Thr Glu Pro
    1805             1810             1815

His Phe Ile Leu Lys Ser Ser Asp Asn Thr Lys Thr Tyr Ser Leu
    1820             1825             1830

Met Pro Ser Ala Pro His Pro Val Lys Glu Ala Ser Pro Gly Phe
    1835             1840             1845

Ser Trp Ser Pro Lys Thr Ala Ser Ala Thr Pro Ala Pro Leu Lys
    1850             1855             1860

Asn Asp Ala Thr Ala Ser Cys Gly Phe Ser Glu Arg Ser Ser Thr
    1865             1870             1875

Pro His Cys Thr Met Pro Ser Gly Arg Leu Ser Gly Ala Asn Ala
    1880             1885             1890

Ala Ala Ala Asp Gly Pro Gly Ile Ser Gln Leu Gly Glu Val Ala
    1895             1900             1905

Pro Leu Pro Thr Leu Ser Ala Pro Val Met Glu Pro Leu Ile Asn
    1910             1915             1920

Ser Glu Pro Ser Thr Gly Val Thr Glu Pro Leu Thr Pro His Gln
    1925             1930             1935

Pro Asn His Gln Pro Ser Phe Leu Thr Ser Pro Gln Asp Leu Ala
    1940             1945             1950

Ser Ser Pro Met Glu Glu Asp Glu Gln His Ser Glu Ala Asp Glu
    1955             1960             1965

Pro Pro Ser Asp Glu Pro Leu Ser Asp Asp Pro Leu Ser Pro Ala
    1970             1975             1980

Glu Glu Lys Leu Pro His Ile Asp Glu Tyr Trp Ser Asp Ser Glu
    1985             1990             1995

His Ile Phe Leu Asp Ala Asn Ile Gly Gly Val Ala Ile Ala Pro
    2000             2005             2010

Ala His Gly Ser Val Leu Ile Glu Cys Ala Arg Arg Glu Leu His
    2015             2020             2025

Ala Thr Thr Pro Val Glu His Pro Asn Arg Asn His Pro Thr Arg
    2030             2035             2040

Leu Ser Leu Val Phe Tyr Gln His Lys Asn Leu Asn Lys Pro Gln
    2045             2050             2055

His Gly Phe Glu Leu Asn Lys Ile Lys Phe Glu Ala Lys Glu Ala
    2060             2065             2070

Lys Asn Lys Lys Met Lys Ala Ser Glu Gln Lys Asp Gln Ala Ala
    2075             2080             2085

Asn Glu Gly Pro Glu Gln Ser Ser Glu Val Asn Glu Leu Asn Gln
    2090             2095             2100

Ile Pro Ser His Lys Ala Leu Thr Leu Thr His Asp Asn Val Val
    2105             2110             2115

Thr Val Ser Pro Tyr Ala Leu Thr His Val Ala Gly Pro Tyr Asn
    2120             2125             2130
```

```
His Trp Val
    2135

<210> SEQ ID NO 3
<211> LENGTH: 6498
<212> TYPE: DNA
<213> ORGANISM: Homo sapiens
<220> FEATURE:
<221> NAME/KEY: CDS
<222> LOCATION: (1)..(6498)

<400> SEQUENCE: 3 atg tct cga tcc cgc cat gca agg cct tcc aga tta gtc agg aag gaa        48
Met Ser Arg Ser Arg His Ala Arg Pro Ser Arg Leu Val Arg Lys Glu
1               5                  10                  15 gat gta aac aaa aaa aag aaa aac agc caa cta cga aag aca acc aag        96
Asp Val Asn Lys Lys Lys Lys Asn Ser Gln Leu Arg Lys Thr Thr Lys
            20                  25                  30 gga gcc aac aaa aat gtg gca tca gtc aag act tta agc cct gga aaa       144
Gly Ala Asn Lys Asn Val Ala Ser Val Lys Thr Leu Ser Pro Gly Lys
        35                  40                  45 tta aag caa tta att caa gaa aga gat gtt aag aaa aaa aca gaa cct       192
Leu Lys Gln Leu Ile Gln Glu Arg Asp Val Lys Lys Lys Thr Glu Pro
    50                  55                  60 aaa cca ccc gtg cca gtc aga agc ctt ctg aca aga gct gga gca gca       240
Lys Pro Pro Val Pro Val Arg Ser Leu Leu Thr Arg Ala Gly Ala Ala
65                  70                  75                  80 cgc atg aat ttg gat agg act gag gtt ctt ttt cag aac cca gag tcc       288
Arg Met Asn Leu Asp Arg Thr Glu Val Leu Phe Gln Asn Pro Glu Ser
                85                  90                  95 tta acc tgc aat ggg ttt aca atg gcg cta cga agc acc tct ctt agc       336
Leu Thr Cys Asn Gly Phe Thr Met Ala Leu Arg Ser Thr Ser Leu Ser
            100                 105                 110 agg cga ctc tcc caa ccc cca ctg gtc gta gcc aaa tcc aaa aag gtt       384
Arg Arg Leu Ser Gln Pro Pro Leu Val Val Ala Lys Ser Lys Lys Val
        115                 120                 125 cca ctt tct aag ggt tta gaa aag caa cat gat tgt gat tat aag ata       432
Pro Leu Ser Lys Gly Leu Glu Lys Gln His Asp Cys Asp Tyr Lys Ile
    130                 135                 140 ctc cct gct ttg gga gta aag cac tca gaa aat gat tcg gtt cca atg       480
Leu Pro Ala Leu Gly Val Lys His Ser Glu Asn Asp Ser Val Pro Met
145                 150                 155                 160 caa ggc acc caa gtc ctt cct gat ata gag act cta att ggt gta caa       528
Gln Gly Thr Gln Val Leu Pro Asp Ile Glu Thr Leu Ile Gly Val Gln
                165                 170                 175 aat ccc tct tta ctt aaa ggt aag agc caa gag aca act cag ttt tgg       576
Asn Pro Ser Leu Leu Lys Gly Lys Ser Gln Glu Thr Thr Gln Phe Trp
            180                 185                 190 tcc caa aga gtt gag gat tcc aag atc aat atc cct acc cac agt ggc       624
Ser Gln Arg Val Glu Asp Ser Lys Ile Asn Ile Pro Thr His Ser Gly
        195                 200                 205 cct gca gct gag atc ctt cct ggg cca ctg gaa ggg aca cgc tgt ggt       672
Pro Ala Ala Glu Ile Leu Pro Gly Pro Leu Glu Gly Thr Arg Cys Gly
    210                 215                 220 gaa gga cta ttc tct gaa gag aca ttg aat gat acc agt ggt tcc cca       720
Glu Gly Leu Phe Ser Glu Glu Thr Leu Asn Asp Thr Ser Gly Ser Pro
225                 230                 235                 240 aaa atg ttt gct cag gac aca gtg tgt gct cct ttt ccc caa aga gca       768
Lys Met Phe Ala Gln Asp Thr Val Cys Ala Pro Phe Pro Gln Arg Ala
                245                 250                 255
```

```
acc ccc aaa gtt acc tct caa gga aac ccc agc att cag tta gaa gag      816
Thr Pro Lys Val Thr Ser Gln Gly Asn Pro Ser Ile Gln Leu Glu Glu
        260                 265                 270 ttg ggt tca cga gta gaa tct ctt aag tta tct gat tct tac ctg gat      864
Leu Gly Ser Arg Val Glu Ser Leu Lys Leu Ser Asp Ser Tyr Leu Asp
            275                 280                 285 ccc att aaa agt gaa cat gat tgc tac ccc acc tcc agt ctt aat aag      912
Pro Ile Lys Ser Glu His Asp Cys Tyr Pro Thr Ser Ser Leu Asn Lys
        290                 295                 300 gtt ata cct gac ttg aac ctt aga aac tgc ttg gct ctt ggt ggg tct      960
Val Ile Pro Asp Leu Asn Leu Arg Asn Cys Leu Ala Leu Gly Gly Ser
305                 310                 315                 320 acg tct cct acc tct gta ata aaa ttc ctc ttg gca ggc tca aaa caa     1008
Thr Ser Pro Thr Ser Val Ile Lys Phe Leu Leu Ala Gly Ser Lys Gln
                325                 330                 335 gcg acc ctt ggt gct aaa cca gat cat caa gag gcc ttc gaa gct act     1056
Ala Thr Leu Gly Ala Lys Pro Asp His Gln Glu Ala Phe Glu Ala Thr
            340                 345                 350 gca aat caa cag gaa gtt tct gat acc acc tct ttc cta gga cag gcc     1104
Ala Asn Gln Gln Glu Val Ser Asp Thr Thr Ser Phe Leu Gly Gln Ala
        355                 360                 365 ttt ggt gct atc cca cat caa tgg gaa ctt cct ggt gct gac cca gtt     1152
Phe Gly Ala Ile Pro His Gln Trp Glu Leu Pro Gly Ala Asp Pro Val
370                 375                 380 cat ggt gag gcc ctg ggt gag acc cca gat cta cca gag att cct ggt     1200
His Gly Glu Ala Leu Gly Glu Thr Pro Asp Leu Pro Glu Ile Pro Gly
385                 390                 395                 400 gct att cca gtc caa gga gag gtc ttt ggt act att tta gac caa caa     1248
Ala Ile Pro Val Gln Gly Glu Val Phe Gly Thr Ile Leu Asp Gln Gln
                405                 410                 415 gaa act ctt ggt atg agt ggg agt gtt gtc cca gac ttg cct gtc ttc     1296
Glu Thr Leu Gly Met Ser Gly Ser Val Val Pro Asp Leu Pro Val Phe
            420                 425                 430 ctt cct gtt cct cca aat cca att gct acc ttt aat gct cct tcc aaa     1344
Leu Pro Val Pro Pro Asn Pro Ile Ala Thr Phe Asn Ala Pro Ser Lys
        435                 440                 445 tgg cct gag ccc caa agc act gtc tca tat gga ctt gca gtc cag ggt     1392
Trp Pro Glu Pro Gln Ser Thr Val Ser Tyr Gly Leu Ala Val Gln Gly
450                 455                 460 gct ata cag att ttg cct ttg ggc tca gga cac act cct caa tca tca     1440
Ala Ile Gln Ile Leu Pro Leu Gly Ser Gly His Thr Pro Gln Ser Ser
465                 470                 475                 480 tca aac tca gag aaa aat tca tta cct cca gta atg gct ata agc aat     1488
Ser Asn Ser Glu Lys Asn Ser Leu Pro Pro Val Met Ala Ile Ser Asn
                485                 490                 495 gta gaa aat gag aag cag gtt cat ata agc ttc ctg cca gct aac act     1536
Val Glu Asn Glu Lys Gln Val His Ile Ser Phe Leu Pro Ala Asn Thr
            500                 505                 510 cag ggg ttc cca tta gcc cct gag aga gga ctc ttc cat gct tca ctg     1584
Gln Gly Phe Pro Leu Ala Pro Glu Arg Gly Leu Phe His Ala Ser Leu
        515                 520                 525 ggt ata gcc caa ctc tct cag gct ggt cct agc aaa tca gac aga ggg     1632
Gly Ile Ala Gln Leu Ser Gln Ala Gly Pro Ser Lys Ser Asp Arg Gly
530                 535                 540 agc tcc cag gtc agt gta acc agc aca gtt cat gtt gtc aac acc aca     1680
Ser Ser Gln Val Ser Val Thr Ser Thr Val His Val Val Asn Thr Thr
545                 550                 555                 560 gtg gtg act atg cca gtg cca atg gtc agt acc tcc tct tct tcc tat     1728
Val Val Thr Met Pro Val Pro Met Val Ser Thr Ser Ser Ser Ser Tyr
                565                 570                 575
```

-continued

| | |
|---|---|
| acc act ttg cta ccg act ttg gaa aag aag aaa aga aag cga tgt ggg<br>Thr Thr Leu Leu Pro Thr Leu Glu Lys Lys Lys Arg Lys Arg Cys Gly<br>              580                      585                    590 | 1776 |
| gtc tgt gaa ccc tgc cag cag aag acc aac tgt ggt gaa tgc act tac<br>Val Cys Glu Pro Cys Gln Gln Lys Thr Asn Cys Gly Glu Cys Thr Tyr<br>      595                      600                    605 | 1824 |
| tgc aag aac aga aag aac agc cat cag atc tgt aag aaa aga aaa tgt<br>Cys Lys Asn Arg Lys Asn Ser His Gln Ile Cys Lys Lys Arg Lys Cys<br>              610                      615                    620 | 1872 |
| gag gag ctg aaa aag aaa cca tct gtt gtt gtg cct ctg gag gtt ata<br>Glu Glu Leu Lys Lys Lys Pro Ser Val Val Val Pro Leu Glu Val Ile<br>625                      630                      635                    640 | 1920 |
| aag gaa aac aag agg ccc cag agg gaa aag aag ccc aaa gtt tta aag<br>Lys Glu Asn Lys Arg Pro Gln Arg Glu Lys Lys Pro Lys Val Leu Lys<br>                        645                      650                    655 | 1968 |
| gca gat ttt gac aac aaa cca gta aat ggc ccc aag tca gaa tcc atg<br>Ala Asp Phe Asp Asn Lys Pro Val Asn Gly Pro Lys Ser Glu Ser Met<br>              660                      665                    670 | 2016 |
| gac tac agt aga tgt ggt cat ggg gaa gaa caa aaa ttg gaa ttg aac<br>Asp Tyr Ser Arg Cys Gly His Gly Glu Glu Gln Lys Leu Glu Leu Asn<br>      675                      680                    685 | 2064 |
| cca cat act gtt gaa aat gta act aaa aat gaa gac agc atg aca ggc<br>Pro His Thr Val Glu Asn Val Thr Lys Asn Glu Asp Ser Met Thr Gly<br>              690                      695                    700 | 2112 |
| atc gag gtg gag aag tgg aca caa aac aag aaa tca cag tta act gat<br>Ile Glu Val Glu Lys Trp Thr Gln Asn Lys Lys Ser Gln Leu Thr Asp<br>705                      710                      715                    720 | 2160 |
| cac gtg aaa gga gat ttt agt gct aat gtc cca gaa gct gaa aaa tcg<br>His Val Lys Gly Asp Phe Ser Ala Asn Val Pro Glu Ala Glu Lys Ser<br>                      725                      730                    735 | 2208 |
| aaa aac tct gaa gtt gac aag aaa cga acc aaa tct cca aaa ttg ttt<br>Lys Asn Ser Glu Val Asp Lys Lys Arg Thr Lys Ser Pro Lys Leu Phe<br>              740                      745                    750 | 2256 |
| gta caa acc gta aga aat ggc att aaa cat gta cac tgt tta cca gct<br>Val Gln Thr Val Arg Asn Gly Ile Lys His Val His Cys Leu Pro Ala<br>      755                      760                    765 | 2304 |
| gaa aca aat gtt tca ttt aaa aaa ttc aat att gaa gaa ttc ggc aag<br>Glu Thr Asn Val Ser Phe Lys Lys Phe Asn Ile Glu Glu Phe Gly Lys<br>770                      775                      780 | 2352 |
| aca ttg gaa aac aat tct tat aaa ttc cta aaa gac act gca aac cat<br>Thr Leu Glu Asn Asn Ser Tyr Lys Phe Leu Lys Asp Thr Ala Asn His<br>785                      790                      795                    800 | 2400 |
| aaa aac gct atg agc tct gtt gct act gat atg agt tgt gat cat ctc<br>Lys Asn Ala Met Ser Ser Val Ala Thr Asp Met Ser Cys Asp His Leu<br>                      805                      810                    815 | 2448 |
| aag ggg aga agt aac gtt tta gta ttc cag cag cct ggc ttt aac tgc<br>Lys Gly Arg Ser Asn Val Leu Val Phe Gln Gln Pro Gly Phe Asn Cys<br>              820                      825                    830 | 2496 |
| agt tcc att cca cat tct tca cac tcc atc ata aat cat cat gct agt<br>Ser Ser Ile Pro His Ser Ser His Ser Ile Ile Asn His His Ala Ser<br>      835                      840                    845 | 2544 |
| ata cac aat gaa ggt gat caa cca aaa act cct gag aat ata cca agt<br>Ile His Asn Glu Gly Asp Gln Pro Lys Thr Pro Glu Asn Ile Pro Ser<br>850                      855                      860 | 2592 |
| aaa gaa cca aaa gat gga tct ccc gtt caa cca agt ctc tta tcg tta<br>Lys Glu Pro Lys Asp Gly Ser Pro Val Gln Pro Ser Leu Leu Ser Leu<br>865                      870                      875                    880 | 2640 |
| atg aaa gat agg aga tta aca ttg gag caa gtg gta gcc ata gag gcc<br>Met Lys Asp Arg Arg Leu Thr Leu Glu Gln Val Val Ala Ile Glu Ala | 2688 |

-continued

|  |  |  |  |  |  |  |  |  |  |  |  |  |  |  |  |
|---|---|---|---|---|---|---|---|---|---|---|---|---|---|---|---|
|  |  |  | 885 |  |  |  |  | 890 |  |  |  |  | 895 |  |  |
| ctg | act | caa | ctc | tca | gaa | gcc | cca | tca | gag | aat | tcc | tcc | cca | tca | aag | 2736 |
| Leu | Thr | Gln | Leu | Ser | Glu | Ala | Pro | Ser | Glu | Asn | Ser | Ser | Pro | Ser | Lys |  |
|  |  |  | 900 |  |  |  |  | 905 |  |  |  |  | 910 |  |  |
| tca | gag | aag | gat | gag | gaa | tca | gag | cag | aga | aca | gcc | agt | ttg | ctt | aat | 2784 |
| Ser | Glu | Lys | Asp | Glu | Glu | Ser | Glu | Gln | Arg | Thr | Ala | Ser | Leu | Leu | Asn |  |
|  |  | 915 |  |  |  |  | 920 |  |  |  |  | 925 |  |  |  |
| agc | tgc | aaa | gct | atc | ctc | tac | act | gta | aga | aaa | gac | ctc | caa | gac | cca | 2832 |
| Ser | Cys | Lys | Ala | Ile | Leu | Tyr | Thr | Val | Arg | Lys | Asp | Leu | Gln | Asp | Pro |  |
|  | 930 |  |  |  |  | 935 |  |  |  |  | 940 |  |  |  |  |
| aac | tta | cag | gga | gag | cca | cca | aaa | ctt | aat | cac | tgt | cca | tct | ttg | gaa | 2880 |
| Asn | Leu | Gln | Gly | Glu | Pro | Pro | Lys | Leu | Asn | His | Cys | Pro | Ser | Leu | Glu |  |
| 945 |  |  |  |  | 950 |  |  |  |  | 955 |  |  |  |  | 960 |
| aaa | caa | agt | tca | tgc | aac | acg | gtg | gtt | ttc | aat | ggg | caa | act | act | acc | 2928 |
| Lys | Gln | Ser | Ser | Cys | Asn | Thr | Val | Val | Phe | Asn | Gly | Gln | Thr | Thr | Thr |  |
|  |  |  |  | 965 |  |  |  |  | 970 |  |  |  |  | 975 |  |
| ctt | tcc | aac | tca | cat | atc | aac | tca | gct | act | aac | caa | gca | tcc | aca | aag | 2976 |
| Leu | Ser | Asn | Ser | His | Ile | Asn | Ser | Ala | Thr | Asn | Gln | Ala | Ser | Thr | Lys |  |
|  |  |  | 980 |  |  |  |  | 985 |  |  |  |  | 990 |  |  |
| tca | cat | gaa | tat | tca | aaa | gtc | aca | aat | tca | tta | tct | ctt | ttt | ata | cca | 3024 |
| Ser | His | Glu | Tyr | Ser | Lys | Val | Thr | Asn | Ser | Leu | Ser | Leu | Phe | Ile | Pro |  |
|  |  | 995 |  |  |  |  | 1000 |  |  |  |  | 1005 |  |  |  |
| aaa | tca | aat | tca | tcc | aag | att | gac | acc | aat | aaa | agt | att | gct | caa |  | 3069 |
| Lys | Ser | Asn | Ser | Ser | Lys | Ile | Asp | Thr | Asn | Lys | Ser | Ile | Ala | Gln |  |  |
|  | 1010 |  |  |  |  | 1015 |  |  |  |  | 1020 |  |  |  |  |
| ggg | ata | att | act | ctt | gac | aat | tgt | tcc | aat | gat | ttg | cat | cag | ttg |  | 3114 |
| Gly | Ile | Ile | Thr | Leu | Asp | Asn | Cys | Ser | Asn | Asp | Leu | His | Gln | Leu |  |  |
|  | 1025 |  |  |  |  | 1030 |  |  |  |  | 1035 |  |  |  |  |
| cca | cca | aga | aat | aat | gaa | gtg | gag | tat | tgc | aac | cag | tta | ctg | gac |  | 3159 |
| Pro | Pro | Arg | Asn | Asn | Glu | Val | Glu | Tyr | Cys | Asn | Gln | Leu | Leu | Asp |  |  |
|  | 1040 |  |  |  |  | 1045 |  |  |  |  | 1050 |  |  |  |  |
| agc | agc | aaa | aaa | ttg | gac | tca | gat | gat | cta | tca | tgt | cag | gat | gca |  | 3204 |
| Ser | Ser | Lys | Lys | Leu | Asp | Ser | Asp | Asp | Leu | Ser | Cys | Gln | Asp | Ala |  |  |
|  | 1055 |  |  |  |  | 1060 |  |  |  |  | 1065 |  |  |  |  |
| acc | cat | acc | caa | att | gag | gaa | gat | gtt | gca | aca | cag | ttg | aca | caa |  | 3249 |
| Thr | His | Thr | Gln | Ile | Glu | Glu | Asp | Val | Ala | Thr | Gln | Leu | Thr | Gln |  |  |
|  | 1070 |  |  |  |  | 1075 |  |  |  |  | 1080 |  |  |  |  |
| ctt | gct | tcg | ata | att | aag | atc | aat | tat | ata | aaa | cca | gag | gac | aaa |  | 3294 |
| Leu | Ala | Ser | Ile | Ile | Lys | Ile | Asn | Tyr | Ile | Lys | Pro | Glu | Asp | Lys |  |  |
|  | 1085 |  |  |  |  | 1090 |  |  |  |  | 1095 |  |  |  |  |
| aaa | gtt | gaa | agt | aca | cca | aca | agc | ctt | gtc | aca | tgt | aat | gta | cag |  | 3339 |
| Lys | Val | Glu | Ser | Thr | Pro | Thr | Ser | Leu | Val | Thr | Cys | Asn | Val | Gln |  |  |
|  | 1100 |  |  |  |  | 1105 |  |  |  |  | 1110 |  |  |  |  |
| caa | aaa | tac | aat | cag | gag | aag | ggc | aca | atg | caa | cag | aaa | cca | cct |  | 3384 |
| Gln | Lys | Tyr | Asn | Gln | Glu | Lys | Gly | Thr | Met | Gln | Gln | Lys | Pro | Pro |  |  |
|  | 1115 |  |  |  |  | 1120 |  |  |  |  | 1125 |  |  |  |  |
| tca | agt | gta | cac | aat | aat | cat | ggt | tca | tca | tta | aca | aaa | caa | aag |  | 3429 |
| Ser | Ser | Val | His | Asn | Asn | His | Gly | Ser | Ser | Leu | Thr | Lys | Gln | Lys |  |  |
|  | 1130 |  |  |  |  | 1135 |  |  |  |  | 1140 |  |  |  |  |
| aac | cca | acc | cag | aaa | aag | aca | aaa | tcc | acc | cca | tca | aga | gat | cgg |  | 3474 |
| Asn | Pro | Thr | Gln | Lys | Lys | Thr | Lys | Ser | Thr | Pro | Ser | Arg | Asp | Arg |  |  |
|  | 1145 |  |  |  |  | 1150 |  |  |  |  | 1155 |  |  |  |  |
| cgg | aaa | aag | aag | ccc | aca | gtt | gta | agt | tat | caa | gaa | aat | gat | cgg |  | 3519 |
| Arg | Lys | Lys | Lys | Pro | Thr | Val | Val | Ser | Tyr | Gln | Glu | Asn | Asp | Arg |  |  |
|  | 1160 |  |  |  |  | 1165 |  |  |  |  | 1170 |  |  |  |  |
| cag | aag | tgg | gaa | aag | ttg | tcc | tat | atg | tat | ggc | aca | ata | tgc | gac |  | 3564 |
| Gln | Lys | Trp | Glu | Lys | Leu | Ser | Tyr | Met | Tyr | Gly | Thr | Ile | Cys | Asp |  |  |
|  | 1175 |  |  |  |  | 1180 |  |  |  |  | 1185 |  |  |  |  |
| att | tgg | ata | gca | tcg | aaa | ttt | caa | aat | ttt | ggg | caa | ttt | tgt | cca |  | 3609 |

|  |  |  |  |  |  |  |  |  |  |  |
|---|---|---|---|---|---|---|---|---|---|---|
| Ile | Trp | Ile | Ala | Ser | Lys | Phe | Gln | Asn | Phe | Gly | Gln | Phe | Cys | Pro |
| 1190 |  |  |  | 1195 |  |  |  |  | 1200 |  |  |  |  |  |

```
cat gat ttt cct act gta ttt ggg aaa att tct tcc tcg acc aaa     3654
His Asp Phe Pro Thr Val Phe Gly Lys Ile Ser Ser Ser Thr Lys
    1205                1210                1215 ata tgg aaa cca ctg gct caa acg agg tcc att atg caa ccc aaa     3699
Ile Trp Lys Pro Leu Ala Gln Thr Arg Ser Ile Met Gln Pro Lys
1220                1225                1230 aca gta ttt cca cca ctc act cag ata aaa tta cag aga tat cct     3744
Thr Val Phe Pro Pro Leu Thr Gln Ile Lys Leu Gln Arg Tyr Pro
    1235                1240                1245 gaa tca gca gag gaa aag gtg aag gtt gaa cca ttg gat tca ctc     3789
Glu Ser Ala Glu Glu Lys Val Lys Val Glu Pro Leu Asp Ser Leu
1250                1255                1260 agc tta ttt cat ctt aaa acg gaa tcc aac ggg aag gca ttc act     3834
Ser Leu Phe His Leu Lys Thr Glu Ser Asn Gly Lys Ala Phe Thr
    1265                1270                1275 gat aaa gct tat aat tct cag gta cag tta acg gtg aat gcc aat     3879
Asp Lys Ala Tyr Asn Ser Gln Val Gln Leu Thr Val Asn Ala Asn
1280                1285                1290 cag aaa gcc cat cct ttg acc cag ccc tcc tct cca cct aac cag     3924
Gln Lys Ala His Pro Leu Thr Gln Pro Ser Ser Pro Pro Asn Gln
    1295                1300                1305 tgt gct aac gtg atg gca ggc gat gac caa ata cgg ttt cag cag     3969
Cys Ala Asn Val Met Ala Gly Asp Asp Gln Ile Arg Phe Gln Gln
1310                1315                1320 gtt gtt aag gag caa ctc atg cat cag aga ctg cca aca ttg cct     4014
Val Val Lys Glu Gln Leu Met His Gln Arg Leu Pro Thr Leu Pro
    1325                1330                1335 ggt atc tct cat gaa aca ccc tta ccg gag tca gca cta act ctc     4059
Gly Ile Ser His Glu Thr Pro Leu Pro Glu Ser Ala Leu Thr Leu
1340                1345                1350 agg aat gta aat gta gtg tgt tca ggt gga att aca gtg gtt tct     4104
Arg Asn Val Asn Val Val Cys Ser Gly Gly Ile Thr Val Val Ser
    1355                1360                1365 acc aaa agt gaa gag gaa gtc tgt tca tcc agt ttt gga aca tca     4149
Thr Lys Ser Glu Glu Glu Val Cys Ser Ser Ser Phe Gly Thr Ser
1370                1375                1380 gaa ttt tcc aca gtg gac agt gca cag aaa aat ttt aat gat tat     4194
Glu Phe Ser Thr Val Asp Ser Ala Gln Lys Asn Phe Asn Asp Tyr
    1385                1390                1395 gcc atg aac ttc ttt act aac cct aca aaa aac cta gtg tct ata     4239
Ala Met Asn Phe Phe Thr Asn Pro Thr Lys Asn Leu Val Ser Ile
1400                1405                1410 act aaa gat tct gaa ctg ccc acc tgc agc tgt ctt gat cga gtt     4284
Thr Lys Asp Ser Glu Leu Pro Thr Cys Ser Cys Leu Asp Arg Val
    1415                1420                1425 ata caa aaa gac aaa ggc cca tat tat aca cac ctt ggg gca gga     4329
Ile Gln Lys Asp Lys Gly Pro Tyr Tyr Thr His Leu Gly Ala Gly
1430                1435                1440 cca agt gtt gct gct gtc agg gaa atc atg gag aat agg tat ggt     4374
Pro Ser Val Ala Ala Val Arg Glu Ile Met Glu Asn Arg Tyr Gly
    1445                1450                1455 caa aaa gga aac gca ata agg ata gaa ata gta gtg tac acc ggt     4419
Gln Lys Gly Asn Ala Ile Arg Ile Glu Ile Val Val Tyr Thr Gly
1460                1465                1470 aaa gaa ggg aaa agc tct cat ggg tgt cca att gct aag tgg gtt     4464
Lys Glu Gly Lys Ser Ser His Gly Cys Pro Ile Ala Lys Trp Val
    1475                1480                1485
```

| | |
|---|---|
| tta aga aga agc agt gat gaa gaa aaa gtt ctt tgt ttg gtc cgg<br>Leu Arg Arg Ser Ser Asp Glu Glu Lys Val Leu Cys Leu Val Arg<br>1490               1495               1500 | 4509 |
| cag cgt aca ggc cac cac tgt cca act gct gtg atg gtg gtg ctc<br>Gln Arg Thr Gly His His Cys Pro Thr Ala Val Met Val Val Leu<br>1505               1510               1515 | 4554 |
| atc atg gtg tgg gat ggc atc cct ctt cca atg gcc gac cgg cta<br>Ile Met Val Trp Asp Gly Ile Pro Leu Pro Met Ala Asp Arg Leu<br>1520               1525               1530 | 4599 |
| tac aca gag ctc aca gag aat cta aag tca tac aat ggg cac cct<br>Tyr Thr Glu Leu Thr Glu Asn Leu Lys Ser Tyr Asn Gly His Pro<br>1535               1540               1545 | 4644 |
| acc gac aga aga tgc acc ctc aat gaa aat cgt acc tgt aca tgt<br>Thr Asp Arg Arg Cys Thr Leu Asn Glu Asn Arg Thr Cys Thr Cys<br>1550               1555               1560 | 4689 |
| caa gga att gat cca gag act tgt gga gct tca ttc tct ttt ggc<br>Gln Gly Ile Asp Pro Glu Thr Cys Gly Ala Ser Phe Ser Phe Gly<br>1565               1570               1575 | 4734 |
| tgt tca tgg agt atg tac ttt aat ggc tgt aag ttt ggt aga agc<br>Cys Ser Trp Ser Met Tyr Phe Asn Gly Cys Lys Phe Gly Arg Ser<br>1580               1585               1590 | 4779 |
| cca agc ccc aga aga ttt aga att gat cca agc tct ccc tta cat<br>Pro Ser Pro Arg Arg Phe Arg Ile Asp Pro Ser Ser Pro Leu His<br>1595               1600               1605 | 4824 |
| acc tac tat gaa aga att act aaa gga cgt aat cca gaa aga aga<br>Thr Tyr Tyr Glu Arg Ile Thr Lys Gly Arg Asn Pro Glu Arg Arg<br>1610               1615               1620 | 4869 |
| tat atg aaa ccg gaa cga atc agt ccg gga cac gag gcc atg gaa<br>Tyr Met Lys Pro Glu Arg Ile Ser Pro Gly His Glu Ala Met Glu<br>1625               1630               1635 | 4914 |
| aaa aac ctt gaa gat aac tta cag agt ttg gct aca cga tta gct<br>Lys Asn Leu Glu Asp Asn Leu Gln Ser Leu Ala Thr Arg Leu Ala<br>1640               1645               1650 | 4959 |
| cca att tat aag cag tat gct cca gta gct tac caa aat cag gtg<br>Pro Ile Tyr Lys Gln Tyr Ala Pro Val Ala Tyr Gln Asn Gln Val<br>1655               1660               1665 | 5004 |
| gaa tat gaa aat gtt gcc cga gaa tgt cgg ctt ggc agc aag gaa<br>Glu Tyr Glu Asn Val Ala Arg Glu Cys Arg Leu Gly Ser Lys Glu<br>1670               1675               1680 | 5049 |
| ggt cgt ccc ttc tct ggg gtc act gct tgc ctg gac ttc tgt gct<br>Gly Arg Pro Phe Ser Gly Val Thr Ala Cys Leu Asp Phe Cys Ala<br>1685               1690               1695 | 5094 |
| cat ccc cac agg gac att cac aac atg aat aat gga agc act gtg<br>His Pro His Arg Asp Ile His Asn Met Asn Asn Gly Ser Thr Val<br>1700               1705               1710 | 5139 |
| gtt tgt acc tta act cga gaa gat aac cgc tct ttg ggt gtt att<br>Val Cys Thr Leu Thr Arg Glu Asp Asn Arg Ser Leu Gly Val Ile<br>1715               1720               1725 | 5184 |
| cct caa gat gag cag ctc cat gtg cta cct ctt tat aag ctt tca<br>Pro Gln Asp Glu Gln Leu His Val Leu Pro Leu Tyr Lys Leu Ser<br>1730               1735               1740 | 5229 |
| gac aca gat gag ttt ggc tcc aag gaa gga atg gaa gcc aag atc<br>Asp Thr Asp Glu Phe Gly Ser Lys Glu Gly Met Glu Ala Lys Ile<br>1745               1750               1755 | 5274 |
| aaa tct ggg gcc atc gag gtc ctg gca ccc cgc cgc aaa aaa aga<br>Lys Ser Gly Ala Ile Glu Val Leu Ala Pro Arg Arg Lys Lys Arg<br>1760               1765               1770 | 5319 |
| acg tgt ttc act cag cct gtt ccc cgt tct gga aag aag agg gct<br>Thr Cys Phe Thr Gln Pro Val Pro Arg Ser Gly Lys Lys Arg Ala<br>1775               1780               1785 | 5364 |

```
gcg atg atg aca gag gtt ctt gca cat aag ata agg gca gtg gaa      5409
Ala Met Met Thr Glu Val Leu Ala His Lys Ile Arg Ala Val Glu
    1790             1795                 1800 aag aaa cct att ccc cga atc aag cgg aag aat aac tca aca aca      5454
Lys Lys Pro Ile Pro Arg Ile Lys Arg Lys Asn Asn Ser Thr Thr
    1805             1810                 1815 aca aac aac agt aag cct tcg tca ctg cca acc tta ggg agt aac      5499
Thr Asn Asn Ser Lys Pro Ser Ser Leu Pro Thr Leu Gly Ser Asn
    1820             1825                 1830 act gag acc gtg caa cct gaa gta aaa agt gaa acc gaa ccc cat      5544
Thr Glu Thr Val Gln Pro Glu Val Lys Ser Glu Thr Glu Pro His
    1835             1840                 1845 ttt atc tta aaa agt tca gac aac act aaa act tat tcg ctg atg      5589
Phe Ile Leu Lys Ser Ser Asp Asn Thr Lys Thr Tyr Ser Leu Met
    1850             1855                 1860 cca tcc gct cct cac cca gtg aaa gag gca tct cca ggc ttc tcc      5634
Pro Ser Ala Pro His Pro Val Lys Glu Ala Ser Pro Gly Phe Ser
    1865             1870                 1875 tgg tcc ccg aag act gct tca gcc aca cca gct cca ctg aag aat      5679
Trp Ser Pro Lys Thr Ala Ser Ala Thr Pro Ala Pro Leu Lys Asn
    1880             1885                 1890 gac gca aca gcc tca tgc ggg ttt tca gaa aga agc agc act ccc      5724
Asp Ala Thr Ala Ser Cys Gly Phe Ser Glu Arg Ser Ser Thr Pro
    1895             1900                 1905 cac tgt acg atg cct tcg gga aga ctc agt ggt gcc aat gca gct      5769
His Cys Thr Met Pro Ser Gly Arg Leu Ser Gly Ala Asn Ala Ala
    1910             1915                 1920 gct gct gat ggc cct ggc att tca cag ctt ggc gaa gtg gct cct      5814
Ala Ala Asp Gly Pro Gly Ile Ser Gln Leu Gly Glu Val Ala Pro
    1925             1930                 1935 ctc ccc acc ctg tct gct cct gtg atg gag ccc ctc att aat tct      5859
Leu Pro Thr Leu Ser Ala Pro Val Met Glu Pro Leu Ile Asn Ser
    1940             1945                 1950 gag cct tcc act ggt gtg act gag ccg cta acg cct cat cag cca      5904
Glu Pro Ser Thr Gly Val Thr Glu Pro Leu Thr Pro His Gln Pro
    1955             1960                 1965 aac cac cag ccc tcc ttc ctc acc tct cct caa gac ctt gcc tct      5949
Asn His Gln Pro Ser Phe Leu Thr Ser Pro Gln Asp Leu Ala Ser
    1970             1975                 1980 tct cca atg gaa gaa gat gag cag cat tct gaa gca gat gag cct      5994
Ser Pro Met Glu Glu Asp Glu Gln His Ser Glu Ala Asp Glu Pro
    1985             1990                 1995 cca tca gac gaa ccc cta tct gat gac ccc ctg tca cct gct gag      6039
Pro Ser Asp Glu Pro Leu Ser Asp Asp Pro Leu Ser Pro Ala Glu
    2000             2005                 2010 gag aaa ttg ccc cac att gat gag tat tgg tca gac agt gag cac      6084
Glu Lys Leu Pro His Ile Asp Glu Tyr Trp Ser Asp Ser Glu His
    2015             2020                 2025 atc ttt ttg gat gca aat att ggt ggg gtg gcc atc gca cct gct      6129
Ile Phe Leu Asp Ala Asn Ile Gly Gly Val Ala Ile Ala Pro Ala
    2030             2035                 2040 cac ggc tcg gtt ttg att gag tgt gcc cgg cga gag ctg cac gct      6174
His Gly Ser Val Leu Ile Glu Cys Ala Arg Arg Glu Leu His Ala
    2045             2050                 2055 acc act cct gtt gag cac ccc aac cgt aat cat cca acc cgc ctc      6219
Thr Thr Pro Val Glu His Pro Asn Arg Asn His Pro Thr Arg Leu
    2060             2065                 2070 tcc ctt gtc ttt tac cag cac aaa aac cta aat aag ccc caa cat      6264
Ser Leu Val Phe Tyr Gln His Lys Asn Leu Asn Lys Pro Gln His
```

```
                2075                  2080                   2085
ggt  ttt  gaa  cta  aac  aag  att  aag  ttt  gag  gct  aaa  gaa  gct  aag            6309
Gly  Phe  Glu  Leu  Asn  Lys  Ile  Lys  Phe  Glu  Ala  Lys  Glu  Ala  Lys
     2090                 2095                      2100 aat  aag  aaa  atg  aag  gcc  tca  gag  caa  aaa  gac  cag  gca  gct  aat            6354
Asn  Lys  Lys  Met  Lys  Ala  Ser  Glu  Gln  Lys  Asp  Gln  Ala  Ala  Asn
     2105                 2110                      2115 gaa  ggt  cca  gaa  cag  tcc  tct  gaa  gta  aat  gaa  ttg  aac  caa  att            6399
Glu  Gly  Pro  Glu  Gln  Ser  Ser  Glu  Val  Asn  Glu  Leu  Asn  Gln  Ile
     2120                 2125                      2130 cct  tct  cat  aaa  gca  tta  aca  tta  acc  cat  gac  aat  gtt  gtc  acc            6444
Pro  Ser  His  Lys  Ala  Leu  Thr  Leu  Thr  His  Asp  Asn  Val  Val  Thr
     2135                 2140                      2145 gtg  tcc  cct  tat  gct  ctc  aca  cac  gtt  gcg  ggg  ccc  tat  aac  cat            6489
Val  Ser  Pro  Tyr  Ala  Leu  Thr  His  Val  Ala  Gly  Pro  Tyr  Asn  His
     2150                 2155                      2160 tgg  gtc  tga                                                                         6498
Trp  Val
     2165

<210> SEQ ID NO 4
<211> LENGTH: 2165
<212> TYPE: PRT
<213> ORGANISM: Homo sapiens

<400> SEQUENCE: 4

Met  Ser  Arg  Ser  Arg  His  Ala  Arg  Pro  Ser  Arg  Leu  Val  Arg  Lys  Glu
1                  5                   10                  15

Asp  Val  Asn  Lys  Lys  Lys  Asn  Ser  Gln  Leu  Arg  Lys  Thr  Thr  Lys
                20                  25                  30

Gly  Ala  Asn  Lys  Asn  Val  Ala  Ser  Val  Lys  Thr  Leu  Ser  Pro  Gly  Lys
            35                  40                  45

Leu  Lys  Gln  Leu  Ile  Gln  Glu  Arg  Asp  Val  Lys  Lys  Thr  Glu  Pro
        50                  55                  60

Lys  Pro  Pro  Val  Pro  Val  Arg  Ser  Leu  Leu  Thr  Arg  Ala  Gly  Ala  Ala
65                  70                  75                  80

Arg  Met  Asn  Leu  Asp  Arg  Thr  Glu  Val  Leu  Phe  Gln  Asn  Pro  Glu  Ser
                85                  90                  95

Leu  Thr  Cys  Asn  Gly  Phe  Thr  Met  Ala  Leu  Arg  Ser  Thr  Ser  Leu  Ser
            100                 105                 110

Arg  Arg  Leu  Ser  Gln  Pro  Pro  Leu  Val  Val  Ala  Lys  Ser  Lys  Lys  Val
        115                 120                 125

Pro  Leu  Ser  Lys  Gly  Leu  Glu  Lys  Gln  His  Asp  Cys  Asp  Tyr  Lys  Ile
130                 135                 140

Leu  Pro  Ala  Leu  Gly  Val  Lys  His  Ser  Glu  Asn  Asp  Ser  Val  Pro  Met
145                 150                 155                 160

Gln  Gly  Thr  Gln  Val  Leu  Pro  Asp  Ile  Glu  Thr  Leu  Ile  Gly  Val  Gln
                165                 170                 175

Asn  Pro  Ser  Leu  Leu  Lys  Gly  Lys  Ser  Gln  Glu  Thr  Thr  Gln  Phe  Trp
            180                 185                 190

Ser  Gln  Arg  Val  Glu  Asp  Ser  Lys  Ile  Asn  Ile  Pro  Thr  His  Ser  Gly
        195                 200                 205

Pro  Ala  Ala  Glu  Ile  Leu  Pro  Gly  Pro  Leu  Glu  Gly  Thr  Arg  Cys  Gly
    210                 215                 220

Glu  Gly  Leu  Phe  Ser  Glu  Glu  Thr  Leu  Asn  Asp  Thr  Ser  Gly  Ser  Pro
225                 230                 235                 240
```

```
Lys Met Phe Ala Gln Asp Thr Val Cys Ala Pro Phe Pro Gln Arg Ala
                    245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
        275                 280                 285

Pro Ile Lys Ser Glu His Asp Cys Tyr Pro Thr Ser Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
            340                 345                 350

Ala Asn Gln Gln Glu Val Ser Asp Thr Thr Ser Phe Leu Gly Gln Ala
        355                 360                 365

Phe Gly Ala Ile Pro His Gln Trp Glu Leu Pro Gly Ala Asp Pro Val
    370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
            420                 425                 430

Leu Pro Val Pro Pro Asn Pro Ile Ala Thr Phe Asn Ala Pro Ser Lys
        435                 440                 445

Trp Pro Glu Pro Gln Ser Thr Val Ser Tyr Gly Leu Ala Val Gln Gly
    450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
            500                 505                 510

Gln Gly Phe Pro Leu Ala Pro Glu Arg Gly Leu Phe His Ala Ser Leu
        515                 520                 525

Gly Ile Ala Gln Leu Ser Gln Ala Gly Pro Ser Lys Ser Asp Arg Gly
    530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Arg Lys Arg Cys Gly
            580                 585                 590

Val Cys Glu Pro Cys Gln Gln Lys Thr Asn Cys Gly Glu Cys Thr Tyr
        595                 600                 605

Cys Lys Asn Arg Lys Asn Ser His Gln Ile Cys Lys Lys Arg Lys Cys
    610                 615                 620

Glu Glu Leu Lys Lys Lys Pro Ser Val Val Val Pro Leu Glu Val Ile
625                 630                 635                 640

Lys Glu Asn Lys Arg Pro Gln Arg Glu Lys Lys Pro Lys Val Leu Lys
                645                 650                 655

Ala Asp Phe Asp Asn Lys Pro Val Asn Gly Pro Lys Ser Glu Ser Met
```

```
            660             665             670
Asp Tyr Ser Arg Cys Gly His Gly Glu Glu Gln Lys Leu Glu Leu Asn
            675             680             685

Pro His Thr Val Glu Asn Val Thr Lys Asn Glu Asp Ser Met Thr Gly
            690             695             700

Ile Glu Val Glu Lys Trp Thr Gln Asn Lys Lys Ser Gln Leu Thr Asp
705             710             715             720

His Val Lys Gly Asp Phe Ser Ala Asn Val Pro Glu Ala Glu Lys Ser
            725             730             735

Lys Asn Ser Glu Val Asp Lys Lys Arg Thr Lys Ser Pro Lys Leu Phe
            740             745             750

Val Gln Thr Val Arg Asn Gly Ile Lys His Val His Cys Leu Pro Ala
            755             760             765

Glu Thr Asn Val Ser Phe Lys Lys Phe Asn Ile Glu Glu Phe Gly Lys
            770             775             780

Thr Leu Glu Asn Asn Ser Tyr Lys Phe Leu Lys Asp Thr Ala Asn His
785             790             795             800

Lys Asn Ala Met Ser Ser Val Ala Thr Asp Met Ser Cys Asp His Leu
            805             810             815

Lys Gly Arg Ser Asn Val Leu Val Phe Gln Gln Pro Gly Phe Asn Cys
            820             825             830

Ser Ser Ile Pro His Ser His Ser Ile Ile Asn His His Ala Ser
            835             840             845

Ile His Asn Glu Gly Asp Gln Pro Lys Thr Pro Glu Asn Ile Pro Ser
            850             855             860

Lys Glu Pro Lys Asp Gly Ser Pro Val Gln Pro Ser Leu Leu Ser Leu
865             870             875             880

Met Lys Asp Arg Arg Leu Thr Leu Glu Gln Val Val Ala Ile Glu Ala
            885             890             895

Leu Thr Gln Leu Ser Glu Ala Pro Ser Glu Asn Ser Ser Pro Ser Lys
            900             905             910

Ser Glu Lys Asp Glu Glu Ser Glu Gln Arg Thr Ala Ser Leu Leu Asn
            915             920             925

Ser Cys Lys Ala Ile Leu Tyr Thr Val Arg Lys Asp Leu Gln Asp Pro
            930             935             940

Asn Leu Gln Gly Glu Pro Pro Lys Leu Asn His Cys Pro Ser Leu Glu
945             950             955             960

Lys Gln Ser Ser Cys Asn Thr Val Val Phe Asn Gly Gln Thr Thr Thr
            965             970             975

Leu Ser Asn Ser His Ile Asn Ser Ala Thr Asn Gln Ala Ser Thr Lys
            980             985             990

Ser His Glu Tyr Ser Lys Val Thr  Asn Ser Leu Ser Leu  Phe Ile Pro
            995             1000             1005

Lys Ser Asn Ser Ser Lys Ile Asp Thr Asn Lys Ser  Ile Ala Gln
   1010             1015             1020

Gly Ile Ile Thr Leu Asp Asn Cys Ser Asn Asp Leu  His Gln Leu
   1025             1030             1035

Pro Pro Arg Asn Asn Glu Val Glu Tyr Cys Asn Gln  Leu Leu Asp
   1040             1045             1050

Ser Ser Lys Lys Leu Asp Ser Asp Asp Leu Ser Cys  Gln Asp Ala
   1055             1060             1065

Thr His Thr Gln Ile Glu Glu Asp Val Ala Thr Gln  Leu Thr Gln
   1070             1075             1080
```

-continued

```
Leu Ala Ser Ile Ile Lys Ile Asn Tyr Ile Lys Pro Glu Asp Lys
1085                1090                1095

Lys Val Glu Ser Thr Pro Thr Ser Leu Val Thr Cys Asn Val Gln
1100                1105                1110

Gln Lys Tyr Asn Gln Glu Lys Gly Thr Met Gln Gln Lys Pro Pro
1115                1120                1125

Ser Ser Val His Asn Asn His Gly Ser Ser Leu Thr Lys Gln Lys
1130                1135                1140

Asn Pro Thr Gln Lys Lys Thr Lys Ser Thr Pro Ser Arg Asp Arg
1145                1150                1155

Arg Lys Lys Lys Pro Thr Val Val Ser Tyr Gln Glu Asn Asp Arg
1160                1165                1170

Gln Lys Trp Glu Lys Leu Ser Tyr Met Tyr Gly Thr Ile Cys Asp
1175                1180                1185

Ile Trp Ile Ala Ser Lys Phe Gln Asn Phe Gly Gln Phe Cys Pro
1190                1195                1200

His Asp Phe Pro Thr Val Phe Gly Lys Ile Ser Ser Ser Thr Lys
1205                1210                1215

Ile Trp Lys Pro Leu Ala Gln Thr Arg Ser Ile Met Gln Pro Lys
1220                1225                1230

Thr Val Phe Pro Pro Leu Thr Gln Ile Lys Leu Gln Arg Tyr Pro
1235                1240                1245

Glu Ser Ala Glu Glu Lys Val Lys Val Glu Pro Leu Asp Ser Leu
1250                1255                1260

Ser Leu Phe His Leu Lys Thr Glu Ser Asn Gly Lys Ala Phe Thr
1265                1270                1275

Asp Lys Ala Tyr Asn Ser Gln Val Gln Leu Thr Val Asn Ala Asn
1280                1285                1290

Gln Lys Ala His Pro Leu Thr Gln Pro Ser Ser Pro Pro Asn Gln
1295                1300                1305

Cys Ala Asn Val Met Ala Gly Asp Asp Gln Ile Arg Phe Gln Gln
1310                1315                1320

Val Val Lys Glu Gln Leu Met His Gln Arg Leu Pro Thr Leu Pro
1325                1330                1335

Gly Ile Ser His Glu Thr Pro Leu Pro Glu Ser Ala Leu Thr Leu
1340                1345                1350

Arg Asn Val Asn Val Val Cys Ser Gly Gly Ile Thr Val Val Ser
1355                1360                1365

Thr Lys Ser Glu Glu Glu Val Cys Ser Ser Ser Phe Gly Thr Ser
1370                1375                1380

Glu Phe Ser Thr Val Asp Ser Ala Gln Lys Asn Phe Asn Asp Tyr
1385                1390                1395

Ala Met Asn Phe Phe Thr Asn Pro Thr Lys Asn Leu Val Ser Ile
1400                1405                1410

Thr Lys Asp Ser Glu Leu Pro Thr Cys Ser Cys Leu Asp Arg Val
1415                1420                1425

Ile Gln Lys Asp Lys Gly Pro Tyr Tyr Thr His Leu Gly Ala Gly
1430                1435                1440

Pro Ser Val Ala Ala Val Arg Glu Ile Met Glu Asn Arg Tyr Gly
1445                1450                1455

Gln Lys Gly Asn Ala Ile Arg Ile Glu Ile Val Val Tyr Thr Gly
1460                1465                1470
```

```
Lys Glu Gly Lys Ser Ser His Gly Cys Pro Ile Ala Lys Trp Val
1475                1480                1485

Leu Arg Arg Ser Ser Asp Glu Glu Lys Val Leu Cys Leu Val Arg
    1490                1495                1500

Gln Arg Thr Gly His His Cys Pro Thr Ala Val Met Val Val Leu
    1505                1510                1515

Ile Met Val Trp Asp Gly Ile Pro Leu Pro Met Ala Asp Arg Leu
    1520                1525                1530

Tyr Thr Glu Leu Thr Glu Asn Leu Lys Ser Tyr Asn Gly His Pro
    1535                1540                1545

Thr Asp Arg Arg Cys Thr Leu Asn Glu Asn Arg Thr Cys Thr Cys
    1550                1555                1560

Gln Gly Ile Asp Pro Glu Thr Cys Gly Ala Ser Phe Ser Phe Gly
    1565                1570                1575

Cys Ser Trp Ser Met Tyr Phe Asn Gly Cys Lys Phe Gly Arg Ser
    1580                1585                1590

Pro Ser Pro Arg Arg Phe Arg Ile Asp Pro Ser Ser Pro Leu His
    1595                1600                1605

Thr Tyr Tyr Glu Arg Ile Thr Lys Gly Arg Asn Pro Glu Arg Arg
    1610                1615                1620

Tyr Met Lys Pro Glu Arg Ile Ser Pro Gly His Glu Ala Met Glu
    1625                1630                1635

Lys Asn Leu Glu Asp Asn Leu Gln Ser Leu Ala Thr Arg Leu Ala
    1640                1645                1650

Pro Ile Tyr Lys Gln Tyr Ala Pro Val Ala Tyr Gln Asn Gln Val
    1655                1660                1665

Glu Tyr Glu Asn Val Ala Arg Glu Cys Arg Leu Gly Ser Lys Glu
    1670                1675                1680

Gly Arg Pro Phe Ser Gly Val Thr Ala Cys Leu Asp Phe Cys Ala
    1685                1690                1695

His Pro His Arg Asp Ile His Asn Met Asn Asn Gly Ser Thr Val
    1700                1705                1710

Val Cys Thr Leu Thr Arg Glu Asp Asn Arg Ser Leu Gly Val Ile
    1715                1720                1725

Pro Gln Asp Glu Gln Leu His Val Leu Pro Leu Tyr Lys Leu Ser
    1730                1735                1740

Asp Thr Asp Glu Phe Gly Ser Lys Glu Gly Met Glu Ala Lys Ile
    1745                1750                1755

Lys Ser Gly Ala Ile Glu Val Leu Ala Pro Arg Arg Lys Lys Arg
    1760                1765                1770

Thr Cys Phe Thr Gln Pro Val Pro Arg Ser Gly Lys Lys Arg Ala
    1775                1780                1785

Ala Met Met Thr Glu Val Leu Ala His Lys Ile Arg Ala Val Glu
    1790                1795                1800

Lys Lys Pro Ile Pro Arg Ile Lys Arg Lys Asn Asn Ser Thr Thr
    1805                1810                1815

Thr Asn Asn Ser Lys Pro Ser Ser Leu Pro Thr Leu Gly Ser Asn
    1820                1825                1830

Thr Glu Thr Val Gln Pro Glu Val Lys Ser Glu Thr Glu Pro His
    1835                1840                1845

Phe Ile Leu Lys Ser Ser Asp Asn Thr Lys Thr Tyr Ser Leu Met
    1850                1855                1860

Pro Ser Ala Pro His Pro Val Lys Glu Ala Ser Pro Gly Phe Ser
```

|       |       |       |       | 1865  |       |       |       |       | 1870  |       |       |       |       | 1875  |       |
|-------|-------|-------|-------|-------|-------|-------|-------|-------|-------|-------|-------|-------|-------|-------|-------|

Trp Ser Pro Lys Thr Ala Ser Ala Thr Pro Ala Pro Leu Lys Asn
    1880            1885                1890

Asp Ala Thr Ala Ser Cys Gly Phe Ser Glu Arg Ser Ser Thr Pro
    1895            1900                1905

His Cys Thr Met Pro Ser Gly Arg Leu Ser Gly Ala Asn Ala Ala
    1910            1915                1920

Ala Ala Asp Gly Pro Gly Ile Ser Gln Leu Gly Glu Val Ala Pro
    1925            1930                1935

Leu Pro Thr Leu Ser Ala Pro Val Met Glu Pro Leu Ile Asn Ser
    1940            1945                1950

Glu Pro Ser Thr Gly Val Thr Glu Pro Leu Thr Pro His Gln Pro
    1955            1960                1965

Asn His Gln Pro Ser Phe Leu Thr Ser Pro Gln Asp Leu Ala Ser
    1970            1975                1980

Ser Pro Met Glu Glu Asp Glu Gln His Ser Glu Ala Asp Glu Pro
    1985            1990                1995

Pro Ser Asp Glu Pro Leu Ser Asp Asp Pro Leu Ser Pro Ala Glu
    2000            2005                2010

Glu Lys Leu Pro His Ile Asp Glu Tyr Trp Ser Asp Ser Glu His
    2015            2020                2025

Ile Phe Leu Asp Ala Asn Ile Gly Gly Val Ala Ile Ala Pro Ala
    2030            2035                2040

His Gly Ser Val Leu Ile Glu Cys Ala Arg Arg Glu Leu His Ala
    2045            2050                2055

Thr Thr Pro Val Glu His Pro Asn Arg Asn His Pro Thr Arg Leu
    2060            2065                2070

Ser Leu Val Phe Tyr Gln His Lys Asn Leu Asn Lys Pro Gln His
    2075            2080                2085

Gly Phe Glu Leu Asn Lys Ile Lys Phe Glu Ala Lys Glu Ala Lys
    2090            2095                2100

Asn Lys Lys Met Lys Ala Ser Glu Gln Lys Asp Gln Ala Ala Asn
    2105            2110                2115

Glu Gly Pro Glu Gln Ser Ser Glu Val Asn Glu Leu Asn Gln Ile
    2120            2125                2130

Pro Ser His Lys Ala Leu Thr Leu Thr His Asp Asn Val Val Thr
    2135            2140                2145

Val Ser Pro Tyr Ala Leu Thr His Val Ala Gly Pro Tyr Asn His
    2150            2155                2160

Trp Val
    2165

<210> SEQ ID NO 5
<211> LENGTH: 4005
<212> TYPE: DNA
<213> ORGANISM: Homo sapiens
<220> FEATURE:
<221> NAME/KEY: CDS
<222> LOCATION: (1)..(4005)

<400> SEQUENCE: 5 atg tct cga tcc cgc cat gca agg cct tcc aga tta gtc agg aag gaa    48
Met Ser Arg Ser Arg His Ala Arg Pro Ser Arg Leu Val Arg Lys Glu
1               5                   10                  15 gat gta aac aaa aaa aag aaa aac agc caa cta cga aag aca acc aag    96
Asp Val Asn Lys Lys Lys Lys Asn Ser Gln Leu Arg Lys Thr Thr Lys

```
                      20                  25                  30
gga gcc aac aaa aat gtg gca tca gtc aag act tta agc cct gga aaa        144
Gly Ala Asn Lys Asn Val Ala Ser Val Lys Thr Leu Ser Pro Gly Lys
         35                  40                  45 tta aag caa tta att caa gaa aga gat gtt aag aaa aaa aca gaa cct        192
Leu Lys Gln Leu Ile Gln Glu Arg Asp Val Lys Lys Lys Thr Glu Pro
 50                  55                  60 aaa cca ccc gtg cca gtc aga agc ctt ctg aca aga gct gga gca gca        240
Lys Pro Pro Val Pro Val Arg Ser Leu Leu Thr Arg Ala Gly Ala Ala
 65                  70                  75                  80 cgc atg aat ttg gat agg act gag gtt ctt ttt cag aac cca gag tcc        288
Arg Met Asn Leu Asp Arg Thr Glu Val Leu Phe Gln Asn Pro Glu Ser
                 85                  90                  95 tta acc tgc aat ggg ttt aca atg gcg cta cga agc acc tct ctt agc        336
Leu Thr Cys Asn Gly Phe Thr Met Ala Leu Arg Ser Thr Ser Leu Ser
            100                 105                 110 agg cga ctc tcc caa ccc cca ctg gtc gta gcc aaa tcc aaa aag gtt        384
Arg Arg Leu Ser Gln Pro Pro Leu Val Val Ala Lys Ser Lys Lys Val
        115                 120                 125 cca ctt tct aag ggt tta gaa aag caa cat gat tgt gat tat aag ata        432
Pro Leu Ser Lys Gly Leu Glu Lys Gln His Asp Cys Asp Tyr Lys Ile
130                 135                 140 ctc cct gct ttg gga gta aag cac tca gaa aat gat tcg gtt cca atg        480
Leu Pro Ala Leu Gly Val Lys His Ser Glu Asn Asp Ser Val Pro Met
145                 150                 155                 160 caa ggc acc caa gtc ctt cct gat ata gag act cta att ggt gta caa        528
Gln Gly Thr Gln Val Leu Pro Asp Ile Glu Thr Leu Ile Gly Val Gln
                165                 170                 175 aat ccc tct tta ctt aaa ggt aag agc caa gag aca act cag ttt tgg        576
Asn Pro Ser Leu Leu Lys Gly Lys Ser Gln Glu Thr Thr Gln Phe Trp
            180                 185                 190 tcc caa aga gtt gag gat tcc aag atc aat atc cct acc cac agt ggc        624
Ser Gln Arg Val Glu Asp Ser Lys Ile Asn Ile Pro Thr His Ser Gly
        195                 200                 205 cct gca gct gag atc ctt cct ggg cca ctg gaa ggg aca cgc tgt ggt        672
Pro Ala Ala Glu Ile Leu Pro Gly Pro Leu Glu Gly Thr Arg Cys Gly
210                 215                 220 gaa gga cta ttc tct gaa gag aca ttg aat gat acc agt ggt tcc cca        720
Glu Gly Leu Phe Ser Glu Glu Thr Leu Asn Asp Thr Ser Gly Ser Pro
225                 230                 235                 240 aaa atg ttt gct cag gac aca gtg tgt gct cct ttt ccc caa aga gca        768
Lys Met Phe Ala Gln Asp Thr Val Cys Ala Pro Phe Pro Gln Arg Ala
                245                 250                 255 acc ccc aaa gtt acc tct caa gga aac ccc agc att cag tta gaa gag        816
Thr Pro Lys Val Thr Ser Gln Gly Asn Pro Ser Ile Gln Leu Glu Glu
            260                 265                 270 ttg ggt tca cga gta gaa tct ctt aag tta tct gat tct tac ctg gat        864
Leu Gly Ser Arg Val Glu Ser Leu Lys Leu Ser Asp Ser Tyr Leu Asp
        275                 280                 285 ccc att aaa agt gaa cat gat tgc tac ccc acc tcc agt ctt aat aag        912
Pro Ile Lys Ser Glu His Asp Cys Tyr Pro Thr Ser Ser Leu Asn Lys
290                 295                 300 gtt ata cct gac ttg aac ctt aga aac tgc ttg gct ctt ggg ggg tct        960
Val Ile Pro Asp Leu Asn Leu Arg Asn Cys Leu Ala Leu Gly Gly Ser
305                 310                 315                 320 acg tct cct acc tct gta ata aaa ttc ctc ttg gca ggc tca aaa caa       1008
Thr Ser Pro Thr Ser Val Ile Lys Phe Leu Leu Ala Gly Ser Lys Gln
                325                 330                 335 gcg acc ctt ggt gct aaa cca gat cat caa gag gcc ttc gaa gct act       1056
Ala Thr Leu Gly Ala Lys Pro Asp His Gln Glu Ala Phe Glu Ala Thr
```

|        |        |        |        |        |        |        |        |        |        |        |        |        |      |
|--------|--------|--------|--------|--------|--------|--------|--------|--------|--------|--------|--------|--------|------|
|        |        |        | Ala<br>Thr | Leu | Gly<br>340 | Ala | Lys | Pro | Asp | His<br>345 | Gln | Glu | Ala | Phe | Glu | Ala<br>350 | Thr |      |

```
gca aat caa cag gaa gtt tct gat acc acc tct ttc cta gga cag gcc    1104
Ala Asn Gln Gln Glu Val Ser Asp Thr Thr Ser Phe Leu Gly Gln Ala
        355                 360                 365 ttt ggt gct atc cca cat caa tgg gaa ctt cct ggt gct gac cca gtt    1152
Phe Gly Ala Ile Pro His Gln Trp Glu Leu Pro Gly Ala Asp Pro Val
370                 375                 380 cat ggt gag gcc ctg ggt gag acc cca gat cta cca gag att cct ggt    1200
His Gly Glu Ala Leu Gly Glu Thr Pro Asp Leu Pro Glu Ile Pro Gly
385                 390                 395                 400 gct att cca gtc caa gga gag gtc ttt ggt act att tta gac caa caa    1248
Ala Ile Pro Val Gln Gly Glu Val Phe Gly Thr Ile Leu Asp Gln Gln
                405                 410                 415 gaa act ctt ggt atg agt ggg agt gtt gtc cca gac ttg cct gtc ttc    1296
Glu Thr Leu Gly Met Ser Gly Ser Val Val Pro Asp Leu Pro Val Phe
        420                 425                 430 ctt cct gtt cct cca aat cca att gct acc ttt aat gct cct tcc aaa    1344
Leu Pro Val Pro Pro Asn Pro Ile Ala Thr Phe Asn Ala Pro Ser Lys
                435                 440                 445 tgg cct gag ccc caa agc act gtc tca tat gga ctt gca gtc cag ggt    1392
Trp Pro Glu Pro Gln Ser Thr Val Ser Tyr Gly Leu Ala Val Gln Gly
450                 455                 460 gct ata cag att ttg cct ttg ggc tca gga cac act cct caa tca tca    1440
Ala Ile Gln Ile Leu Pro Leu Gly Ser Gly His Thr Pro Gln Ser Ser
465                 470                 475                 480 tca aac tca gag aaa aat tca tta cct cca gta atg gct ata agc aat    1488
Ser Asn Ser Glu Lys Asn Ser Leu Pro Pro Val Met Ala Ile Ser Asn
                485                 490                 495 gta gaa aat gag aag cag gtt cat ata agc ttc ctg cca gct aac act    1536
Val Glu Asn Glu Lys Gln Val His Ile Ser Phe Leu Pro Ala Asn Thr
            500                 505                 510 cag ggg ttc cca tta gcc cct gag aga gga ctc ttc cat gct tca ctg    1584
Gln Gly Phe Pro Leu Ala Pro Glu Arg Gly Leu Phe His Ala Ser Leu
        515                 520                 525 ggt ata gcc caa ctc tct cag gct ggt cct agc aaa tca gac aga ggg    1632
Gly Ile Ala Gln Leu Ser Gln Ala Gly Pro Ser Lys Ser Asp Arg Gly
530                 535                 540 agc tcc cag gtc agt gta acc agc aca gtt cat gtt gtc aac acc aca    1680
Ser Ser Gln Val Ser Val Thr Ser Thr Val His Val Val Asn Thr Thr
545                 550                 555                 560 gtg gtg act atg cca gtg cca atg gtc agt acc tcc tct tct tcc tat    1728
Val Val Thr Met Pro Val Pro Met Val Ser Thr Ser Ser Ser Ser Tyr
                565                 570                 575 acc act ttg cta ccg act ttg gaa aag aag aaa aga aag cga tgt ggg    1776
Thr Thr Leu Leu Pro Thr Leu Glu Lys Lys Lys Arg Lys Arg Cys Gly
            580                 585                 590 gtc tgt gaa ccc tgc cag cag aag acc aac tgt ggt gaa tgc act tac    1824
Val Cys Glu Pro Cys Gln Gln Lys Thr Asn Cys Gly Glu Cys Thr Tyr
        595                 600                 605 tgc aag aac aga aag aac agc cat cag atc tgt aag aaa aga aaa tgt    1872
Cys Lys Asn Arg Lys Asn Ser His Gln Ile Cys Lys Lys Arg Lys Cys
610                 615                 620 gag gag ctg aaa aag aaa cca tct gtt gtt gtg cct ctg gag gtt ata    1920
Glu Glu Leu Lys Lys Lys Pro Ser Val Val Val Pro Leu Glu Val Ile
625                 630                 635                 640 aag gaa aac aag agg ccc cag agg gaa aag aag ccc aaa gtt tta aag    1968
Lys Glu Asn Lys Arg Pro Gln Arg Glu Lys Lys Pro Lys Val Leu Lys
                645                 650                 655
```

```
gtt tta aga aga agc agt gat gaa gaa aaa gtt ctt tgt ttg gtc cgg    2016
Val Leu Arg Arg Ser Ser Asp Glu Glu Lys Val Leu Cys Leu Val Arg
        660             665                 670 cag cgt aca ggc cac cac tgt cca act gct gtg atg gtg gtg ctc atc    2064
Gln Arg Thr Gly His His Cys Pro Thr Ala Val Met Val Val Leu Ile
    675             680                 685 atg gtg tgg gat ggc atc cct ctt cca atg gcc gac cgg cta tac aca    2112
Met Val Trp Asp Gly Ile Pro Leu Pro Met Ala Asp Arg Leu Tyr Thr
690             695                 700 gag ctc aca gag aat cta aag tca tac aat ggg cac cct acc gac aga    2160
Glu Leu Thr Glu Asn Leu Lys Ser Tyr Asn Gly His Pro Thr Asp Arg
705             710                 715                 720 aga tgc acc ctc aat gaa aat cgt acc tgt aca tgt caa gga att gat    2208
Arg Cys Thr Leu Asn Glu Asn Arg Thr Cys Thr Cys Gln Gly Ile Asp
            725                 730                 735 cca gag act tgt gga gct tca ttc tct ttt ggc tgt tca tgg agt atg    2256
Pro Glu Thr Cys Gly Ala Ser Phe Ser Phe Gly Cys Ser Trp Ser Met
        740                 745                 750 tac ttt aat ggc tgt aag ttt ggt aga agc cca agc ccc aga aga ttt    2304
Tyr Phe Asn Gly Cys Lys Phe Gly Arg Ser Pro Ser Pro Arg Arg Phe
    755                 760                 765 aga att gat cca agc tct ccc tta cat acc tac tat gaa aga att act    2352
Arg Ile Asp Pro Ser Ser Pro Leu His Thr Tyr Tyr Glu Arg Ile Thr
770             775                 780 aaa gga cgt aat cca gaa aga aga tat atg aaa ccg gaa cga atc agt    2400
Lys Gly Arg Asn Pro Glu Arg Arg Tyr Met Lys Pro Glu Arg Ile Ser
785             790                 795                 800 ccg gga cac gag gcc atg gaa aaa aac ctt gaa gat aac tta cag agt    2448
Pro Gly His Glu Ala Met Glu Lys Asn Leu Glu Asp Asn Leu Gln Ser
            805                 810                 815 ttg gct aca cga tta gct cca att tat aag cag tat gct cca gta gct    2496
Leu Ala Thr Arg Leu Ala Pro Ile Tyr Lys Gln Tyr Ala Pro Val Ala
        820                 825                 830 tac caa aat cag gtg gaa tat gaa aat gtt gcc cga gaa tgt cgg ctt    2544
Tyr Gln Asn Gln Val Glu Tyr Glu Asn Val Ala Arg Glu Cys Arg Leu
    835                 840                 845 ggc agc aag gaa ggt cgt ccc ttc tct ggg gtc act gct tgc ctg gac    2592
Gly Ser Lys Glu Gly Arg Pro Phe Ser Gly Val Thr Ala Cys Leu Asp
850                 855                 860 ttc tgt gct cat ccc cac agg gac att cac aac atg aat aat gga agc    2640
Phe Cys Ala His Pro His Arg Asp Ile His Asn Met Asn Asn Gly Ser
865             870                 875                 880 act gtg gtt tgt acc tta act cga gaa gat aac cgc tct ttg ggt gtt    2688
Thr Val Val Cys Thr Leu Thr Arg Glu Asp Asn Arg Ser Leu Gly Val
            885                 890                 895 att cct caa gat gag cag ctc cat gtg cta cct ctt tat aag ctt tca    2736
Ile Pro Gln Asp Glu Gln Leu His Val Leu Pro Leu Tyr Lys Leu Ser
        900                 905                 910 gac aca gat gag ttt ggc tcc aag gaa gga atg gaa gcc aag atc aaa    2784
Asp Thr Asp Glu Phe Gly Ser Lys Glu Gly Met Glu Ala Lys Ile Lys
    915                 920                 925 tct ggg gcc atc gag gtc ctg gca ccc cgc cgc aaa aaa aga acg tgt    2832
Ser Gly Ala Ile Glu Val Leu Ala Pro Arg Arg Lys Lys Arg Thr Cys
930                 935                 940 ttc act cag cct gtt ccc cgt tct gga aag aag agg gct gcg atg atg    2880
Phe Thr Gln Pro Val Pro Arg Ser Gly Lys Lys Arg Ala Ala Met Met
945             950                 955                 960 aca gag gtt ctt gca cat aag ata agg gca gtg gaa aag aaa cct att    2928
Thr Glu Val Leu Ala His Lys Ile Arg Ala Val Glu Lys Lys Pro Ile
            965                 970                 975
```

```
ccc cga atc aag cgg aag aat aac tca aca aca aca aac aac agt aag      2976
Pro Arg Ile Lys Arg Lys Asn Asn Ser Thr Thr Thr Asn Asn Ser Lys
            980                 985                 990 cct tcg tca ctg cca acc tta ggg agt aac act gag acc gtg caa cct      3024
Pro Ser Ser Leu Pro Thr Leu Gly Ser Asn Thr Glu Thr Val Gln Pro
            995                1000                1005 gaa gta aaa agt gaa acc gaa ccc cat ttt atc tta aaa agt tca          3069
Glu Val Lys Ser Glu Thr Glu Pro His Phe Ile Leu Lys Ser Ser
        1010                1015                1020 gac aac act aaa act tat tcg ctg atg cca tcc gct cct cac cca          3114
Asp Asn Thr Lys Thr Tyr Ser Leu Met Pro Ser Ala Pro His Pro
        1025                1030                1035 gtg aaa gag gca tct cca ggc ttc tcc tgg tcc ccg aag act gct          3159
Val Lys Glu Ala Ser Pro Gly Phe Ser Trp Ser Pro Lys Thr Ala
        1040                1045                1050 tca gcc aca cca gct cca ctg aag aat gac gca aca gcc tca tgc          3204
Ser Ala Thr Pro Ala Pro Leu Lys Asn Asp Ala Thr Ala Ser Cys
        1055                1060                1065 ggg ttt tca gaa aga agc agc act ccc cac tgt acg atg cct tcg          3249
Gly Phe Ser Glu Arg Ser Ser Thr Pro His Cys Thr Met Pro Ser
        1070                1075                1080 gga aga ctc agt ggt gcc aat gca gct gct gct gat ggc cct ggc          3294
Gly Arg Leu Ser Gly Ala Asn Ala Ala Ala Ala Asp Gly Pro Gly
        1085                1090                1095 att tca cag ctt ggc gaa gtg gct cct ctc ccc acc ctg tct gct          3339
Ile Ser Gln Leu Gly Glu Val Ala Pro Leu Pro Thr Leu Ser Ala
        1100                1105                1110 cct gtg atg gag ccc ctc att aat tct gag cct tcc act ggt gtg          3384
Pro Val Met Glu Pro Leu Ile Asn Ser Glu Pro Ser Thr Gly Val
        1115                1120                1125 act gag ccg cta acg cct cat cag cca aac cac cag ccc tcc ttc          3429
Thr Glu Pro Leu Thr Pro His Gln Pro Asn His Gln Pro Ser Phe
        1130                1135                1140 ctc acc tct cct caa gac ctt gcc tct tct cca atg gaa gaa gat          3474
Leu Thr Ser Pro Gln Asp Leu Ala Ser Ser Pro Met Glu Glu Asp
        1145                1150                1155 gag cag cat tct gaa gca gat gag cct cca tca gac gaa ccc cta          3519
Glu Gln His Ser Glu Ala Asp Glu Pro Pro Ser Asp Glu Pro Leu
        1160                1165                1170 tct gat gac ccc ctg tca cct gct gag gag aaa ttg ccc cac att          3564
Ser Asp Asp Pro Leu Ser Pro Ala Glu Glu Lys Leu Pro His Ile
        1175                1180                1185 gat gag tat tgg tca gac agt gag cac atc ttt ttg gat gca aat          3609
Asp Glu Tyr Trp Ser Asp Ser Glu His Ile Phe Leu Asp Ala Asn
        1190                1195                1200 att ggt ggg gtg gcc atc gca cct gct cac ggc tcg gtt ttg att          3654
Ile Gly Gly Val Ala Ile Ala Pro Ala His Gly Ser Val Leu Ile
        1205                1210                1215 gag tgt gcc cgg cga gag ctg cac gct acc act cct gtt gag cac          3699
Glu Cys Ala Arg Arg Glu Leu His Ala Thr Thr Pro Val Glu His
        1220                1225                1230 ccc aac cgt aat cat cca acc cgc ctc tcc ctt gtc ttt tac cag          3744
Pro Asn Arg Asn His Pro Thr Arg Leu Ser Leu Val Phe Tyr Gln
        1235                1240                1245 cac aaa aac cta aat aag ccc caa cat ggt ttt gaa cta aac aag          3789
His Lys Asn Leu Asn Lys Pro Gln His Gly Phe Glu Leu Asn Lys
        1250                1255                1260 att aag ttt gag gct aaa gaa gct aag aat aag aaa atg aag gcc          3834
Ile Lys Phe Glu Ala Lys Glu Ala Lys Asn Lys Lys Met Lys Ala
```

|  |  |  |  |  |  |  |  |  |  |  |  |  |  |  |
|---|---|---|---|---|---|---|---|---|---|---|---|---|---|---|
|  |  | 1265 |  |  |  | 1270 |  |  |  | 1275 |  |  |  |  |
| tca | gag | caa | aaa | gac | cag | gca | gct | aat | gaa | ggt | cca | gaa | cag | tcc | 3879 |
| Ser | Glu | Gln | Lys | Asp | Gln | Ala | Ala | Asn | Glu | Gly | Pro | Glu | Gln | Ser |  |
|  | 1280 |  |  |  | 1285 |  |  |  |  | 1290 |  |  |  |  |  |
| tct | gaa | gta | aat | gaa | ttg | aac | caa | att | cct | tct | cat | aaa | gca | tta | 3924 |
| Ser | Glu | Val | Asn | Glu | Leu | Asn | Gln | Ile | Pro | Ser | His | Lys | Ala | Leu |  |
|  | 1295 |  |  |  | 1300 |  |  |  |  | 1305 |  |  |  |  |  |
| aca | tta | acc | cat | gac | aat | gtt | gtc | acc | gtg | tcc | cct | tat | gct | ctc | 3969 |
| Thr | Leu | Thr | His | Asp | Asn | Val | Val | Thr | Val | Ser | Pro | Tyr | Ala | Leu |  |
|  | 1310 |  |  |  | 1315 |  |  |  |  | 1320 |  |  |  |  |  |
| aca | cac | gtt | gcg | ggg | ccc | tat | aac | cat | tgg | gtc | tga |  |  |  | 4005 |
| Thr | His | Val | Ala | Gly | Pro | Tyr | Asn | His | Trp | Val |  |  |  |  |  |
|  | 1325 |  |  |  | 1330 |  |  |  |  |  |  |  |  |  |  |

<210> SEQ ID NO 6
<211> LENGTH: 1334
<212> TYPE: PRT
<213> ORGANISM: Homo sapiens

<400> SEQUENCE: 6

Met Ser Arg Ser Arg His Ala Arg Pro Ser Arg Leu Val Arg Lys Glu
1               5                   10                  15

Asp Val Asn Lys Lys Lys Asn Ser Gln Leu Arg Lys Thr Thr Lys
            20                  25                  30

Gly Ala Asn Lys Asn Val Ala Ser Val Lys Thr Leu Ser Pro Gly Lys
        35                  40                  45

Leu Lys Gln Leu Ile Gln Glu Arg Asp Val Lys Lys Thr Glu Pro
    50                  55                  60

Lys Pro Pro Val Pro Val Arg Ser Leu Leu Thr Arg Ala Gly Ala Ala
65                  70                  75                  80

Arg Met Asn Leu Asp Arg Thr Glu Val Leu Phe Gln Asn Pro Glu Ser
                85                  90                  95

Leu Thr Cys Asn Gly Phe Thr Met Ala Leu Arg Ser Thr Ser Leu Ser
            100                 105                 110

Arg Arg Leu Ser Gln Pro Pro Leu Val Val Ala Lys Ser Lys Lys Val
        115                 120                 125

Pro Leu Ser Lys Gly Leu Glu Lys Gln His Asp Cys Asp Tyr Lys Ile
    130                 135                 140

Leu Pro Ala Leu Gly Val Lys His Ser Glu Asn Asp Ser Val Pro Met
145                 150                 155                 160

Gln Gly Thr Gln Val Leu Pro Asp Ile Glu Thr Leu Ile Gly Val Gln
                165                 170                 175

Asn Pro Ser Leu Leu Lys Gly Lys Ser Gln Glu Thr Thr Gln Phe Trp
            180                 185                 190

Ser Gln Arg Val Glu Asp Ser Lys Ile Asn Ile Pro Thr His Ser Gly
        195                 200                 205

Pro Ala Ala Glu Ile Leu Pro Gly Pro Leu Glu Gly Thr Arg Cys Gly
    210                 215                 220

Glu Gly Leu Phe Ser Glu Glu Thr Leu Asn Asp Thr Ser Gly Ser Pro
225                 230                 235                 240

Lys Met Phe Ala Gln Asp Thr Val Cys Ala Pro Phe Pro Gln Arg Ala
                245                 250                 255

Thr Pro Lys Val Thr Ser Gln Gly Asn Pro Ser Ile Gln Leu Glu Glu
            260                 265                 270

Leu Gly Ser Arg Val Glu Ser Leu Lys Leu Ser Asp Ser Tyr Leu Asp
        275                 280                 285

```
Pro Ile Lys Ser Glu His Asp Cys Tyr Pro Thr Ser Leu Asn Lys
    290                 295                 300

Val Ile Pro Asp Leu Asn Leu Arg Asn Cys Leu Ala Leu Gly Gly Ser
305                 310                 315                 320

Thr Ser Pro Thr Ser Val Ile Lys Phe Leu Leu Ala Gly Ser Lys Gln
                325                 330                 335

Ala Thr Leu Gly Ala Lys Pro Asp His Gln Glu Ala Phe Glu Ala Thr
                340                 345                 350

Ala Asn Gln Gln Glu Val Ser Asp Thr Thr Ser Phe Leu Gly Gln Ala
                355                 360                 365

Phe Gly Ala Ile Pro His Gln Trp Glu Leu Pro Gly Ala Asp Pro Val
                370                 375                 380

His Gly Glu Ala Leu Gly Glu Thr Pro Asp Leu Pro Glu Ile Pro Gly
385                 390                 395                 400

Ala Ile Pro Val Gln Gly Glu Val Phe Gly Thr Ile Leu Asp Gln Gln
                405                 410                 415

Glu Thr Leu Gly Met Ser Gly Ser Val Val Pro Asp Leu Pro Val Phe
                420                 425                 430

Leu Pro Val Pro Pro Asn Pro Ile Ala Thr Phe Asn Ala Pro Ser Lys
                435                 440                 445

Trp Pro Glu Pro Gln Ser Thr Val Ser Tyr Gly Leu Ala Val Gln Gly
                450                 455                 460

Ala Ile Gln Ile Leu Pro Leu Gly Ser Gly His Thr Pro Gln Ser Ser
465                 470                 475                 480

Ser Asn Ser Glu Lys Asn Ser Leu Pro Pro Val Met Ala Ile Ser Asn
                485                 490                 495

Val Glu Asn Glu Lys Gln Val His Ile Ser Phe Leu Pro Ala Asn Thr
                500                 505                 510

Gln Gly Phe Pro Leu Ala Pro Glu Arg Gly Leu Phe His Ala Ser Leu
                515                 520                 525

Gly Ile Ala Gln Leu Ser Gln Ala Gly Pro Ser Lys Ser Asp Arg Gly
                530                 535                 540

Ser Ser Gln Val Ser Val Thr Ser Thr Val His Val Val Asn Thr Thr
545                 550                 555                 560

Val Val Thr Met Pro Val Pro Met Val Ser Thr Ser Ser Ser Ser Tyr
                565                 570                 575

Thr Thr Leu Leu Pro Thr Leu Glu Lys Lys Arg Lys Arg Cys Gly
                580                 585                 590

Val Cys Glu Pro Cys Gln Gln Lys Thr Asn Cys Gly Glu Cys Thr Tyr
                595                 600                 605

Cys Lys Asn Arg Lys Asn Ser His Gln Ile Cys Lys Lys Arg Lys Cys
610                 615                 620

Glu Glu Leu Lys Lys Lys Pro Ser Val Val Pro Leu Glu Val Ile
625                 630                 635                 640

Lys Glu Asn Lys Arg Pro Gln Arg Glu Lys Pro Lys Val Leu Lys
                645                 650                 655

Val Leu Arg Arg Ser Ser Asp Glu Glu Lys Val Leu Cys Leu Val Arg
                660                 665                 670

Gln Arg Thr Gly His His Cys Pro Thr Ala Val Met Val Val Leu Ile
                675                 680                 685

Met Val Trp Asp Gly Ile Pro Leu Pro Met Ala Asp Arg Leu Tyr Thr
                690                 695                 700
```

-continued

```
Glu Leu Thr Glu Asn Leu Lys Ser Tyr Asn Gly His Pro Thr Asp Arg
705                 710                 715                 720

Arg Cys Thr Leu Asn Glu Asn Arg Thr Cys Thr Cys Gln Gly Ile Asp
            725                 730                 735

Pro Glu Thr Cys Gly Ala Ser Phe Ser Phe Gly Cys Ser Trp Ser Met
        740                 745                 750

Tyr Phe Asn Gly Cys Lys Phe Gly Arg Ser Pro Ser Pro Arg Arg Phe
    755                 760                 765

Arg Ile Asp Pro Ser Ser Pro Leu His Thr Tyr Tyr Glu Arg Ile Thr
770                 775                 780

Lys Gly Arg Asn Pro Glu Arg Arg Tyr Met Lys Pro Glu Arg Ile Ser
785                 790                 795                 800

Pro Gly His Glu Ala Met Glu Lys Asn Leu Glu Asp Asn Leu Gln Ser
            805                 810                 815

Leu Ala Thr Arg Leu Ala Pro Ile Tyr Lys Gln Tyr Ala Pro Val Ala
        820                 825                 830

Tyr Gln Asn Gln Val Glu Tyr Glu Asn Val Ala Arg Glu Cys Arg Leu
    835                 840                 845

Gly Ser Lys Glu Gly Arg Pro Phe Ser Gly Val Thr Ala Cys Leu Asp
850                 855                 860

Phe Cys Ala His Pro His Arg Asp Ile His Asn Met Asn Asn Gly Ser
865                 870                 875                 880

Thr Val Val Cys Thr Leu Thr Arg Glu Asp Asn Arg Ser Leu Gly Val
            885                 890                 895

Ile Pro Gln Asp Glu Gln Leu His Val Leu Pro Leu Tyr Lys Leu Ser
        900                 905                 910

Asp Thr Asp Glu Phe Gly Ser Lys Glu Gly Met Glu Ala Lys Ile Lys
    915                 920                 925

Ser Gly Ala Ile Glu Val Leu Ala Pro Arg Arg Lys Lys Arg Thr Cys
930                 935                 940

Phe Thr Gln Pro Val Pro Arg Ser Gly Lys Lys Arg Ala Ala Met Met
945                 950                 955                 960

Thr Glu Val Leu Ala His Lys Ile Arg Ala Val Glu Lys Lys Pro Ile
            965                 970                 975

Pro Arg Ile Lys Arg Lys Asn Asn Ser Thr Thr Thr Asn Asn Ser Lys
        980                 985                 990

Pro Ser Ser Leu Pro Thr Leu Gly Ser Asn Thr Glu Thr Val Gln Pro
    995                 1000                1005

Glu Val Lys Ser Glu Thr Pro His Phe Ile Leu Lys Ser Ser
    1010                1015                1020

Asp Asn Thr Lys Thr Tyr Ser Leu Met Pro Ser Ala Pro His Pro
    1025                1030                1035

Val Lys Glu Ala Ser Pro Gly Phe Ser Trp Ser Pro Lys Thr Ala
    1040                1045                1050

Ser Ala Thr Pro Ala Pro Leu Lys Asn Asp Ala Thr Ala Ser Cys
    1055                1060                1065

Gly Phe Ser Glu Arg Ser Thr Pro His Cys Thr Met Pro Ser
    1070                1075                1080

Gly Arg Leu Ser Gly Ala Asn Ala Ala Ala Ala Asp Gly Pro Gly
    1085                1090                1095

Ile Ser Gln Leu Gly Glu Val Ala Pro Leu Pro Thr Leu Ser Ala
    1100                1105                1110

Pro Val Met Glu Pro Leu Ile Asn Ser Glu Pro Ser Thr Gly Val
```

```
              1115                1120                1125

Thr Glu Pro Leu Thr Pro His Gln Pro Asn His Gln Pro Ser Phe
        1130                1135                1140

Leu Thr Ser Pro Gln Asp Leu Ala Ser Ser Pro Met Glu Glu Asp
    1145                1150                1155

Glu Gln His Ser Glu Ala Asp Glu Pro Pro Ser Asp Glu Pro Leu
1160                1165                1170

Ser Asp Asp Pro Leu Ser Pro Ala Glu Glu Lys Leu Pro His Ile
    1175                1180                1185

Asp Glu Tyr Trp Ser Asp Ser Glu His Ile Phe Leu Asp Ala Asn
        1190                1195                1200

Ile Gly Gly Val Ala Ile Ala Pro Ala His Gly Ser Val Leu Ile
            1205                1210                1215

Glu Cys Ala Arg Arg Glu Leu His Ala Thr Thr Pro Val Glu His
                1220                1225                1230

Pro Asn Arg Asn His Pro Thr Arg Leu Ser Leu Val Phe Tyr Gln
                    1235                1240                1245

His Lys Asn Leu Asn Lys Pro Gln His Gly Phe Glu Leu Asn Lys
                        1250                1255                1260

Ile Lys Phe Glu Ala Lys Glu Ala Lys Asn Lys Lys Met Lys Ala
                            1265                1270                1275

Ser Glu Gln Lys Asp Gln Ala Ala Asn Glu Gly Pro Glu Gln Ser
                                1280                1285                1290

Ser Glu Val Asn Glu Leu Asn Gln Ile Pro Ser His Lys Ala Leu
                                    1295                1300                1305

Thr Leu Thr His Asp Asn Val Val Thr Val Ser Pro Tyr Ala Leu
                                        1310                1315                1320

Thr His Val Ala Gly Pro Tyr Asn His Trp Val
                                            1325                1330

<210> SEQ ID NO 7
<211> LENGTH: 68
<212> TYPE: DNA
<213> ORGANISM: Artificial sequence
<220> FEATURE:
<223> OTHER INFORMATION: Artificially synthesized primer sequence

<400> SEQUENCE: 7
gcaagaattc ctcgagccac catggactac aaagacgatg acgacaagtc tcgatcccgc     60
catgcaag                                                             68

<210> SEQ ID NO 8
<211> LENGTH: 38
<212> TYPE: DNA
<213> ORGANISM: Artificial sequence
<220> FEATURE:
<223> OTHER INFORMATION: Artificially synthesized primer sequence

<400> SEQUENCE: 8
gagtgaattc ctcgatcaga cccaatggtt atagggcc                             38

<210> SEQ ID NO 9
<211> LENGTH: 41
<212> TYPE: DNA
<213> ORGANISM: Artificial sequence
<220> FEATURE:
<223> OTHER INFORMATION: Artificially synthesized primer sequence

<400> SEQUENCE: 9
```

```
gcaagaattc ctcgagccac catgtctcga tcccgccatg c                          41

<210> SEQ ID NO 10
<211> LENGTH: 52
<212> TYPE: DNA
<213> ORGANISM: Artificial sequence
<220> FEATURE:
<223> OTHER INFORMATION: Artificially synthesized primer sequence

<400> SEQUENCE: 10
gagtgaattc ctcgattact tgtcgtcatc gtctttgtag tcgacccaat gg             52

<210> SEQ ID NO 11
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 11
agccacatcg ctcagacac                                                   19

<210> SEQ ID NO 12
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 12
gcccaatacg accaaatcc                                                   19

<210> SEQ ID NO 13
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 13
ctttgaggct ctgcagctta g                                                21

<210> SEQ ID NO 14
<211> LENGTH: 22
<212> TYPE: DNA
<213> ORGANISM: Artificial sequence
<220> FEATURE:
<223> OTHER INFORMATION: Artificially synthesized primer sequence

<400> SEQUENCE: 14
tctgctttgc atatctcctg aa                                               22

<210> SEQ ID NO 15
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 15
gggggaatgg accttgtata g                                                21

<210> SEQ ID NO 16
<211> LENGTH: 20
<212> TYPE: DNA
```

```
<213> ORGANISM: Artificial sequence
<220> FEATURE:
<223> OTHER INFORMATION: Artificially synthesized primer sequence

<400> SEQUENCE: 16
gcaaagctcc taccgtacca                                              20

<210> SEQ ID NO 17
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 17
tctccaacat cctgaacctc a                                            21

<210> SEQ ID NO 18
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 18
ttgctattct tcggccagtt                                              20

<210> SEQ ID NO 19
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 19
gctgtgacag gtacccaacc                                              20

<210> SEQ ID NO 20
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 20
catgcaggtg agttgtcaga a                                            21

<210> SEQ ID NO 21
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 21
ggctgagcac cactacgact                                              20

<210> SEQ ID NO 22
<211> LENGTH: 25
<212> TYPE: DNA
<213> ORGANISM: Artificial sequence
<220> FEATURE:
<223> OTHER INFORMATION: Artificially synthesized primer sequence

<400> SEQUENCE: 22
gcattataaa atttcccaaa tcatc                                        25
```

<210> SEQ ID NO 23
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 23
atttcccgct ctggttcag                                                  19

<210> SEQ ID NO 24
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 24
gttttctcca cggatgttgc                                                 20

<210> SEQ ID NO 25
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 25
acgccgagtt gagcaaga                                                   18

<210> SEQ ID NO 26
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 26
tctgcctcct ccacgaag                                                   18

<210> SEQ ID NO 27
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 27
ggtaccccga catccactt                                                  19

<210> SEQ ID NO 28
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 28
gcctgttctg gaaccatacc t                                               21

<210> SEQ ID NO 29
<211> LENGTH: 20
<212> TYPE: DNA
<213> ORGANISM: Artificial sequence
<220> FEATURE:

<223> OTHER INFORMATION: Artificially synthesized primer sequence

<400> SEQUENCE: 29
ccgcttgtta ggtcgccgca                                              20

<210> SEQ ID NO 30
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 30
tgggctgagg gccggagaaa                                              20

<210> SEQ ID NO 31
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 31
acacgcacca ccaccacaac a                                            21

<210> SEQ ID NO 32
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 32
ccggcgagtt tgccaagagc                                              20

<210> SEQ ID NO 33
<211> LENGTH: 21
<212> TYPE: DNA
<213> ORGANISM: Artificial sequence
<220> FEATURE:
<223> OTHER INFORMATION: Artificially synthesized primer sequence

<400> SEQUENCE: 33
cgacttcacc aactggttct g                                            21

<210> SEQ ID NO 34
<211> LENGTH: 18
<212> TYPE: DNA
<213> ORGANISM: Artificial sequence
<220> FEATURE:
<223> OTHER INFORMATION: Artificially synthesized primer sequence

<400> SEQUENCE: 34
atgcaggttg tgcgatca                                                18

<210> SEQ ID NO 35
<211> LENGTH: 22
<212> TYPE: DNA
<213> ORGANISM: Artificial sequence
<220> FEATURE:
<223> OTHER INFORMATION: Artificially synthesized primer sequence

<400> SEQUENCE: 35
tgggatattc aggttcatgt tg                                           22

```
<210> SEQ ID NO 36
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 36
actggagttt ggcaggagag                                           20

<210> SEQ ID NO 37
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 37
gcggccacga cacgaggaat                                           20

<210> SEQ ID NO 38
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 38
cgcccatcag cccactctcg                                           20

<210> SEQ ID NO 39
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 39
ccaagcccca gaagattag                                            19

<210> SEQ ID NO 40
<211> LENGTH: 17
<212> TYPE: DNA
<213> ORGANISM: Artificial sequence
<220> FEATURE:
<223> OTHER INFORMATION: Artificially synthesized primer sequence

<400> SEQUENCE: 40
tggagctaat cgtgtag                                              17

<210> SEQ ID NO 41
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 41
ggtgcactga aatggaaagg                                           20

<210> SEQ ID NO 42
<211> LENGTH: 18
<212> TYPE: DNA
<213> ORGANISM: Artificial sequence
<220> FEATURE:
<223> OTHER INFORMATION: Artificially synthesized primer sequence
```

```
<400> SEQUENCE: 42
actggcacgc tccatgac                                                    18

<210> SEQ ID NO 43
<211> LENGTH: 19
<212> TYPE: DNA
<213> ORGANISM: Artificial sequence
<220> FEATURE:
<223> OTHER INFORMATION: Artificially synthesized primer sequence

<400> SEQUENCE: 43
ggtgcactga gctcgaaag                                                   19

<210> SEQ ID NO 44
<211> LENGTH: 20
<212> TYPE: DNA
<213> ORGANISM: Artificial sequence
<220> FEATURE:
<223> OTHER INFORMATION: Artificially synthesized primer sequence

<400> SEQUENCE: 44
aagaggtgtc ggatgacagg                                                  20

<210> SEQ ID NO 45
<211> LENGTH: 27
<212> TYPE: DNA
<213> ORGANISM: Artificial sequence
<220> FEATURE:
<221> NAME/KEY: CDS
<222> LOCATION: (1)..(27)
<223> OTHER INFORMATION: Sequence of FLAG tag

<400> SEQUENCE: 45 atg gac tac aaa gac gat gac gac aag                                    27
Met Asp Tyr Lys Asp Asp Asp Asp Lys
1               5

<210> SEQ ID NO 46
<211> LENGTH: 9
<212> TYPE: PRT
<213> ORGANISM: Artificial sequence
<220> FEATURE:
<223> OTHER INFORMATION: Sequence of FLAG tag

<400> SEQUENCE: 46

Met Asp Tyr Lys Asp Asp Asp Asp Lys
1               5
```

METHOD FOR PRODUCING PLURIPOTENT STEM CELLS

This application is a divisional, and claims priority of co-pending U.S. application Ser. No. 14/439,037, filed Apr. 28, 2015, now issued as U.S. Pat. No. 9,868,934, which is a U.S. National Stage application, and claims priority of International Application No. PCT/JP2013/079311, filed Oct. 29, 2013, which claims priority of Japan Application No. 2012-237734, filed Oct. 29, 2012. The contents of all of the prior applications are incorporated herein by reference in their entirety.

TECHNICAL FIELD

The present invention relates to a method of producing pluripotent stem cells (PSCs), more specifically to a method of producing pluripotent stem cells with enhanced differentiation efficacies. Also included in this invention are the proteins used to realize this process.

BACKGROUND ART

PSCs are defined as cell entities which have both the capacity to differentiate toward multiple cell lineages non-identical to themselves (pluripotency) and a capability of producing a cell having an identical capacity to the originated cell as a daughter cell when they divide (self-renewal), which is considered to include embryonic stem (ES) cell and induced pluripotent stem (iPS) cell. And because of these characteristics, ES cell and iPS cell are strongly anticipated to play important roles in regenerative medicine and/or drug screening.

However, it has been recently reported that mouse PSCs and human PSCs do not share some of their fundamental properties and moreover, human PSCs are generally considered to have lower differentiation capabilities when compared to mouse PSCs.

Mouse PSCs can be challenged experimentally for their pluripotency with some accuracy. For example, mouse ES cells can be injected into a cavity of blastocyst where the injected cells intermingle with the host inner cell mass (ICM), followed by a normal development of ES cell-derived cells in an embryo, which is called as chimera formation. The fact that mouse ES cells can synchronize their development with a timing-matched ICM is a good verdict for pluripotency. In this case, as development further proceeds, it is known that part of the injected ES cells might also contribute to the germline. This germline transmission means that these cells can contribute to the next generation and further corroborates the compatibility as normal cells in a more generic term.

There also exists an "ultimate" way to show pluripotency. When we inhibit the first cell cleavage of a mouse fertilized egg transiently and culture it in a culture dish, we can obtain a tetraploid blastocyst. The tetraploid blastocyst looks almost normal but will not continue development into embryo further. Therefore, just by putting tetraploid embryos back to a uterus of pseudo-pregnant female mouse would not produce a live pup. But if we inject stem cells with differentiation capabilities into these tetraploid blastocysts and let them contribute to the chimera formation as mentioned above, the PSCs now would be fully responsible to contribute to development as they are the sole cells with normal karyotype. In this way, we can obtain a completely PSC-derived body in a single generation. This methodology is called the tetraploid-complementation assay and the obtained pups are called as all-iPS mice, according to the PSCs injected. This multiple tests enable strict assessment of pluripotencies in mouse and mouse iPS cells have been shown to exhibit strict pluripotencies using the battery of such multiple tests.

In sharp contrast, human pluripotencies cannot be scrutinized in these fashions because of ethical issues. An alternative way to show pluripotency in human contexts is teratoma formation. When stem cells are transplanted into nude mice subcutaneously, these cells when supported by the host blood supply, do differentiate at random to form an organ. The formed stem cell-derived tumor mass will be pathologically examined to find ectoderm, mesoderm and endoderm, and thereby, the originated stem cells are qualified as pluripotent. However, this methodology whereby we assess pluripotency by teratoma formation is inherently problematic. That is, even if the original stem cells have insufficient efficacy of differentiation, any differentiation efficacy above zero could be judged as "pluripotency" if three germ layers are observed. Teratoma assay would judge the pluripotency without considering the existence of residual undifferentiated cells within the teratoma. With the current paradigm of teratoma assay, the mere presence of a limited number of bona fide pluripotent cells within the cell population would be sufficient and the current teratoma assay has no implication about the quantitative trait of pluripotency. For example, mouse iPS cells derived using c-Myc, albeit showing three-germ-layer differentiation in teratoma assays, were prone to give iPS cell-derived tumors upon chimera formation. An alternative to teratoma assay would be to independently direct cell differentiation toward the three germ layers. However, there is no "golden standard" in any cell differentiation protocol making this strategy inapplicable for quantitative analysis.

There is also a more profound and fundamental problem with human PSCs. This is about the possible absence of an ideal PSC for human which bears the capacity to be amenable to equally robust differentiation toward all the cell lineages. Osafune et al. have reported that no two human ES cell lines showed quasi-identical gene expression profile, and thus each ES cell line has own propensity to differentiate into a specific germ layer, and further, suggested that human ES cells do not have sufficient pluripotency in terms of quantitative evaluation (non-patent literature1).

It took 17 years after the discovery of mouse ES cell to establish human ES cell. In retrospect, the major reason for this delay was that human ES cell could not be established in the same way as in the mouse ES cell. Although mouse ES cells are dependent to leukemia inhibitory factor (LIF) for their self-renewal, human ES cell cannot show self-renewal ability in a medium added with LIF. Thomson et al. found that human ES cell requires fibroblast growth factor (FGF) and Activin/Nodal for its maintenance (non-patent literature2). These differential requirements for mouse and human ES cell self-renewal diversify into different intracellular signaling pathways: JAK/STAT signaling and SMAD2/3 signaling for mouse and human ES cell, respectively. The currently major view is that SMAD2/3 signaling in human PSCs activates the expression of NANOG. In parallel, SMAD2/3 signaling is a critical factor for the mesendoderm development in mammals and therefore a high concentration of Activin is required for proper mesendoderm differentiation of PSCs. It is therefore interesting to note that the current human PSC self-renewal signaling crossovers with the signal which would induce its mesendodermal differentiation.

Mouse and human ES cells both originate from blastocysts. However, most probably owing to their difference in the culture conditions, their characteristics significantly differ. A major contrast is albeit mouse ES cells retain characteristics of their originated blastocyst inner cells, human ES cells are more akin to the primitive ectoderm of the epiblast, which appears after some development of the blastocyst. Then, the epiblast stem cell (EpiSC) was established directly from mouse epiblasts using culture condition equivalent to human ES cells (non-patent literature 3 and 4). This had led the stem cell biologists to discriminate two stages of pluripotency. One is the blastocyst-type pluripotency, represented by mouse ES as well as iPS cells and the other is the epiblast-type pluripotency, which includes human ES, human iPS cells and mouse EpiSCs. The former pluripotency is now called "naive" and the latter "primed", originally coined by Smith et al. (non-patent literature 5).

Naive and primed pluripotencies share the three germ layer differentiation capabilities and teratoma assay-compatibilities upon transplantation into nude mouse. However, naive PSCs are more similar to the earlier stage (blastocyst) of development closer to fertilized ovum, are easier to be established in culture and possess fuller pluripotency in that an individual body completely derived from these cells can be generated. In contrast, primed PSCs are more akin to the epiblast, an embryonic stage following the blastocyst, and are empirically tougher to establish. Additionally, as described above, primed PSCs have clear differentiation propensities (non-patent literature 1). Finally, it has been recognized that primed PSCs poorly synchronize their development with early embryo and therefore do not produce chimera, and thus it is known that primed human PSCs are inferior to mouse naive PSCs in differentiation efficacy including pluripotency.

In practicing regenerative medicine and drug development, human PSCs are being anticipated to exert their high differentiation capabilities in order to supply various cell types, tissues and organogenesis. In this line, it seems desirable to enhance differentiation efficacy of primed human PSCs. However, this kind of innovation remains to be developed.

PRIOR ART DOCUMENTS

Non-Patent Literature

[Non-patent literature1] Osafune, K. et al., *Nat Biotechnol.* 2008, 26, 313-315.
[Non-patent literature2] Thomson, J. A. et al., *Science* 1998, 282, 1145-7.
[Non-patent literature3] Brons, I. et al., *Nature* 2007, 448, 191-5.
[Non-patent literature4] Tesar, P. J. et al., *Nature* 2007, 448, 196-9.
[Non-patent literature5] Nichols, J., *Cell Stem Cell* 2009, 4, 487-92.

DISCLOSURE OF THE INVENTION

Problems to be Solved by the Invention

The present invention has been made to address the other problems referred to in the cited art above, and objects of the invention are to provide a method for producing PSCs with improved differentiation capabilities and also substances which enable such production.

Measures to Solve the Referred Problems

In order to achieve the purposes, the present inventors have comparatively studied the differences in the characteristics of mouse PSCs and human PSCs.

Mouse PSCs bear characteristics close to inner clump of cells of the pre-implantation blastocyst. In contrast, human PSCs are most akin to the primitive ectodermal cells of the post-implantation epiblast. We can assume by this difference between mouse and human pluripotencies that human PSCs is inherently inferior to mouse PSCs for its differentiation capabilities.

There are two distinct phases of reprogramming during development. One occurs during the transition from a fertilized egg to a pre-implantation embryo (which we shall refer to as "reprogramming during early development") and another happens post-implantation during the establishment of the germ cell lineage ("germline reprogramming"). From this viewpoint, the present inventors examined factors expressed in the "germline reprogramming" to reset cell memories acquired from the blastocyst to the epiblast stage, and thereby the present inventors have come up with TET1.

It has been shown that TET1 protein is an enzyme involved in hydroxylation of methyl group of 5-methylcytosine (5mC) to convert 5mC to 5-hydroxymethylcytosine (5hmC). It has been recently shown that TET1 is involved in demethylation of 5mC to cytosine. It is also supposed that TET1 protein can competitively inhibit the binding of the DNA methyltransferases such as DNMT1, DNMT3a and DNMT3b to their target DNA methylation sites leading to a hypomethylated genome. Therefore, TET1 protein function is strongly suggested in the process of DNA demethylation and/or the maintenance of a hypomethylated state. Moreover, in mice, TET1 protein expression can be observed in the development of early embryo from the fertilized egg to the blastocyst onward, in the primordial germ cells and in ES cells established from blastocysts. Coupled with its function in DNA demethylation, TET1 protein is strongly suggested to be involved in reprogramming processes. However, the role of TET1 protein in the human is totally unexplored.

Given the situation, the present inventors investigated the expression of TET1 at the transcriptional as well as translational levels. As a result, the present inventors found that human iPS cells, just like mouse ES cells, abundantly express TET1 mRNA. The present inventors have also identified two novel TET1 mRNA (cDNA) sequences which differed from the known sequences in terms of the presence or absence of a part of exons and therefore the present inventors succeeded in finding novel splice variants for TET1.

However, to their surprises, the present inventors were unable to detect TET1 at the protein level in human iPS cells, unlike in mouse ES cells. The inventors have deduced that this differential expressivity of TET1 protein between mouse PSCs and human PSCs might be causal for the observed difference in the differentiation capacities of these two cell entities and have therefore investigated a way to overexpress TET1 protein in human PSCs. In this line of investigations, the inventors have found that placing a peptide-tag at the wild-type TET1 protein's N-terminus allowed them to stably express TET1 protein in human PSCs. The inventors have further demonstrated that simply replacing its second amino acid to another one renders the protein more stable.

The inventors succeeded in forcing TET1 expression in hiPSCs by exploiting the mutant TET1 protein (modified TET1 protein) which can be stably expressed in hiPSCs, which led them to notice that expression of T and SOX17, mesendodermal markers usually expressed in conventional hiPSCs, was missing. This showed that the mutant TET1 protein can cancel some of the differentiation biases (propensities), an inherent nature of the current human iPSCs.

When mutant TET1-introduced hiPSCs were induced toward neuroectoderm (ectoderm), the expression of OCT3/4 and NANOG which operate in resisting cell differentiation were rapidly diminished. Especially, NANOG operates by counteracting differentiation signals to most kinds of cells and therefore, the swift down-regulation of this factor upon mutant-TET1 introduction could be a reason for the observed decrease in the differentiation resistance by this factor and the enhanced pluripotency. Moreover, the inventors demonstrated that mutant-TET1 introduction renders hiPSCs more amenable to neural differentiation judged by the enhanced up-regulation of the neural markers SOX2 and SOX1. Especially, SOX1 up-regulation was mostly sensitive to the mutant TET1-introduction as shown by the 60-fold upregulation of SOX1 when compared to their parental control cells produced without TET1 introduction, which suggests that differentiation capacity to neurons of PSCs increased about 60-fold by introduction of this protein.

In corroboration with these transcription factors' regulations, conditions which would poorly produce neurons from conventional TET1-non-expressing hiPSC were able to induce neurons at 100% efficiency for mutant TET1-expressing iPSCs. In addition to this ectodermal differentiation, the inventors showed that the mutant-TET1 introduction allowed them to increase the efficacy of definitive endoderm differentiation.

Even more surprisingly, the effect on differentiation efficacy of TET1 was also exerted when the second amino acid was simply replaced with another amino acid and furthermore, even when the dioxygenase catalytic domain was omitted. This indicates the observed effect of TET1 introduction does not rely on the DNA demethylating activity that the dioxygenase domain is responsible for but rather on the DNA-binding properties of TET1.

The present inventors further demonstrate that the mutant-TET1, when introduced together with the so-called reprogramming factors (Oct3/4, Sox2, Klf4 and c-Myc) into somatic cells not only enhance the differentiation efficacy of the obtained iPSCs but also the yield (production efficacy) of such iPSC clones.

The inventors also found that the TET1-introduced iPSCs have significantly reduced levels of various cancer-related markers (such as GPC4, GAGE2B and GAGE7) when compared to the parental cell line which indicates that, in addition to improving the differentiation potentials (and/or the production efficiency of such cells), TET1-introduced iPSCs bear enhanced safety.

This invention was completed according to the mentioned experimental results obtained by the inventors and provides a method which allows the production of PSCs with enhanced efficacies for cell differentiation. Furthermore, this invention also provides materials to practice the production of PSCs such as mutant TET1 proteins, novel TET1 protein isoforms which can be used as raw material for these mutant TET1 proteins as well as nucleic acids which code for such proteins. More in details, the present invention provides the following aspects.

<1> A method for producing pluripotent stem cells, comprising:
  introducing at least one molecule selected from the group consisting of (a) to (c) into pluripotent stem cells (PSCs) or somatic cells which are to be induced toward PSCs;
  (a) TET1 protein,
  (b) a nucleic acid that encodes TET1 protein, and
  (c) a vector into which a nucleic acid that encodes TET1 protein has been inserted.
<2> The method of <1>, wherein said TET1 protein is a mutant TET1 protein which has enhanced stability as compared to a wild type TET1 protein.
<3> The method of <2>, wherein said mutant TET1 protein is a mutant TET1 protein in which the second amino acid from their N-terminus differs from the wild-type TET1's second amino acid from their N-terminus.
<4> The method of <2> or <3>, wherein said mutant TET1 protein lacks its dioxygenase domain.
<5> The method of <1>, wherein said TET1 protein is a protein consisting of the amino acid sequence of SEQ ID NO: 2, 4 or 6.
<6> A mutant TET1 protein which has enhanced stability as compared to a wild type TET1 protein.
<7> The protein of <6>, wherein the second amino acid from their N-terminus differs from the wild-type TET1's second amino acid from their N-terminus.
<8> The protein of <7>, which lacks its dioxygenase domain.
<9> A protein consisting of the amino acid sequence of SEQ ID NO: 4 or 6.
<10> A nucleic acid encoding the protein as described in any one of <6> to <9>.
<11> A vector into which the nucleic acid of <10> has been inserted.
<12> A pluripotent stem cell (PSC) or somatic cell which is to be induced toward PSC into which at least one molecule selected from the group consisting of (a) to (c) has been introduced;
  (a) TET1 protein,
  (b) a nucleic acid that encodes TET1 protein, and
  (c) a vector into which a nucleic acid that encodes TET1 protein has been inserted.

The Effects of the Invention

The invention accordingly provides a way to enhance the differentiation efficacy of PSCs. Furthermore, the invention can also allow increasing the production efficacy of iPS cell reprogramming. Moreover, it is also possible to produce highly safe PSCs with suppressed tumorigenicity.

EMBODIMENTS FOR CARRYING OUT THE INVENTION

Figure 1:
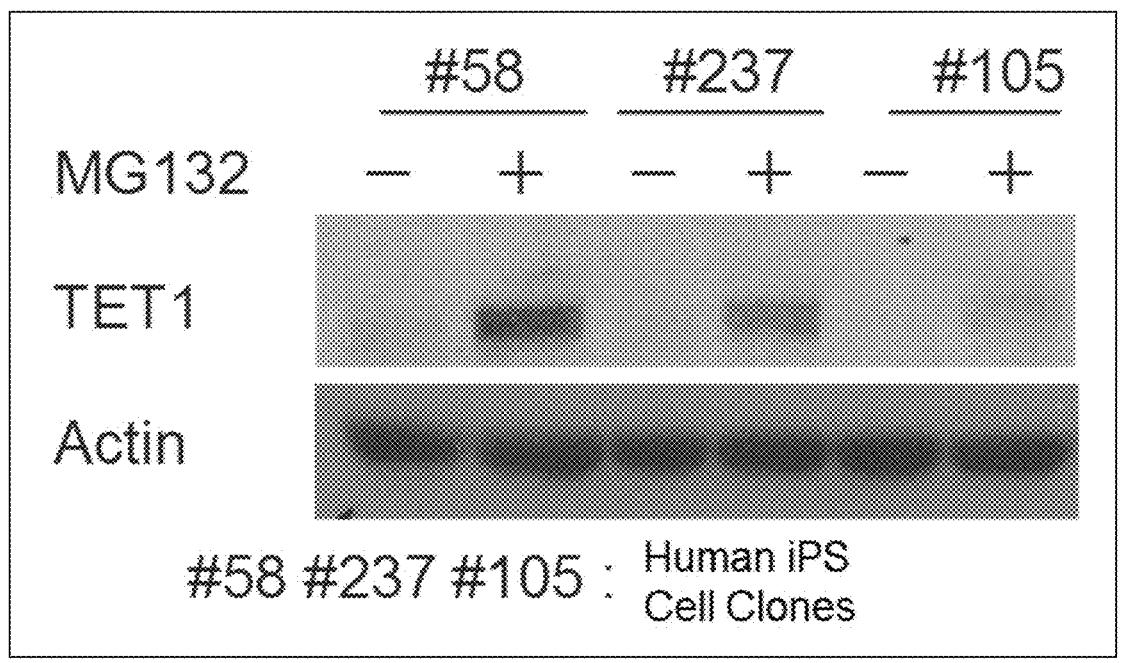
FIG. 1 The picture shows the result of the western blotting for analyzing the expression amount of TET1 protein in individual human iPS cells (#58, #237 and #105) with or without proteasome inhibitor (MG132).

<The Method for Producing PSCs of this Invention>

This invention provides the methods for producing PSCs which comprises introducing at least one molecule selected from the group consisting of (a) to (c) into pluripotent stem cells (PSCs) or somatic cells which are to be induced toward PSCs;

(a) TET1 protein,
(b) a nucleic acid that encodes TET1 protein, and
(c) a vector into which a nucleic acid that encodes TET1 protein has been inserted.

Furthermore, according to the production method, PSCs with enhanced differentiation capacity can be produced. Furthermore, according to the production method, by introducing the TET1 protein etc. into the somatic cells, it becomes possible to produce iPS cells with higher efficacy. Moreover, it is also possible to produce highly safe PSCs with suppressed tumorigenicity.

In this invention, "pluripotent stem cell (PSC)" denotes for a cell with a dual capacity of being able to differentiate into multiple cell lineages different from itself (pluripotency) and at the same time being able to divide into daughter cells which bear the same capacity with itself (self-renewal).

In this invention, "differentiation capacity" denotes for a cell capacity to change into a different kind of cell. And an "enhancement of differentiation efficacy" in this invention specifically denotes not only an increase of cell differentiation probability as monitored by increased differentiation marker expression (in case of neural induction the markers could be SOX2, SOX1, NEUROGENIN1, NEUROGENIN2, NEUROD1, ASCL1, PAX6, ZNF521 or OTX2) but also a significant repression of other cell lineage choice (in case where ectoderm specification is required such other lineage markers could be T and SOX17) as well as significant repression of factors which act to resist differentiation signals such as NANOG. As shown in the following examples, the differentiation capacities of a PSC are in a repressed state which can be expressed as differentiation resistance and also proper differentiation can be blocked by an inherent differentiation propensity toward an undesired cell fate. To this line, the present invention provides a way to cancel these robust differentiation resistance or propensity enabling a PSC to faithfully execute its pluripotency. In this way, when mentioning about the enhancement of differentiation capacity, this will automatically include an improvement in the pluripotency.

Candidate pluripotent stem cell lines where the invention could be applied to enhance the differentiation capacities includes embryonic stem cell (ES cell), epiblast stem cell (EpiSC), embryonal carcinoma cell (EC cell), embryonic germ cell (EG cell), multipotent germ stem cell (mGS cell) and MUSE cell (refer to Kuroda Y. et al., Proc. Natl. Acad. Sci. U.S.A., 2010. 107, 8639-43.), cells which can be obtained from various sources of the organism. Moreover, the list includes cells such as iPS cells which have been induced to obtain pluripotency artificially from somatic cells obtained from the organism.

There is no specific restriction for the source organism of these cells and examples thereof include human as well as non-human (mouse, rat, cattle, horse, porcine, goat, monkey, dog, cat, bird, etc.) animals.

PSCs can be staged either in an earlier developmental stage (blastocyst) where the corresponding PSCs are called naïve PSCs or also in a developmental stage which appears after the blastocyst and called the epiblast in which case the PSCs are called primed PSCs. It is generally believed that the latter PSCs have lower differentiation capacities compared to the former PSCs. Therefore, it is conceivable that the production method presented in the invention will impact more the primed PSCs. Examples of primed PSCs in this context include ES cells and iPS cells from human, monkey, porcine, ovine, dog and cow and also include EpiSC obtained from human as well as non-human sources.

In the production method described in this invention, the preferred "TET1 protein" used to be introduced in pluripotent stem cells or a somatic cell to be induced to pluripotent stem cells is a "mutant TET1 protein".

In this present invention, the "mutant TET1 protein" may be a protein obtained by artificially introducing a mutation into the wild type TET1 protein as described below or a protein whereby a mutation naturally (non-artificially) occurred in the wild type TET1 protein as long as it has a function of enhancing differentiation efficacy of PSCs when it is introduced into the PSCs. In order to assess such enhancement of a PSC differentiation efficacy, one can for example introduce the TET1 protein into PSCs and evaluate the expression of factors which induce differentiation into different cell lineage, differentiation markers, factors which represent the differentiation propensity or factors which exhibit differentiation resistance, during various differentiation paradigms.

As for the mutant TET1 protein, it is preferred that the TET1 protein has an increased stability when expressed in a primed pluripotent stem cell. One can assess if the protein is more stable or not by known protein detection method such as Western blotting as shown in Examples shown below.

Preferred examples of "a mutant protein having enhanced stability as compared to the wild type TET1 protein" include a protein in which the second amino acid from the N-terminus is different from that of the wild type TET1 protein.

The TET1 protein which differs from the wild type TET1 in its second N-terminus amino acid can be obtained, as shown below, by artificially introducing a mutation to the wild type TET1 protein. Such a mutant TET1 protein may be a mutant protein having the mutation that occurred naturally.

An example of the TET1 mutant having amino acid substitution includes a TET1 protein in which the second amino acid from the N-terminus (which is a serine in the case of human TET1 protein) has been replaced with a different amino acid (for an example glycine). Although there is no particular restriction about the method to change the second amino acid from the N-terminus of TET1 protein, we can for example use site-directed mutagenesis (Kramer W. & Fritz H J., Methods Enzymol., 1987. 154, 350).

An example of the TET1 mutant having amino acid insertion or addition includes a TET1 protein in which one or plural amino acids have been inserted between the first and the second amino acid of the N-terminus of the wild type TET1 protein or a TET1 protein in which one or plural amino acids have been added to the N-terminus of the wild type TET1 protein. In these cases, plural amino acids could be any plural number for example two to 100 amino acids (preferably 2 to 50 or even more preferably 2 to 10 amino acids). There is no restriction for the method used to insert or add amino acids in the way and so, polymerase chain reaction (PCR) can be performed by using a primer containing an oligonucleotide encoding an amino acid or a peptide to be inserted or added.

An example of the TET1 mutant having amino acid deletion includes a TET1 protein in which one or plural amino acids have been deleted from the N-terminal portion of the wild type TET1 protein. In this case, from the perspective of retaining the functions of the TET1 protein without impairing the DNA binding region, it is preferable that one or plural amino acids have been deleted in the region from amino acid number 1 to 584 counted from the N-terminus of the wild type TET1 protein. In this case too, there is no restriction of the number of "plural" amino acids to be deleted, but the number is for example 2 to 100 (preferably 2 to 50 and more preferably 2 to 10). There is no restriction for the method used to delete amino acids in the way and so, a DNA encoding a TET1 protein having a deletion can be obtained by PCR.

Also as will be shown in the working example 9, it is possible to obtain an enhancement of the differentiation efficacy of the PSCs if the DNA binding motif of TET1 is preserved and therefore the de-methylating activity is redundant. Therefore, the mutant TET1 protein may be a mutant having a deletion of a region locating C-terminus side from the DNA binding region (CXXC domain), and more specifically may be a mutant TET1 protein which lacks its dioxygenase domain or may be a mutant TET1 protein which lacks both the cysteine-rich and the dioxygenase domains.

In this invention, the DNA-binding domain of TET1 protein refers to the amino acid stretch encompassing the lysine 585 to lysine 613 of the human TET1 protein (SEQ ID NO: 2, 4 or 6). The dioxygenase domain refers to the amino acid stretch encompassing amino acids 1611 to 2074 in SEQ ID NO: 2, amino acids 1640 to 2103 in SEQ ID NO: 4 or amino acids 809 to 1272 in SEQ ID NO: 6. Also the cysteine-rich domain refers to the amino acid stretch encompassing amino acids 1418 to 1610 in SEQ ID NO: 2, amino acids 1418 to 1608 and 1638 to 1639 in SEQ ID NO: 4 or amino acids 657 to 777 and 807 to 808 in SEQ ID NO: 6.

So far mentioned are examples of the preferred examples for the mutant proteins used in this invention, however, as far as that by introducing it into a pluripotent stem cell, the cell exhibit enhanced differentiation capability, one can also use TET1 proteins which bear other mutation. For example, considering that TET1, TET2 and TET3 proteins all share quasi-equivalent catalytic (dioxygenase) domains, one can swap the TET1-dioxygenase domain with that of TET2 or TET3 protein, or can directly or indirectly combine the TET1-DNA-binding domain and the dioxygenase domain of TET2 or TET3 protein for such purpose.

For the production method of this invention, it is also conceivable to introduce the wild-type TET1 protein into a pluripotent stem cell. The "wild-type TET1 protein" in this invention typically refers to proteins of SEQ ID NO: 2, 4 or 6 or their naturally occurring homologues which are supposedly degraded in primed pluripotent stem cells. When using such wild-type TET1 protein, it is preferable to use an excess amount of the protein in such a way it exceeds the capacity of a given pluripotent stem cell to degrade it. Or from the point of view of inhibiting such degradation in a pluripotent stem cell, one may additionally use a decoy of TET1 protein. For such a decoy, one may use a polypeptide derived from the N-terminus of the wild-type TET1 protein.

As shown in the examples described later, in order to enhance the differentiation potential of pluripotent stem cells, it is necessary that the function of the DNA-binding domain of the protein having the amino acid sequence of SEQ ID NO: 2, 4 or 6 is maintained. Therefore, such homolog of the protein having the amino acid sequence of SEQ ID NO: 2, 4 or 6 is preferably a natural protein with sequence homology of over 70% (for example, 75%, 80% 85%, 90%, 95%, 97%, over 99%) to the DNA-binding domain (CXXC domain) of the protein. Such natural proteins can be listed as identified by accession number XP_003359270, XP_004777901, XP_005602635, XP_002805756, XP_003928828, XP_002735044, XP_005168673, of CG43444, and the like.

In this invention, a "homology in amino acid sequence" denotes a perfect match and the proportion (in %) of the matched amino acids (similar amino acids) regarding their physical-chemical properties including basicity and acidity and can be determined by using BLASTP program (Altschul et al. J. Mol. Biol., 215: 403-410, 1990), and the like. The program is based on the BLAST algorithm originally proposed by Karlin and Altschul (Proc. Natl. Acad. Sci. USA, 87:2264-2268, 1990, Proc. Natl. Acad. Sci. USA, 90:5873-5877, 1993). More specifically, BLAST homology search of the NCBI page (http://blast.ncbi.nlm.nih.gov/Blast.cgi), the default parameters, the program including "protein blast" and "blastx" can be used to determine homology. These methods for analyses are well known to those in the art.

Also, in case that the mutant TET1 protein described in this invention may be degraded in primed pluripotent stem cells, one may use excess amount overexpression or decoy strategy described above for wild-type TET1 protein.

For the preparation of mutant TET1 proteins in this invention, we previously mentioned methods where one can modify nucleic acids which code for wild-type TET1 protein. Those in the art may for example be able to produce such mutant TET1 proteins by introducing the nucleic acids encoding the mutant TET1 proteins by baculovirus-infection of Sf9 insect cells. Moreover, besides such genetically mutant preparations, one may directly synthesize mutant TET1 proteins used in this invention by a commercially available poly-peptide synthesizer in a chemical fashion.

To prepare such wild-type TET1 protein, those skilled in the art can obtain nucleic acid coding for said protein by using know method such as hybridization technologies onto cDNA library or genomic DNA library obtained from human or non-human tissues which express TET1 protein and then, use the preparation method mentioned for the preparation of the mutant TET1 protein such as introducing the nucleic acid obtained as above into an insect cell. Alternatively, one can also synthesize such wild-type TET1 protein using a commercially available polypeptide synthesizer according the amino acid sequence shown in SEQ ID NO: 2.

For the methods to introduce the nucleic acids encoding the mutant TET1 proteins into PSCs or the after-mentioned somatic cells which will be utilized to induce PSCs, we do not have any particular restrictions and therefore are able to use methods such as viral infection, lipofection, liposome introduction, electroporation, Ca phosphate, DEAE dextran or microinjection of the expression vectors which bear the nucleic acids encoding the TET1 proteins (for example its cDNA) within appropriate expression vectors which are known to function in the desired cell types.

Such expression vectors include, for examples, viral expression systems such as lentivirus, retrovirus, adenovirus, adeno-associated virus, herpes virus, Sendai virus as well as mammalian expression plasmid vectors such as episomal vectors, PiggyBac transposon vectors. Among these, from the standpoint that the nucleic acids encoding the TET1 proteins are not integrated into the cell's genome, it is preferable to use episomal vectors or Sendai virus. Moreover, from the standpoint that the nucleic acids are temporarily introduced in the genome but will be able to be removed away by transposase, it is preferable to use PiggyBac transposon vector.

For such expression vectors, we can exploit promoters such as CAG; SRα, SV40, LTR, CMV, RSV or HSV-TK promoters. Such promoter selection can include promoters where the expression of the genes introduced beneath can be controlled by the presence or absence of the added agents (for example tetracycline). The expression vectors can also bear, in addition to the promoter, enhancer, poly A addition signal, selection markers (for examples, puromycin-resistance or neomycin-resistance genes) or SV40 replication origin.

The modes of expression of the aforementioned TET1 protein-encoding nucleic acids introduced into PSCs can either be transient, inducible or constitutive. However, regarding its function in extinguishing the expression of NANOG, an inhibitory factor for differentiation induction, and also that differentiation may be hindered if the so-called reprogramming signal by TET1 persists during differentiation process from PSCs produced by the method of this invention to other cell lineage, the preferred expression modes should be transient or inducible. Such controlled expression period is preferably between one day before the commencement of the differentiation of PSCs produced by the method of this invention and 4 days after it.

Methods wherein we can introduce the TET1 protein into each cells include the use of protein cell transfection agents, introducing a protein transduction domain (PTD) fused to the mutant protein, electroporation or direct microinjection.

For the culture conditions used on or after introduction of the mutant TET1 proteins or the nucleic acid encoding it or a vector inserted with the nucleic acid, there is no specific restriction but could be specified by conditions used by those in the art such as culture media constituents, culture temperature, culture humidity, carbon dioxide and/or oxygen tension. Regarding the hydroxylation reaction that the TET1 may provide, it is preferable that Fe, α-ketoglutarate or ascorbic acid (vitamin C) are included in the culture media.

The types of somatic cells to be reprogrammed to PSCs by introduction of the TET1 protein can be anything, and examples thereof include fibroblasts, epithelial cells, blood cells, arbitrary cells derived from an animal. Reprogramming of such cells toward PSCs (especially toward iPS cells) can be achieved by introducing such "reprogramming factors" into somatic cells to erase the cellular memory of each somatic cell.

Such "reprogramming factors" denote any factors with the capacity of harnessing pluripotency to the somatic cells when introduced singly or in concert with other factors such as OCT3/4, c-MYC, L-MYC, N-MYC, SOX2, KLF4, KLF5, KLF2, LIN28, NANOG, ECAT1, ESG1, FBX15, ERAS, ECAT7, ECAT8, GDF3, SOX15, ECAT15-1, ECAT15-2, Fthl17, SALL1, SALL4, REX1, UTF1, TCL1, STELLA, β-catenin, ESRRB, PRDM14, TBX3, STAT3, GATA3 and GRB2 proteins as well as miR-199a-3p, miR-291-3p, miR-294, miR-295 (miR-290 cluster) as well as miR-302 cluster microRNA. Among all these factors, from the viewpoint that the reprogramming occurs with relatively small number of factors, it is preferred to introduce OCT3/4, c-MYC, SOX2 and KLF4 (the so-called Yamanaka factors) into somatic cells. To reduce the tumorigenicity of the obtained PSCs, it is also preferable to replace c-MYC with L-MYC from the four factors or to introduce OCT3/4, SOX2 and KLF4 (3 factors). Moreover, from the standpoint of the induction efficacy of the PSCs, it is preferable to introduce OCT3/4, L-MYC, SOX2, KLF4 and LIN28 and also, chemical compounds or nucleic acids which can inhibit the function of p53 or p21 into the somatic cells. Meanwhile, the "reprogramming factor" does not necessarily have to be the above-described proteins and the like, and may be a low-molecular-weight compound having an alternative function to these or capable of inducing these expressions. Examples of such a low-molecular-weight compound include histone deacetylase (HDAC) inhibitors such as valproic acid (VPA), GSK-3β inhibitors such as CHIR99021, TGF-β1 type receptor inhibitors such as 616452, histone demethylase inhibitors such as tranylcypromine, cAMP production promoters such as forskolin, histone methyltransferase inhibitors such as 3-deazaneplanocin (DZNep), and combinations thereof.

In this present invention, the methods to introduce reprogramming factors into somatic cells can be anything as being discussed about the methods for introducing the TET1 proteins; by selecting the relevant publicly known method, if a protein is to be introduced, the embodiment could be the protein itself or the nucleic acids encoding such protein and if a microRNA is desired, we can introduce it as nucleic acid molecules. But if such reprogramming factors persist within the obtained PSCs, the cells may acquire some resistance against cell differentiation to other cell lineage and makes it difficult to stably harnessing new cell memories. From this point, it is preferable to introduce nucleic acids encoding the reprogramming factors through the use of episomal vectors, Sendai virus or PiggyBac transposon vector.

The timing of such introduction of reprogramming factors can be before, simultaneous or after the introduction of the TET1 proteins or the nucleic acids coding the proteins.

The culture conditions after the introductions of reprogramming factors into somatic cells can be suitably selected by those in the art among the publicly known cell culture methods. An example of such cell culture methods is to culture the cells onto feeder cells in a culture medium suited for somatic cells and then to gradually switch to media suitable for PSCs.

"Feeder cells" can be any cell lines which support the growth and the maintenance of PSCs such as mouse embryonic fibroblasts (MEFs), OP-9 cells, PA6 cells, NIH3T3 cells, M15 cells, 10T/2 cells, STO cells or SNL cells. It is also preferable that the growth of such cells are reduced by antibiotic treatment (like Mitomycin C treatment) or by irradiation.

"A culture medium suited for somatic cells" can be anything publicly known to those in the art and be further selected according the kind of somatic cells used. For examples as basic culture media, we can list Roswell Park Memorial Institute (RPMI) 1640 medium, Minimally Essential Medium (α-MEM), Dulbecco's modified Eagle Medium (DMEM) and F12 medium and to these basic media we can add supplements such as human sera, cytokines, amino acids needed to cell culture (for example L-glutamine) and antibiotics (such as streptomycin, penicillin, puromycin) to prepare "a culture medium suited for somatic cells".

"Media suitable for PSCs" can be selected according to the originated animal from a battery of publicly known media. To give an example of such media for human PSCs, DMEM/F12 supplemented with Knockout Serum Replacement (KSR; Life Technologies), L-glutamine, non-essential amino acids, 2-mercaptoethanol and FGF2 can be one option.

The aforementioned co-culture method with feeder cells is a preferred method for inducing and maintaining PSCs as it provides an easy way to maintain the undifferentiated state of the cells. However, from the standpoint of enhancing the differentiation efficacies to ectoderm lineage such as nerve cells and enabling tight control over the cell densities of the PSCs, non-feeder culture and passaging by trituration is the preferred method for the PSCs in this invention. For such non-feeder trituration passaging culture, we can use methods discussed below.

Once the reprogramming factors are introduced to somatic cells, these cells are cultured in E8 medium developed by Thomson's group (Chen G. et al., Nat Methods, 2011, vol. 8, 424-429). Once iPS cell colonies become discernible, the obtained PSCs are dispersed into culture media containing KSR, FGF2, Activin A, ROCK inhibitor and fibronectin and then seeded onto collagen type I-coated culture dishes which will produce such non-feeder trituration passaging.

For such trituration passaging, the basic culture media to which KSR, FGF2 and Activin A and so on are to be supplemented can be, for example, DMEM/F12 medium or CDM medium. For the concentrations of KSR, FGF2 and Activin A added to these basic media can be within the ranges of 15-25%, 4 to 100 ng/ml and 0.01 to 20 ng/ml, respectively. In a more preferred embodiment, the concentrations are 20%, 15 ng/ml and 10 ng/ml, respectively. In addition to these supplements, other constituents such as L-glutamine, non-essential amino acids or antibiotics (such as streptomycin, penicillin or puromycin) can be added.

In addition, to enhance the efficacy of inducing PSCs, regardless the presence or absence of feeder cells, chemicals which inhibit the function of HDAC (small molecule inhibitors such as valproic acid (VPA), trichostatin A, sodium butyrate, MC1293 or M344), chemicals which inhibit the function of G9a histone methyltransferase (small molecule inhibitors such as BIX-01294), chemicals which inhibit the function of p53 (small molecule inhibitors such as Pifithrin-α (PFT-α)), chemicals which inhibit the function of p21, compounds which inhibit the function of micro RNAs including, let-7 cluster, miR-17-92, miR-21, miR-29a, miR-106a-363 or miR-106b-25, are preferably to be added when or after the reprogramming factors are introduced into somatic cells. From a similar perspective in which we anticipate that the induction efficacy of PSCs may increase upon inhibition of such factors, we can also introduce to the somatic cells nucleic acids with inhibitory effects toward HDAC, G9a, p53, p21 or micro RNAs such as let-7 cluster (siRNA, shRNA, antisense, aptamers and so on) using publicly know methods for nucleic acid delivery.

Moreover, although the aforementioned culture methods including culture conditions (such as culture temperature, oxygen and carbon dioxide concentrations) can suitably be set by those in the art, from the standpoint that it may enhance the induction efficacy of PSCs, it is preferred to culture in hypoxic condition (oxygen concentration: 5%).

Thus far, we have explained the production methods of PSCs in this present invention. For comparatively evaluating the differentiation efficacies between the PSCs induced by such methods and PSCs in which the mutant TET1 are not introduced, as will be explained in the working example 7 later, one can judge the differentiation efficacy by indexing the efficacy of cell differentiation toward the desired cell lineage (for example by dividing the cell number of the desired cell type after differentiation by the total number of PSCs before such differentiation). Moreover, as will be described in the working examples 5 and 6 later, we can measure the expression levels of differentiation markers (such as SOX1, NEUROGENIN1, NEUROGENIN2, NEUROD1, ASCL1, PAX6, ZNF521 or OTX2 for nerve cells), factors which induce differentiation to other cell lineage (for example, SOX2 when nerve differentiation is desired), factors which mark the differentiation propensities (for example, when ectoderm differentiation is desired, markers such as T and SOX17) or factors which resist proper differentiation (for examples, NANOG and OCT3/4) during the cell differentiation process and deduce and judge from these expression data whether the differentiation efficacy has been improved or not. Moreover, as will be shown in Example 11, the current human iPSCs without TET1-introduction tend to express higher levels of the differentiation markers such as FOXA2, LHX1, LIM2, SOX17, EOMES or T, in addition to undifferentiation markers such as GPC4, GAGE2B and GAGE7. Therefore, those markers can be utilized to assess the enhancement of differentiation capacities.

Also, of these markers, GPC4, GAGE2B and GAGE7 are also known as cancer-related markers. Therefore, this invention can also provide a way of assessing the "safety" (the propensity for tumorigenesis upon transplantation) of the given pluripotent stem cells by evaluating at least one marker out of GPC4, GAGE2B and GAGE7.

<Proteins, Nucleic Acids, Vectors and Cells of this Invention>

As described above, for the production method of PSC of this invention, the TET1 protein which is resistant to degradation in primed PSCs is useful. Therefore, this invention provides a mutant TET1 protein having enhanced stability as compared to a wild type TET1 protein, preferably a mutant TET1 protein in which its second amino acid from the N-terminus is different from the second amino acid from the N-terminus of the wild type TET1 protein.

Moreover, the described amino acid sequence of SEQ ID NO: 4 or 6 which denote TET1 protein sequence first described by the inventors and are useful to prepare the mutant TET1 proteins as well as to provide a wild type TET1 protein to be used in the production method of this invention. Therefore, the present invention also provides these TET1 proteins.

Furthermore, as described above, to express the mutant TET1 proteins having enhanced stability as compared to a wild type TET1 protein in the PSCs, the nucleic acids encoding such proteins are useful. Also, to prepare the mutant TET1 proteins and the nucleic acids encoding such proteins as well as to provide a wild type TET1 protein to be used in the production method of this invention, the nucleic acids which encode the amino acid sequences 4 or 6 of TET1 are also useful. Therefore, this present invention also provides such nucleic acids.

As mentioned above, to introduce the nucleic acids into somatic cells, it is preferable to insert the nucleic acid sequence into a vector. Therefore, this invention also provides vectors which bear a nucleic acid sequence coding the mutant TET1 protein with enhanced stability as compared to a wild type TET1 protein or a nucleic acid sequence encoding the amino acid sequence of SEQ ID NO: 4 or 6.

Moreover, according to the production method of this invention, as mentioned above, one can obtain a pluripotent stem cell with enhanced differentiation capacity. Therefore, this invention also provides pluripotent stem cells and/or somatic cells aimed to be induced to the stem cell which had been introduced by at least one molecule selected by the group (a) to (c) below:

(a) TET1 protein
(b) a nucleic acid coding for TET1 protein
(c) a vector into which a nucleic acid that encodes TET1 protein has been inserted

EXAMPLES

From here on, we are going to discuss our invention in details. However, the present invention is not restricted to the working examples shown below. The materials and methods used in these working examples are as follows.

<Human iPSC Production Using Episomal DNA Vectors>

The human iPSCs used in these working examples were derived using the method described by Okita K. et al. (Nat Methods, 2011, vol. 8, 409-412). Three pairs of reprogramming factors, namely a short-hairpin RNA against p53 (shp53) and POU5F1 (OCT3/4), SOX2 and KLF4, L-MYC and LIN28 are introduced in independent episomal pCXLE vectors and three vector DNAs were prepared.

In this process of the production of such iPS cells, cellular reprogramming which is a process to erase the cellular memories of the somatic cells was performed by overexpressing the so-called Yamanaka four factors (OCT3/4, SOX2, KLF4 and c-MYC). In these working examples, to decrease the likelihood of iPS cell-derived tumorigenesis which is an inherent characteristic of the introduced reprogramming factors, we have replaced c-MYC by L-MYC, a reprogramming factor which is known to bear less tumorigenic property. Also, to enhance the efficacy of human iPS cell induction, LIN28 which is known to enhance induction efficacy of human iPS cells was also introduced to somatic cells. Also, as p53 acts to repress reprogramming, this factor was repressed by RNA interference (RNAi) against p53 using shp53.

If the reprogramming factors used to induce iPS cells are retained in the derived iPS cells during the course of producing of iPS cells, such iPS cells may exhibit some resistance against a certain differentiation signal such as neural induction (differentiation resistance) and have difficulty of gaining a novel cell memory. To this end, in these working examples, we chose episomal vector system to introduce genes which allow us to avoid genomic integration of the reprogramming vectors and persistent factor expression.

Next, the inventors introduced 1 µg of each the 3 vector DNA into $1.0 \times 10^5$ human neonatal fibroblasts using DNA transfection reagents (Human fibroblast Nucleofector™ kit) and a DNA transfection apparatus (Nucleofector™) (both from Lonza). Subsequently, the transfected cells have been maintained in E8 media, developed by Thomson et al., capable to induce iPS cells at a feeder-free condition (Chen, G et al., Nat Methods, 2011, Vol. 8, No. 5, pp 424-429). During the first 5 to 10 days after transfection, hydrocortisone with fibroblast-proliferative activity was added to the E8 medium at a concentration of 100 nM, but afterward, both hydrocortisone and TGFβ were removed from the E8 medium to allow iPS cell reprogramming to occur. Cell culture media was replaced every one or two days and throughout this reprogramming process, cells were maintained in a hypoxic condition of 5% oxygen and 5% carbon dioxide within a hypoxic cell incubator.

Through these cultures, the authors were able to obtain multiple iPS cell colonies typically 25 to 30 days later after the introduction of vector DNA. Next, as will be mentioned afterward, the iPS cell colonies were individually picked up and cultured into a culture medium containing KnockOut Serum Replacement (KSR), Fibroblast Growth Factor 2 (FGF2), Activin A, ROCK inhibitor and Fibronectin and plated onto Collagen type I-coated culture dishes to isolate iPS cell clones. Examples of the obtained human iPS cell clones which were stably maintained and shown here are YMhiPSC058, YMhiPSC105 and YMhiPSC237.

When single cell-derived subclones from these original iPS cell clones were obtained and their differentiation potential were individually checked, the authors have found significant variations in the propensities of each subclones, which strongly suggests that the human iPS cell colonies induced as above are not homogeneous in terms of differentiation potential (data not shown). In the following working examples, results obtained from the YMhiPSC058sbc6 subclone, which exhibited the lowest differentiation biases among the obtained subclones, are displayed.

[Trituration Cell Passaging of Human iPS Cells at a Non-Feeder Condition]

In these working examples, human iPS cells were cultured in DMEM/F12 media (Kohjin-Bio) containing 20% KSR (Invitrogen), 15 ng/ml human FGF2 (Peprotech), 10 ng/ml heparin sulfate (SIGMA), 0.03% L-glutamine (MP Biochemicals), 1× non-essential amino acids (Invitrogen), 1× penicillin (Invitrogen) and 1× streptomycin (Invitrogen) (KFA medium hereafter), and maintained at a feeder-free condition.

At cell passaging, human iPS cells were single-cell triturated using 0.01% trypsin/0.1 mM EDTA and replated in KFA medium containing 2 µM ROCK inhibitor (Thiazovivin, WAKO) and 5 µg/ml human Fibronectin (BD Biosciences), followed by seeding onto a collagen type I-coated culture dish.

The non-feeder, trituration cell passaging method for human iPS cells has been independently established by the inventors themselves for the first time. This means that the inventors have performed pilot experiments to deduce adequate conditions which allow this non-feeder, trituration passaging of human iPS cells prior to these working examples. The reason why such pilot experiments were needed was as follows: The current lab routine for maintaining human ES cells or iPS cells alike uses mouse feeder cells which is relatively easy to keep the cells in an undifferentiated state. However, the authors have independently found that such cultures were rendering the stem cells more intractable to cell differentiation especially toward the neuroectoderm lineage. Moreover, although it is commonly accepted that trituration during human pluripotent stem cell passaging is more difficult, the inventors reckoned that such procedure is essential in controlling the cell density for proper cell differentiation.

Using a human iPS cell line (rvhiPSC08) reprogrammed by retrovirus-mediated expression of reprogramming factors (POU5F1, SOX2, KLF4 and c-MYC), the present inventors have addressed the following two points.
 (1) the growth factor(s) to be added and its (their) concentration(s), and
 (2) the combination of the cell signaling inhibitors and the extracellular matrices to be used at the passage with trypsin.

At the time of these experiments, one of the conventional ways for culturing human pluripotent stem cells (PSCs) was to culture the cells in basal media supplemented chiefly with KSR, an Invitrogen reagent, and with human FGF2 at a concentration between 4 and 5 ng/ml and onto mouse embryonic fibroblast (MEF) feeders. In this circumstance, the MEF is supposed to provide the extracellular matrix and hence to help the attachability of PSCs onto culture surfaces but also to support cell growth by supplementing FGF2 and/or NODAL secreted by these cells, when judged by the published literature and the authors' own unpublished observations. Therefore, the inventors have investigated especially the effects of FGF2 and Activin A with NODAL-like activity to be added on top of KSR to their media. They have investigated the concentrations of FGF2 and Activin A by assessing the expression of markers such as POU5F1, SOX2 or NANOG which indicate the undifferentiated status, a mesendodermal marker T (also known as BRACHYURY) and a neuroectodermal marker SOX1. The inventors have come up with final concentrations of approximately 15 ng/ml for FGF2 and 10 ng/ml for Activin A which gave best results in stable cell proliferation of these cells, and by using KFA medium, the inventors succeeded in easily culturing human iPS cells at a non-feeder fashion.

Although the routine passaging procedure was to loosely detach human iPS cell colonies enzymatically which gave cell aggregates of average size of several tens of cells, from the viewpoints presented earlier, the inventors went on to devise a way to allow such cell trituration. It has been known that human ES cells could be single-cell passaged using ROCK inhibitors (Watanabe, K. et al., Nat Biotechnol., 2007, Vol. 25, No. 6, pp 681-686; Lin, T. et al., Nat Methods, 2009, Vol. 6, No. 11, pp 805-808). However, in these known literatures, the use of artificial extracellular matrices such as MatriGel for coating a culture dish is mandatory and therefore these methods were not user-friendly. The inventors have found a paper in which such use of artificial extracellular matrices is replaced by fibronectin which could be added directly into the culture medium to help trituration passaging (Kitajima, H. et al., Biochem Biophys Res Commun, 2010, Vol. 396, No. 4, pp 933-938). Collectively, the present inventors have deduced that by combining the KFA media, ROCK inhibitor and fibronectin to maintain human iPS cells after trypsin-single-cell passaging in collagen type I-coated culture dishes would be a feasible culture methods which finally led them to establish their own non-feeder, trituration-passaging culture method of the cells.

[Quantitative RT-PCR]

RNA was extracted using RNeasy mini kits (QIAGEN). To avoid genomic DNA contamination, RNase-free-DNase set (QIAGEN) was also used for DNase treatment. Using 1 μg of total RNA as a template, cDNA was reverse-transcribed using oligo-dT primer (TOYOBO) and Revertra Ace (TOYOBO). The cDNA was diluted 20 times in distilled water and quantitative PCR (qPCR) was performed using Fast SYBR green master mix reagent (ABI) and primers listed in Table 1 on an ABI apparatus. For each RNA sample, a triplicate of reactions were performed to obtain each mean value and values normalized against GAPDH internal controls were shown as graphs (FIGS. 2, 5, and 8-23).

TABLE 1

| Gene name of amplification target | Forward primer Sequence | SEQ ID NO: | Reverse primer Sequence | SEQ ID NO: |
|---|---|---|---|---|
| GAPDH | agccacatcgctcagacac | 11 | gcccaatacgaccaaatcc | 12 |
| POU5F1 | catgaggctctgcagcttag | 13 | tctgctttgcatatctcctgaa | 14 |
| SOX2 | gggggaatggaccttgtatag | 15 | gcaaagctcctaccgtacca | 16 |
| NANOG | tctccaacatcctgaacctca | 17 | ttgctattctaggccagtt | 18 |
| T(Brachury) | gctgtgacaggtacccaacc | 19 | catgcaggtgagttgtcagaa | 20 |
| SOX1 | ggctgagcaccactacgact | 21 | gcattataaaatttcccaaatcatc | 22 |
| PAX6 | atttcccgctctggttcag | 23 | gttttctccacggatgttgc | 24 |
| SOX17 | acgccgagttgagcaaga | 25 | tctgcctcctccacgaag | 26 |
| MIXL1I | ggtaccccgacatccactt | 27 | gcctgttctggaaccatacct | 28 |

TABLE 1-continued

| Gene name of amplification target | Forward primer Sequence | SEQ ID NO: | Reverse primer Sequence | SEQ ID NO: |
|---|---|---|---|---|
| NEUROGENIN1 | ccgcttgttaggtcgccgca | 29 | tgggctgagggccggagaaa | 30 |
| NEUROGENIN2 | acacgcaccaccaccacaaca | 31 | ccggcgagtttgccaagagc | 32 |
| ASCL1 | cgacttcaccaactggttctg | 33 | atgcaggttgtgcgatca | 24 |
| ZNF521 | tgggatattcaggttcatgttg | 35 | actggagtttggcaggagag | 36 |
| NUROD1 | gcggccacgacacgaggaat | 37 | cgcccatcagcccactctcg | 38 |
| TET1 | ccaagccccagaagattag | 39 | tggagctaatcgtgtag | 40 |
| DNMT3A | ggtgcactgaaatggaaagg | 41 | actggcacgctccatgac | 42 |
| DNMT3B | ggtgcactgagctcgaaag | 43 | aagaggtgtcggatgacagg | 44 |

[Western Blotting]

To reproducibly detect TET1 protein using Western blotting, the authors have performed sets of pilot experiments to optimize the method for protein extraction. It turned out that Tet1 molecules were strongly bound to DNA. The inventors have found that by cell-fractionating cell nuclei followed by protein extraction using NER solution (PIERCE) allowed them to quantitatively detect TET1 protein. It was known later that TET1 protein binds to DNA with an unprecedented affinity, which may explain the requirement of such special extraction method.

For western blotting, protein was extracted with the method and was size-fractionated using SDS-PAGE followed by electro-transfer onto a PVDF membrane. Anti-human TET1 antibody (SIGMA) and anti-human β-actin antibody (SANTA CRUZ) were diluted ×1,000 in 0.3% Triton-X100, 3% BSA and 1% normal-goat serum in PBS(−) (antibody diluting solution). Next, the membrane was incubated in the diluted primary antibody solution overnight at 4° C. After stringent washing, the membrane was incubated with HRP-conjugated secondary antibody at room temperature for one hour. After washing, ECL (GE Healthcare) was reacted with HRP present on the membrane surface, and the resulting fluorescence was developed on a film.

[Neural Differentiation of Human iPS Cells]

The neural differentiation of human iPS cells were basically performed according to the improved protocol the inventors have previously developed for mouse ES cells in that these cells efficiently differentiated to neurons (Bouhon, I. et al., Brain Res Bull, 2005, vol. 68 (1-2), pp. 62 to 75). The details are as follows:

(1) Adaptation Culture

Before each cell differentiation, human iPS cells routinely maintained in KFA at a feeder-free condition were transferred to a CDM-based medium, a step which the authors call adaptation culture. The novel CFA medium used for this adaptation culture consists of CDM medium supplemented with 40 ng/ml human recombinant FGF2 and 2 ng/ml human recombinant Activin A and was developed herein especially to switch the human PSCs from maintenance culture to neural differentiation. The details of the CDM medium can be found in Bouhon, I A et al., Brain Res Bull, 2005, Vol. 68 (1-2), pp 62-75. As cells are slightly more vulnerable to oxidative stress originated from atmospheric oxygen in this culture medium, this adaptation culture was performed in a low-oxygen $CO_2$ incubator (hypoxic condition: oxygen concentration 5%).

(2) Neural Precursor Cell Differentiation of Human iPS Cells

When confluency is attained, CFA-cultured human iPS cells were dissociated with trypsin treatment as mentioned above and resuspended at a cell density of $5 \times 10^4$ cells/ml in CDM medium supplemented with 10 μM Y27632 (a ROCK inhibitor) and plated down onto a low-attachment culture dish (bacterio-grade Petri dish).

Four days after the induction of differentiation, the formed cell aggregates ("spheres" hereafter) were collected and were single-cell dissociated back with Accutase (BD Biosciences). The dissociated cells were then transferred to the neural induction medium (10 μM SB431542, 30 nM IWR-1endo and 10 μM Y276732 in CDM) and plated onto Petri dishes as above. After additional four days, the collected spheres were dissociated as above and resuspended in CDM containing 10 μM SB431542 and 10 μM Y27632.

In the above procedure, SB431542 and IWR-1endo were deliberately added to the original CDM differentiation medium by taking into account the difference between mouse ES cells and human PSCs. This is because from the naïve mouse ES cells, a primitive endoderm cell population can be derived which can become a source of expressing antagonizing factors against the anti-neural TGFβ/Nodal and WNT signaling according to the inventors' previous reports. In contrast, primitive endoderm cells cannot be normally induced from human PSCs and therefore their differentiation toward neural cells would be expected to be defective if the mouse ES cell neural differentiation protocol is applied without modification. Therefore, in order to assess the neural differentiation potentials of the given human iPS cells in the following Examples, the inventors have deliberately added the small molecule SB542431 to block the TGFβ/Nodal signaling and IWR-1endo, a WNT signaling antagonizing small molecule to their neural differentiation media.

After the cells were treated in CDM supplemented with SB542431 and Y27632, at similar intervals, the spheres were passaged in CDM plus Y27632 or passed to the maturation procedure as follows. In the inventors' hands, maintaining the differentiated neural precursors in CDM did not let these cells mature into neurons but kept proliferating as precursors.

(3) Maturation of Neurons

Neurons are post-mitotic and therefore do not divide anymore. With the neural differentiation protocol, proliferating neural precursor cells could be differentiated out of human PSCs. To obtain functional post-mitotic neurons with characteristic neurites, we have to keep these cells individually attached onto substrates on the bottom of a culture dish out of the formed precursor spheres (This step whereby the precursors are let to mature in a culture dish into neurons can be called as "neuron-maturation culture").

At the neuron-maturation culture, culture dish surfaces were transferred from non-attaching Petri dish plastic to neuron-permissive collagen type IV (IWAKI). For culture, the inventors have further pre-treated it with poly-L-ornithine (SIGMA) and recombinant laminin (BD Biosciences) for a certain period of time. The spheres were dissociated using Accutase as mentioned earlier. Moreover, during this maturation culture, cells were maintained in CDM containing 3 µM CHIR99021, 10 µM DAPT and 10 µM forskolin. The culture medium was replaced every second day, and after about a week, neurons with prominent neurites were observed.

Working Example 1

<Endogenous TET1 Dynamics in Human Pluripotent Stem Cells>

The mouse PSCs bear similar characteristics of the pre-implantation blastocyst's inner cell mass. In contrast, human PSCs are most akin to the post-implantation epiblast's primitive ectodermal cells. From this difference in developmental stages, it is generally assumed that human PSCs are less pluripotent than mouse PSCs. Therefore, the inventors aimed to enhance the pluripotency of human PSCs by further de-differentiating (or reprogramming) these cells from an epiblast-like (primed) state toward a blastocyst-like (naive) state.

During development, there are two kind of reprogramming. One occurs from fertilization to implantation and called the "early embryonic reprogramming" and the other occurs after implantation during the specification of the germline which is called the "germline reprogramming". From these, the inventors considered that the cell memories acquired during the process of blastocyst to epiblast transition should be erased and have come up with TET1 which seemed to be a strong candidate after examining various factors expressing during the "early embryonic reprogramming".

The expression profile for Tet1/TET1 in mammals is only reported for mice. According to these information, mouse Tet1 is known to be expressed during the early development within the nuclei of the fertilized eggs up to blastocysts (Ito S., Nature, 2010, vol. 466, 1129-1133). Another paper described this factor is also expressed specifically in the primordial germ cells in which the germ cells are specified (Hajkova P., Science, 2010, vol. 329, 78-82). Moreover, Tet1 protein is also abundantly expressed in mouse ES cells which are derived from the Tet1-expressing blastocysts. However, there was no information available about the expression profile of the human TET1 thus far.

First, the inventors investigated the expression of TET1 mRNA and protein in human iPS cells. For the detection of TET1 protein, the inventors have noticed that this protein is strongly bound to DNA and therefore exploited a strong elution method which for the first time allowed them to quantitatively detect this protein by western blotting. The results are shown in FIGS. 1 and 2.

Figure 2:
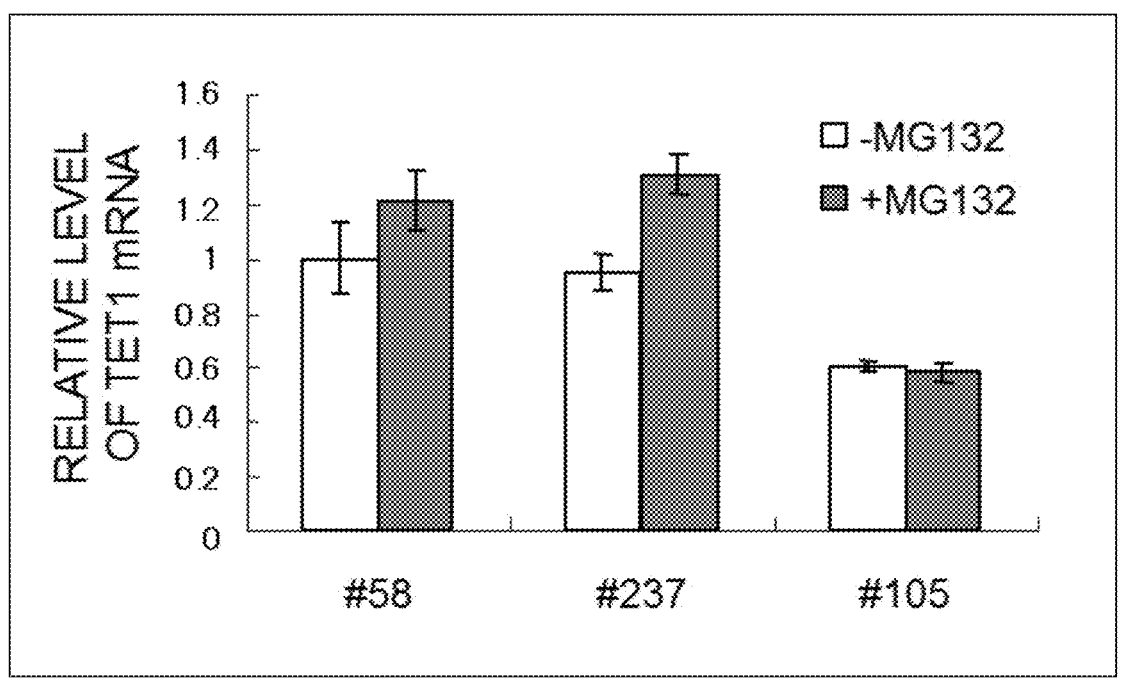
FIG. 2 The graph shows the result of the quantitative RT-PCR for analyzing the expression amount of TET1 mRNA in individual human iPS cells (#58, #237 and #105) with or without proteasome inhibitor (MG132). On the vertical axis are represented relative mean values of each sample in triplicates when normalized against GAPDH expression values of the same sample. Error bars represent standard deviations (so are in FIGS. 5, 8 to 23).

As clearly shown in FIGS. 1 and 2, albeit the fact that TET1 is expressed at the transcript level, its protein was not detected in normal conditions, a situation which contrasts to the one observed for mouse ES cells.

Therefore, the inventors went on to transiently inhibit the function of the major protein degradation pathway, the proteasome, and tried to detect TET1 with western blotting. Independent human iPS cell lines (#58, #237 and #105) were cultured in KFA medium in a routine fashion but 7 hours before nuclear extract sampling, the cells were treated with MG132 5 µM with 0.1% of DMSO as a solvent and processed for western blots. As control, cells were also treated with 0.1% DMSO alone for 7 hours before nuclear extraction and processed for western blots.

As shown in FIGS. 1 and 2, TET1 being actively transcribed in human iPS cells, was swiftly degraded at the protein level through the proteasome system. Upon MG132 treatment, although the transcription levels of TET1 were also up-regulated, these were clearly not causative of the drastic changes observed at the protein levels. Together, these results indicate that human PSCs under a normal condition do not bear TET1 protein or otherwise, its protein level in these cells stayed under the detection limit by western blots.

Working Example 2

<Determination of the Structure for Human TET1 Gene>

As has been clearly shown in the Working example 1, TET1 protein was not stabilized in human PSCs. When considering the process of human iPS cell induction, it is unlikely that the cells in the process have spent enough time under conditions similar to blastocyst- or germline-stage embryos where TET1 protein can be stably expressed and therefore, in this induction process, it is feasible to think that TET1 activity has not been sufficiently transferred to the genome. It is also noticeable that this presence or absence of TET1-genome interaction may be decisive for the difference in the differentiation efficacies between the naive mouse PSCs and the primed human PSCs.

In order to forcefully express TET1 protein in human PSCs, the inventors sought to obtain the full-length cDNA encoding human TET1 by RT-PCR. Using a human iPS cell line (rvhiPSC08), the inventors obtained the TET1 cDNA by RT-PCR using PrimeSTAR Max DNA polymerase (Takara Bio). In this step, according to the available TET1 cDNA sequence (Refseq: NM_030625), the inventors designed their PCR primers so that they can express TET1 protein which would bear FLAG tag either at its N-terminus or C-terminus as shown below and used them for RT-PCRs.

```
(N-terminus FLAG primers)
XhoI-Flag-hTet1-S:
                                           (SEQ ID NO: 7)
GCAAGAATTCCTCGAGCCACCATGGACTACAAAGACGATGACGACAAGTC

TCGATCCCGCCATGCAAG

XhoI-hTet1-AS:
                                           (SEQ ID NO: 8)
GAGTGAATTCCTCGATCAGACCCAATGGTTATAGGGCC (N-terminus FLAG primers)
XhoI-hTet1-5:
                                           (SEQ ID NO: 9)
GCAAGAATTCCTCGAGCCACCATGTCTCGATCCCGCCATGC
```

-continued

XhoI-hTet1-Flag-AS:

(SEQ ID NO: 10)
GAGTGAATTCCTCGATTACTTGTCGTCATCGTCTTTGTAGTCGACCCAAT
GG

Figure 3:
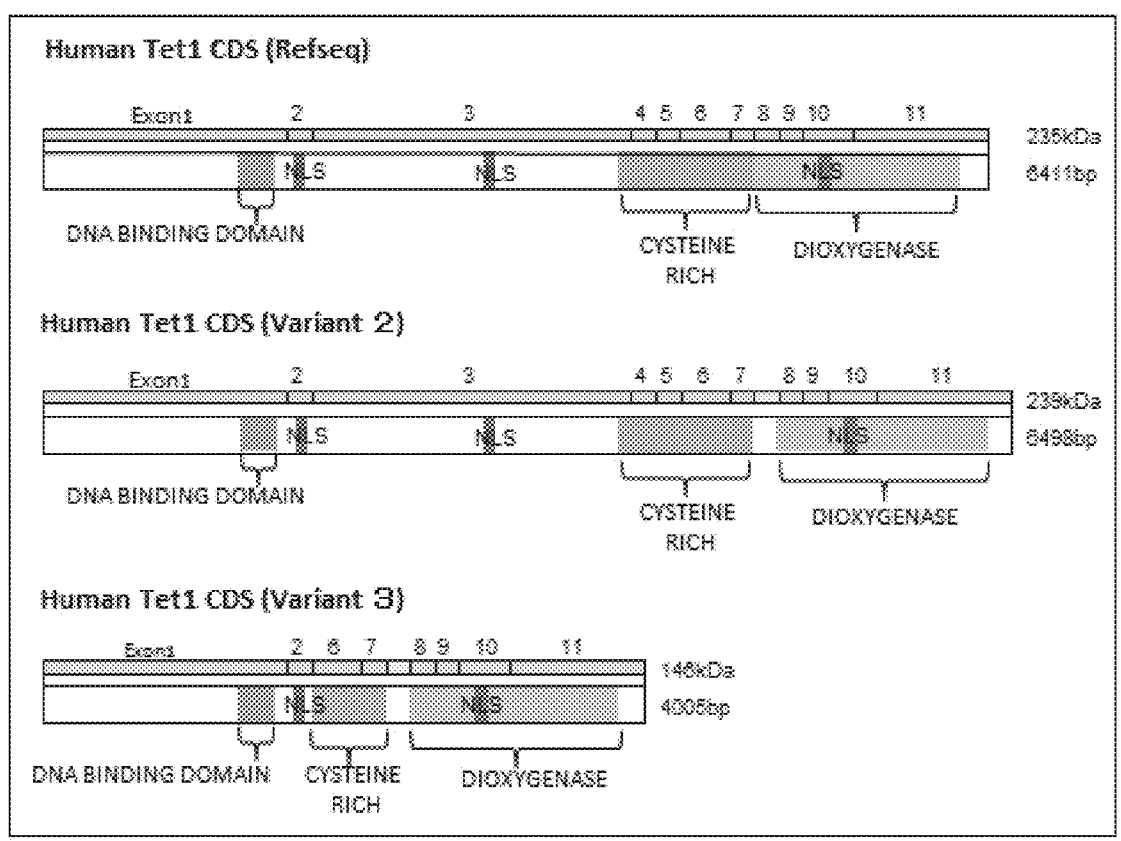
FIG. 3 The structures of the three TET1 proteins expressed in human iPS cells. At the top are shown the TET1 gene coding region (CDS) from the sequence deposited as Refseq and protein structures encoded by the CDS. At the middle and bottom are the two TET1 splice variants' CDSs and protein structures encoded by the CDSs.

The results of these RT-PCR, as depicted in FIG. 3, showed two PCR products both of which turned out to be TET1 variants but differed from the Refseq sequence (human TET1, variant 1), and therefore these two variants represent novel splice variants in PSCs.

The longer of the novel variants (human TET1, variant 2), when compared to the Refseq sequence, bears an additional sequence between the 7$^{th}$ exon and the 8$^{th}$ exon with a length of 87 bases. The exon sequence was confirmed to be a single exon from the comparison with the genomic sequence. This part of the TET1 protein corresponds to the N-terminal portion of the catalytic (dioxygenase) domain of TET1 deduced by crystallography. Interestingly, the corresponding exon is present in the mouse Tet1 sequence.

The shorter of the novel variants (human TET1, variant 3) turned out to miss the third to the fifth exons. As these three exons consist of 2493 base pairs, this deletion is supposed to be an in-frame deletion. Within the portion missing in variant 3 when compared to variants 1 and 2, it is reported that two nuclear localization signals are present.

Although not presented here as a figure, variant 2 appeared to be the majorly expressed form in human iPS cells by RT-PCR. In contrast, variant 1 expression, albeit in a more limited amount, was also detectable in human iPS cells. Variant 3 was also expressed in a modest way. Also not shown as a figure was the fact that all three corresponding variants were detectable in the mouse at the mRNA level.

In the sequence listing are shown: human TET1 variant 1 sequence as SEQ ID NO: 1 and the amino acid sequence encoded by this as SEQ ID NO: 2; human TET1 variant 2 sequence as SEQ ID NO: 3 and the amino acid sequence encoded by this as SEQ ID NO: 4; human TET1 variant 3 sequence as SEQ ID NO: 5 and the amino acid sequence encoded by this as SEQ ID NO: 6.

Working Example 3

<Expression of the Mutant TET1 Protein: Part1>

The inventors have tried in expressing human TET1 (variant 2) which was amplified in the Working example 2 in human PSCs by introducing it in human PSCs.

As mentioned previously, N-terminal or C-terminal FLAG tag-containing TET1 cDNAs were amplified using human iPS cell cDNA as template using RT-PCR. The obtained 2 modified TET1 cDNAs were then independently inserted into a XhoI site in a mammalian expression vector (pCAG-ires-puro; a gift from Niwa lab at RIKEN CDB) using In-fusion HD cloning kit (Takara Bio).

Next, these expression vectors were independently transfected into the human iPS cell line (YMhiPSC058 subclone) using Nucleofector. The transfection was performed by suspending iPS cells with Human Stem Cell Nucleofector Kit 1 (Lonza) and applying electric pulse under the program B-016 which was previously shown to exhibit highest transfection efficiency toward human iPS cells.

The aforementioned expression vectors were introduced into human iPS cells and by selecting the transfected cells under the pressure of puromycin (1 μg/ml), the inventors obtained several stable transformants for both N-terminal and C-terminal FLAG-tagged TET1 clones. TET1 mRNA and protein expression levels were analyzed and shown in FIGS. 4 and 5.

Figure 4:
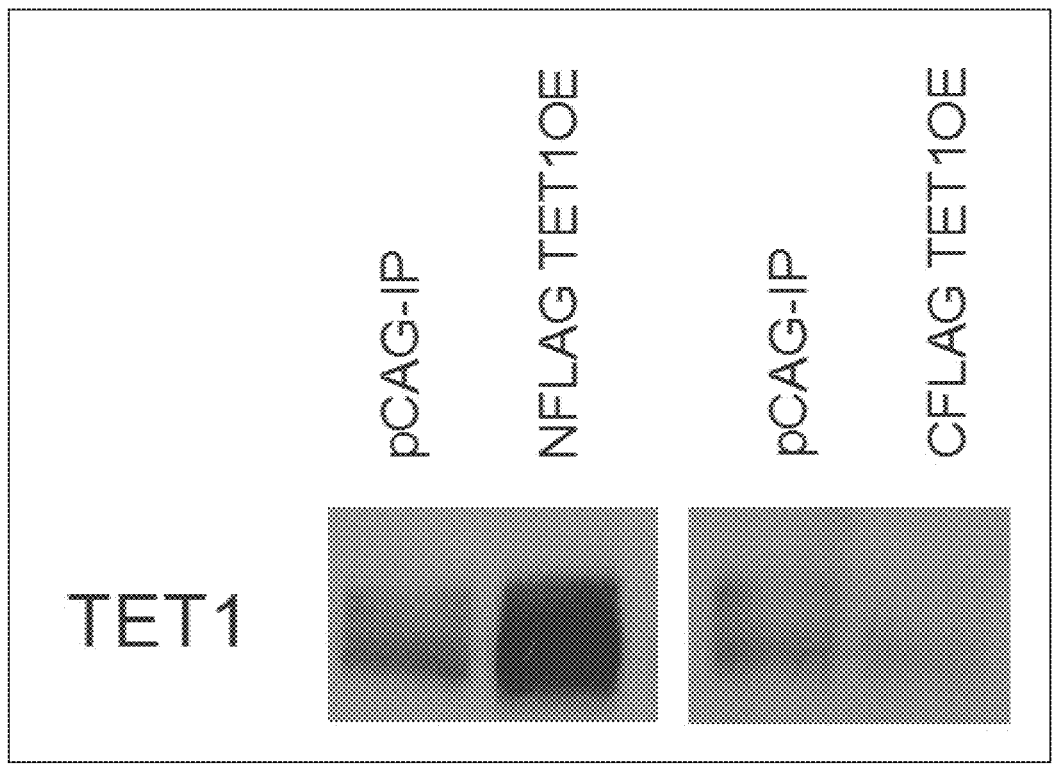
FIG. 4 The picture shows the result of the western blot for analyzing the expression amount of TET1 in control human iPS cell line which expresses a mock vector (pCAG-IP), a human iPS cell line expressing an N-terminally FLAG-tagged (NFLAG TET0E) and a human iPS cell line expressing a C-terminally FLAG-tagged (CFLAG TET0E).
Figure 5:
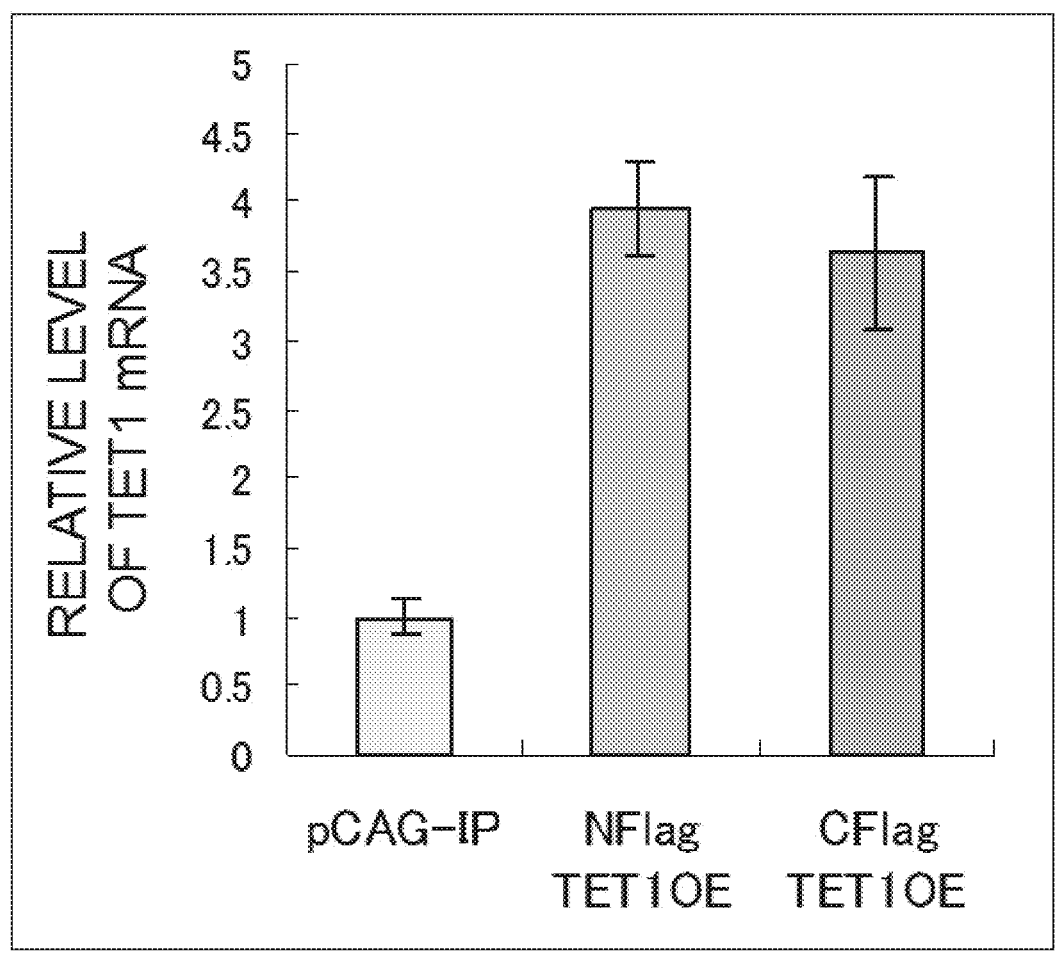
FIG. 5 The graph shows the result of quantitative RT-PCR for analyzing the expression amount of TET1 mRNA in NFLAG TET1OE, CFLAG TET1OE and pCAG-IP.

As clearly shown in FIGS. 4 and 5, TET1-expressing clones of both tags exhibited significant increases of TET1 transcription (FIG. 5). However, very interestingly, TET1 protein signal detection by western blots only showed TET1 band from the N-terminal FLAG-tagged TET1 clones (FIG. 4). This suggests that a degradation signal for TET1 protein is present at its N-terminal end.

Working Example 4

<Expression of the Mutant TET1 Protein: Part2>

According to the results obtained in the Working example 3, the inventors evaluated the stability of the mutant TET1 protein for identifying a sequence involved in destabilization of the TET1 protein as follows.

The N-terminal portion of TET1 protein (about 600 amino acids) were fused through its C-terminus to a GFP resulting a mutant TET1 protein which was expressed in human iPS cells by the aid of Nucleofector. The GFP used in this example (Tag-GFP; Evrogen) has a shorter translation-coloring time lag compared to the conventional GFP which allows a real-time analysis of the appearance-disappearance dynamics of the fused protein.

Figure 6:
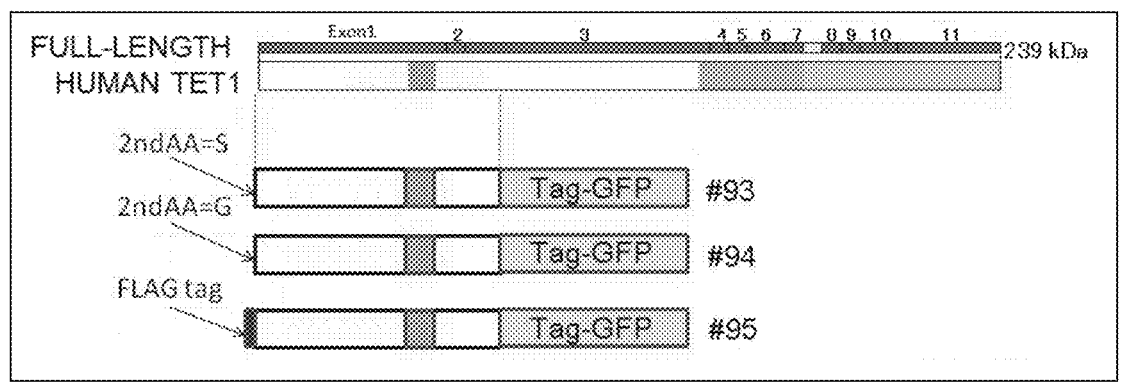
FIG. 6 Schematic figure showing the structures of the mutant TET1 proteins which were used to show the relationship between the stability and the modification in TET1 protein. At the top is shown the CDS of the human TET1 gene for the variant 2 and the protein structure encoded by the CDS. Second from the top is shown the structure for a fusion protein of the N-terminal portion of the human TET1 protein (the protein consisting of 670 amino acids) fused to GFP (#93). At the third position from the top is shown the structure for a fusion protein of the N-terminal portion of the human TET1 protein (the protein consisting of 670 amino acids) with the second amino acid serine converted to glycine, fused to GFP (#94). At the fourth position from the top is shown the structure for a fusion protein of the N-terminal portion of the human TET1 protein (the protein consisting of 670 amino acids) with a FLAG tag inserted between the first methionine and the second serine, fused to GFP (#95).

As shown in FIG. 6, the fused mutant TET1 proteins are, the wild-type TET1 N-terminal portion fused to Tag-GFP (#93), a TET1 protein N-terminal portion in which its second amino acid form the N-terminus (S: serine) has been experimentally switched to G: glycine and then fused to Tag-GFP (#94) and finally, as described in the Working example 3, TET1 N-terminal portion with a stabilizing N-terminal FLAG tag fused to Tag-GFP (#95). These were independently introduced into iPS cells. It was confirmed that all these GFP fluorescence emanating from the fused proteins were discernible within the cell nuclei of the transfected cells. To quantitatively analyze the fluorescent intensities of the individual expression constructs in each cell, human iPS cells expressing each mutant TET1-fusion protein were analyzed by FACS analyses. The results are shown in FIG. 7.

Figure 7:
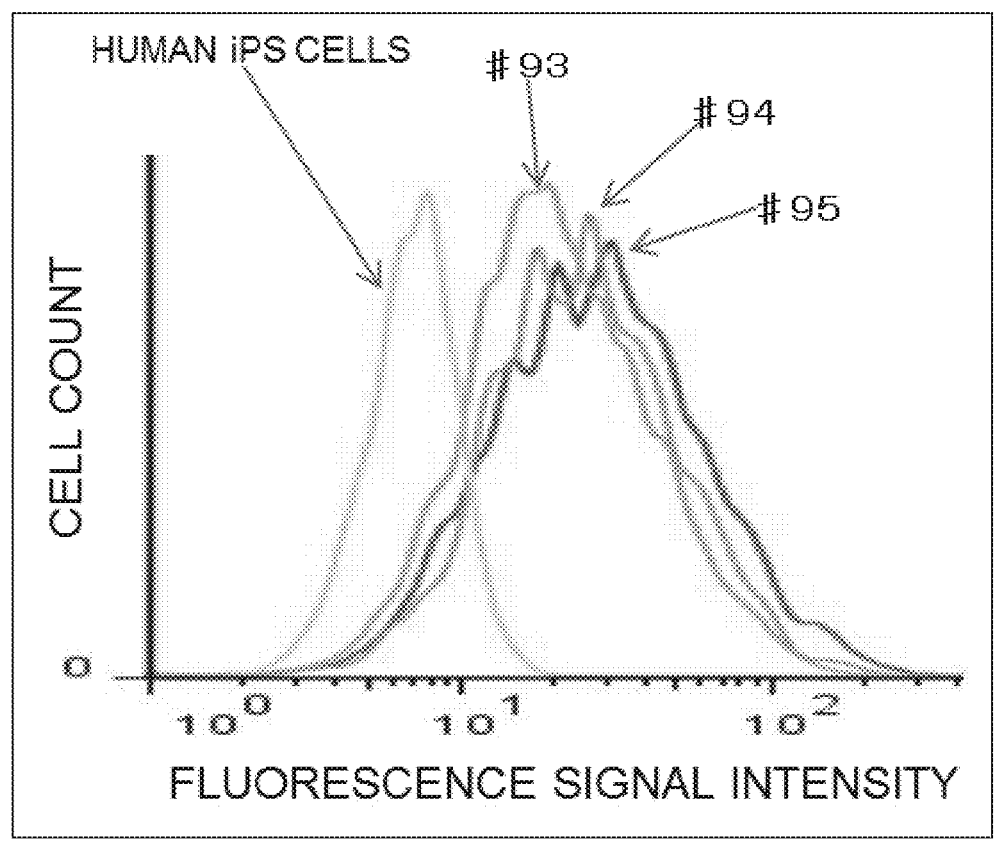
FIG. 7 A histogram showing FACS result obtained from the hiPSCs bearing the GFP-fusion protein depicted in FIG. 6 independently (#93, #94 and #95). The histogram depicted as "hiPSC" represents a negative control using human iPS cells with no GFP expression.

As clearly depicted in FIG. 7, the geometric means of the auto-fluorescence signals of the negative control non-GFP expressing iPS cells was 7.2. The geometric means of the wild-type TET1 N-terminal portion-GFP fusion expressing iPS cells (#93) was 26.3. In contrast and interestingly, the fluorescence intensity jumped up for the fusion protein in which the second amino acid from the N-terminus of TET1 was switched from serine to glycine (signal intensity: 31.6; #94 in FIG. 6). Moreover, as expected from the results shown in the Working example 3, in case where the inventors have replaced the first methionine of the wild-type TET1 by a FLAG tag, the signal intensity was significantly increased (signal intensity: 37.7; #95 in FIG. 6).

Therefore, it was concluded that the second amino acid from its N-terminus, serine, is critical in determining the stability of this protein. According to this result, it would be possible to deduce that the observed enhanced stability of the TET1 protein in the Working examples 3 and 4, where its second amino acid from its N-terminus has been replaced from serine to the second amino acid of a FLAG tag, an aspartate, was operational for this change (for the amino acid sequence of a FLAG tag, refer to SEQ ID NO: 46).

Working Example 5

\<Analyses of Human iPS Cells Overexpressing the Mutant TET1 Protein (TET1-hiPSC) at their Undifferentiated State\>

As been shown in the Working example 1, TET1 protein is not normally expressed in the human PSCs which are presumed to be equivalent to an epiblast-like embryonic stage. Therefore, the human iPS cells overexpressing the mutant TET1 protein (TET1-hiPSCs) can be assumed that these cells do not exist during development.

Although it is not shown as a Figure, surprisingly, TET1-hiPSC cultured in KFA medium, when maintained in an undifferentiated state, does not exert any physiological difference such as cell morphology or cell growth when compared to conventional human iPSC which does not express the mutant TET1 protein and is rather identical in appearance. Therefore, the inventors have tried to evaluate the TET1-hiPSC using the expressivities of mRNA for transcription factors which are thought to be strongly correlated with the characteristics of PSCs by RT-PCR. The obtained results are shown as "Day 0" in FIGS. 8 to 23.

Figure 8:
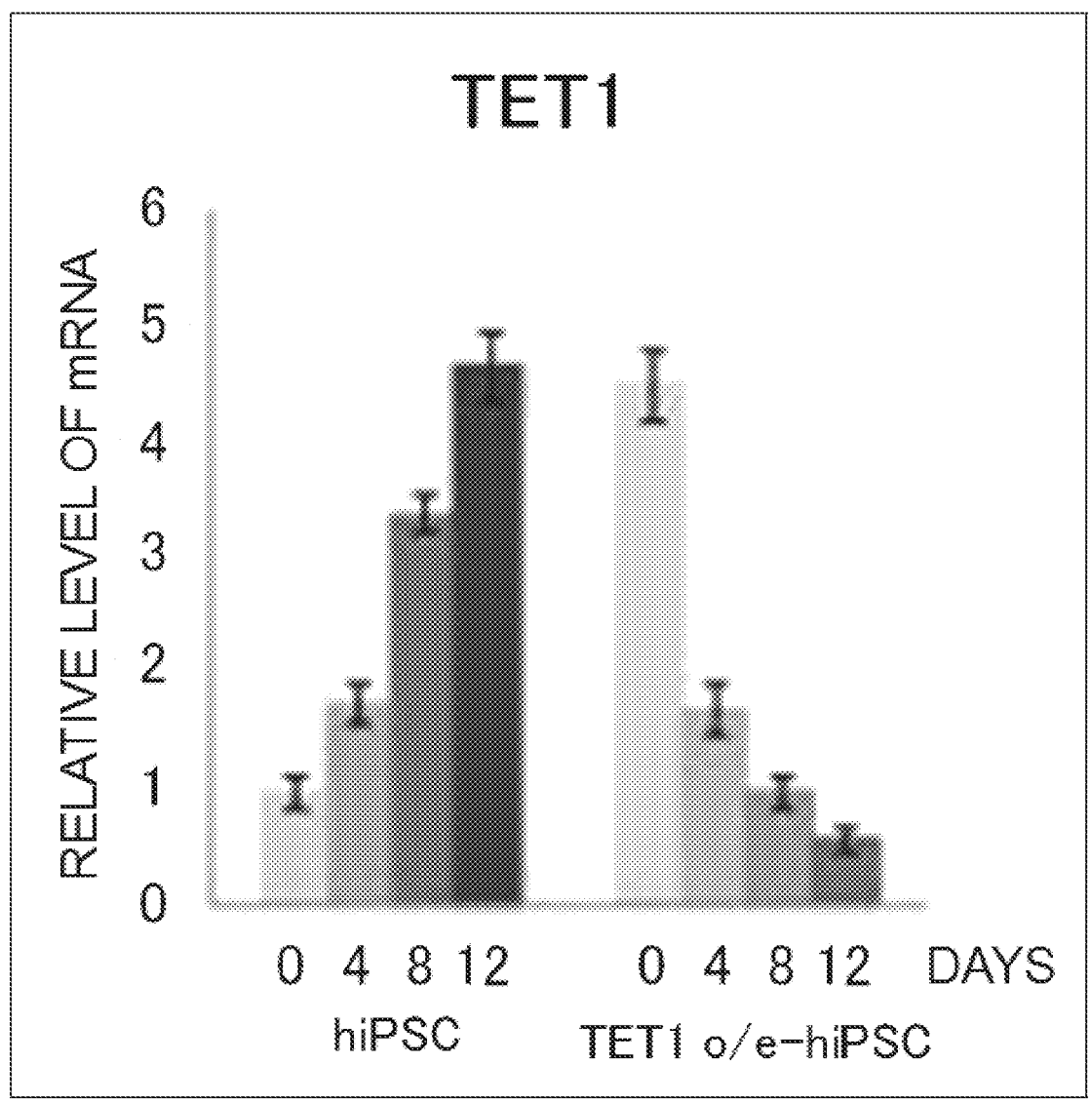
FIG. 8 The graph shows the time course of TET1 mRNA expression during the neural induction of control human iPS cell (depicted as "hiPSC" in the figure) and human iPS cell expressing N-terminally FLAG-tagged TET1 protein ("TET1o/e-hiPSC"). The vertical axis of the graph represents the days after the commencement of neural induction (also in FIGS. 9 to 23).
Figure 9:
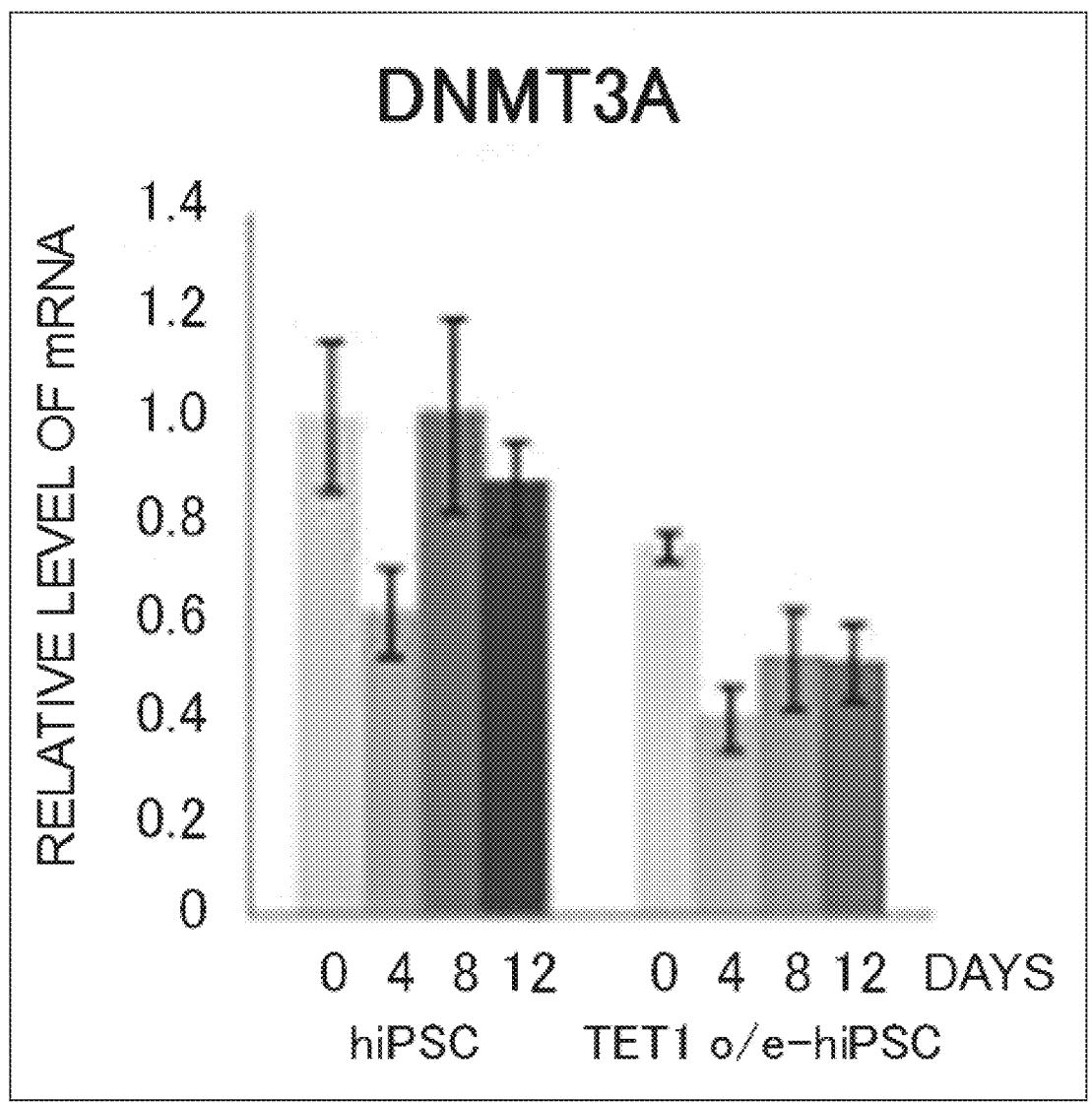
FIG. 9 The graph shows the time course of DNMT3A mRNA expression during the neural induction of hiPSC and human iPS cell expressing N-terminally FLAG-tagged TET1 protein.
Figure 10:
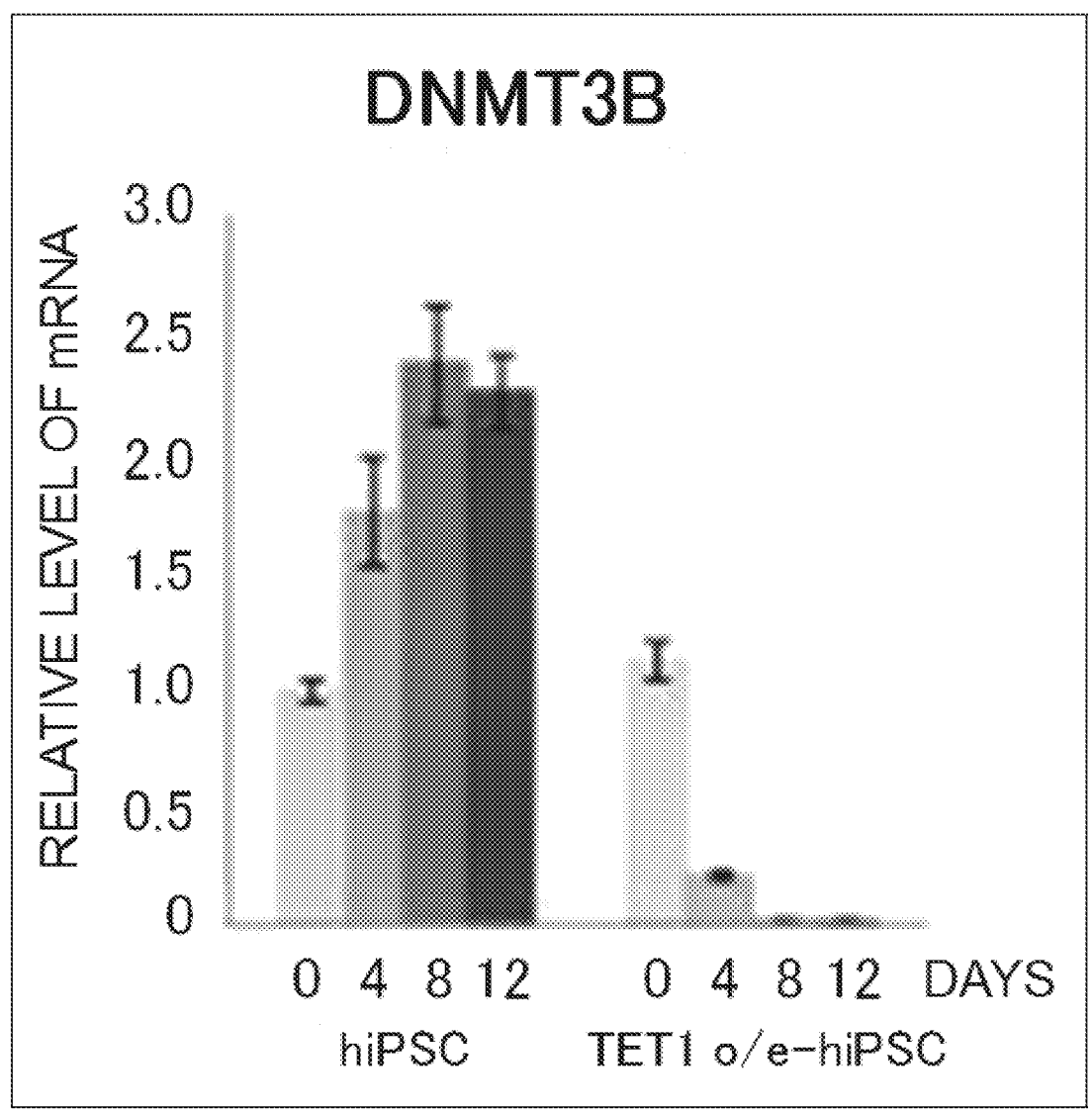
FIG. 10 The graph shows the time course of DNMT3B mRNA expression during the neural induction of hiPSC and human iPS cell expressing N-terminally FLAG-tagged TET1 protein.
Figure 11:
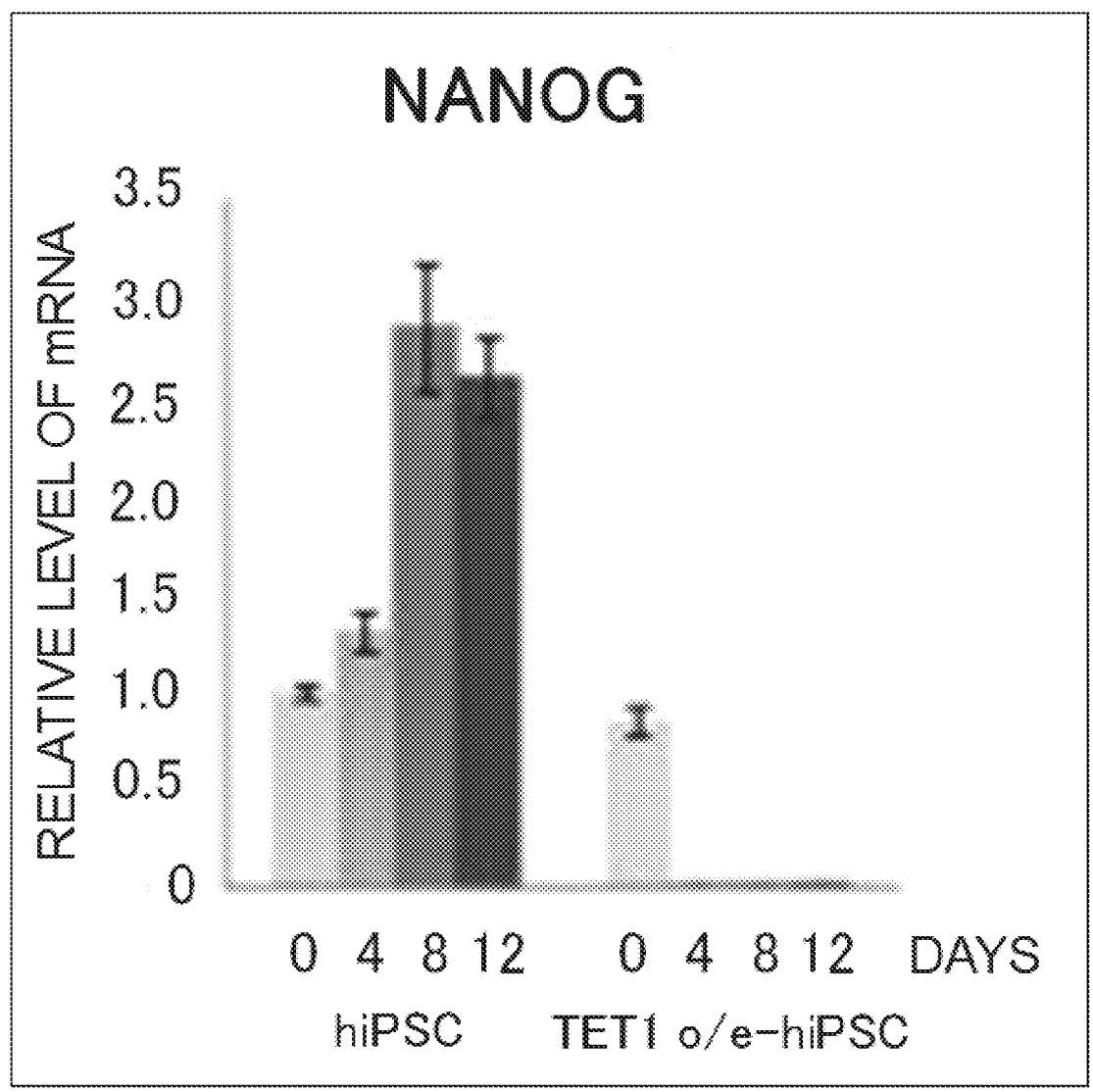
FIG. 11 The graph shows the time course of NANOG mRNA expression during the neural induction of hiPSC and human iPS cell expressing N-terminally FLAG-tagged TET1 protein.
Figure 12:
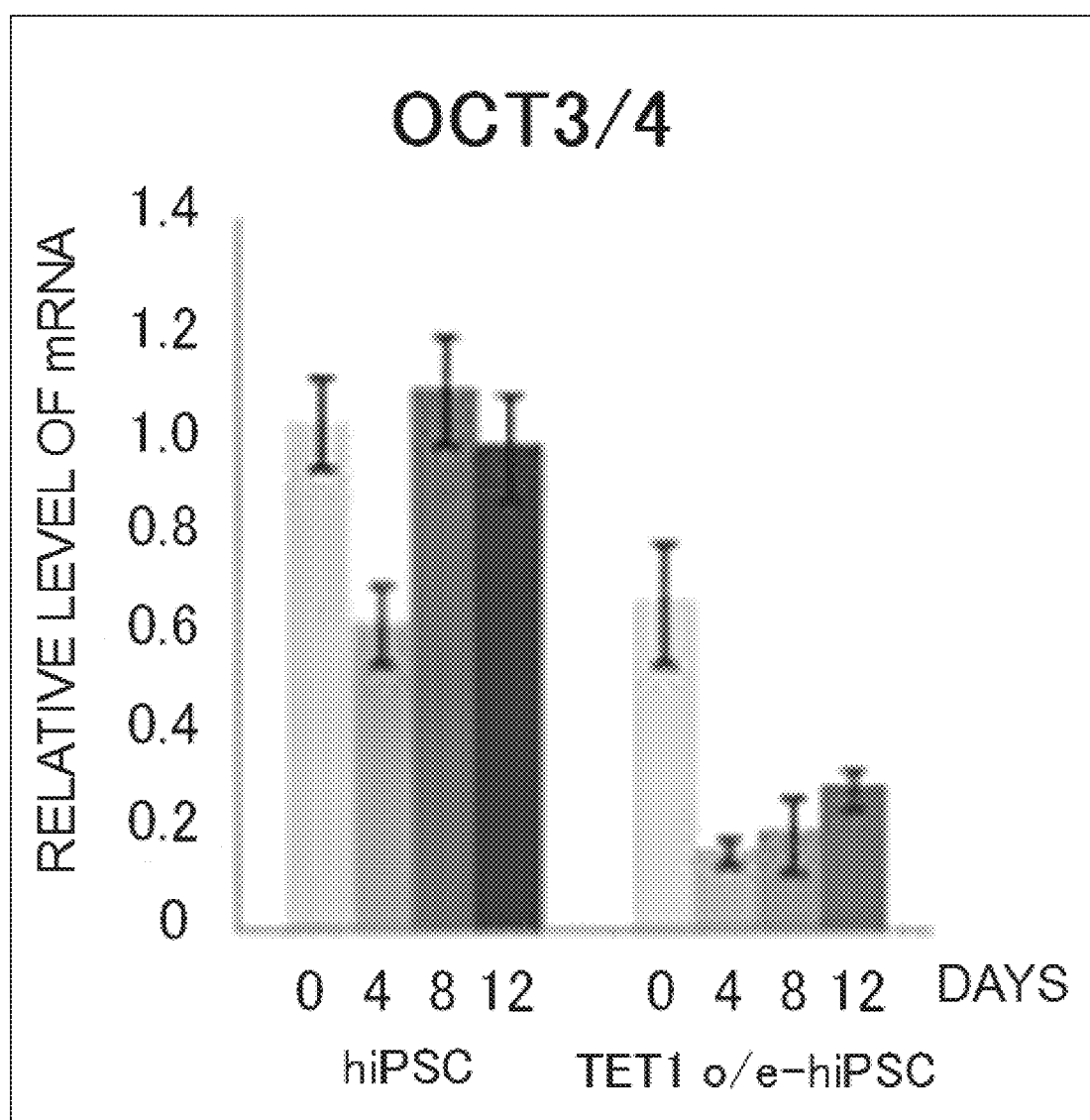
FIG. 12 The graph shows the time course of OCT3/4 mRNA expression during the neural induction of hiPSC and human iPS cell expressing N-terminally FLAG-tagged TET1 protein.
Figure 13:
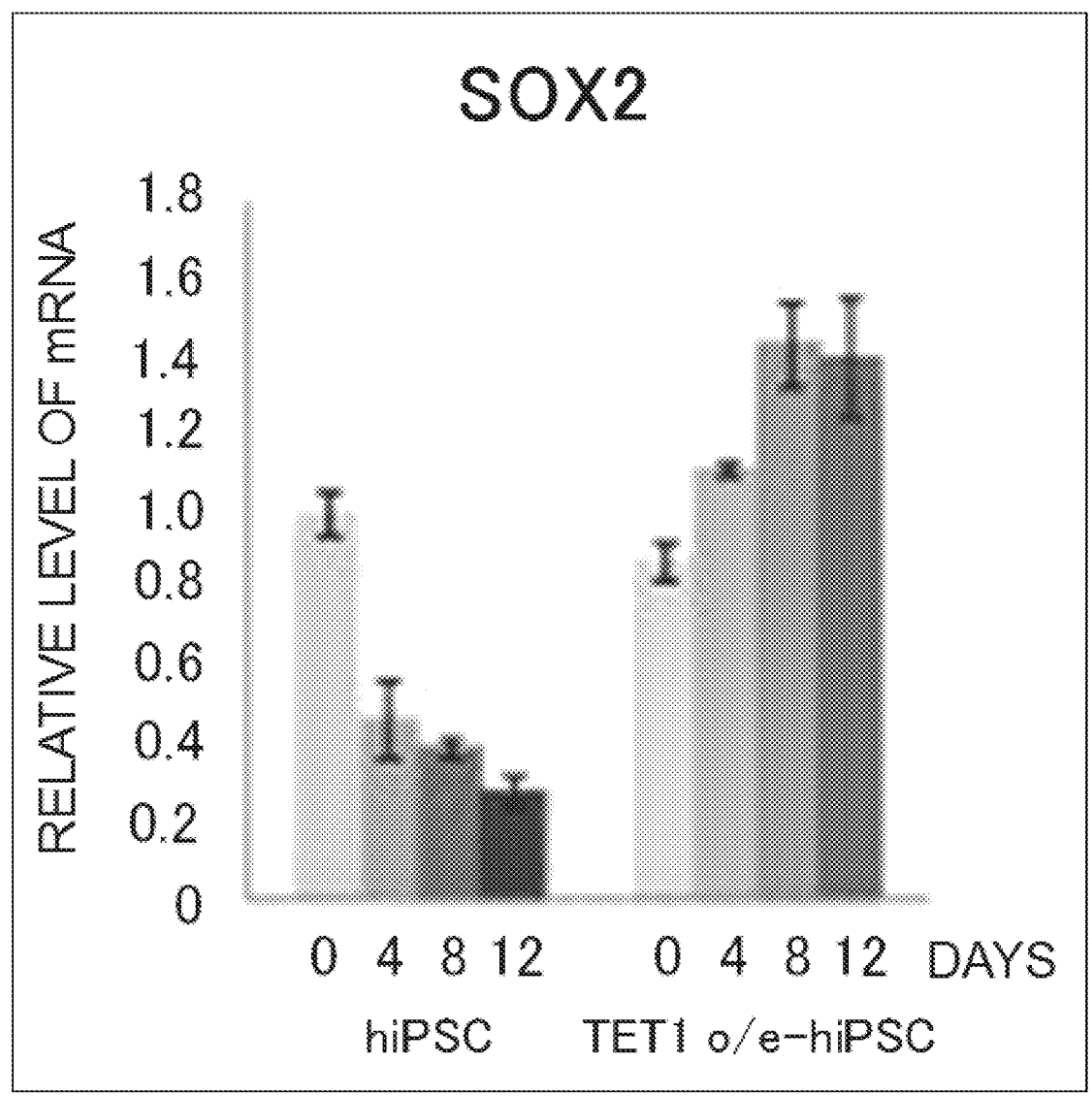
FIG. 13 The graph shows the time course of SOX2 mRNA expression during the neural induction of hiPSC and human iPS cell expressing N-terminally FLAG-tagged TET1 protein.
Figure 14:
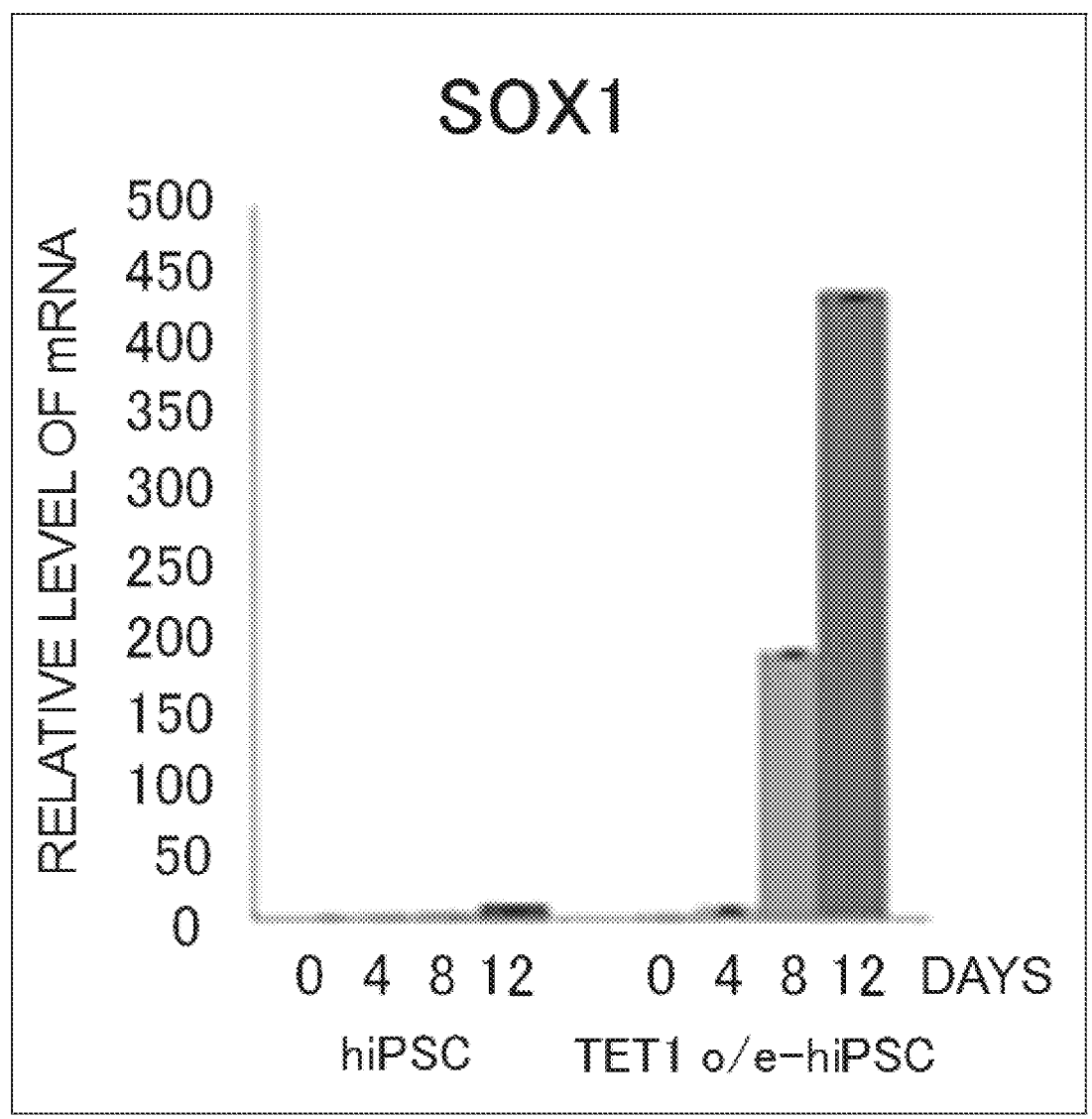
FIG. 14 The graph shows the time course of SOX1 mRNA expression during the neural induction of hiPSC and human iPS cell expressing N-terminally FLAG-tagged TET1 protein.
Figure 15:
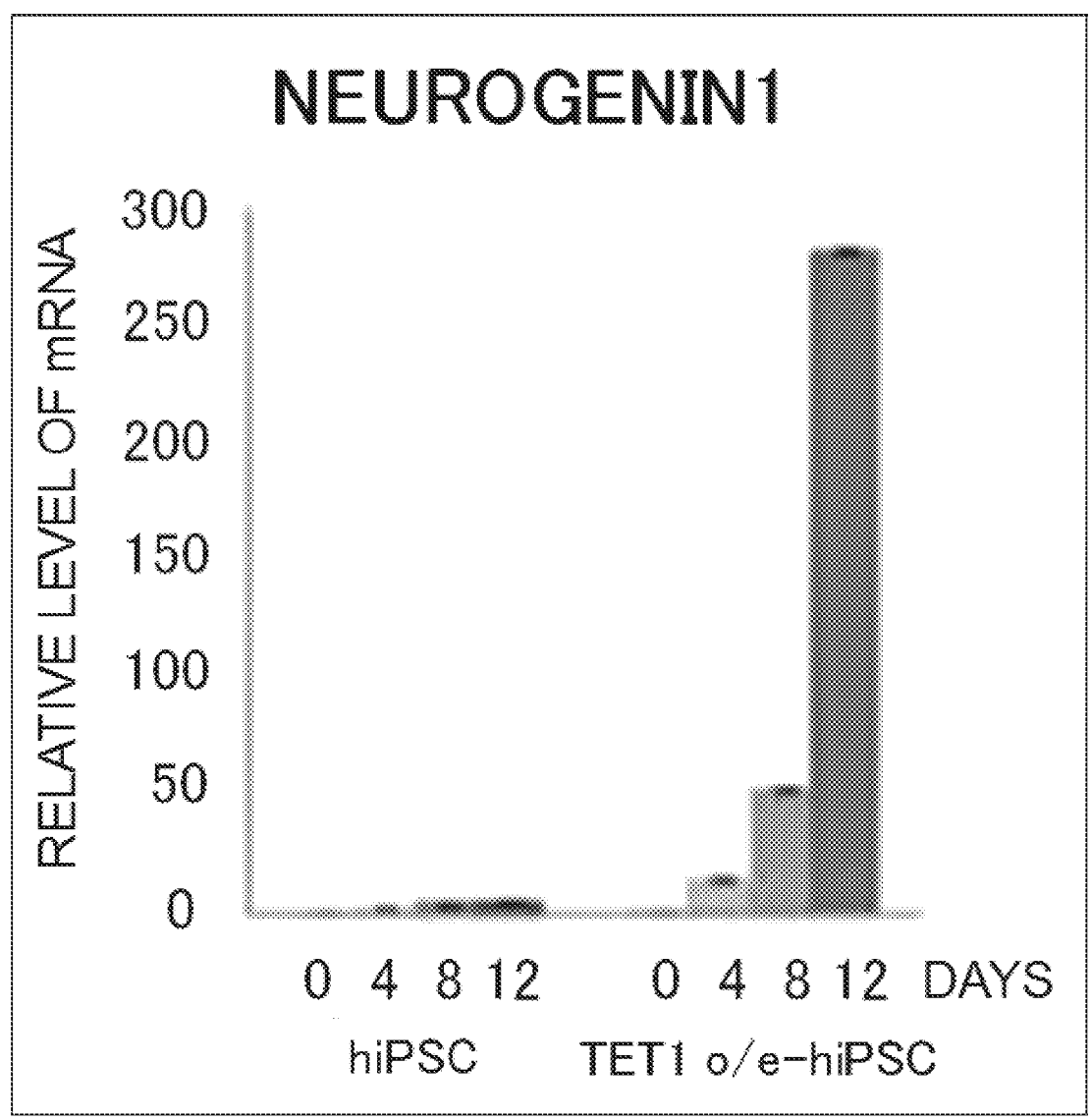
FIG. 15 The graph shows the time course of NEUROGENIN1 mRNA expression during the neural induction of hiPSC and human iPS cell expressing N-terminally FLAG-tagged TET1 protein.
Figure 16:
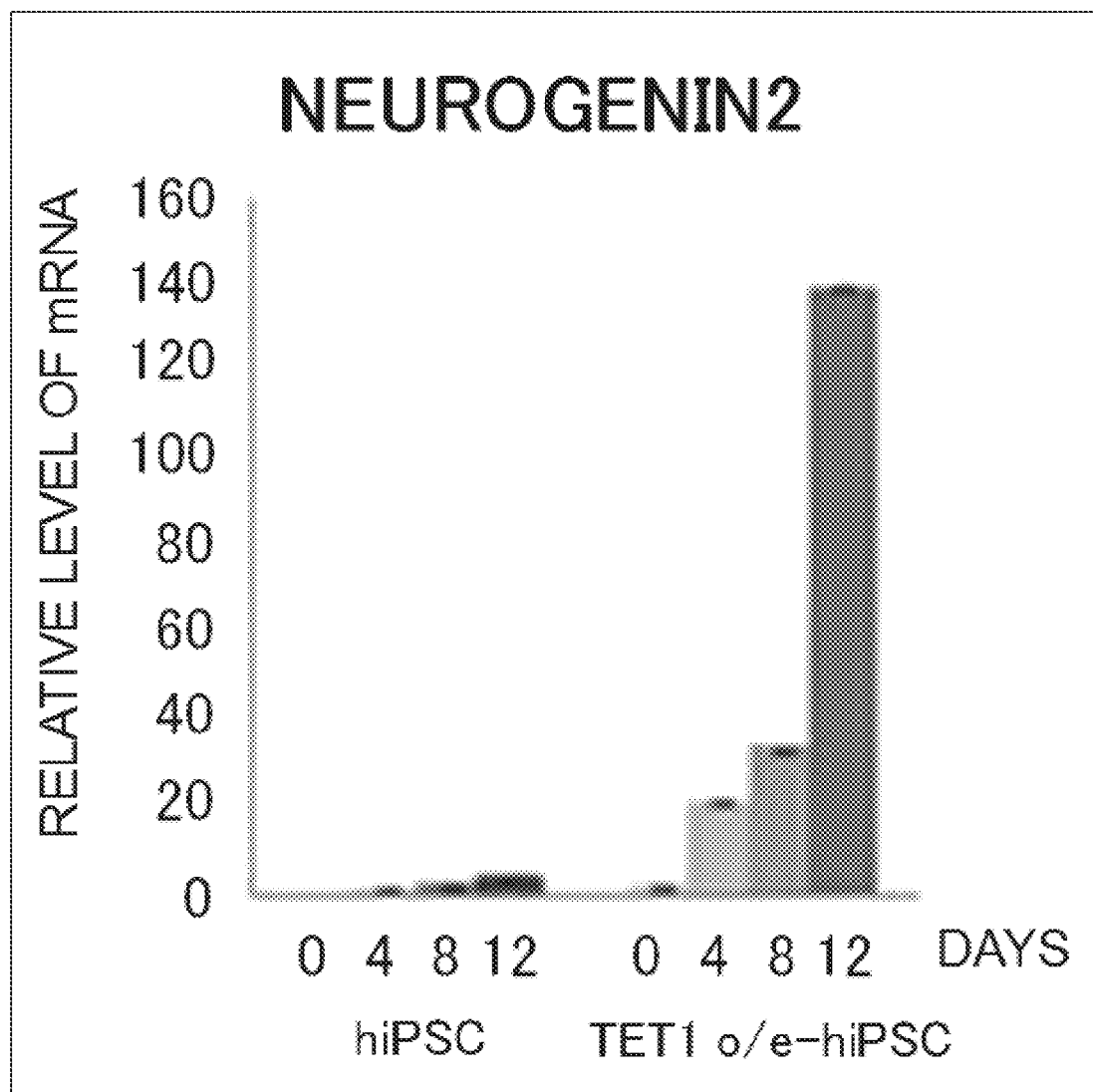
FIG. 16 The graph shows the time course of NEUROGENIN2 mRNA expression during the neural induction of hiPSC and human iPS cell expressing N-terminally FLAG-tagged TET1 protein.
Figure 17:
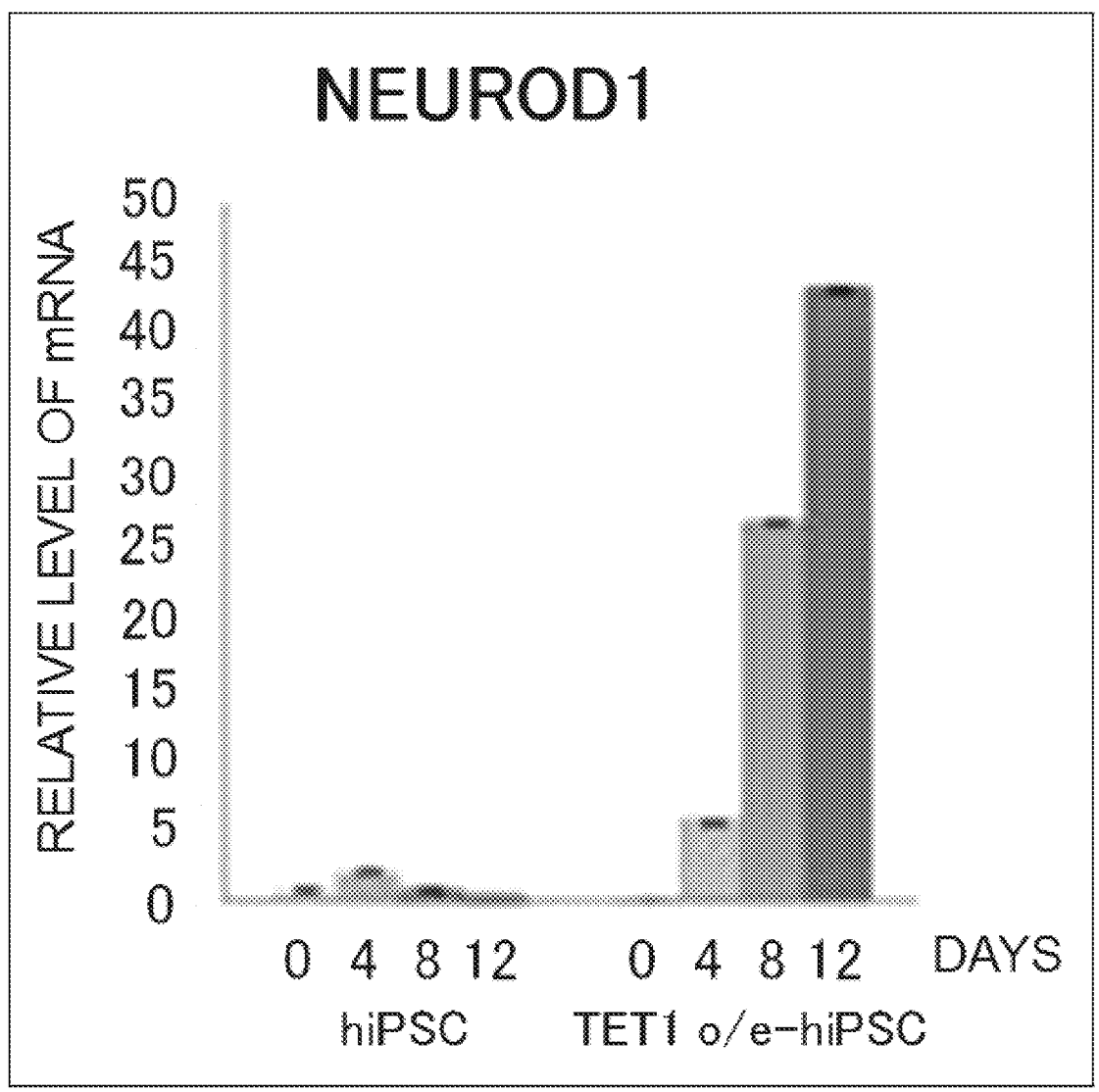
FIG. 17 The graph shows the time course of NEUROD1 mRNA expression during the neural induction of hiPSC and human iPS cell expressing N-terminally FLAG-tagged TET1 protein.
Figure 18:
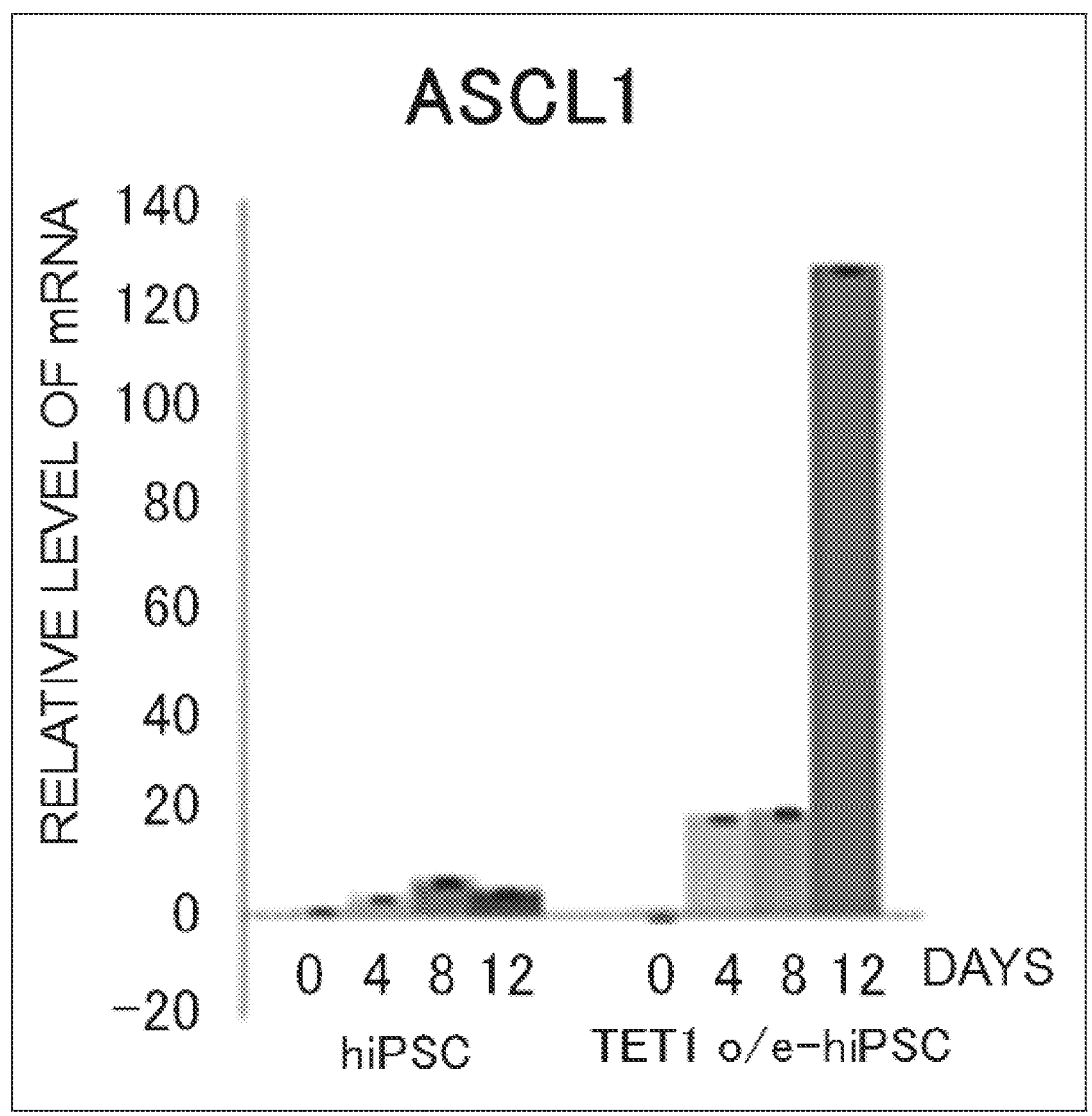
FIG. 18 The graph shows the time course of ASCL1 mRNA expression during the neural induction of hiPSC and human iPS cell expressing N-terminally FLAG-tagged TET1 protein.
Figure 19:
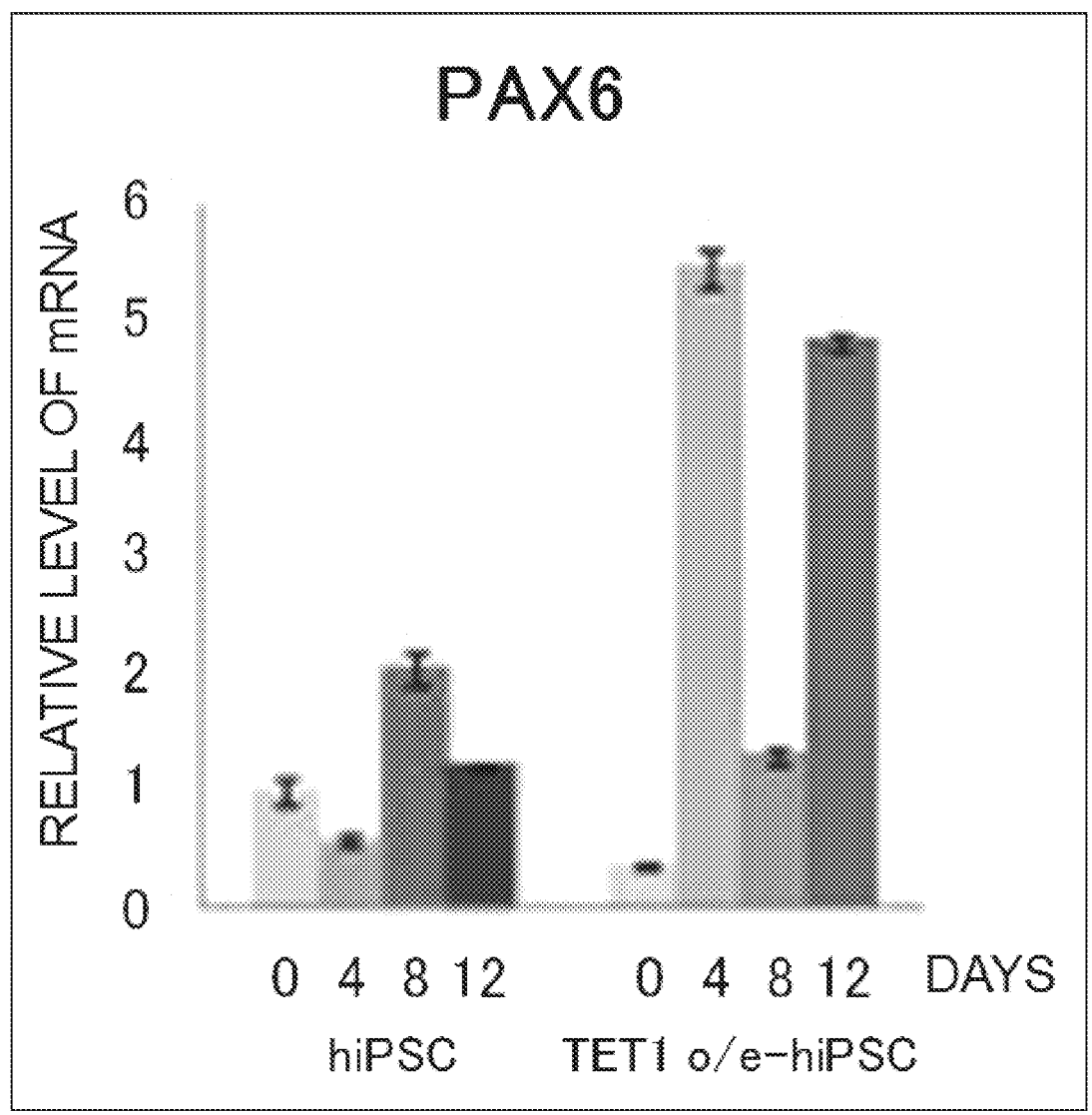
FIG. 19 The graph shows the time course of PAX6 mRNA expression during the neural induction of hiPSC and human iPS cell expressing N-terminally FLAG-tagged TET1 protein.
Figure 20:
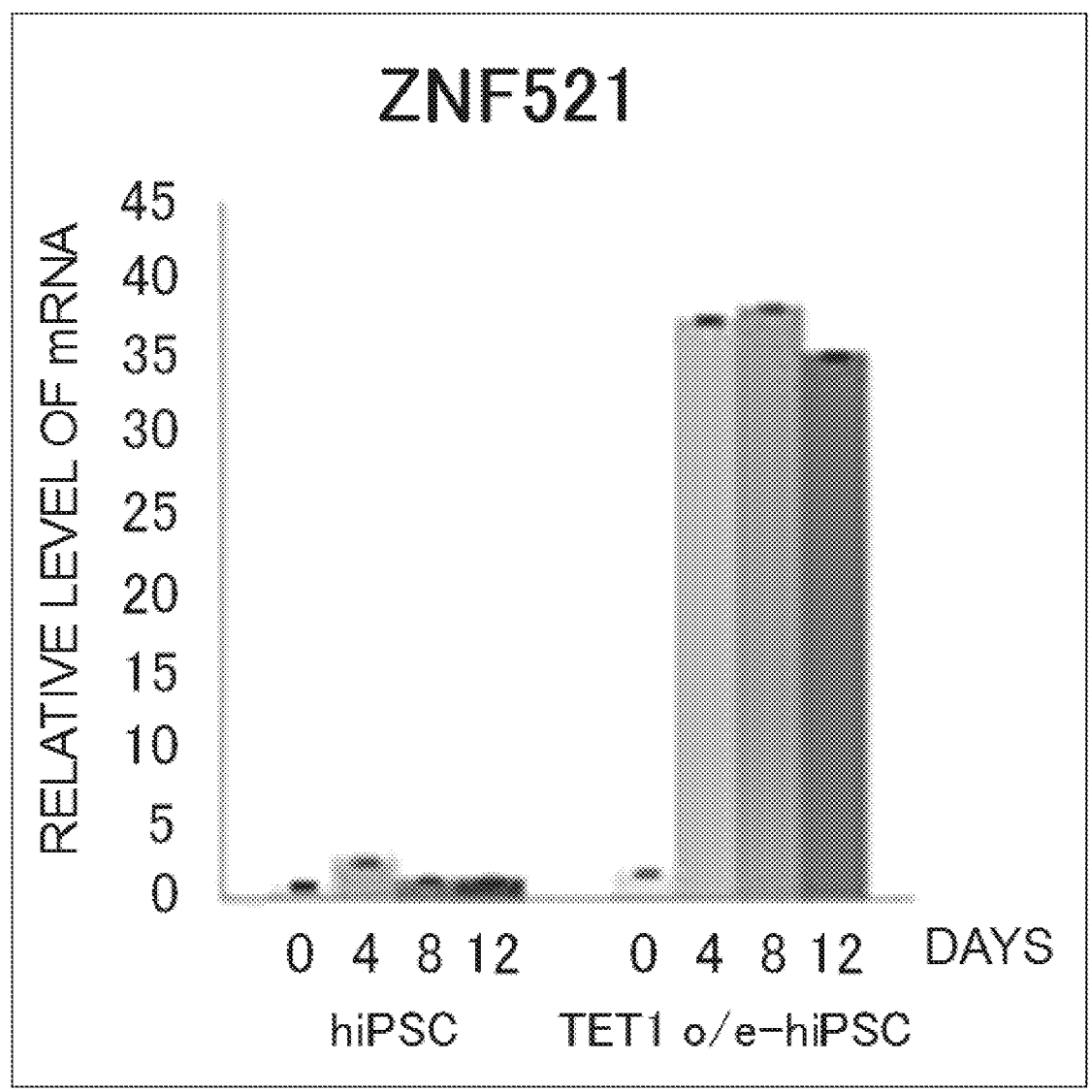
FIG. 20 The graph shows the time course of ZNF521 mRNA expression during the neural induction of hiPSC and human iPS cell expressing N-terminally FLAG-tagged TET1 protein.

As clearly shown in FIG. 8, the level of TET1 mRNA expression in TET1-hiPSC prior to differentiation (Day 0), when compared to the control hiPSC which only expresses the pCAG-IP vector alone, is more than four times and from this, one can deduce that a three-fold expression of the endogenous expression was attained from the transgene expression. Compared to this change, the expression levels of the factors which are believed to correlate to the self-renewality of PSCs at undifferentiated state such as OCT3/4, NANOG or SOX2 mRNA did not significantly differ between hiPSCs with or without TET1-overexpression (FIGS. 11-13; see data at Day 0).

Primed PSCs, which are supposed to be quasi-equivalent to epiblast-stage embryonic cells, are also supposed to have capacities to differentiation toward ectoderm or mesendoderm. To this end, interestingly, the expressivity of ectodermal differentiation markers (markers for neural differentiation: SOX1, NEUROGENIN1, NEUROGENIN2, NEUROD1, ASCL1, PAX6, ZNF521 and OTX2) did not differ between hiPSCs at their undifferentiated states regardless the presence or absence of TET1-overexpression (FIGS. 14-21; refer to Day 0 data).

Figure 22:
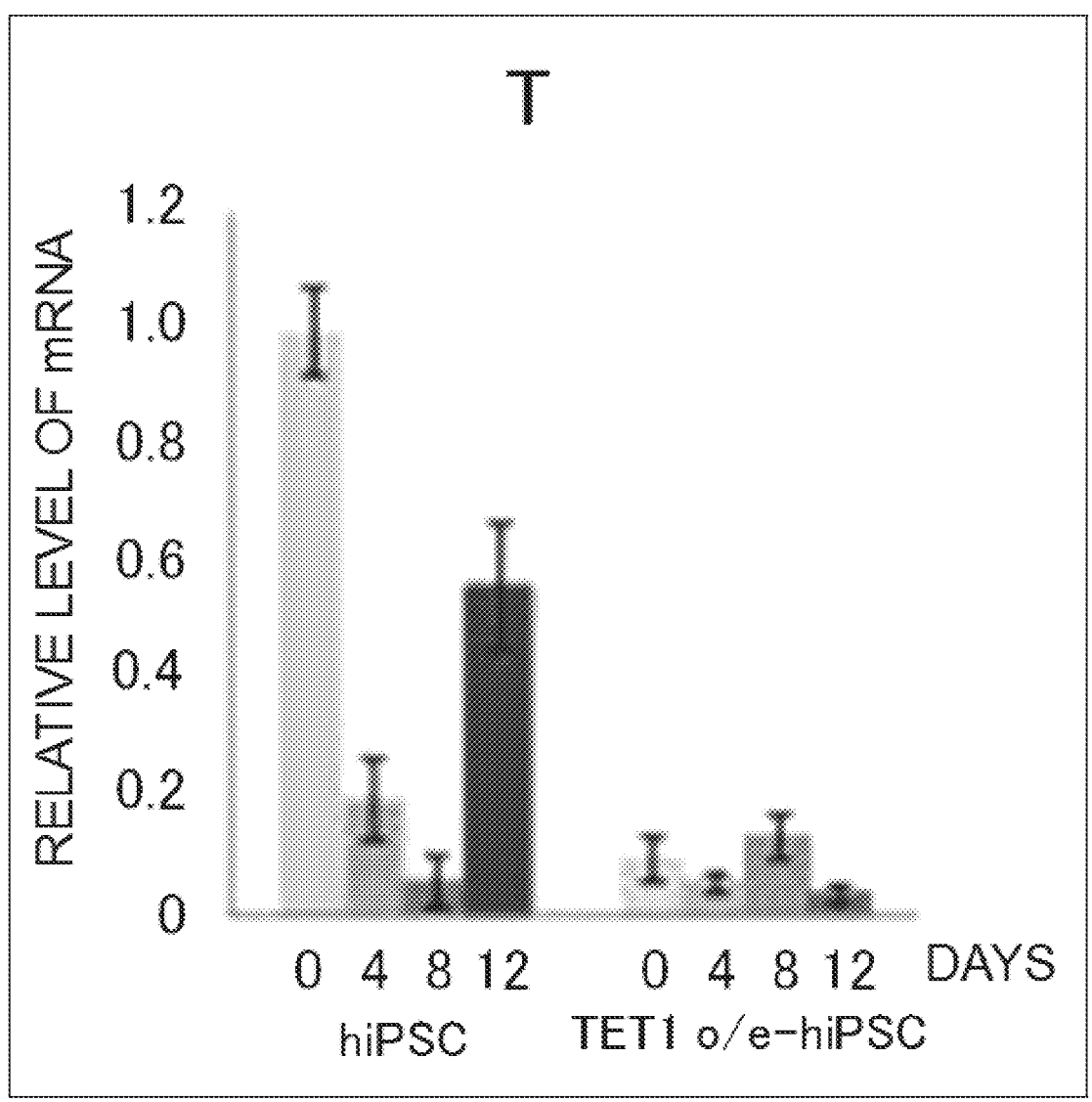
FIG. 22 The graph shows the time course of T mRNA expression during the neural induction of hiPSC and human iPS cell expressing N-terminally FLAG-tagged TET1 protein.
Figure 23:
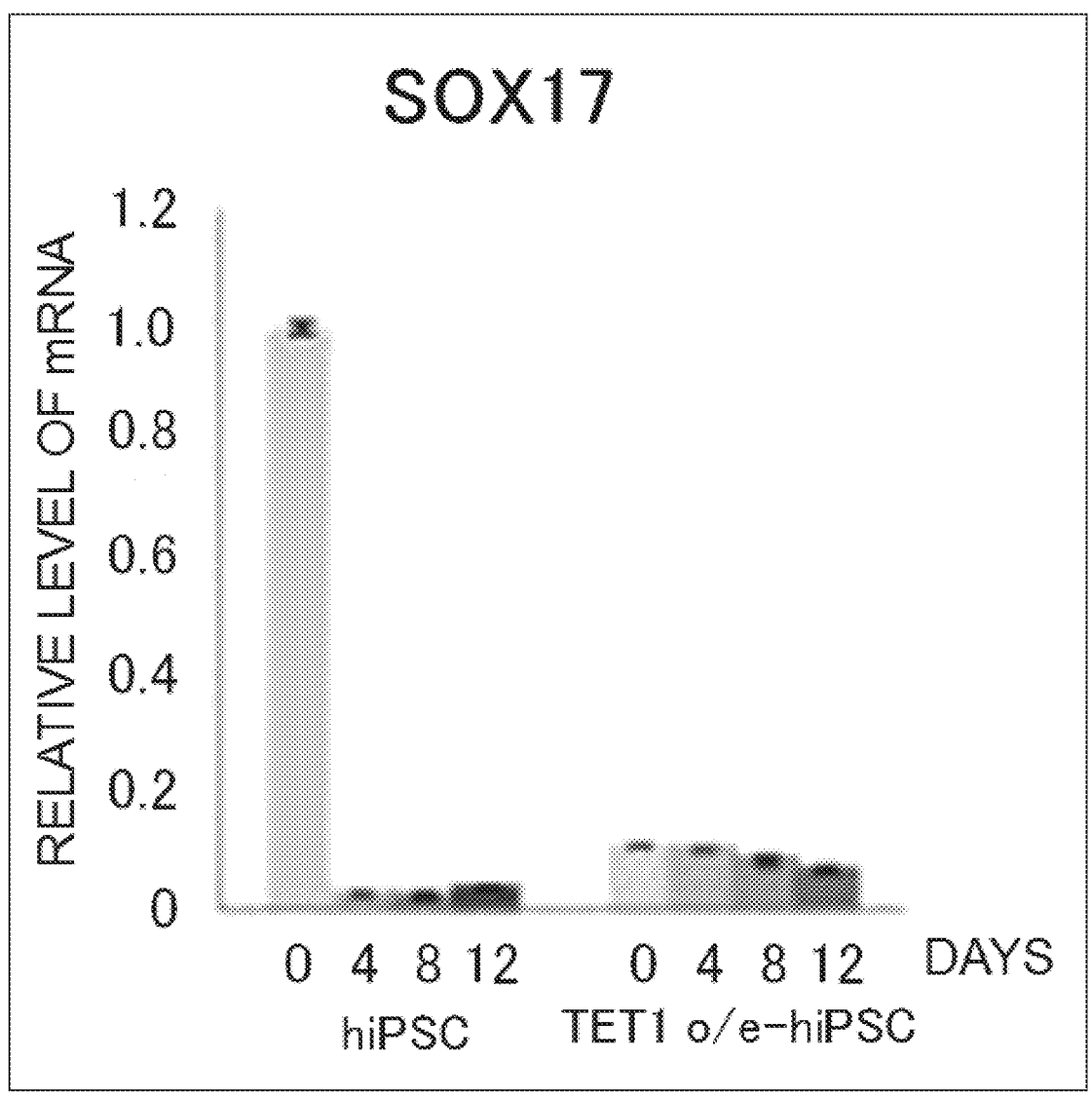
FIG. 23 The graph shows the time course of SOX17 mRNA expression during the neural induction of hiPSC and human iPS cell expressing N-terminally FLAG-tagged TET1 protein.

However, the expression levels of T and SOX17, markers for mesendoderm differentiation, differed significantly between hiPSCs with and without the TET1-overexpression. Whereas hiPSCs, where the mutant TET1 protein is not overexpressed, expressed these markers, TET1-hiPSCs which were maintained in an identical culture condition did hardly express these markers (FIGS. 22 and 23; see the data of Day 0).

It is generally believed that T or SOX17 marks that the cells are already differentiated and in principle, should not be expressed in stem cells which are supposed to be in an undifferentiated state. This is suggestive that in human iPS cells induced in a conventional method over-reacted toward Activin A, which mimics the mesendodermal inducer NODAL activity, and exited from their undifferentiated state to reach mesendodermal cell lineage characteristics. In other words, one can deduce from these facts that the conventional human PSCs bear propensity toward mesendodermal differentiation and in the strict sense of the word, are not "undifferentiated".

Working Example 6

\<Validating Neural Inducibility of TET1-hiPSC: Part 1\>

Evolutionarily conserved phenomena in the early development of vertebrates are that the cell differentiation is set to differentiate toward neural cells by default (default neurogenesis; Levine A J. et al., Dev. Biol., 2007, vol. 308, 247-256.). If early developing cells are dissociated in medium which does not have any inductive signaling molecules, the cells are to differentiate toward neurons. Mouse ES cells were known to follow this default neurogenesis rule (Smukler S R. et al, J Cell Biol, 2006, vol. 172, 79-90). The present inventor has also previously developed a protocol to efficiently induce neural cells from mouse ES cells based on this default pathway idea (Bouhon I A. et al, Brain Res Bull, 2005, vol. 68, 62-75). To date, however, the default status of the human PSCs totally remained to be a mystery.

In order to test the differentiation capacity of TET1-hiPSC, similar to a condition which would allow a mouse ES cell to follow the default neurogenesis, the inventors analyzed their differentiation directions. To this end, as previously mentioned, TET1-hiPSC and hiPSC were maintained in parallel in KFA, and then cultured in a developmentally neutral CDM medium for 4 days, followed by a condition where Activin A/Nodal was inhibited for neurogenesis. The default differentiation was followed up to 12 days and cell samples were collected every 4 days to analyze the dynamics of transcription factors' mRNA expression. The results were shown in FIGS. 8 to 23.

During neural differentiation, OCT3/4 and NANOG expression ought to be swiftly down-regulated during the process (Zheng W. et al, Cell Stem Cell, 2012, vol. 10, 440-454). Relevant to this, as clearly shown in FIGS. 11 and 12, during the first four days of differentiation, TET1-overexpression seemed to strongly impact the expressivity of OCT3/4 and NANOG Especially for NANOG, its expression dropped down below to one-hundredth within the first four days of differentiation in TET1-hiPSCs. In sharp contrast, the conventional human iPSCs (hiPSCs) failed to down-regulate these factor expressions but up-regulated when following the default differentiation. Although not shown in a Figure, in hiPSCs, the OCT3/4 and NANOG expressions went down gradually over a period of one month but to only one-tenth of the original expression values.

As shown in FIG. 13, SOX2 expression in differentiating TET1-hiPSC was gradually up-regulated after the beginning of differentiation induction. SOX2 represents a transcription factor whose expression is observed in the undifferentiated PSC as well as being an essential factor for the development of the nervous systems. Therefore, one can deduce that the consistent expression of SOX2 in TET1-hiPSC during its course of differentiation into the nervous systems might have been a driver for the neural differentiation. Compared to this, in hiPSC, SOX2 expression went down.

Moreover, as clearly shown in FIGS. 14 to 21, we could observe marked up-regulation of neural markers in TET1-hiPSCs (SOX1, NEUROGENIN1, NEUROGENIN2, NEUROD1, ASCL1, PAX6, ZNF521 and OTX2). In contrast, such marker expressivities were not observed for hiPSCs. Especially, the expression of SOX1 in differentiating TET1-hiPSCs at Day 12 of differentiation was 60 times than that of hiPSCs which do not express the TET1 protein. Judging from these, the overexpression of the mutant TET1 into human iPS cells renders these cells 60 times more amenable to neural differentiation.

Figure 21:
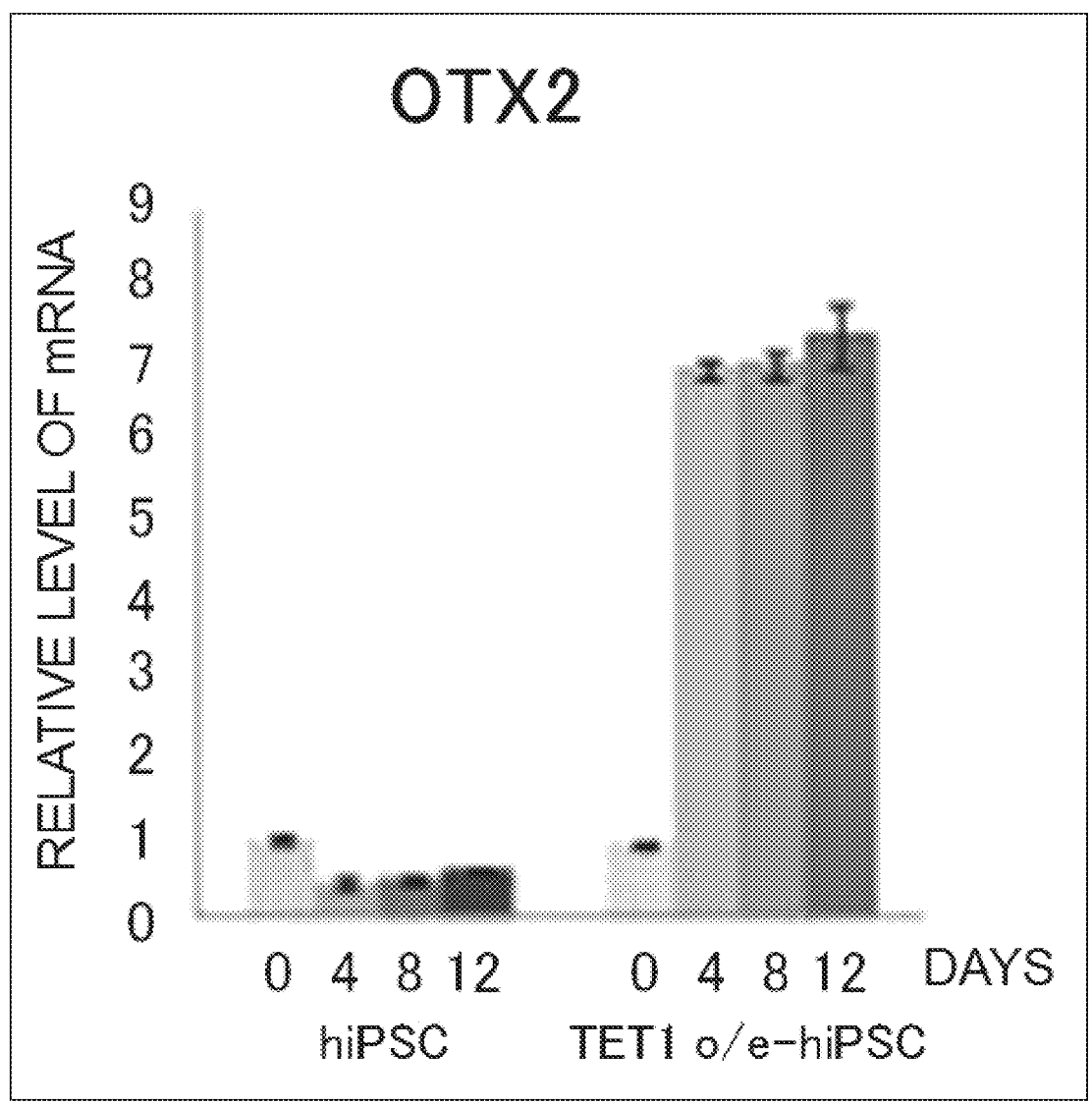
FIG. 21 The graph shows the time course of OTX2 mRNA expression during the neural induction of hiPSC and human iPS cell expressing N-terminally FLAG-tagged TET1 protein.

It is also established that the neurons induced through the default neurogenesis pathway bear the phenotypes of forebrain neurons. In close relation, as shown in FIG. 21, the mutant TET1 protein overexpression clearly allowed a marked induction of the forebrain marker OTX2. This result is therefore supportive of the fact that the mutant TET1 protein overexpression makes the human iPSCs conducive for default neurogenesis toward forebrain neurons.

As mentioned above, TET1 protein overexpression also allowed a swift down-regulation of NANOG. NANOG-down-regulation, not only for swift neural induction, is known to be prerequisites for proper differentiation into multiple cell lineages. Therefore, although here in the Working example 6 we focused on the effects of the mutant TET1 protein during neural (ectodermal) differentiation, the effects of the methods or the proteins in the present invention are not restricted to ectodermal differentiation but have larger impacts as will be shown in the Working examples 8. That is to say that the swift down-regulation of NANOG by the overexpressed TET1 protein is mechanically linked to a release of differentiation resistance and therefore operates in enhancing the pluripotency of the PSCs.

Working Example 7

<Validating Neural Inducibility of TET1-hiPSC: Part 2>

Figure 24:
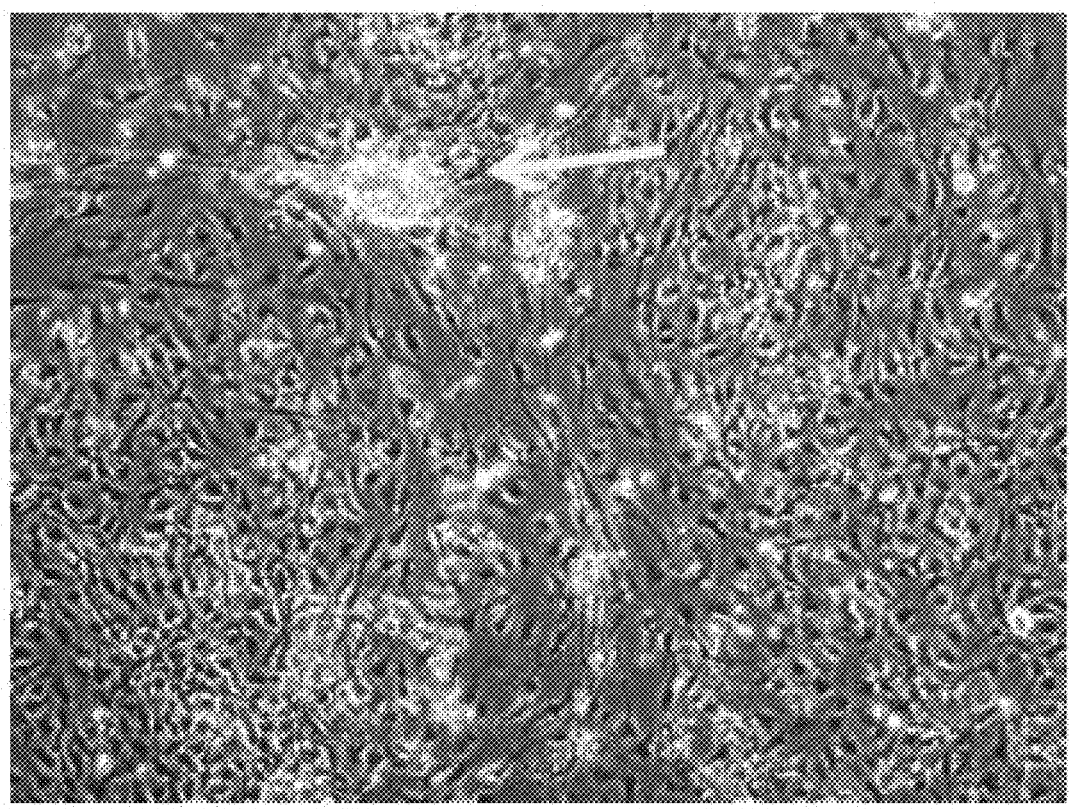
FIG. 24 A micrograph of human iPS cells plated onto laminin-coated culture dishes after 12 days of neural induction. The picture was taken 14 days after the plating of the induced cells. The arrow in the picture shows the position where an aggregate of neuron's cell somata were formed.

Here, the inventors have plated down the neural progenitor cells induced in the Working example 6 onto a laminin-coated culture dishes to observe their maturation to neurite-bearing mature neurons. The results are shown in FIGS. 24 and 25.

Figure 25:
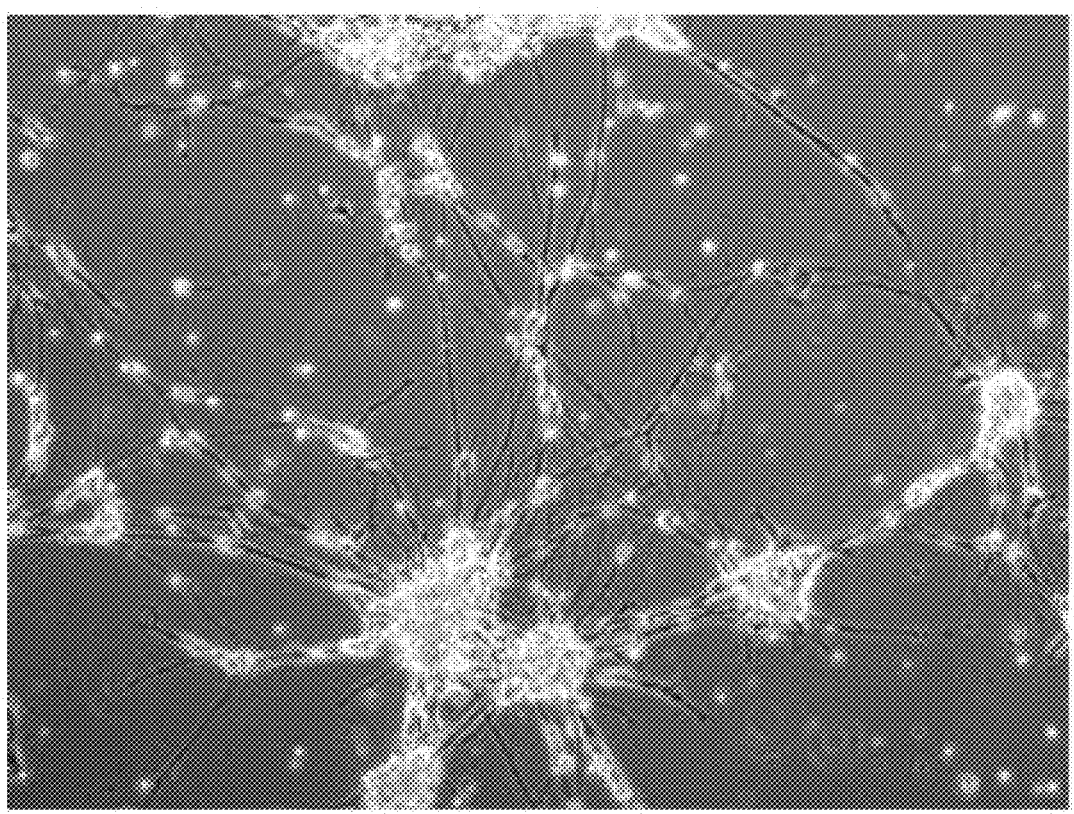
FIG. 25 A micrograph of human iPS cell expressing N-terminally FLAG-tagged TET1 protein plated onto laminin-coated culture dishes after 12 days of neural induction. The picture was taken 14 days after the plating of the induced cells.
Figure 26:
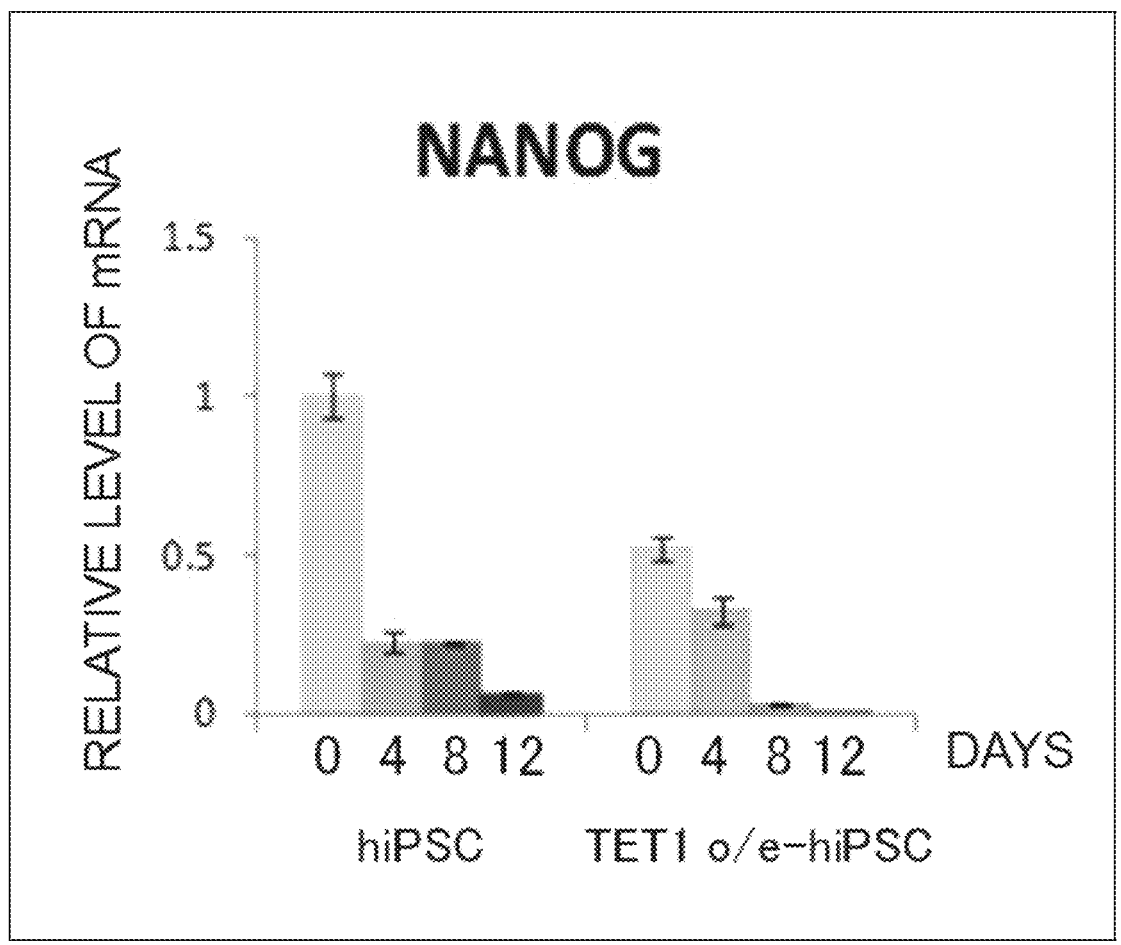
FIG. 26 The graph shows the time course of NANOG mRNA expression during the definitive endoderm induction of control human iPS cell (depicted as "hiPSC" in the figure) and human iPS cell expressing N-terminally FLAG-tagged TET1 protein ("TET1o/e-hiPSC"). The vertical axis represents a relative level obtained when the expression level in the human iPS cells before the differentiation induction is taken as 1. The horizontal axis of the graph represents the days after the commencement of definitive endoderm induction (also in FIGS. 27 to 29).
Figure 27:
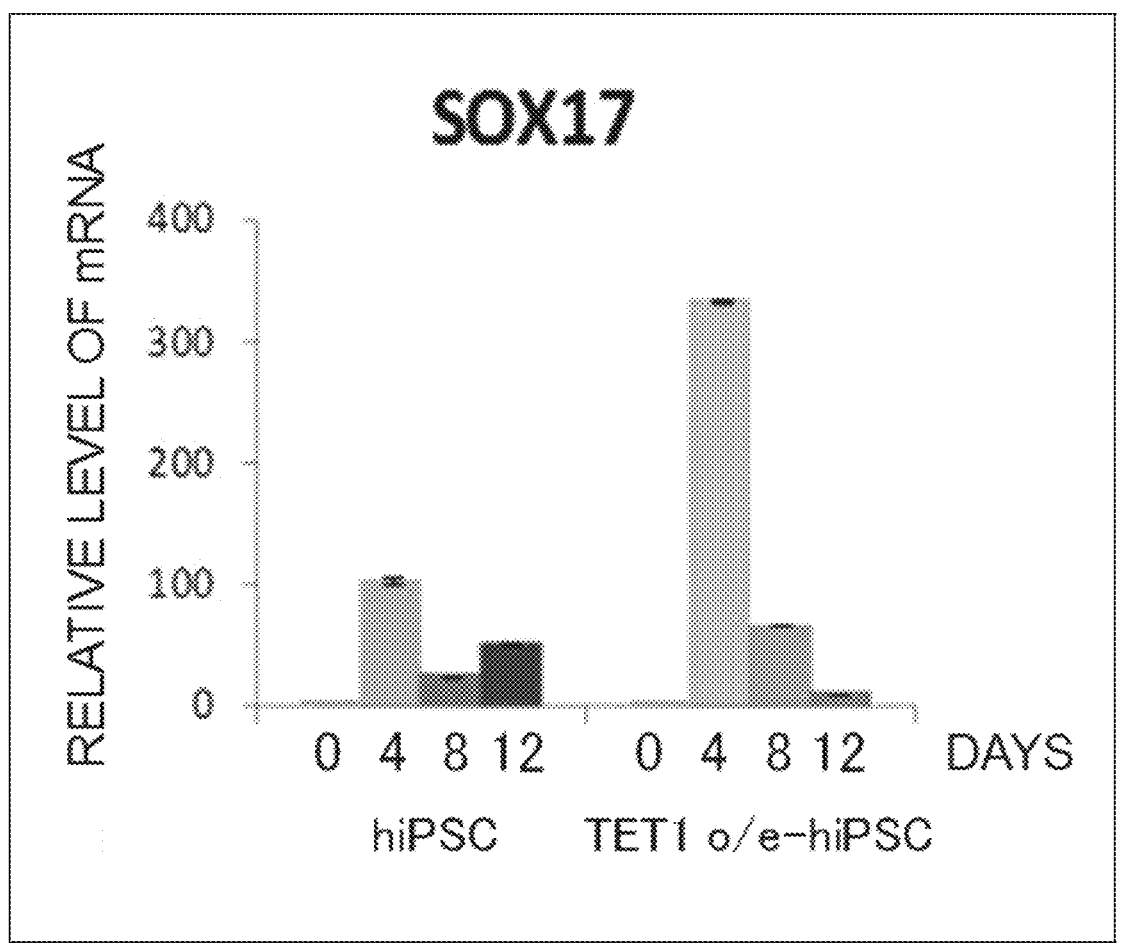
FIG. 27 The graph shows the time course of SOX17 mRNA expression during the definitive endoderm induction of hiPSC and human iPS cell expressing N-terminally FLAG-tagged TET1 protein.
Figure 28:
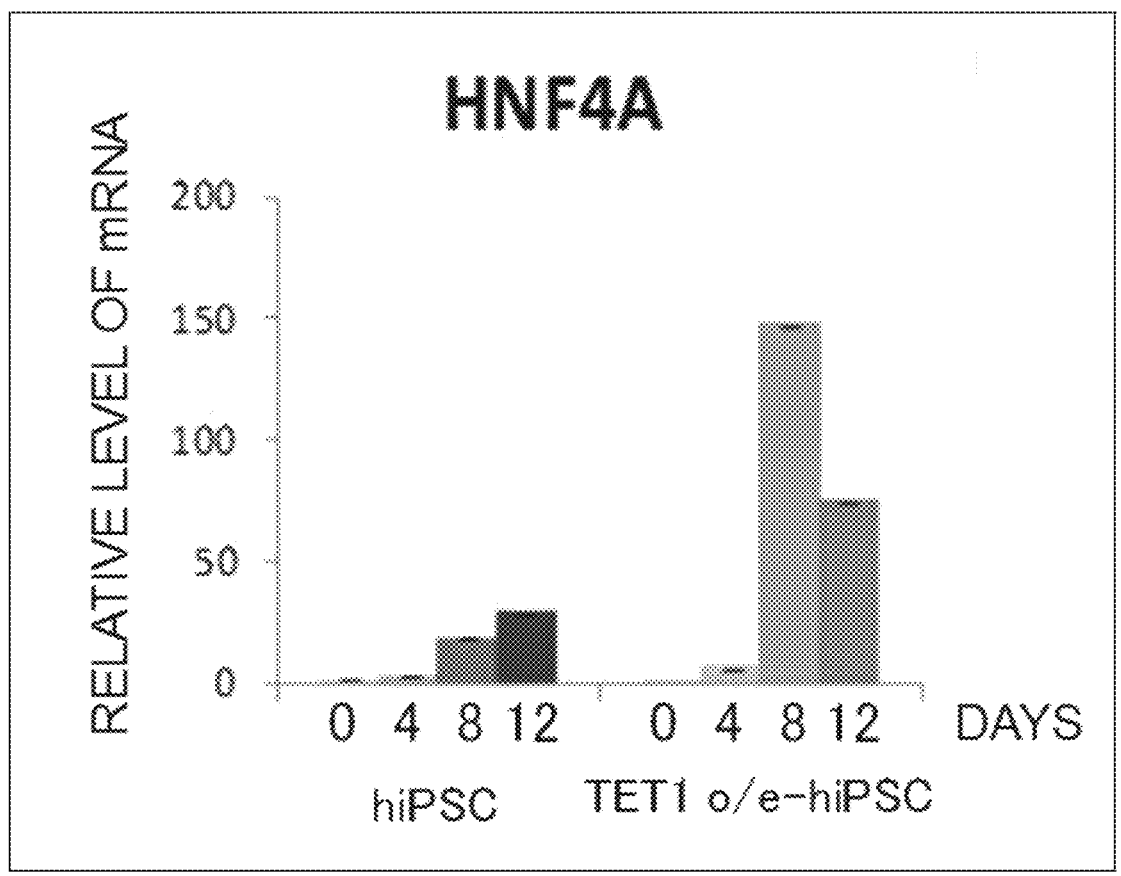
FIG. 28 The graph shows the time course of HNF4A mRNA expression during the definitive endoderm induction of hiPSC and human iPS cell expressing N-terminally FLAG-tagged TET1 protein.
Figure 29:
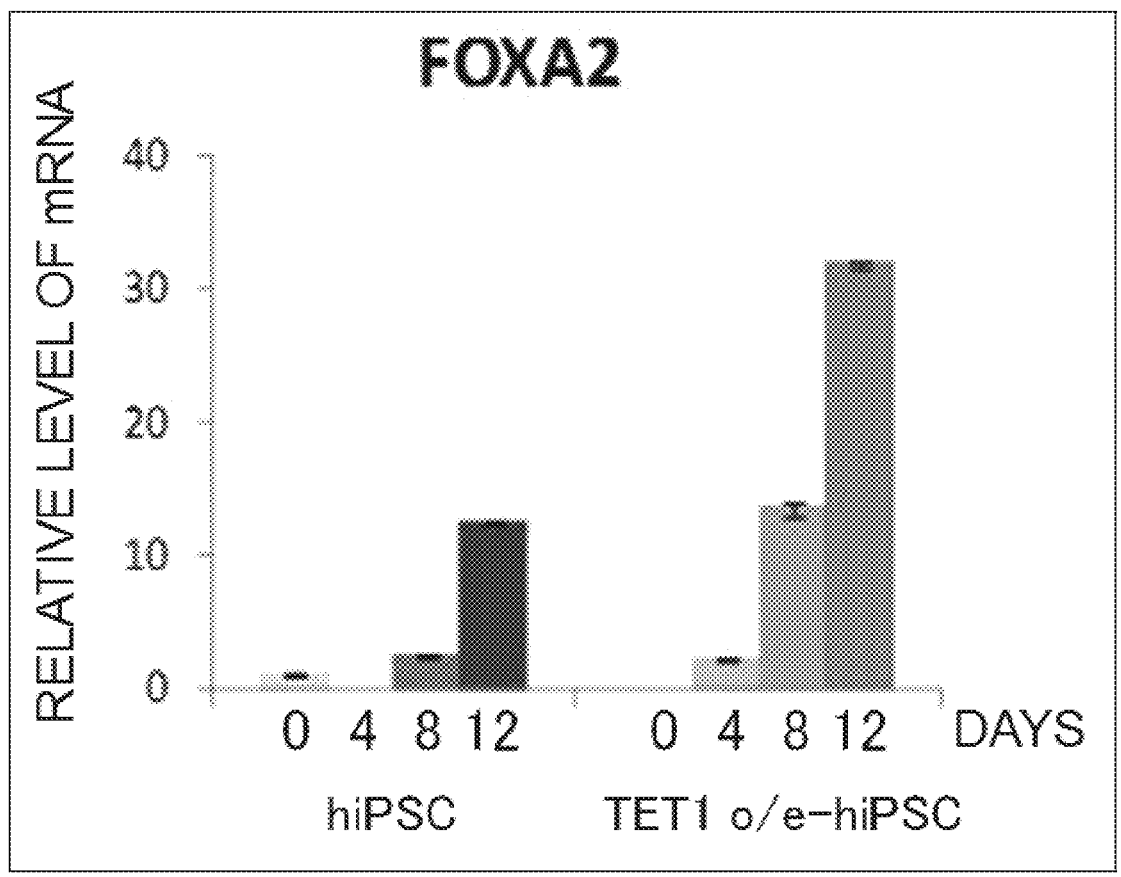
FIG. 29 The graph shows the time course of FOXA2 mRNA expression during the definitive endoderm induction of hiPSC and human iPS cell expressing N-terminally FLAG-tagged TET1 protein.

As clearly shown in FIG. 25, when TET1-hiPSCs were let to differentiate to neurons, a nearly 100% of the cells turned to neurons and no other cells were discernible in the culture. In contrast, from the conventional human iPS cells (hiPSCs), as shown in FIG. 24 by an arrow, although some neuron-aggregates were discernible, the culture became overwhelmed by growing non-neural cells leaving the proportion of neurons in a dish fairly low (FIG. 24).

Working Example 8

<Validating TET1-hiPSCs for Endodermal Differentiation>

The early mammalian development in its simplified form is a binary cell lineage choice between ectoderm which will eventually diversify into neural or dermal tissues or alternatively mesendoderm which will later diversify into mesoderm (blood, muscle, skeletal tissues) and endoderm (lung, digestive tracts). Therefore, the inventors sought to investigate the differentiation capacity to endoderm by TET1 in addition to its effect to the ectodermal differentiation.
<Endoderm Differentiation of Human iPS Cells>

Among endodermal organs, the pancreas which is related to diabetes mellitus and the liver which is the central organ for metabolism and detoxification have attracted major medical concerns and as a consequence, developments for protocols deriving these organs are under intensive investigation. The inventors have therefore modified a differentiation protocol originally devised for inducing the insulin-secreting pancreatic 13 cells (D'Amour K A, Nat Biotech, 2006, vol. 24, 1392-1401) to execute the differentiation of the definitive endoderm cells.

The modifications made to the original protocol are as follows. The basic medium RPMI used in the paper was replaced to CDM medium which the inventors have used for differentiating neurons; Wnt3a recombinant proteins were replaced with a small molecule compound CHIR99021 which also transduces through the same signaling pathway; and Cyclopamine (a hedgehog signaling antagonist) which was used to derive pancreatic lineages was omitted in the example here. The last modification is expected to orient human iPS cells toward a liver cell lineage instead.

Below, this differentiation method is explained for each stage.

Stage 1: Determination of the Definitive Endoderm (4 Days)

Human iPS cells (human iPS cell line overexpressing the mutant TET1 protein (TET1-hiPSC) and YMhiPSC058sbc6 subclone as described in the Working example 3) were routinely maintained for undifferentiated condition in KFA medium and passaged by trypsin-dissociation. After adequate treatment of trypsin, its activity was stopped using trypsin inhibitor. About 2,000 single cells obtained in this manner were individually seeded into separate non-attaching wells (Nunclon Sphera, Thermo) in CDM medium supplemented with Activin A (100 ng/ml), CHIR99021 (3 µM) and ROCK inhibitor (Y27632; 10 µM) and let them to form cell spheres. 48 hours later, the medium was changed to fresh CDM supplemented with Activin A (100 ng/ml). After another 48 hours, the cells are supposed to be determined to the definitive endoderm stage (stage marker: SOX17).

Stage 2: Primitive Gut Formation (4 Days)

Once using the differentiation procedure, cells which have fixed their cell lineage into endoderm are formed, and these cells are further induced toward the primitive anlage of the digestive organs called primitive gut. The cell spheres collected from the Stage 1 above, are now seeded into CDM supplemented with FGF10 (50 ng/ml). After 4 days of culture, the cells are supposed to differentiate into primitive gut cells (marker: HNF4A).

Stage 3: Foregut Formation (4 Days)

The descendants of the primitive gut form rostrally the thyroid and the lungs and more caudally the digestive organs. Among these, the common ancestors for all digestive organs are the foregut cells. The spheres collected from the Stage 2 will be passed into fresh CDM medium supplemented with FGF10 (50 ng/ml) and all-trans retinoic acid (2 µM) and left for additional 4 days. As a result, cells are supposed to acquire foregut characteristics (marker: FOXA2).

The conventional human iPS cells and TET1-hiPSCs were in parallel processed using the differentiation protocol mentioned above and RNA samples were collected every 4 days. The collected RNAs were used as templates for qPCR to analyze the markers of each differentiation stage described above. Moreover, NANOG expression was also monitored to assess the undifferentiated status of the cells. The obtained results are shown in FIGS. 26 to 29.

The conventionally induced human iPS cells can also be differentiated toward endoderm at least to some degree as shown in FIGS. 26 to 29. In contrast, from the TET1-hiPSCs, we could clearly observe a marked down-regulation of NANOG together with an eminent up-regulation of the endodermal markers (SOX17, HNF4A and FOXA2). Collectively from these marker expression analyses, one can deduce that TET1-iPSCs, in comparison to conventionally made iPSCs, have roughly 3-time enhanced differentiation capability toward the endoderm lineages. Therefore, in addition to the enhanced differentiation efficacy for ectoderm as described above, the differentiation efficacy toward endoderm of a PSC can also be enhanced by the introduction of the mutant TET1 protein.

Working Example 9

<Validation of the Mutant TET1 Proteins>

As described above, the inventors so far have exploited an N-terminal FLAG tagged TET1 protein (full length) as their mutant TET1 protein and observed its effects. Now, they are exploring here for another illustrative embodiment for their mutant TET1 protein which is equally capable of enhancing the differentiation efficacy of PSCs as will be shown below: this alternative embodiment is the first, N-terminal 670 amino acids of the wild-type TET1 where its second amino acid from the N-terminus was changed from serine to glycine and then fused a GFP tag (#94) as shown in FIG. 6.

First, four different human iPS cell lines were prepared as follows.

TET1o/e: YMhiPSC058sbc6 subclone (the mutant TET1 introduced hiPSCs in the Working example 3) which was introduced with the N-terminally FLAG-tagged full length TET1 protein

93: YMhiPSC058sbc subclone which was introduced with the N-terminal 670 amino acids of the wild-type TET1 which is fused to a Tag-GFP protein as shown in FIG. 6 #94: YMhiPSC058sbc subclone which was introduced with the N-terminal 670 amino acids of the wild-type TET1 where its second amino acid from the N-terminus was changed from serine to glycine as shown in FIG. 6 pCAG-IP: YMhiPSC058sbc Subclone which was Introduced with a Mock Vector (pCAG-IP) to Acquire the Antibiotics Resistance (Serving as Control Cell Line)

As shown in the Working example 3, #93-, #94-, and pCAG-IP were prepared by constructing pCAG-IP vector encoding each mutant TET1 expressing protein or pCAG-IP (mock vector) and introducing them into YMhiPSC058sbc6 subclone cells using Nucleofector, and thereby, drug-resistant clones were collected.

These iPS cell lines were processed according to the aforementioned neural differentiation protocol and marker expression was evaluated for 8 days of differentiation. The results are shown in FIGS. 30 to 32.

Figure 30:
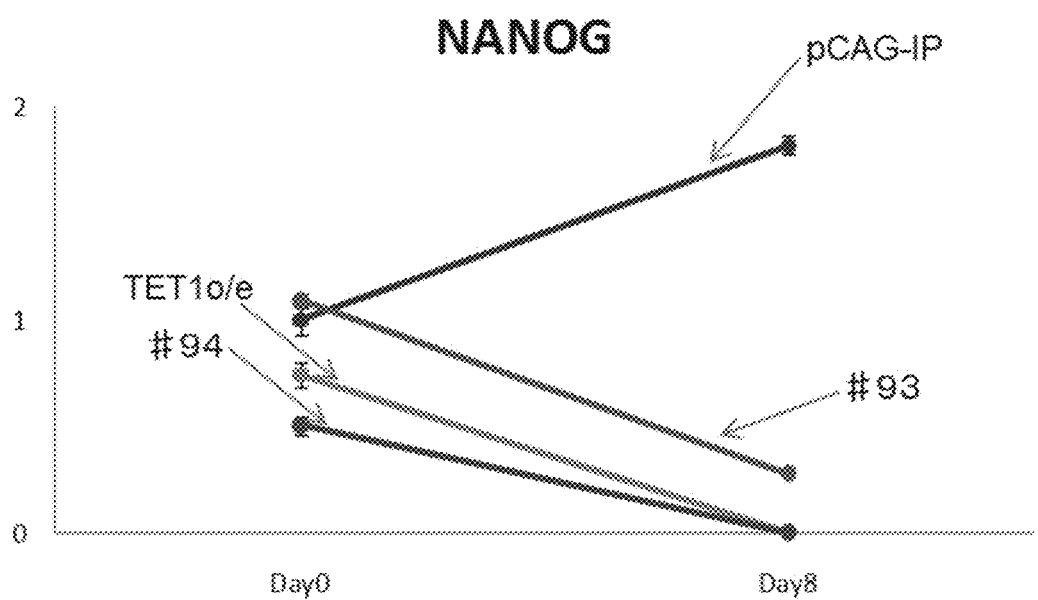
FIG. 30 The graph shows the time course of NANOG mRNA expression during the neural induction of human iPS cell bearing various transgenes: a mock vector expressing human iPS cell (pCAG-IP), human iPS cell expressing a fusion protein of the N-terminal portion of the human TET1 protein (the protein consisting of 670 amino acids) fused to GFP (#93), human iPS cell expressing a fusion protein of the N-terminal portion of the human TET1 protein (the protein consisting of 670 amino acids) with the second amino acid serine converted to glycine, fused to GFP (#94), and human iPS cell expressing N-terminally FLAG-tagged TET1 protein (full-length) ("TET1o/e-hiPSC"). The vertical axis represents a relative level obtained when the expression level in pCAG-IP before the differentiation induction is taken as 1. The horizontal axis of the graph represents the days after the commencement of neural induction (also in FIGS. 31 and 32).
Figure 31:
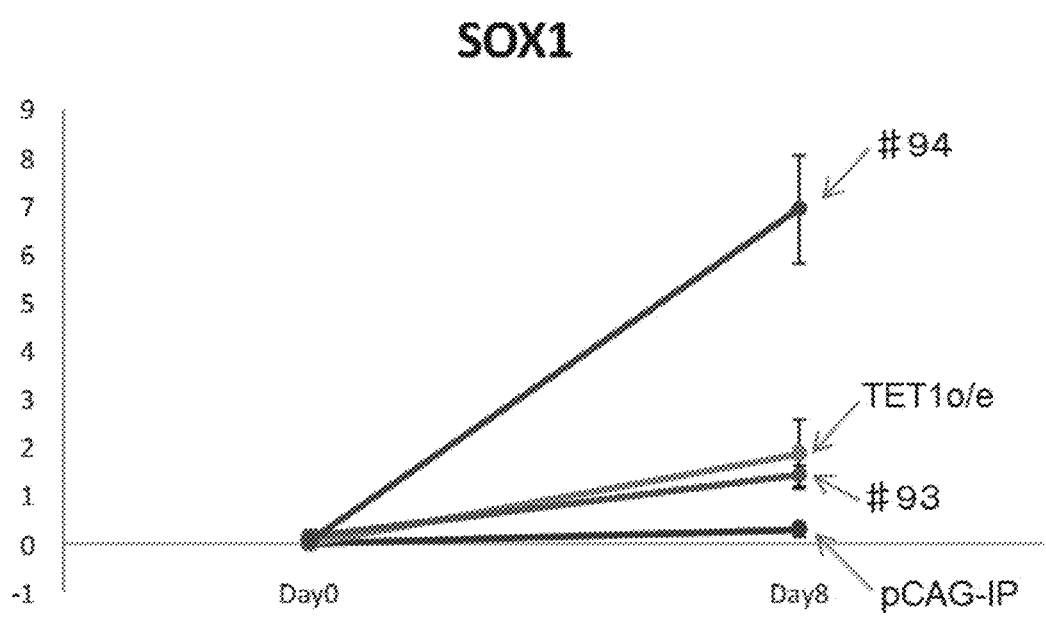
FIG. 31 The graph shows the time course of SOX1 mRNA expression during the neural induction of human iPS cell bearing various transgenes: a mock vector expressing human iPS cell, human iPS cell a fusion protein of the N-terminal portion of the human TET1 protein (the protein consisting of 670 amino acids) fused to GFP, human iPS cell expressing a fusion protein of the N-terminal portion of the human TET1 protein (the protein consisting of 670 amino acids) with the second amino acid serine converted to glycine, fused to GFP, and human iPS cell expressing N-terminally FLAG-tagged TET1 protein (full-length). In the figure, the vertical axis represents certain relative values because the value of the mock vector expressing human iPS cells (pCAGIP) before the differentiation was below the detection level.
Figure 32:
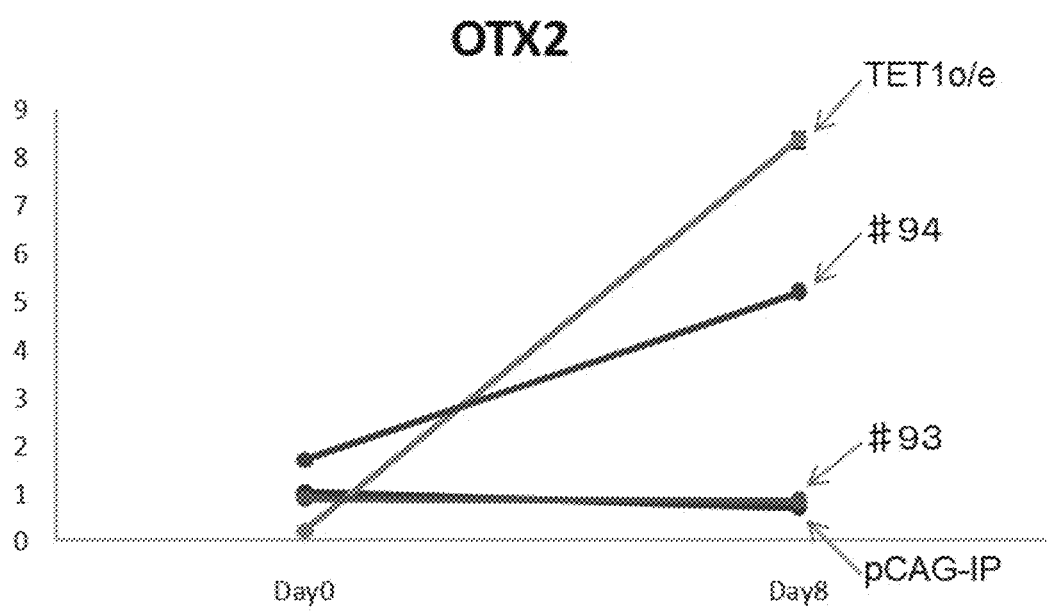
FIG. 32 The graph shows the time course of OTX2 mRNA expression during the neural induction of human iPS cell bearing various transgenes: a mock vector expressing human iPS cell (pCAG-IP), human iPS cell a fusion protein of the N-terminal portion of the human TET1 protein (the protein consisting of 670 amino acids) fused to GFP, human iPS cell expressing a fusion protein of the N-terminal portion of the human TET1 protein (the protein consisting of 670 amino acids) with the second amino acid serine converted to glycine, fused to GFP, and human iPS cell expressing N-terminally FLAG-tagged TET1 protein (full-length).

As clearly shown in FIGS. 30 to 32, not only the human iPS cell line which has received an N-terminally FLAG-tagged full length TET1 protein (TET1o/e) but also the human iPS cell line, which is the alternative embodiment of this invention and was introduced with the N-terminal 670 amino acids of the wild-type TET1 where its second amino acid from the N-terminus was changed from serine to glycine fused to a Tag-GFP protein (#94), equally displayed enhanced differentiation efficacies toward neurons. Therefore, for the enhancement in the differentiation efficacy of PSCs, DNA demethylating activity exerted by the C-terminally situated dioxygenase domain of TET1 is redundant and therefore, we can deduce that DNA-binding ability of the DNA-binding domain which is situated at the N-terminal portion of TET1 is sufficient.

Working Example 10

<Validating the Effect of the Mutant TET1 Protein in the Enhancement of the Production Efficacy of iPS Cells>

The rates of reprogramming toward iPS cells, especially human ones, are fairly low. Good quality fully-reprogrammed iPS cell, i.e., those forming sharply delimited colonies under microscope observation, lines are practically tough to obtain. Also, it is empirically known that iPSC colonies with said good morphology highly expressed transcription factors (such as OCT3/4 and SOX2) related to pluripotency, and are known to self-renew while maintaining its characteristics.

Therefore, the inventors next investigated whether introducing the mutant TET1 protein of the present invention together with the so-called reprogramming factors to somatic cells for iPS cells induction would enhance the production efficacy of iPS cells using the experiment as follows.

iPSC induction was performed as described above by introducing 6 factors (Oct3/4, Sox2, Klf4, L-MYC, LIN28 and shp53) but using the episomal vector system established by Okita et al. N-terminally FLAG-tagged full length TET1 was introduced into the same vector as used in the system and iPS cells were induced based on the presence or absence thereof.

Figure 33:
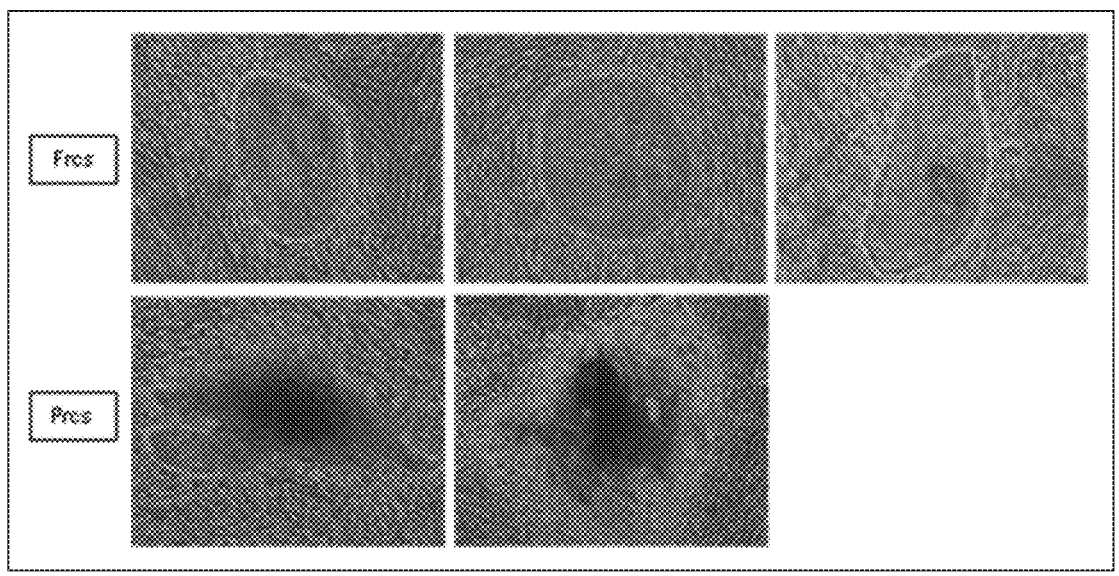
FIG. 33 Phase contrast micrographs of colonies composed of iPS cells of high quality (Frcs) and colonies composed of iPS cells of low quality (Pres).

The resulting iPS cell colonies were observed and their numbers were counted. The result is shown in Table 2. In Table 2, "6 factors" shows the result of iPS cell induction by introducing the above-described 6 factors and "6 factors+ Flag-TET1" shows the result of iPS cell induction by introducing the above-described 6 factors plus the mutant TET1 protein of this invention. "Frcs" denotes the number of colonies composed of iPS cells with high quality and "Prcs" denotes the number of colonies composed of iPS cells with low quality. In FIG. 33, we have displayed examples of "Frcs" and "Prcs".

TABLE 2

| vector | Frcs | Prcs |
| --- | --- | --- |
| 6 factors | 10 | 12 |
| 6 factors + Flag-TET1 | 40 | 7 |

As shown in Table 2, compared to the conventional iPS cell induction without TET1, the number of iPS cell colonies significantly increased (from 22 colonies to 47 colonies) by the method of inducing iPS cells in which the TET1 protein of this invention is introduced. Moreover, although the conventional induction method gave equal numbers for Frcs and Prcs, using the iPS induction method of this invention, the inventors could also raise the proportion of Frcs (the proportion of Frcs increased from 10/22 to 40/47).

Collectively, by the method for producing PSCs by introducing the TET1 protein of this invention, it has been shown that it is now possible not only to enhance the differentiation efficacy of the obtained PSCs but also to enhance the production efficacy of such PSCs.

Working Example 11

<Evaluation of the Human iPSCs Overexpressing Mutant-TET1 at their Undifferentiated State2>

The inventors further analyzed their mutant-TET1 overexpressing human iPSC (TET1-hiPSC) at its undifferentiated state in terms of its proliferability and by surveying its gene expression profile.

Figure 34:
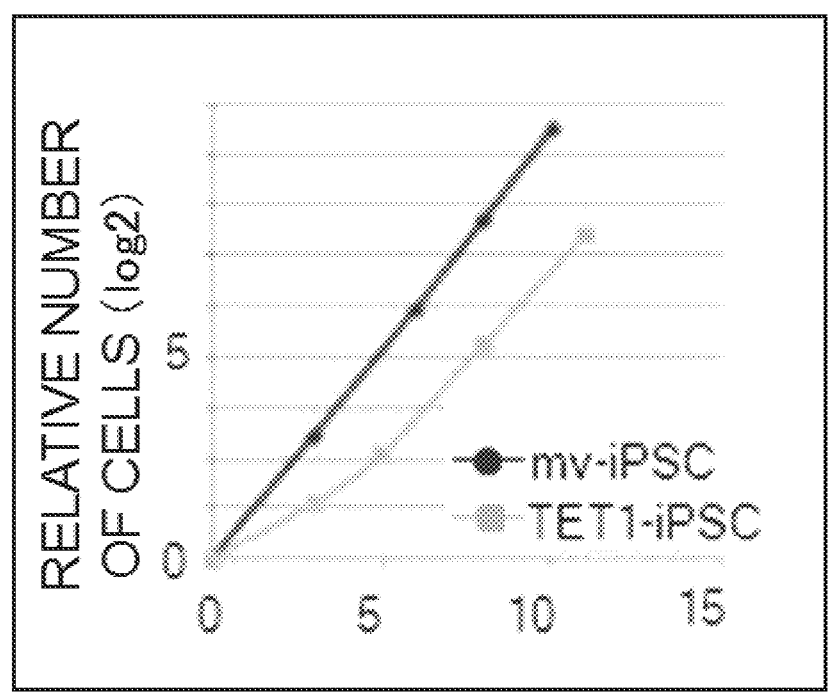
FIG. 34 The graph shows the cell proliferation curves for mock-vector introduced human iPS cells ("mv-iPSC"; same in FIG. 35 and FIG. 36) and human iPS cells with overexpression of N-terminal FLAG-tagged TET1 protein ("TET1-iPSC"; same in FIG. 35 and FIG. 36). The horizontal axis denotes days in culture.
Figure 35:
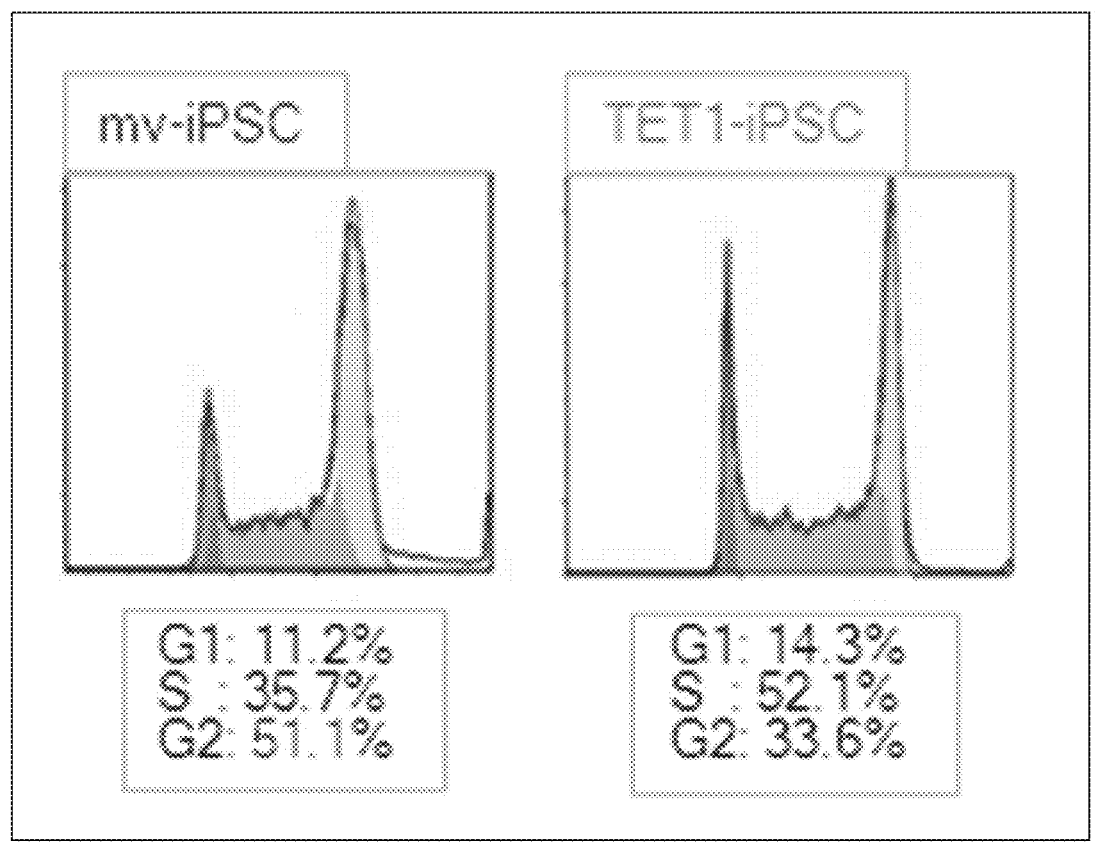
FIG. 35 Histograms showing cell cycle profiles of mv-iPSC and TET1-iPSC analyzed using FACS. In the figure, cell number ratios for G1, S and G2 phase are shown in percentiles.

Although not displayed as a figure, TET1-hiPSCs grew for at least 20 passages after its establishment in a stable fashion. Also, when compared with mock-vector-expressing hiPSCs (mv-iPSC), the cells proliferated more slowly (FIG. 34). Moreover, when their cell cycle were analyzed, TET1-iPSCs spent less time in G2 phase but tend to be more in S phase when compared to mv-iPSCs (FIG. 35). As shown, TET1-iPSCs were more likely in S phase and less likely in G1/G2/M, a hallmark of a stem cell's cell cycle profile.

Figure 36:
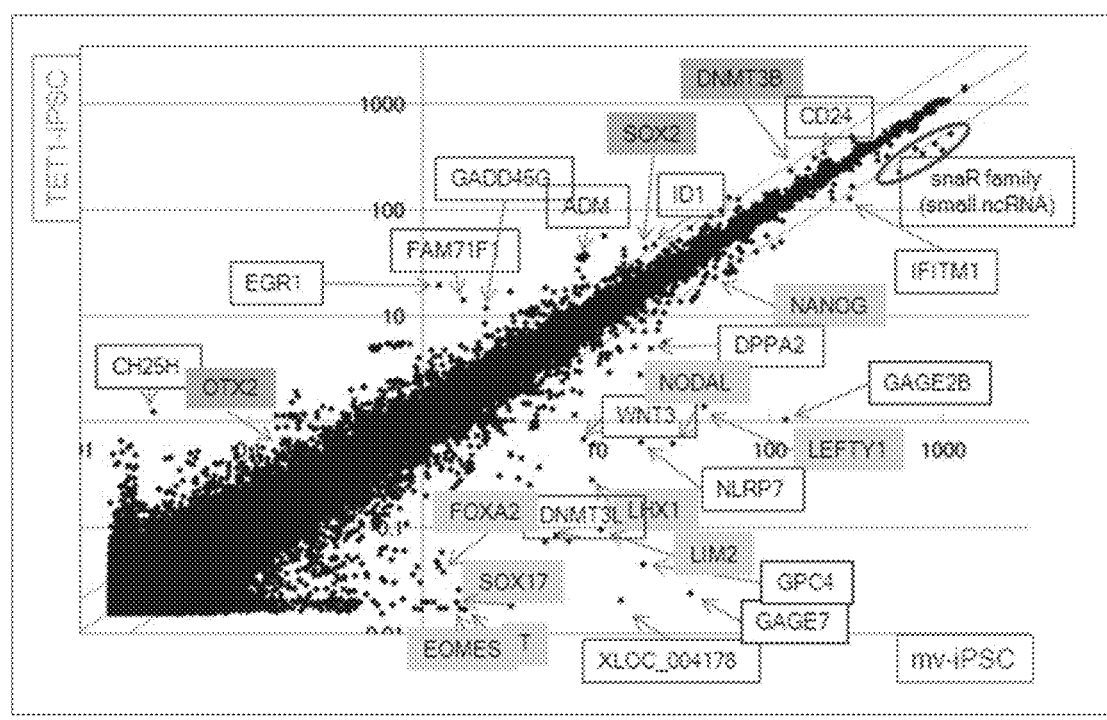
FIG. 36 Gene expression scattered plots of DNA microarray analysis showing genes whose expression differs between mv-iPSC and TET1-iPSC. DNA microarray analysis was performed on SurePrint G3 Human GE 8×60K v2 one-color platform (Agilent) and data analysis was done using 75-percentile shift method.

Moreover, when the transcriptome of TET1-iPSCs were analyzed globally using DNA microarray, the cells exhibited an expression profile which better fits a primed rather than a naïve stem cell (FIG. 36). For example, albeit the fact that no naïve-ness-related factors were over-represented, DNMT3B and OTX2, both a determinant of primed-ness were over-expressed in TET1-iPSCs. Also, except for increase in the expression of SOX2 and slight decrease in the expression of NANOG, factors which are related to pluripotency did not significantly change between the two cell populations. Although not shown as a figure, culturing the TET1-hiPSCs in LIF did not turn them into a naïve status.

And also, globally viewed, TET1-hiPSC gene expression profile indicated that the cell is more undifferentiated compared to its control mv-iPSC. That is, the overexpression of TET1 was able to significantly decrease the expression of NODAL and its direct target genes (LEFTY1 and LEFTY2) as well as some mesendodermal markers (T, SOX17, MIXL1, EOMES, LHX1, LIM2 and FOXA2). Moreover, the NODAL down-regulation by TET1-introduction was by a factor of 45, contrary to the mesendoderm-differentiation propensity of the conventional hiPSCs without TET1 as show above. Also not shown are quantitative RT-PCR data which confirmed the up-regulation of DNMT3B and the significant down-regulation of mesendodermal factors in TET1-hiPSCs. And, the fact that cancer-related markers (GPC4, GAGE2B and GAGE7) are over-represented in the conventional hiPSCs when compared to TET1-hiPSCs is indicative that the conventional hiPSCs without TET1 bear endogenous carcinogenic property (FIG. 36). Although the definitive neuroectodermal marker SOX1 was not expressed in both the TET1-hiPSCs and mv-iPSC, TET1-hiPSCs showed enhanced expression of DNMT3B, SOX2 and OTX2 which may explain their higher differentiation capability toward a neural fate.

Working Example 12

<Evaluation of the Transition of the Tet1-Knockdown Mouse ES Cell to the Primed Stage>

Figure 37:
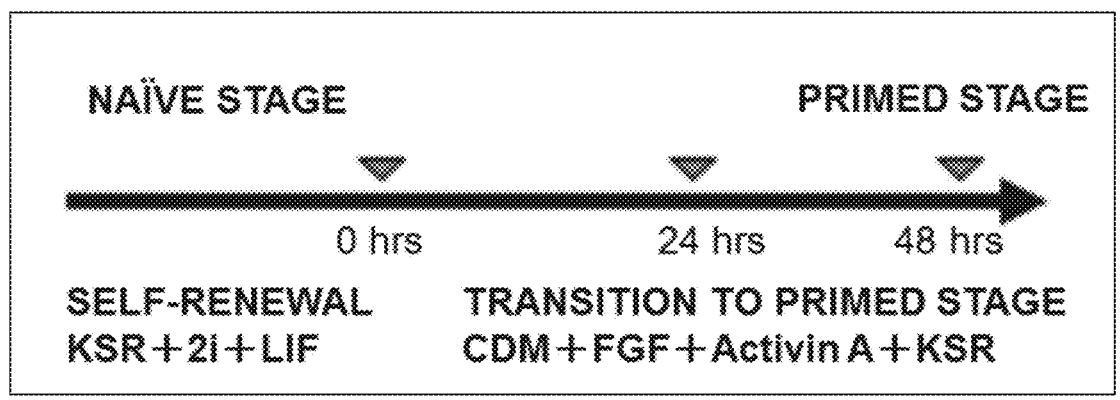
FIG. 37 A schematic drawing showing the transition from mouse ES cell's naïve stage to primed stage. From a naïve culture of mouse ES cells, leukemia inhibitory factor (LIF) and other agents preventing the transition to the naïve stage were removed and then said cells were transferred to FGF2 and Activin A (TGFβ/Nodal agonist) containing media which allow them to transition to the primed stage's status.
Figure 38:
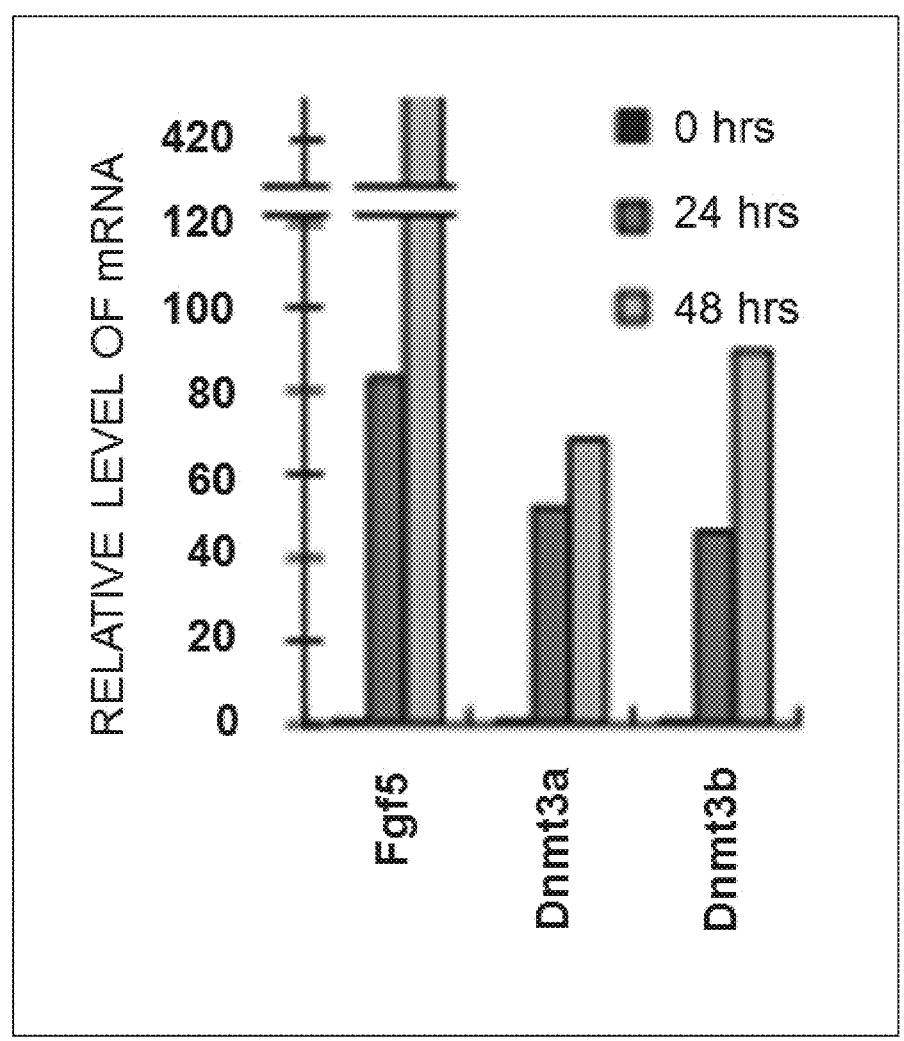
FIG. 38 The graph shows qPCR results which show up-regulation of epiblast markers during the naïve to primed transition. Each bar from left to right represents data of 0 hour, 24 hours and 48 hours after transition induction, respectively (The same applies to FIGS. 40 to 54).
Figure 40:
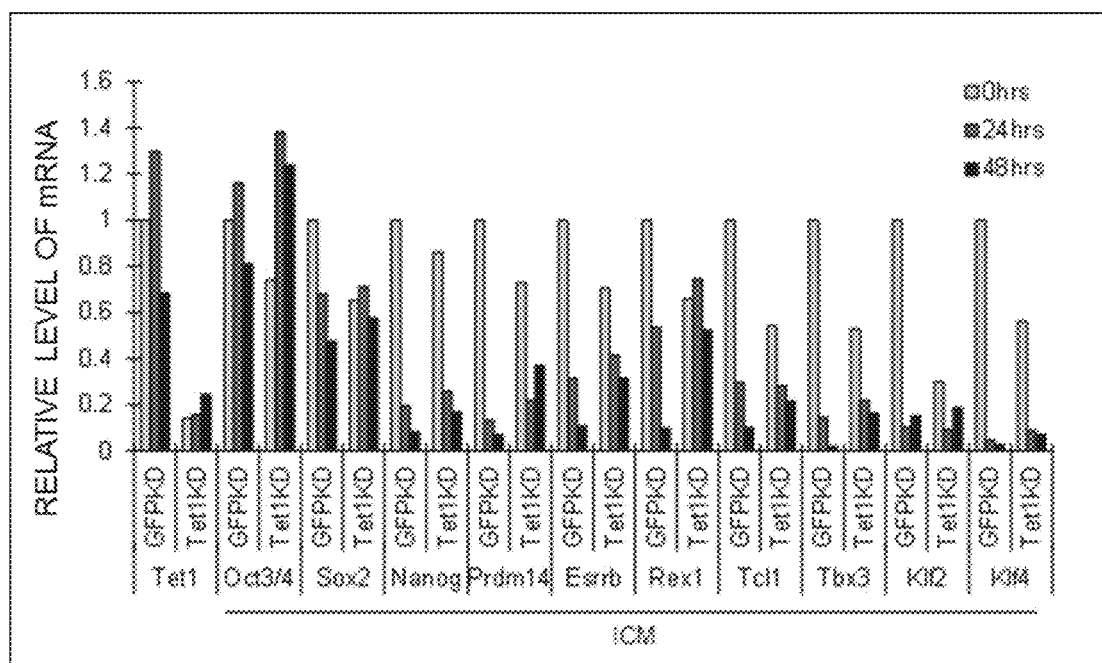
FIG. 40 The graph shows the qPCR results for the naïve to primed transition of mouse ES cells showing the effect of Tet1 knockdown. Tet1KD denotes for mouse ES cells in which Tet1 was knockdown and GFPKD is for mouse ES cells introduced with GFP-targeting shRNA which are used as control ES cells. ICM stands for the results of analysis for transcription levels of ICM/naïve stage markers.

As described above, by introducing TET1 proteins, it was possible to improve the differentiation potential of human iPS cells. So, the inventors further analyzed in details this aspect of Tet1 function using an in vitro mouse model of naïve-to-primed transition. In other words, according to the description of "K. Hayashi, H. Ohta, K. Kurimoto, S. Aramaki, M. Saitou, Cell 146, 519 (Aug. 19, 2011)" and "G Guo et al., Development 136, 1063 (April, 2009)", the inventors switched the culture conditions of the naïve mouse ES cells and let the cells proceed to an epiblast-like stage in 48 hours (called EpiLCs) (FIG. 37). In fact, the EpiLCs obtained this way showed increased expression of the primitive ectoderm cell markers Dnmt3b and Fgf5, Dnmt3a (FIG. 38) and diminished expression of a battery of naïve factors (FIG. 40).

Figure 39:
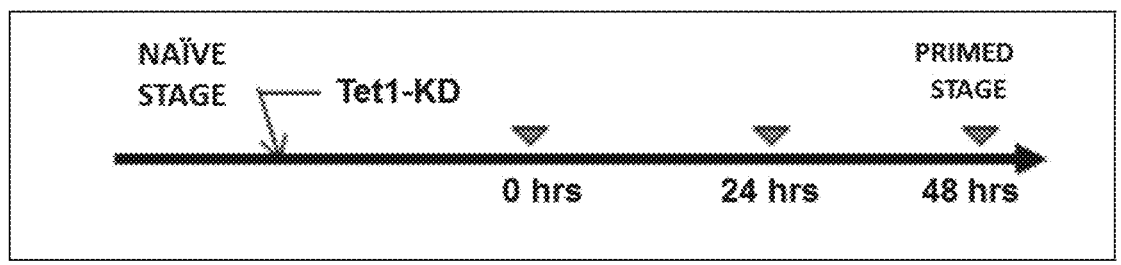
FIG. 39 Schematic drawing of the stages of the transition to epiblast-like stem cells (EpiLC) from Tet1-knockdown (Tet1-KD) mouse ES cells. Tet1-KD mouse ES cells were established by introducing shRNA against Tet1 and by selecting for puromycin resistance (Ref.: K. Williams et al., Nature 473, 343 (May 19, 2011)).

Then, in order to explore the role of Tet1 in establishing pluripotency, short hairpin RNA (shRNA) that targets all the Tet1 transcripts were used to decrease Tet1 expression in the in vitro model system (FIG. 39, please refer to K. Williams et al., Nature 473, 343 (May 19, 2011)).

Upon the knockdown (KD) of Tet1 in mouse ES cells, the expression levels of pluripotency-related marker such as Oct3/4 (Pou5f1), Sox2 and Nanog did not change (data not shown). And for the cell cycle, Tet1-KD ES cells exhibited typical stem-like cell cycle profile, indicating that as previously shown, Tet1 is not important in the self-renewability of the mouse ES cells (K. Williams et al., Nature 473, 343 (May 19, 2011), K. P. Koh et al., Cell Stem Cell 8,200 (Feb. 4, 2011), G Ficz et al., Nature 473, 398 (May 19, 2011), M. M. Dawlaty et al., Cell Stem Cell 9, 166; M. M. Dawlaty et al., Dev Cell 24, 310 and (Aug. 5, 2011) (Feb. 11, 2013)).

Figure 41:
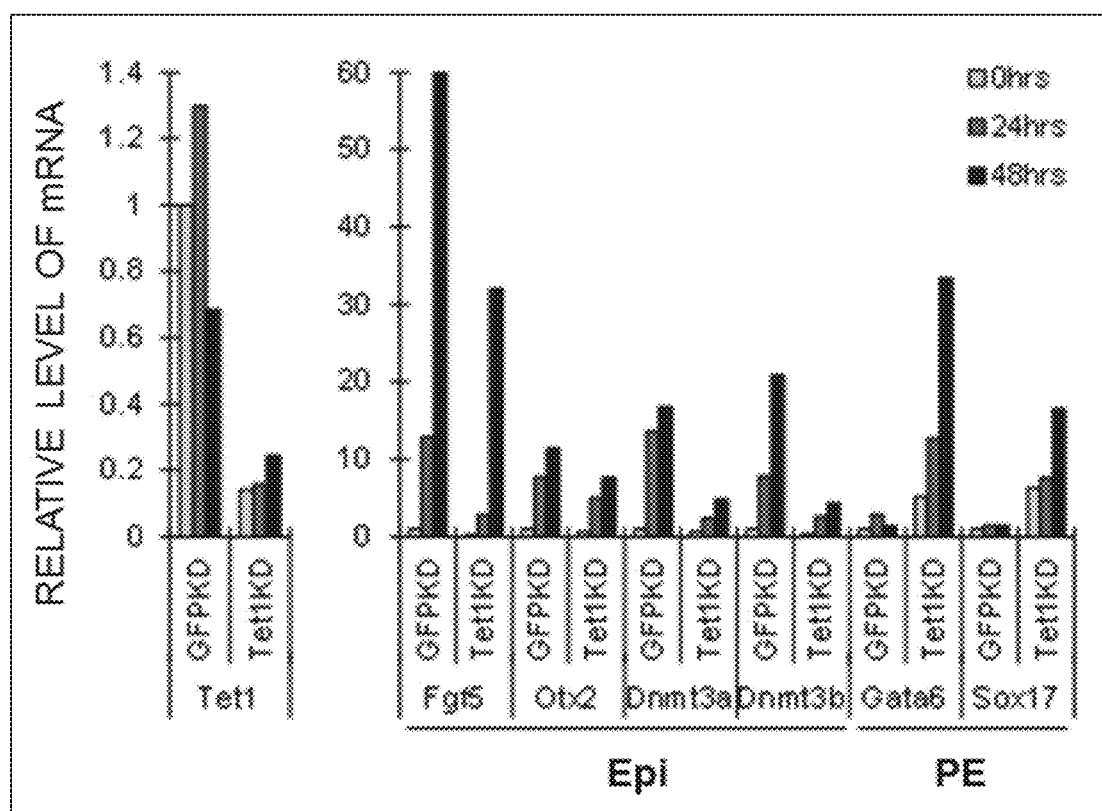
FIG. 41 The graph shows the results of qPCR data during the transition from the naïve to primed stage for the transcription levels of Tet1, Epiblast-related (Epi) and primitive endodermal (PE) markers by comparing Tet1-KD mouse ES cells (Tet1KD) and their control (GFP-KD) cells.

However, Tet1-KD mouse ES cells were unable to transit to the primed EpiLC pluripotent status like untreated cell. Instead, genes which are known to be highly expressed at the primed stage, especially the de novo DNA methyltransferases (Dnmt3a and Dnmt3b) were expressed in significantly lower levels in Tet1-KD EpiLCs (FIGS. 41 to 43).

Figure 42:
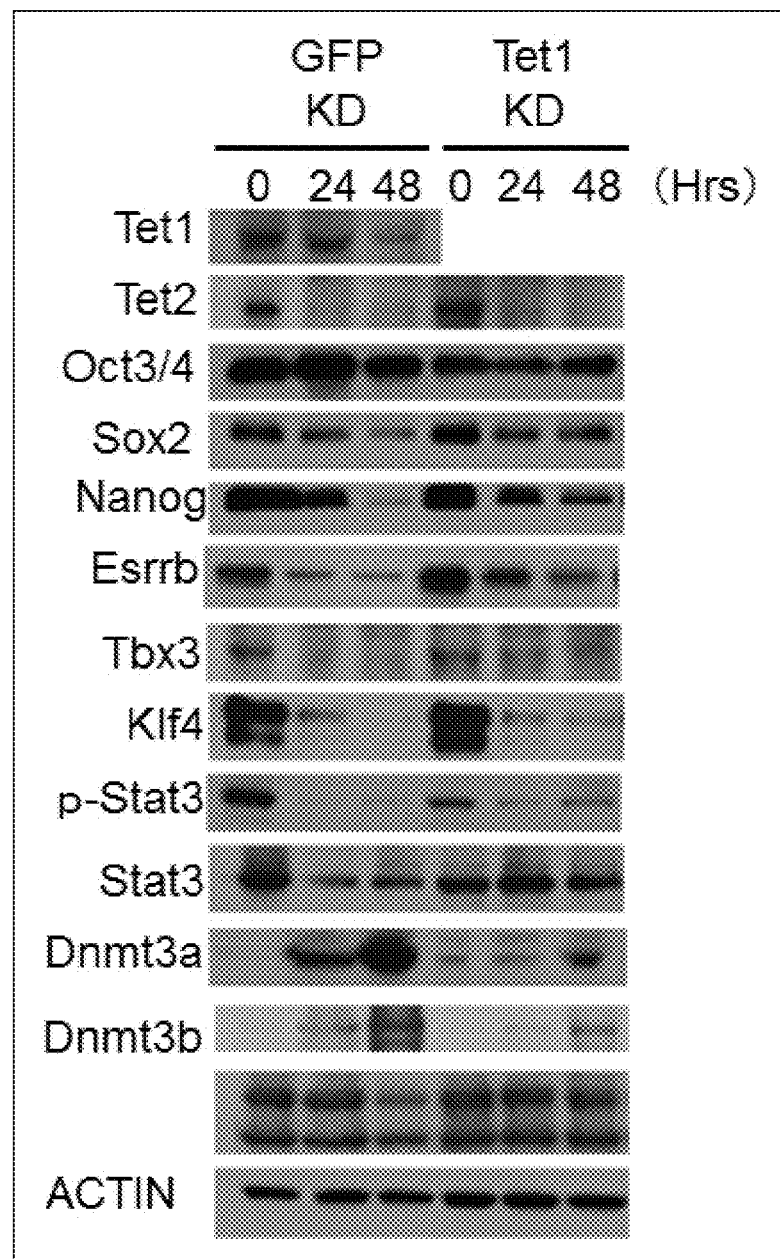
FIG. 42 The photograph shows the results of western blots for the protein levels of Tet1, Tet2, ICM markers and epiblast markers in Tet1-KD mouse ES cells (Tet1-KD) and GFP-KD mouse ES cells (GFP-KD). Of note, protein expression levels of naïve factors (such as Nanog, Esrrb, Tbx3 and Stat3) were largely maintained through the transition in Tet1-KD EpiLCs.
Figure 43:
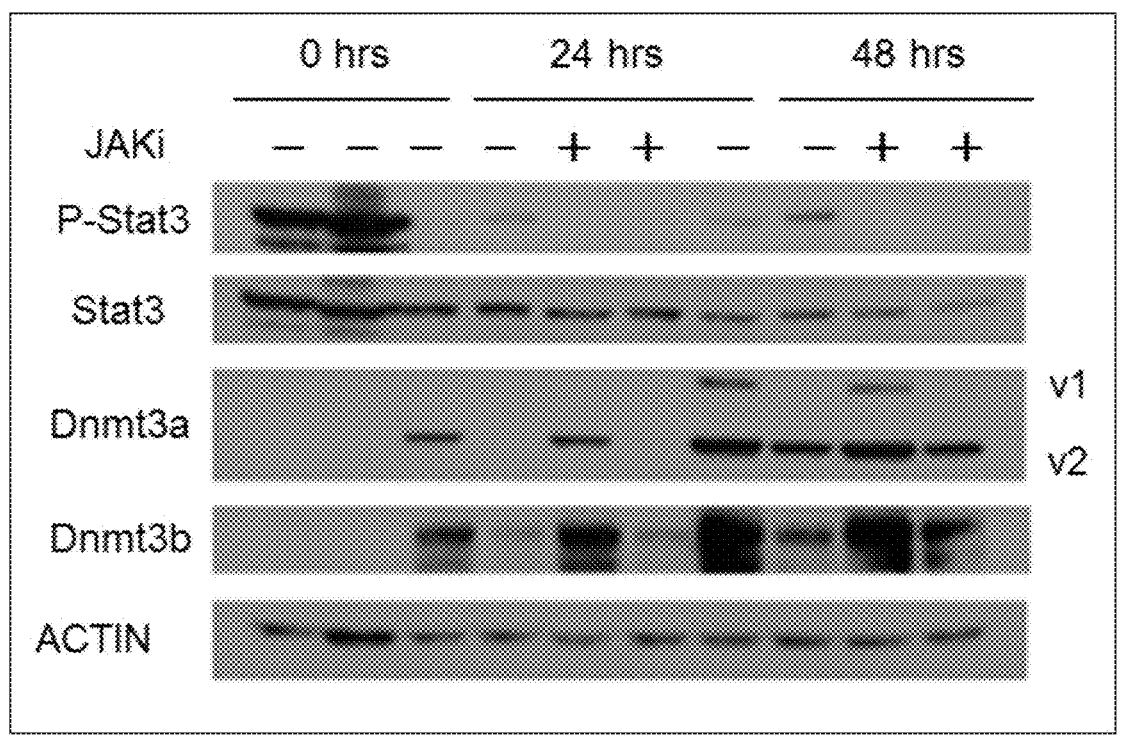
FIG. 43 The photograph shows the results of western blots for the protein expression levels of Stat3, Dnmt3a and Dnmt3b in the presence (JAKi+) or absence (JAKi−) of JAK inhibitor during the naïve to primed transition. As a JAKi, JAK Inhibitor I (Calbiochem, added at 1 μM) was used. For Dnmt3a, two bands appeared on the blots which correspond to v1 and v2 variants.

Moreover, the expression levels of the naïve factors (Nanog, Prdm14, Esrrb, Rex1/Zfp42, Tcl1, Tbx3, Klf2, Klf4 and Stat3) were maintained in Tet1-KD EpiLCs (FIG. 42 and FIG. 40).

Overall, the proteome and transcriptome of the Tet1-KD EpiLCs indicates that the cells expressed markers typical of an earlier developmental stage but also that, without Tet1 expression, mouse ES cells cannot transit to a primed pluripotency anymore within 48 hours.

Figure 44:
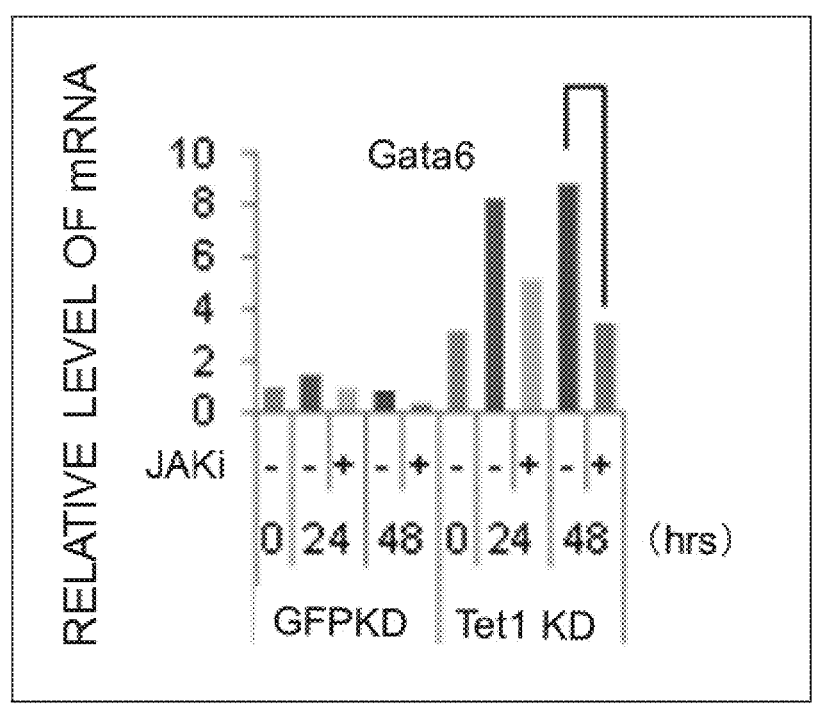
FIG. 44 The graph shows the qPCR results for Gata6 transcription levels upon naïve to primed transition in the presence (JAKi+) or absence (JAKi−) of JAK inhibitor.

Moreover, some transcription factors typically expressed in the primitive endoderm (such as Gata6 and Sox17) have been found to be expressed in the Tet1-KD EpiLCs. These signals are normally found in the preimplantation naïve cells of the blastocyst ICM. Furthermore, even when forced to transit to the epiblast (primed stage) by inhibiting the JAK signaling pathway which normally acts in the maintenance of the naïve status, Tet1-KD EpiLCs did not transit to the (epiblast) primitive ectodermal stage 48 hours after induction (FIG. 44).

Working Example 13

<TET1 Degradation at the Primed Pluripotency>

Figure 45:
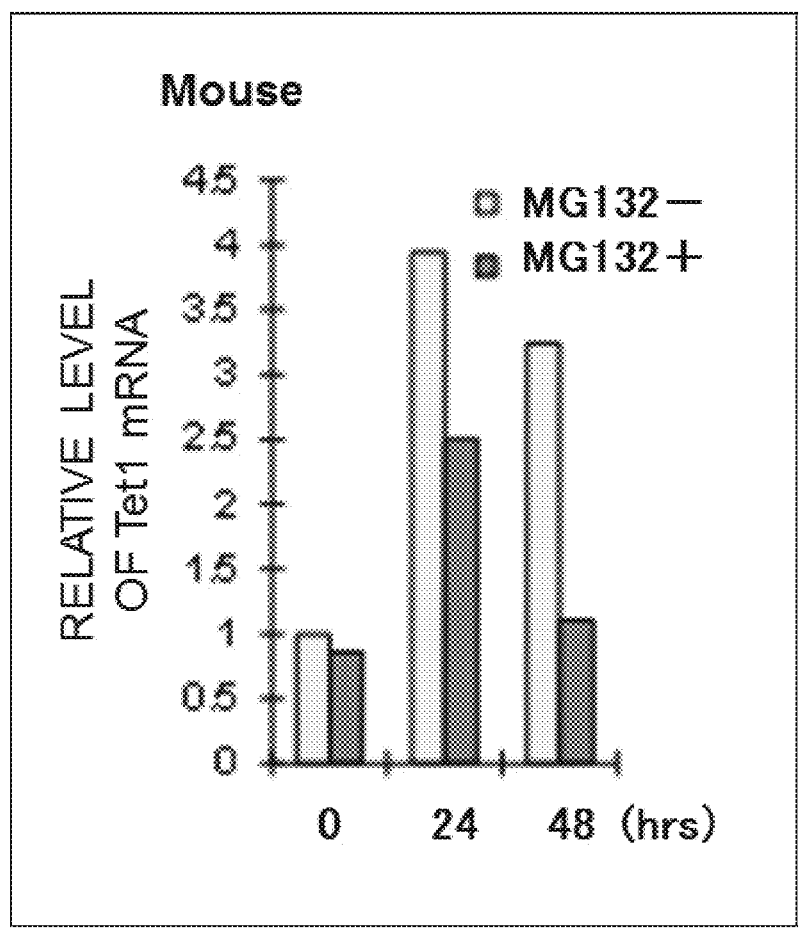
FIG. 45 The graph shows the qPCR results showing Tet1 mRNA levels upon naïve to primed transition of mouse ES cells in the presence (MG132+) or absence (MG132−) of MG132.
Figure 46:
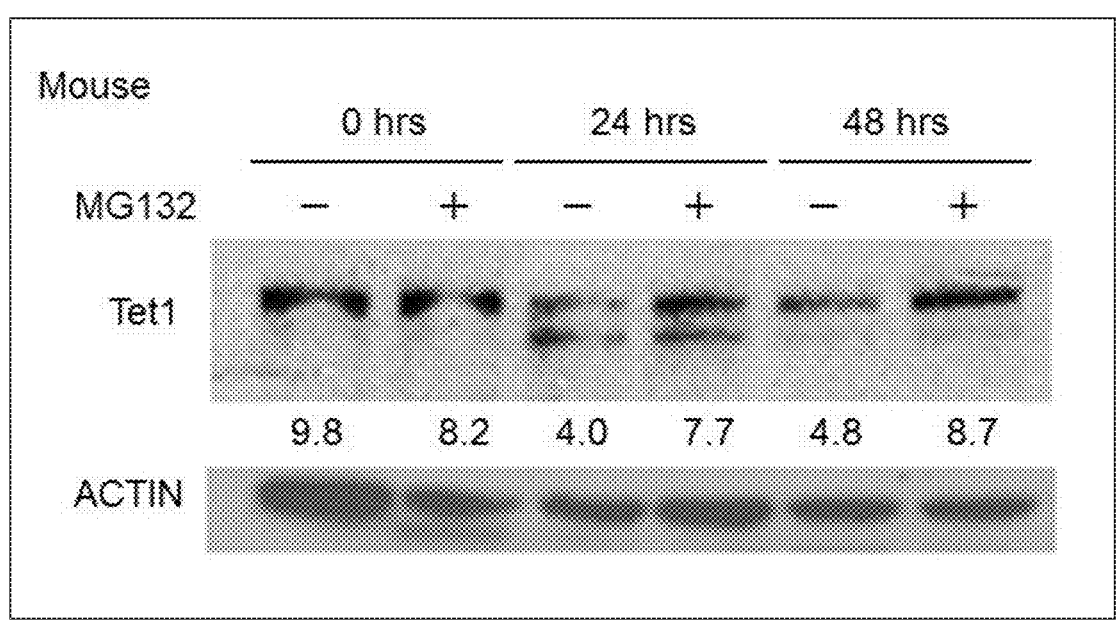
FIG. 46 The photograph shows the results of western blots for the protein expression levels of Tet1 upon naïve to primed transition of mouse ES cells in the presence (MG132+) or absence (MG132−) of MG132. Numbers shown in the figure are TET1 expression amount normalized against the actin expression amount.

When analyzed through the transition period of naïve-to-primed, as reported in "S. Ito et al., Nature 466, 1129 (Aug. 26, 2010)", Tet1 was highly expressed in the undifferentiated mouse ES cells (FIG. 45, FIG. 46 and FIG. 41). Upon transition to a primed stage, albeit that Tet1 mRNA level is maintained, their protein levels went significantly down (FIG. 45, FIG. 46, FIG. 41 and FIG. 42). However, upon applying the proteasome inhibitor MG132 and inhibiting protein degradation, the inventors were now able to detect Tet1 proteins (FIG. 46). In contrast, such regulation of Tet1 protein levels were not observed when the naïve undifferentiated ES cells were used.

As aforementioned, TET1 protein is hardly detectable in human iPSCs and therefore phenotypically, the cells can be supposed to be equivalent to the mouse primed EpiLCs in terms of its protein regulatory dynamics. Moreover, TET1 protein levels in hiPSCs were significantly up-regulated upon MG132 treatment (FIG. 1).

Thus, it became clear that TET1 protein is unable to be stabilized in a primed pluripotent stem cell as much as in a naïve pluripotent stem cell. In addition, the observed down-regulation of Tet1 protein in an in vitro model of development mimicking the naïve-to-primed transition suggests that Tet1 protein is programmed during development to down-regulate its expression during the transition from blastocyst to epiblast.

Working Example 14

<Validation of the Effect of Tet1 on Dnmt3 Expressivity>

As Tet1 is known to execute demethylation, Tet1-KD mouse ES cells or EpiLCs are anticipated to bear hypermethylated genomes.

Figure 47:
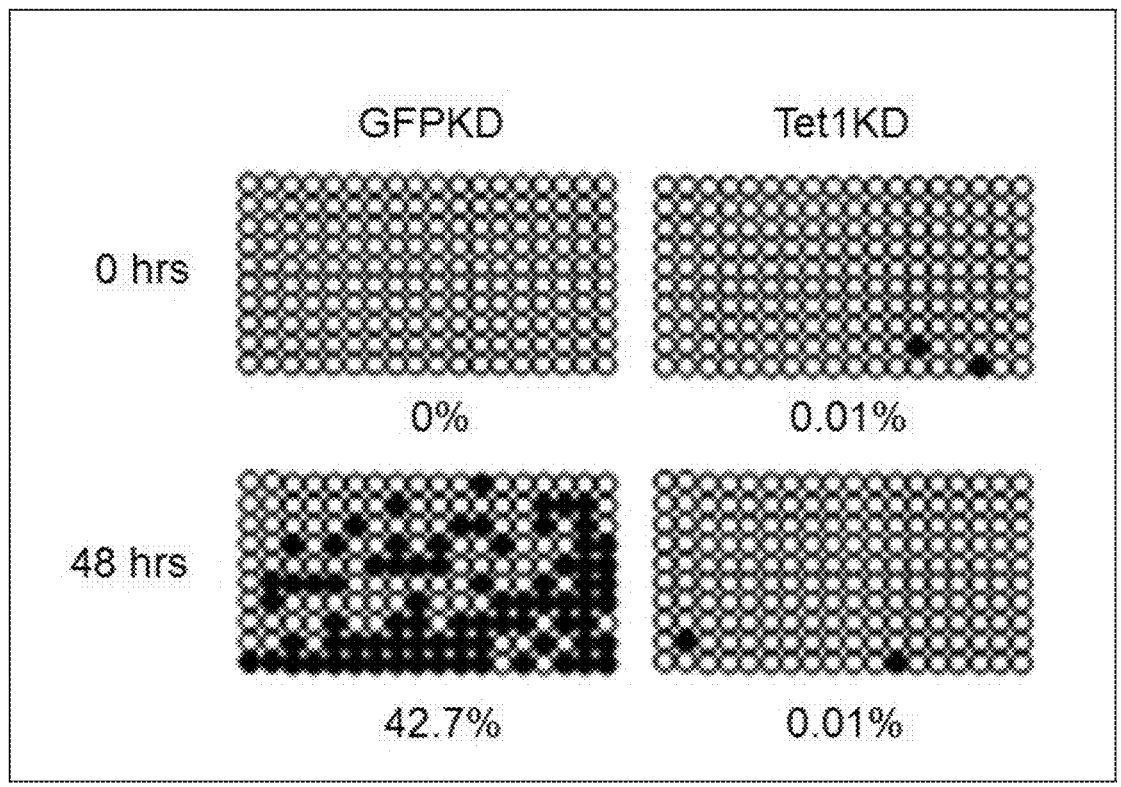
FIG. 47 Bisulfite sequencing results showing the DNA methylation statuses of the Tcl1 differentially methylated region (DMR) upon naïve to primed transition. Black circles denote for methylated (or hydroxymethylated) CpG sites and open (white) circles are for unmethylated (or unhydroxymethylated) CpG sites. Bisulfite sequencing of the selected CpG sites was performed according to H. Wu et al., Nature 473, 389 (May 19, 2011).

However, when the differentially-methylated region (DMR) of a gene of a naïve factor Tcl1 was analyzed, Tet1 loss did not affect the methylation status of the Tcl1-DMR in mouse ES cells. It should be noted that, however, the Tcl1-DMR has been reported as a region which acquires de novo methylation post-implantationally during blastocysts to epiblasts, as a part of a genome-wide methylation process (J. Borgel et al., Nat Genet 42, 1093 (December, 2010)). Furthermore, although the Tcl1 DMR acquired methylation in the process of transition to EpiLCs in control EpiLCs, Tet1-KD EpiLCs remained hypomethylated (FIG. 47).

Therefore, although Tet1 does not seem to directly affect the Tcl1-DMR methylation status through its demethylating activity, Tet1 expression at a naïve stage seems to affect the expressivity of the de novo DNA methyltransferases (Dnmt3a and Dnmt3b) important for the genome-wide re-methylation in an indirect fashion. In fact, as shown in FIG. 41, the expression levels of the DNA methyltransferases are fairly low in Tet1-KD EpiLCs.

So, the inventors went to look if the observed global hypomethylation and the dysregulation of Dnmt3a/b in the Tet1-KD EpiLCs could be explained by an aberration of the methylation status of Dnmt3b promoter region. The bisulfite sequencing of the supposed DMR of the Dnmt3b showed a hypermethylation at the region −866 to −576 of the transcription start site in Tet1-KD mouse ES cells and therefore this dysregulation seemed to be in accordance with the loss of the Tet1-demethylating activity.

However, this difference in the methylation status was rather subtle and therefore, the inventors went to look at a dioxygenase-independent molecular mechanism.

Prdm14, a naïve factor, is known to inhibit the expression of Dnmt3b and to be partly responsible in harnessing the mouse ES cells their pluripotency (Z. Ma, T. Swigut, A. Valouev, A. Rada-Iglesias, J. Wysocka, Nat Struct Mol Biol 18, 120; M. Yamaji et al., Cell Stem Cell 12, 368 and (February, 2011) (Mar. 7, 2013) reference). Therefore, the inventors analyzed Prdm14 expression in the process of naïve-to-primed transition.

As a result, Prdm14 mRNA was observed to be highly expressed at the naïve stage in mouse ES cells but went down upon EpiLC differentiation. However, upon Tet1-KD, Prdm14-down-regulation was attenuated upon EpiLC differentiation (FIG. 40). Tet1 is involved in the down-regulation of Prdm14 expression and as an effect, can be supposed to be involved in the up-regulation of Dnmt3a/b, and moreover, this result concords well with the observed down-regulation of Dnmt3a/b in the Tet1-KD EpiLCs.

Figure 48:
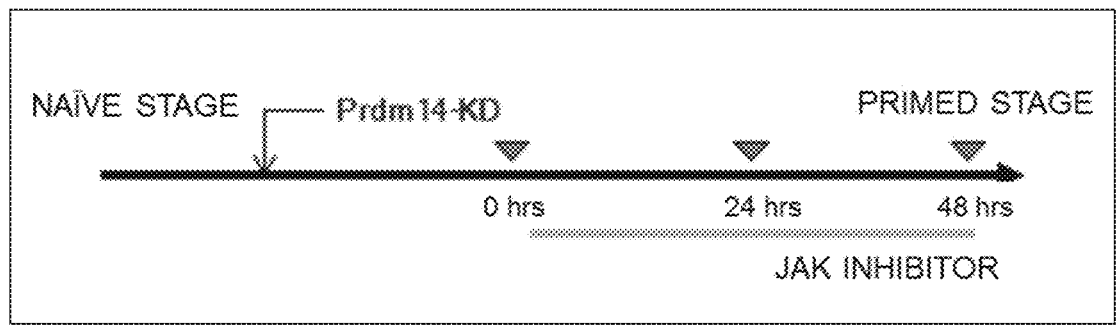
FIG. 48 Schematic drawing depicting the experimental scheme of the naïve to primed transition using Tet1/Prdm14 double knockdown mouse ES cells.
Figure 49:
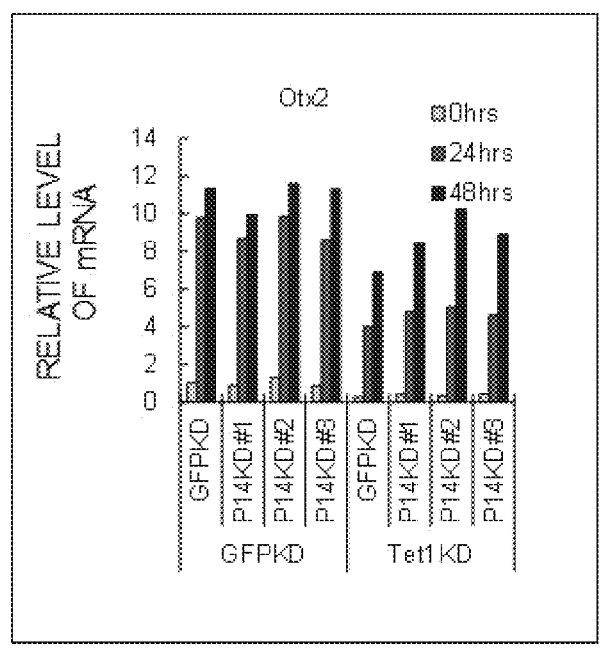
FIG. 49 The graph shows the qPCR results for Otx2 mRNA expression levels during the naïve to primed transition of Tet1/Prdm14 double knockdown mouse ES cells. "GFPKD" is the control cell line used here in which only GFP-targeting shRNA was introduced, "GFPKD P14KD #1 to 3" are cell lines in which both GFP and Prdm14 are targeted by shRNA, "Tet1KD GFPKD" are cell lines in which both GFP and Tet1 are targeted by shRNA and "Tet1KD P14KD #1 to 3" are cell lines in which both Tet1 and Prdm14 are targeted by shRNA. (These notations are also valid for FIGS. 50 to 52.)
Figure 50:
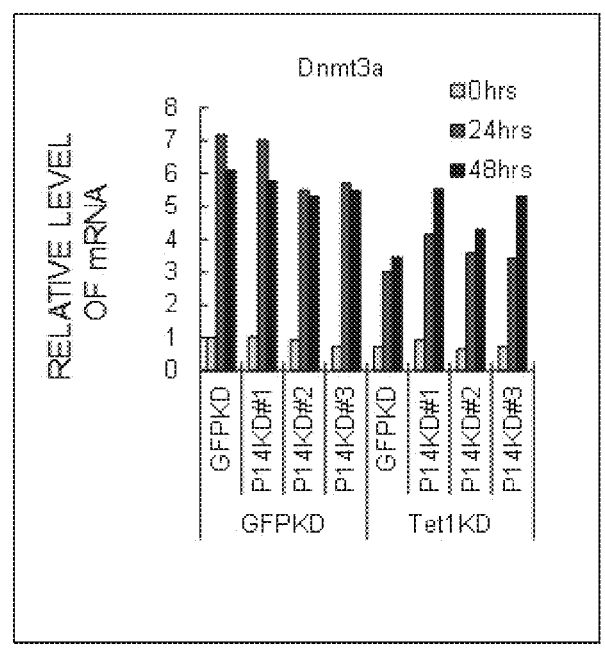
FIG. 50 The graph shows the qPCR results for Dnmt3a mRNA expression levels upon naïve to primed transition of Tet1/Prdm14 double knockdown mouse ES cells.
Figure 51:
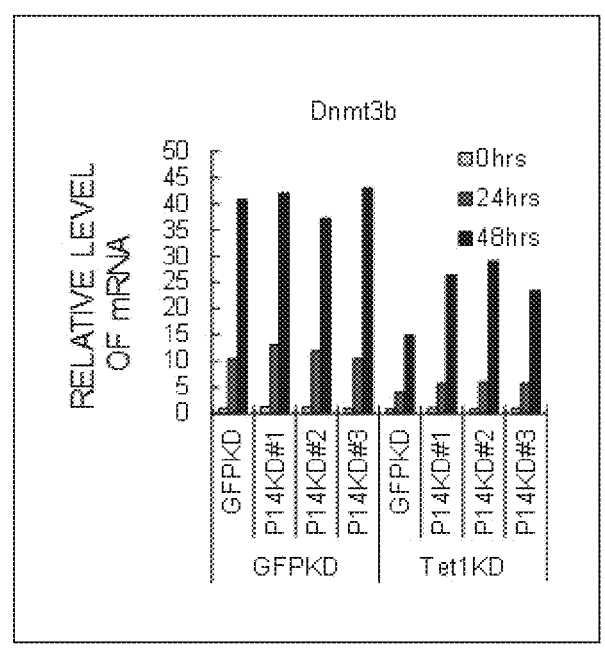
FIG. 51 The graph shows the qPCR results for Dnmt3b mRNA expression levels upon naïve to primed transition of Tet1/Prdm14 double knockdown mouse ES cells.
Figure 52:
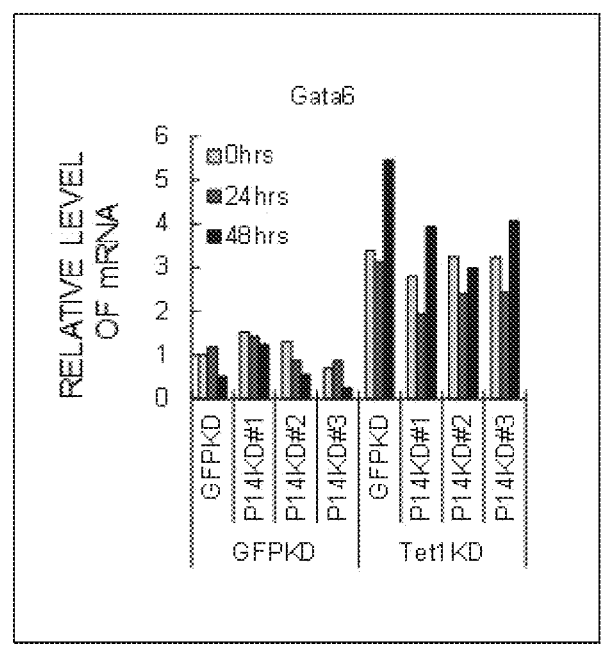
FIG. 52 The graph shows the qPCR results for Gata6 mRNA expression levels upon naïve to primed transition of Tet1/Prdm14 double knockdown mouse ES cells.

Next, the effect of knocking down both Prdm14 and Tet1 (Tet1/Prdm14-double KD) was analyzed in EpiLC for reversal of decreased Dnmt3b expression due to Tet1 loss (FIG. 48).

When compared to Tet1-KD, Tet1/Prdm14-double KD EpiLC expressed higher levels of Otx2, Dnmt3a and Dnmt3b transcripts (all indicators of the primed stage of development) but expressed lower level of the (extraembryonic) primitive endoderm marker Gata6 (FIGS. 49 to 52).

Collectively, the induction of decreased expression of Dnmt3a and Dnmt3b during naïve-to-primed transition of Tet1-KD and the concomitant hypomethylated genome of Tet1-KDEpiLC is suggestive that Tet1 is involved in this process in a dioxygenase-dependent as well as independent manner.

Next, to evaluate the differential contribution of the Dnmt3 isoforms during the naïve-to-primed transition, various Dnmt3 isoforms were introduced into the Tet1-KD cells.

Figure 53:
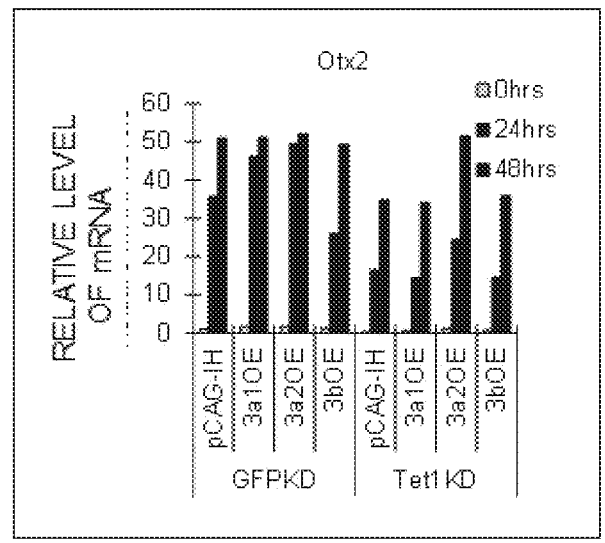
FIG. 53 The graph shows the qPCR results for Otx2 mRNA upon naïve to primed transition of mouse ES cells over-expressing Dnmt3a1 (3a1OE), Dnmt3a2 (3a2OE) and Dnmt3b (3bOE). "GFPKD pCAG-IH" is the control cell line in which a mock vector (pCAG-IH) and an shRNA targeting GFP are introduced, "GFPKD 3a1OE" is the cell line in which an shRNA targeting GFP and a Dnmt3a1-expressing pCAG-IH vector are introduced, "GFPKD 3a2OE" is the cell line in which an shRNA targeting GFP and a Dnmt3a2-expressing pCAG-IH vector are introduced, "GFPKD 3bOE" is the cell line in which an shRNA targeting GFP and a Dnmt3b-expressing pCAG-IH vector are introduced. "Tet1KD pCAG-IH" is a cell line in which an shRNA targeting Tet1 and a mock vector are introduced, "Tet1KD 3a1OE" is a cell line in which an shRNA targeting Tet1 and a pCAG-IH vector encoding Dnmt3a1 are introduced, "Tet1KD 3a2OE" is a cell line in which an shRNA targeting Tet1 and a pCAG-IH vector encoding Dnmt3a2 are introduced and "Tet1KD 3bOE" is a cell line in which an shRNA targeting Tet1 and a pCAG-IH vector encoding Dnmt3b are introduced. (These notations are also valid for FIG. 54.)
Figure 54:
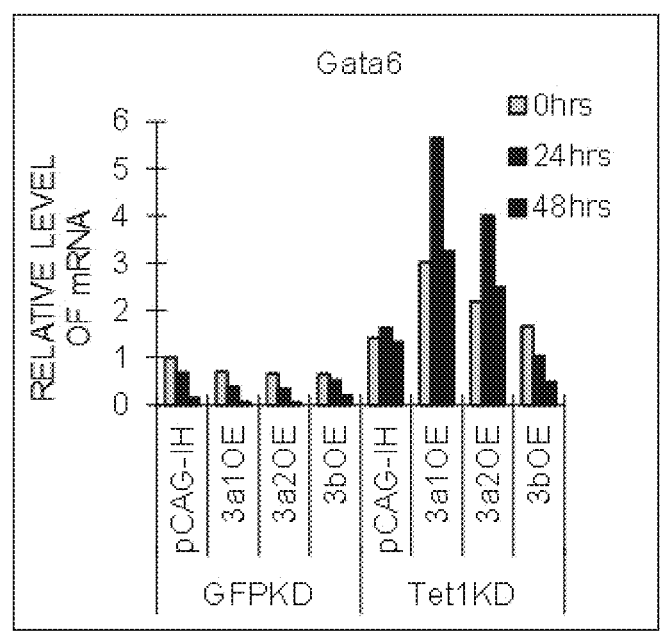
FIG. 54 The graph shows the qPCR results for Gata6 mRNA upon naïve to primed transition of mouse ES cells over-expressing Dnmt3a1 (3a1OE), Dnmt3a2 (3a2OE) and Dnmt3b (3bOE).

The ectopic expression of Dnmt3a2 into the Tet1-KDs recovered the Otx2 expression level to a similar level of the wild-type cells (FIG. 53). In contrast, Gata6 over-expression observed in the Tet1-KD cells was cancelled upon Dnmt3b ectopic expression (FIG. 54).

Therefore, the inventors concluded that Tet1 was actively responsible for the naïve-to-primed transition of pluripotencies in mouse ES cells through its regulation of Dnmt3a/b.

As aforementioned in the Working examples 1 to 9 and 11, by introducing a mutant TET1 protein where its second amino acid from the N-terminus was replaced from its wild-type amino acid into human PSCs, it was made clear that it is possible now to drastically enhance their differentiation efficacies. Furthermore, it was made clear that to drastically enhance their differentiation efficacies of human PSCs by expressing the mutant TET1 protein in human PSCs where normal TET1 protein is actively degraded. Moreover, by this enhancement of the differentiation efficacy of the PSCs, it has been shown that it is possible to resolve the differentiation biases inherent to the conventional human iPS cells (for example, the differentiation propensity toward the mesendoderm shown in the Working example 5). Moreover, such enhancement of the differentiation efficacy has been proven to be achievable by using a mutant TET1 protein where its second amino acid from its N-terminus has been replaced and also where its dioxygenase region has been deleted. Therefore, one can deduce from this result that the DNA demethylating activity exerted by the dioxygenase region of TET1 is redundant and that the DNA-binding domain of TET1 protein is sufficient for such effects.

Moreover, as shown in the Working example 10, by this invention, it is now possible not only to enhance the differentiation efficacy of a given PSC but also to enhance the production efficacy of such PSC.

As mentioned previously, TET1 protein is expressed throughout from the fertilized egg to the blastocyst in the naive embryonic cells. This fact, in combination with the discovery of this invention that TET1 protein is not expressed in primed human PSCs, together with the differentiation efficacy enhancing effect of introducing the mutant TET1 into such PSCs, strongly suggests that TET1 protein's function is to facilitate the transition of the naive blastocyst to the primed epiblast in early development and further toward differentiation into each germ lineages. Actually, as described in Examples 12 to 14, the present invention revealed that a TET1 protein actively led mouse ES cells from the naive stage to the primed pluripotent stage by controlling the expressions of Dnmt3a/b.

Therefore, TET1 protein functions as a lubricant for cell differentiation in general, or in other words, TET1 harnesses the robustness for the development to proceed. It is therefore strongly suggested that the observed effect of the TET1 protein on the enhancement of differentiation efficacy of PSCs is a consequence of an increase of robustness for differentiation.

INDUSTRIAL APPLICABILITY

As explained so far, the introduction of the mutant TET1 protein not only swiftly down-regulates the differentiation resistant factor NANOG but also, can enhance cell differentiation efficacy by up-regulating factors which actively promote cell differentiation.

The TET1 proteins and the methods for producing pluripotent stem cells which utilize these TET1 proteins of this invention are superior in that they can release the PSCs from the differentiation resistance by NANOG or differentiation propensities exhibited by endoderm/mesoderm marker T and SOX17 expression and allow one to obtain only the desired cell type at high efficacy. Therefore, this invention is useful in regenerative medicine, drug discovery and reproductive medicine where the supplies of various cell types, tissues or organs are strongly desired.

[Sequence Listing Free Text]

SEQ ID NOs: 7 to 44

<223> artificially synthesized primer sequences

SEQ ID NOs: 45 and 46

<223> sequences of FLAG tag

What is claimed is:

1. An isolated nucleic acid that encodes a mutant human TET1 protein having the amino acid sequence selected from the group consisting of SEQ ID NO: 2, 4 and 6, and partial sequences thereof having at least amino acids 1 through 613 of SEQ ID NO: 2, 4 and 6, said amino acid sequence incorporating the binding domain at amino acids 585 to 613 and said mutant human TET1 protein having the second amino acid from the N-terminus substituted with another amino acid, wherein said mutant human TET1 protein has enhanced stability as compared to the corresponding non-mutant human TET1 protein selected from the group consisting of SEQ ID NO: 2, 4 and 6, wherein said enhanced stability is determined by Western blotting.

2. The isolated nucleic acid of claim 1, wherein said mutant human TET1 protein is the mutant human TET1 protein in which the second amino acid from the N-terminus is substituted with glycine in the amino acid sequence of SEQ ID NO: 2, 4 and 6 or the partial sequence thereof comprising at least amino acids 1 through 613 of SEQ ID Nos. 2, 4 or 6, and incorporating the binding domain at amino acids 585 to 613.

3. An isolated vector into which the nucleic acid of claim 1 has been inserted.

4. An isolated vector into which the nucleic acid of claim 1 has been inserted, further comprising a regulatory sequence for expression and the nucleic acid of claim 1 is operably linked to the regulatory sequence for expression.

5. An isolated nucleic acid that encodes a mutant human TET1 protein having the amino acid sequence selected from the group consisting of SEQ ID NO: 2, 4 and 6, and partial sequences thereof having at least amino acids 1 through 613 of SEQ ID NO: 2, 4 and 6, said amino acid sequence incorporating the binding domain at amino acids 585 to 613 and said mutant human TET1 protein having the amino acid sequence of SEQ ID NO: 46 inserted between the first and second amino acid from the N-terminus, wherein said insertion results in the substitution of the serine at the second position with another amino acid, wherein said expressed mutant human TETI protein has enhanced stability as compared to the corresponding non-mutant human TETI protein selected from the group consisting of SEQ ID NO: 2, 4 and 6, wherein said enhanced stability is determined by Western blotting.

6. An isolated vector into which the nucleic acid of claim 5 has been inserted.

7. An isolated vector into which the nucleic acid of claim 5 has been inserted, further comprising a regulatory sequence for expression and the nucleic acid of claim 5 is operably linked to the regulatory sequence for expression.

* * * * *

UNITED STATES PATENT AND TRADEMARK OFFICE
CERTIFICATE OF CORRECTION

PATENT NO. : 10,851,342 B2
APPLICATION NO. : 15/842701
DATED : December 1, 2020
INVENTOR(S) : Hidemasa Kato et al.

Page 1 of 1

It is certified that error appears in the above-identified patent and that said Letters Patent is hereby corrected as shown below:

In the Claims

Column 119, Line 60, in Claim 1:
Delete "TETl" and insert -- TET1 --, therefor.

Column 119, Line 62, in Claim 1:
Delete "TETl" and insert -- TET1 --, therefor.

Column 121, Line 6, in Claim 5:
Delete "TETl" and insert -- TET1 --, therefor.

Column 121, Line 7, in Claim 5:
Delete "TETl" and insert -- TET1 --, therefor.

Signed and Sealed this
Thirteenth Day of April, 2021

Drew Hirshfeld
*Performing the Functions and Duties of the*
*Under Secretary of Commerce for Intellectual Property and*
*Director of the United States Patent and Trademark Office*